(12) United States Patent
Miwa et al.

(10) Patent No.: US 7,087,597 B1
(45) Date of Patent: Aug. 8, 2006

(54) PYRIMIDINE 5-CARBOXAMIDE COMPOUNDS, PROCESS FOR PRODUCING THE SAME AND USE THEREOF

(75) Inventors: Tetsuo Miwa, Kobe (JP); Mitsuo Yamamoto, Nishinomiya (JP); Takayuki Doi, Izumi (JP); Naoki Tarui, Nara (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 636 days.

(21) Appl. No.: 10/110,381

(22) PCT Filed: Oct. 11, 2000

(86) PCT No.: PCT/JP00/07048

§ 371 (c)(1),
(2), (4) Date: Apr. 10, 2002

(87) PCT Pub. No.: WO01/27105

PCT Pub. Date: Apr. 19, 2001

(30) Foreign Application Priority Data

Oct. 12, 1999 (JP) .................................. 11-289868

(51) Int. Cl.
| | |
|---|---|
| *C07D 403/04* | (2006.01) |
| *C07D 405/14* | (2006.01) |
| *C07D 409/14* | (2006.01) |
| *A61K 31/506* | (2006.01) |
| *A61K 31/5377* | (2006.01) |

(52) U.S. Cl. ..................... 514/212.08; 514/255.05; 514/273; 544/320; 544/321; 540/524

(58) Field of Classification Search ................ 544/320, 544/321; 540/524; 514/212.08, 255.05, 514/273

See application file for complete search history.

(56) References Cited

U.S. PATENT DOCUMENTS

| 4,959,368 A | 9/1990 | Awaya et al. ................ 514/252 |
| 6,432,963 B1 * | 8/2002 | Hisamichi et al. ........... 514/256 |

FOREIGN PATENT DOCUMENTS

| DE | 19636487 | 3/1998 |
| EP | 0012361 | 6/1980 |
| EP | 0188094 | 7/1986 |
| EP | 0557877 | 9/1993 |
| EP | 0557879 | 9/1993 |
| EP | 0640599 | 3/1995 |
| EP | 0816358 | 1/1998 |
| EP | 0816359 | 1/1998 |
| EP | 1054004 | 11/2000 |
| GB | 901749 | 7/1962 |
| GB | 933159 | 8/1963 |
| JP | 61087672 | 5/1986 |
| WO | WO 99/06046 | 2/1999 |
| WO | WO 99/31073 | * 6/1999 |

OTHER PUBLICATIONS

Damasio, Alzheimer's Disease, Cecil Textbook of Medicine, 20th Edition, vol. 2, pp. 1992-1996, 1996.*
Layzer, Degenerative Diseases of the Nervous System, Cecil Textbook of Medicine, 20th Edition, vol. 2, pp. 2050-2057, 1996.*
Jacob et al., PubMed Abstract (Therapie 57(2):163-8), 2002.*
Rosen et al., PubMed Abstract (Annu Rev Sex Res 13:36-88), 2002.*
Torphy, Phosphodiesterase Isozymes, Am J Respir Crit Care Med. vol. 157, pp. 351-370, 1998.*
Reffelmann et al., Therapeutic Potential of Phsophodiesterase 5 Inhibition for Cardiovascular Disease, Circulation, pp. 239-244, 2003 (www.circulationaha.org).*
Maurice et al., Cyclic Nucleotide Phosphodiesterase Activity, Expression, and Targeting in Cells of the Cardiovascular System, Molecular Pharmacology, vol. 64, No. 3, pp. 533-546, 2003.*
Taylor, et al. "Heterocyclic Compounds" Chemical Abstracts 55:Columns 6489 and 6491 (1961).
Xiang, et al. "Synthesis and Biological Examination of New Pyrimidine Type Derivatives as Potential Phosphodiesterase(PDE) V Inhibitors" Korean J. of Med. Chem 8: 6-9(1998) No. 1.

* cited by examiner

Primary Examiner—Deepak Rao
(74) Attorney, Agent, or Firm—Elaine M. Ramesh; Mark Chao

(57) ABSTRACT

Compounds of the formula

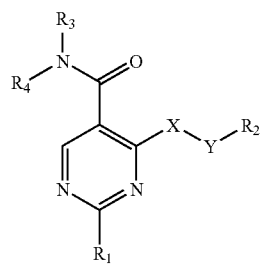

wherein $R_1$, $R_2$, $R_3$, $R_4$, X and Y are as defined, which have a superior cGMP specific phosphodiesterase (PDE) inhibitory activity, and can be used as an agent for the treatment of cardiovascular diseases such as angina pectoris, heart failure, cardiac infarction, hypertension, arteriosclerosis, and the like; allergic diseases such as asthma, or disorders of male or female genital function and the like.

28 Claims, No Drawings

SEQUENCE LISTING

<160> NUMBER OF SEQ ID NOS: 2

<210> SEQ ID NO 1
<211> LENGTH: 833
<212> TYPE: PRT
<213> ORGANISM: Human

<400> SEQUENCE: 1

```
Met Leu Pro Phe Gly Asp Lys Thr Arg Glu Met Val Asn Ala Trp Phe
  1               5                  10                  15

Ala Glu Arg Val His Thr Ile Pro Val Cys Lys Glu Gly Ile Arg Gly
             20                  25                  30

His Thr Glu Ser Cys Ser Cys Pro Leu Gln Gln Ser Pro Arg Ala Asp
         35                  40                  45

Asn Ser Val Pro Gly Thr Pro Thr Arg Lys Ile Ser Ala Ser Glu Phe
     50                  55                  60

Asp Arg Pro Leu Arg Pro Ile Val Val Lys Asp Ser Glu Gly Thr Val
 65                  70                  75                  80

Ser Phe Leu Ser Asp Ser Glu Lys Lys Glu Gln Met Pro Leu Thr Pro
                 85                  90                  95

Pro Arg Phe Asp His Asp Glu Gly Asp Gln Cys Ser Arg Leu Leu Glu
                100                 105                 110

Leu Val Lys Asp Ile Ser Ser His Leu Asp Val Thr Ala Leu Cys His
            115                 120                 125

Lys Ile Phe Leu His Ile His Gly Leu Ile Ser Ala Asp Arg Tyr Ser
        130                 135                 140

Leu Phe Leu Val Cys Glu Asp Ser Ser Asn Asp Lys Phe Leu Ile Ser
145                 150                 155                 160

Arg Leu Phe Asp Val Ala Glu Gly Ser Thr Leu Glu Glu Val Ser Asn
                165                 170                 175

Asn Cys Ile Arg Leu Glu Trp Asn Lys Gly Ile Val Gly His Val Ala
                180                 185                 190

Ala Leu Gly Glu Pro Leu Asn Ile Lys Asp Ala Tyr Glu Asp Pro Arg
            195                 200                 205

Phe Asn Ala Glu Val Asp Gln Ile Thr Gly Tyr Lys Thr Gln Ser Ile
        210                 215                 220

Leu Cys Met Pro Ile Lys Asn His Arg Glu Glu Val Val Gly Val Ala
225                 230                 235                 240

Gln Ala Ile Asn Lys Lys Ser Gly Asn Gly Gly Thr Phe Thr Glu Lys
                245                 250                 255

Asp Glu Lys Asp Phe Ala Ala Tyr Leu Ala Phe Cys Gly Ile Val Leu
            260                 265                 270

His Asn Ala Gln Leu Tyr Glu Thr Ser Leu Leu Glu Asn Lys Arg Asn
        275                 280                 285

Gln Val Leu Leu Asp Leu Ala Ser Leu Ile Phe Glu Glu Gln Gln Ser
    290                 295                 300

Leu Glu Val Ile Leu Lys Lys Ile Ala Ala Thr Ile Ile Ser Phe Met
```

```
                305                 310                 315                 320
Gln Val Gln Lys Cys Thr Ile Phe Ile Val Asp Glu Asp Cys Ser Asp
                    325                 330                 335
Ser Phe Ser Ser Val Phe His Met Glu Cys Glu Glu Leu Glu Lys Ser
                340                 345                 350
Ser Asp Thr Leu Thr Arg Glu His Asp Ala Asn Lys Ile Asn Tyr Met
                355                 360                 365
Tyr Ala Gln Tyr Val Lys Asn Thr Met Glu Pro Leu Asn Ile Pro Asp
            370                 375                 380
Val Ser Lys Asp Lys Arg Phe Pro Trp Thr Thr Glu Asn Thr Gly Asn
385                 390                 395                 400
Val Asn Gln Gln Cys Ile Arg Ser Leu Leu Cys Thr Pro Ile Lys Asn
                405                 410                 415
Gly Lys Lys Asn Lys Val Ile Gly Val Cys Gln Leu Val Asn Lys Met
                420                 425                 430
Glu Glu Asn Thr Gly Lys Val Lys Pro Phe Asn Arg Asn Asp Glu Gln
            435                 440                 445
Phe Leu Glu Ala Phe Val Ile Phe Cys Gly Leu Gly Ile Gln Asn Thr
450                 455                 460
Gln Met Tyr Glu Ala Val Glu Arg Ala Met Ala Lys Gln Met Val Thr
465                 470                 475                 480
Leu Glu Val Leu Ser Tyr His Ala Ser Ala Ala Glu Glu Thr Arg
                485                 490                 495
Glu Leu Gln Ser Leu Ala Ala Ala Val Val Pro Ser Ala Gln Thr Leu
            500                 505                 510
Lys Ile Thr Asp Phe Ser Phe Ser Asp Phe Glu Leu Ser Asp Leu Glu
            515                 520                 525
Thr Ala Leu Cys Thr Ile Arg Met Phe Thr Asp Leu Asn Leu Val Gln
            530                 535                 540
Asn Phe Gln Met Lys His Glu Val Leu Cys Arg Trp Ile Leu Ser Val
545                 550                 555                 560
Lys Lys Asn Tyr Arg Lys Asn Val Ala Tyr His Asn Trp Arg His Ala
                565                 570                 575
Phe Asn Thr Ala Gln Cys Met Phe Ala Ala Leu Lys Ala Gly Lys Ile
            580                 585                 590
Gln Asn Lys Leu Thr Asp Leu Glu Ile Leu Ala Leu Leu Ile Ala Ala
            595                 600                 605
Leu Ser His Asp Leu Asp His Arg Gly Val Asn Asn Ser Tyr Ile Gln
        610                 615                 620
Arg Ser Glu His Pro Leu Ala Gln Leu Tyr Cys His Ser Ile Met Glu
625                 630                 635                 640
His His His Phe Asp Gln Cys Leu Met Ile Leu Asn Ser Pro Gly Asn
                    645                 650                 655
Gln Ile Leu Ser Gly Leu Ser Ile Glu Glu Tyr Lys Thr Thr Leu Lys
                660                 665                 670
Ile Ile Lys Gln Ala Ile Leu Ala Thr Asp Leu Ala Leu Tyr Ile Lys
                675                 680                 685
Arg Arg Gly Glu Phe Phe Glu Leu Ile Arg Lys Asn Gln Phe Asn Leu
            690                 695                 700
Glu Asp Pro His Gln Lys Glu Leu Phe Leu Ala Met Leu Met Thr Ala
705                 710                 715                 720
Cys Asp Leu Ser Ala Ile Thr Lys Pro Trp Pro Ile Gln Gln Arg Ile
                    725                 730                 735
```

```
Ala Glu Leu Val Ala Thr Glu Phe Phe Asp Gln Gly Asp Arg Glu Arg
        740                 745                 750

Lys Glu Leu Asn Ile Glu Pro Thr Asp Leu Met Asn Arg Glu Lys Lys
        755                 760                 765

Asn Lys Ile Pro Ser Met Gln Val Gly Phe Ile Asp Ala Ile Cys Leu
        770                 775                 780

Gln Leu Tyr Glu Ala Leu Thr His Val Ser Glu Asp Cys Phe Pro Leu
785                 790                 795                 800

Leu Asp Gly Cys Arg Lys Asn Arg Gln Lys Trp Gln Ala Leu Ala Glu
                805                 810                 815

Gln Gln Glu Lys Met Leu Ile Asn Gly Glu Ser Gly Gln Ala Lys Arg
        820                 825                 830

Asn

<210> SEQ ID NO 2
<211> LENGTH: 2499
<212> TYPE: DNA
<213> ORGANISM: Human

<400> SEQUENCE: 2
atgttgccct tggagacaa aacaagagaa atggtcaatg catggtttgc tgagagagtt      60
cacaccatcc ctgtgtgcaa ggaaggtatc agaggccaca ccgaatcttg ctcttgtccc    120
ttgcagcaga gtcctcgtgc agataacagt gtccctggaa caccaaccag gaaaatctct    180
gcctctgaat tgaccggcc tcttagaccc attgttgtca aggattctga gggaactgtg     240
agcttcctct ctgactcaga aagaaggaa cagatgcctc taaccctcc aaggtttgat      300
catgatgaag ggaccagtg ctcaagactc ttggaattag tgaaggatat ttctagtcat     360
ttggatgtca cagccttatg tcacaaaatt ttcttgcata ccatggact gatatctgct     420
gaccgctatt ccctgttcct tgtctgtgaa gacagctcca atgacaagtt tcttatcagc    480
cgcctctttg atgttgctga aggttcaaca ctggaagaag tttcaaataa ctgtatccgc    540
ttagaatgga caaaggcat tgtgggacat gtggcagcgc ttggtgagcc cttgaacatc     600
aaagatgcat atgaggatcc tcggttcaat gcagaagttg accaaattac aggctacaag    660
acacaaagca ttcttttgta tgccaattaag aatcataggg aagaggttgt tggtgtagcc   720
caggccatca acaagaaatc aggaaacggt gggacattta ctgaaaaaga tgaaaaggac    780
tttgctgctt atttggcatt ttgtggtatt gttcttcata tgctcagct ctatgagact     840
tcactgctgg agaacaagag aaatcaggtg ctgcttgacc ttgctagttt aattttttgaa  900
gaacaacaat cattagaagt aattttgaag aaaatagctg ccactattat ctctttcatg   960
caagtgcaga atgcaccat tttcatagtg gatgaagatt gctccgattc ttttttctagt  1020
gtgtttcaca tggagtgtga ggaattagaa aaatcatctg atacattaac aagggaacat  1080
gatgcaaaca aaatcaatta catgtatgct cagtatgtca aaaatactat ggaaccactt  1140
aatatcccag atgtcagtaa ggataaaaga tttccctgga caactgaaaa tacaggaaat  1200
gtaaaccagc agtgcattag aagtttgctt tgtacaccta taaaaaatgg aaagaagaat  1260
aaagttatag ggtttgcca acttgttaat aagatggagg agaatactgg caaggttaag   1320
cctttcaacc gaaatgacga acagtttctg gaagcttttg tcatctttttg tggcttgggg  1380
atccagaaca cgcagatgta tgaagcagtg gagagagcca tggccaagca aatggtcaca  1440
ttggaggttc tgtcgtatca tgcttcagca gcagaggaag aaacaagaga gctacagtcg  1500
```

```
ttagcggctg ctgtggtgcc atctgcccag acccttaaaa ttactgactt tagcttcagt    1560
gactttgagc tgtctgatct ggaaacagca ctgtgtacaa ttcggatgtt tactgacctc    1620
aaccttgtgc agaacttcca gatgaaacat gaggttcttt gcagatggat tttaagtgtt    1680
aagaagaatt atcggaagaa tgttgcctat cataattgga gacatgcctt taatacagct    1740
cagtgcatgt ttgctgctct aaaagcaggc aaaattcaga acaagctgac tgacctggag    1800
atacttgcat tgctgattgc tgcactaagc cacgatttgg atcaccgtgg tgtgaataac    1860
tcttacatac agcgaagtga acatccactt gcccagcttt actgccattc aatcatggaa    1920
caccatcatt ttgaccagtg cctgatgatt cttaatagtc caggcaatca gattctcagt    1980
ggcctctcca ttgaagaata taagaccacg ttgaaaataa tcaagcaagc tattttagct    2040
acagacctag cactgtacat taagaggcga ggagaatttt ttgaacttat aagaaaaaat    2100
caattcaatt tggaagatcc tcatcaaaag gagttgtttt tggcaatgct gatgacagct    2160
tgtgatcttt ctgcaattac aaaaccctgg cctattcaac aacggatagc agaacttgta    2220
gcaactgaat tttttgatca aggagacaga gagagaaaag aactcaacat agaacccact    2280
gatctaatga acaggagaa gaaaaacaaa atcccaagta tgcaagttgg gttcatagat    2340
gccatctgct tgcaactgta tgaggccctg acccacgtgt cagaggactg tttccctttg    2400
ctagatggct gcagaaagaa caggcagaaa tggcaggccc ttgcagaaca gcaggagaag    2460
atgctgatta atggggaaag cggccaggcc aagcggaac                           2499
```

PYRIMIDINE 5-CARBOXAMIDE COMPOUNDS, PROCESS FOR PRODUCING THE SAME AND USE THEREOF

This application is the National Phase filing of International Patent Application No. PCT/JP00/07048, filed Oct. 11, 2000.

TECHNICAL FIELD

The present invention relates to a novel pyrimidine-5-carboxamide compound or a salt thereof, a production method and a pharmaceutical product containing the same. The pyrimidine-5-carboxamide compound and a salt thereof of the present invention have a potent and selective cyclic guanosine-3',5'-monophosphoric acid (hereinafter cGMP) phosphodiesterase (hereinafter PDE) inhibitory activity, and are useful as an agent for the prophylaxis or therapy of a disease for which its action is effective.

BACKGROUND ART cGMP is biosynthesized from guanosine triphosphate (GTP) by the action of guanylate cyclase and metabolized to 5'-GMP by the action of cGMP-PDE, during which cGMP plays various roles as a secondary transmitter in cellular signal transduction in the body. Particularly the action of cGMP, which is of critical importance in the functional modulation of cardiovascular system, is well known. Therefore, inhibition of the action of cGMP-PDE leads to the prophylaxis or treatment of the diseases caused by the promotion of metabolism of cGMP. Examples of such diseases include angina pectoris, heart failure, cardiac infarction, hypertension, pulmonary hypertension, arteriosclerosis, allergic diseases, asthma, renal diseases, cerebral function disorders, immunodeficiency, ophthalmic diseases, disorders of male or female genital function and the like.

There are a number of reports on a compound having a PDE inhibitory activity (e.g., WO9853819 and references cited therein). However, only a small number of reports deal with a compound having a monocyclic pyrimidine skeleton and showing a PDE inhibitory activity, which are limited to JP-A-2-295978, JP-A-3-145466, JP-A-7-89958, Korean J. of Med. Chem., vol. 8, p. 6 (1998) and the like.

PDE is known to include at least 7 isoenzymes [e.g., Annual Reports in Medicinal Chemistry, vol. 31, p. 61 (1996), Academic Press, San Diego]. Of those isoenzymes, PDE I, II, III, IV and V are widely distributed in the body. It is well known that inhibition of plural isoenzymes results in unpreferable occurrence of side effects.

It is therefore an object of the present invention to provide a potent and selective PDE inhibitor.

DISCLOSURE OF INVENTION

For the purpose of achieving the above-mentioned object, the present inventors have synthesized various compounds and succeeded in creating a compound having a novel structure represented by the formula (I) and found that the compound has a potent and selective PDE inhibitory activity, which resulted in the completion of the present invention.

Accordingly, the present invention provides

[1] a compound of the formula (I)

wherein $R_1$ is a heterocycle having a skeleton consisting of 3 to 15 atoms including 1 to 5 nitrogen atom(s), which heterocycle is attached by a secondary nitrogen atom constituting the heterocycle;

X is an oxygen atom, a nitrogen atom optionally substituted by a hydrocarbon group having 1 to 5 carbon atom(s) or a sulfur atom optionally oxidized with 1 or 2 oxygen, Y is a bond or a ($C_{1-5}$ alkylene group, $R_2$ is (1) a hydrogen atom, (2) a hydroxy group, (3) a $C_{1-5}$ alkoxy group, (4) a ($C_{1-5}$ alkylthio group, (5) a carbocycle having 3 to 15 carbon atoms or (6) a heterocycle having a skeleton consisting of 3 to 15 atoms including 1 to 5 heteroatom(s), provided that when Y is a bond, $R_2$ is a carbocycle having 3 to 15 carbon atoms or a heterocycle having a skeleton consisting of 3 to 15 atoms including 1 to 5 heteroatom(s) and;

one of $R_3$ and $R_4$ is a hydrogen atom or a group of the formula: —Z—$R_5$ (Z is a bond or $C_{1-10}$ alkylene group optionally having substituent(s) and $R_5$ is (1) a hydrogen atom, (2) a hydroxy group, (3) a $C_{1-5}$ alkoxy group, (4) a nitrile group, (5) a $C_{1-5}$ alkoxy-carbonyl group, (6) a carboxyl group, (7) a carbamoyl group, (8) a (mono or di-$C_{1-5}$ alkyl)carbamoyl group, (9) an amino group, (10) a (di or mono-$C_{1-5}$ alkyl)amino group, (11) a ($C_{1-5}$ alkoxy-carbonyl)amino group, (12) a ($C_{1-5}$ alkylthio group, (13) a carbocycle having 3 to 15 carbon atoms or (14) a heterocycle having a skeleton consisting of 3 to 15 atoms including 1 to 5 heteroatom(s));

the other is a group of the formula: —Z—$R_5$ (Z and $R_5$ are as defined above); and $R_3$ and $R_4$ may form, together with the adjacent nitrogen atom, a heterocycle having a skeleton consisting of 3 to 15 atoms, which heterocycle is attached by a secondary nitrogen atom constituting the heterocycle, wherein the above-mentioned heterocycle and a carbocycle having 3 to 15 carbon atoms are each optionally substituted by substituent(s) selected from the group consisting of $C_{1-8}$ alkyl, $C_{2-8}$ alkenyl, $C_{2-8}$ alkynyl, $C_{7-16}$ aralkyl, $C_{3-8}$ cycloalkyl, $C_{3-8}$ cycloalkenyl, $C_{6-14}$ aryl, $C_{1-8}$ alkoxy, $C_{1-3}$ alkylenedioxy, hydroxy, halogen atom, amino, (di or mono-$C_{1-5}$ alkyl)amino, ($C_{1-5}$ alkoxy-carbonyl)amino, ($C_{1-5}$ acyl)amino, ($C_{1-5}$ acyl) ($C_{1-5}$ alkyl)amino, ($C_{1-5}$ alkylthio, nitrile, nitro, ($C_{1-5}$ alkoxy-carbonyl, carboxyl, $C_{1-5}$ alkyl-carbonyloxy, oxo, thioxo, $C_{1-6}$ acyl group, sulfamoyl and (di or mono-$C_{1-5}$ alkyl)sulfamoyl, or a salt thereof,

[2] the compound of [1], wherein, when Z is a $C_{2-10}$ alkylene group optionally having substituent(s), $R_5$ is a hydrogen atom, a hydroxy group, a $C_{1-5}$ alkoxy group, a nitrile group, a $C_{1-5}$ alkoxy-carbonyl, a carboxyl group, a carbamoyl group, a (mono or di-$C_{1-5}$ alkyl)carbamoyl group, an amino group, a (di or mono-$C_{1-5}$ alkyl)amino group, a ($C_{1-5}$ alkoxy-carbonyl)amino group, a $C_{1-5}$ alkylthio group, a carbocycle having 3 to 15 carbon atoms, or a heterocycle having a skeleton consisting of 3 to 15 atoms including 1 to 5 heteroatom(s) and, when Z is a methylene group optionally having substituents, $R_5$ is a nitrile group, a $C_{1-5}$ alkoxy-carbonyl group, a carboxyl group, a carbamoyl group, a (mono or di-$C_{1-5}$ alkyl)carbamoyl group, a carbocycle having 3 to 15 carbon atoms, or a heterocycle having a skeleton consisting of 3 to 15 atoms including 1 to 5 heteroatom(s) and,

[3] the compound of [1], wherein X is a nitrogen atom optionally substituted by a hydrocarbon group having 1 to 5 carbon atom(s) or a sulfur atom optionally oxidized with 1 or 2 oxygen,

[4] the compound of [1], wherein Y is a $C_{2-5}$ alkylene group,

[5] the compound of [1], wherein Y is a $C_{1-5}$ alkylene group, $R_2$ is a hydroxy group, a $C_{1-5}$ alkoxy group or a $C_{1-5}$ alkylthio group,

[6] the compound of [1], wherein $R_5$ is (1) a non-aromatic carbocycle having 3 to 15 carbon atoms or (2) a non-aromatic heterocycle having a skeleton consisting of 3 to 15 atoms including 1 to 5 heteroatom(s),

[7] the compound of [1], wherein Z is a $C_{2-10}$ alkylene group optionally having substituent(s), and $R_5$ is a hydroxy group, a nitrile group, a $C_{1-5}$ alkoxy-carbonyl, a carboxyl group, a carbamoyl group, a (mono or di-($C_{1-5}$ alkyl)carbamoyl group, a ($C_{1-5}$ alkoxy-carbonyl)amino group or a $C_{1-5}$ alkylthio group,

[8] the compound of [1], wherein Z is a methylene group optionally having substituent(s), and $R_5$ is a nitrile group, a $C_{1-5}$ alkoxy-carbonyl group, a carboxyl group, a carbamoyl group or a (mono or di-$C_{1-5}$ alkyl)carbamoyl group,

[9] the compound of [1], wherein the substituent(s) of the heterocycle and the carbocycle having 3 to 15 carbon atoms is selected from the group consisting of $C_{2-8}$ alkenyl, $C_{2-8}$ alkynyl, $C_{7-16}$ aralkyl, $C_{3-8}$ cycloalkyl, $C_{3-8}$ cycloalkenyl, $C_{6-14}$ aryl, $C_{1-3}$ alkylenedioxy, hydroxy, ($C_{1-5}$ alkoxy-carbonyl)amino, ($C_{1-5}$ acyl)amino, ($C_{1-5}$ acyl)($C_{1-5}$ alkyl)amino, $C_{1-5}$ alkylthio, nitrile, $C_{1-5}$ alkoxy-carbonyl, carboxyl, ($C_{1-5}$ alkyl-carbonyloxy, oxo, thioxo, $C_{1-6}$ acyl group, sulfamoyl and (di or mono-($C_{1-5}$ alkyl)sulfamoyl,

[10] the compound of [1], wherein $R_1$ is a heterocycle having a skeleton consisting of 5 to 12 atoms including 1 or 2 nitrogen atom(s) and optionally substituted by substituent(s) selected from the group consisting of $C_{1-8}$ alkyl, $C_{2-8}$ alkenyl, $C_{2-8}$ alkynyl, $C_{7-16}$ aralkyl, $C_{3-8}$ cycloalkyl, $C_{3-8}$ cycloalkenyl, $C_{6-14}$ aryl, $C_{1-8}$ alkoxy, $C_{1-3}$ alkylenedioxy, hydroxy, halogen atom, amino, (di or mono-$C_{1-5}$ alkyl) amino, ($C_{1-5}$ alkoxy-carbonyl)amino, ($C_{1-5}$ acyl)amino, ($C_{1-5}$ acyl) ($C_{1-5}$ alkyl)amino, $C_{1-5}$ alkylthio, nitrile, nitro, $C_{1-5}$ alkoxy-carbonyl, carboxyl, ($C_{1-5}$ alkyl-carbonyloxy, oxo, thioxo, $C_{1-6}$ acyl group, sulfamoyl and (di or mono-$C_{1-5}$ alkyl)sulfamoyl,

[11] the compound of [1], wherein $R_1$ is a heterocycle having a skeleton consisting of 8 to 12 atoms including a nitrogen atom and optionally substituted by substituent(s) selected from the group consisting of $C_{1-8}$ alkyl, $C_{2-8}$ alkenyl, $C_{2-8}$ alkynyl, $C_{7-16}$ aralkyl, $C_{3-8}$ cycloalkyl, $C_{3-8}$ cycloalkenyl, $C_{6-14}$ aryl, $C_{1-8}$ alkoxy, $C_{1-3}$ alkylenedioxy, hydroxy, halogen atom, amino, (di or mono-$C_{1-5}$ alkyl)amino, ($C_{1-5}$ alkoxy-carbonyl)amino, ($C_{1-5}$ acyl)amino, ($C_{1-5}$ acyl) ($C_{1-5}$ alkyl)amino, $C_{1-5}$ alkylthio, nitrile, nitro, $C_{1-5}$ alkoxy-carbonyl, carboxyl, $C_{1-5}$ alkyl-carbonyloxy, oxo, thioxo, $C_{1-6}$ acyl group, sulfamoyl and (di or mono-$C_{1-5}$ alkyl)sulfamoyl,

[12] the compound of [1], wherein $R_1$ is 1-indolinyl optionally substituted by substituent(s) selected from the group consisting of $C_{1-8}$ alkyl, $C_{2-8}$ alkenyl, $C_{2-8}$ alkynyl, $C_{7-16}$ aralkyl, $C_{3-8}$ cycloalkyl, $C_{3-8}$ cycloalkenyl, $C_{6-14}$ aryl, $C_{1-8}$ alkoxy, $C_{1-3}$ alkylenedioxy, hydroxy, halogen atom, amino, (di or mono-($C_{1-5}$ alkyl)amino, ($C_{1-5}$ alkoxy-carbonyl) amino, ($C_{1-5}$ acyl)amino, ($C_{1-5}$ acyl)($C_{1-5}$ alkyl)amino, ($C_{1-5}$ alkylthio, nitrile, nitro, $C_{1-5}$ alkoxy-carbonyl, carboxyl, $C_{1-5}$ alkyl-carbonyloxy, oxo, thioxo, $C_{1-6}$ acyl group, sulfamoyl and (di or mono-($C_{1-5}$ alkyl)sulfamoyl,

[13] the compound of [1], wherein $R_2$ is a carbocycle having 5 to 7 carbon atoms or a heterocycle having a skeleton consisting of 5 to 7 atoms including 1 or 2 heteroatom(s), which heterocycle is optionally substituted by substituent(s) selected from the group consisting of $C_{1-8}$ alkyl, $C_{2-8}$ alkenyl, $C_{2-8}$ alkynyl, $C_{7-16}$ aralkyl, $C_{3-8}$ cycloalkyl, $C_{3-8}$ cycloalkenyl, $C_{6-14}$ aryl, $C_{1-8}$ alkoxy, $C_{1-3}$ alkylenedioxy, hydroxy, halogen atom, amino, (di or mono-$C_{1-5}$ alkyl) amino, ($C_{1-5}$ alkoxy-carbonyl)amino, ($C_{1-5}$ acyl)amino, ($C_{1-5}$ acyl) ($C_{1-5}$ alkyl)amino, $C_{1-5}$ alkylthio, nitrile, nitro, $C_{1-5}$ alkoxy-carbonyl, carboxyl, $C_{1-5}$ alkyl-carbonyloxy, oxo, thioxo, $C_{1-6}$ acyl group, sulfamoyl and (di or mono-($C_{1-5}$ alkyl)sulfamoyl,

[14] the compound of [1], wherein $R_2$ is phenyl optionally substituted by substituent(s) selected from the group consisting of $C_{1-8}$ alkyl, $C_{2-8}$ alkenyl, $C_{2-8}$ alkynyl, $C_{7-16}$ aralkyl, $C_{3-8}$ cycloalkyl, $C_{3-8}$ cycloalkenyl, $C_{6-14}$ aryl, $C_{1-8}$ alkoxy, $C_{1-3}$ alkylenedioxy, hydroxy, halogen atom, amino, (di or mono-$C_{1-5}$ alkyl)amino, ($C_{1-5}$ alkoxy-carbonyl)amino, ($C_{1-5}$ acyl)amino, ($C_{1-5}$ acyl)($C_{1-5}$ alkyl)amino, $C_{1-5}$ alkylthio, nitrile, nitro, ($C_{1-5}$ alkoxy-carbonyl, carboxyl, ($C_{1-5}$ alkyl-carbonyloxy, oxo, thioxo, $C_{1-6}$ acyl group, sulfamoyl and (di or mono-$C_{1-5}$ alkyl)sulfamoyl,

[15] the compound of [1], wherein X is an oxygen atom or NH, and Y is a $C_{1-3}$ alkylene group,

[16] the compound of [1], wherein X is an oxygen atom, and Y is a methylene group,

[17] the compound of [1], wherein $R_3$ is a hydrogen atom and $R_4$ is a group of the formula: —Z—$R_5$,

[18] the compound of [17], wherein Z is a bond or a $C_{1-4}$ alkylene group, $R_5$ is a carbocycle having 5 to 8 carbon atoms or a heterocycle having a skeleton consisting of 5 to 11 atoms having 1 to 5 heteroatom(s), which heterocycle is optionally substituted by substituent(s) selected from the group consisting of $C_{1-8}$ alkyl, $C_{2-8}$ alkenyl, $C_{2-8}$ alkynyl, $C_{7-16}$ aralkyl, $C_{3-8}$ cycloalkyl, $C_{3-8}$ cycloalkenyl, $C_{6-14}$ aryl, $C_{1-8}$ alkoxy, $C_{1-3}$ alkylenedioxy, hydroxy, halogen atom, amino, (di or mono-$C_{1-5}$ alkyl)amino, ($C_{1-5}$ alkoxy-carbonyl)amino, ($C_{1-5}$ acyl)amino, ($C_{1-5}$ acyl)($C_{1-5}$ alkyl)amino, $C_{1-5}$ alkylthio, nitrile, nitro, $C_{1-5}$ alkoxy-carbonyl, carboxyl, $C_{1-5}$ alkyl-carbonyloxy, oxo, thioxo, $C_{1-6}$ acyl group, sulfamoyl and (di or mono-$C_{1-5}$ alkyl)sulfamoyl,

[19] the compound of [1], wherein $R_1$ is a group selected from
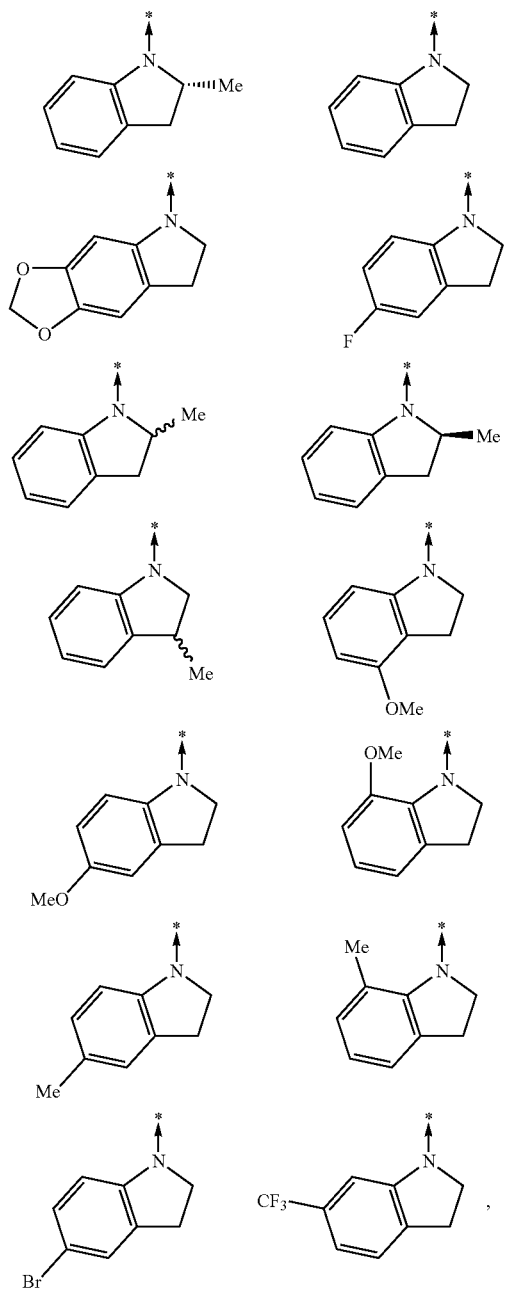
—X—Y—$R_2$ is a group selected from
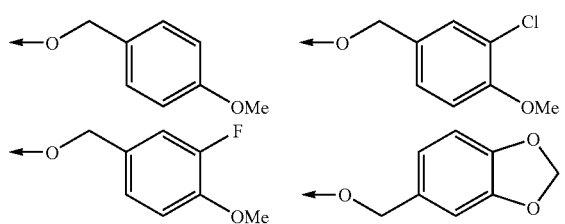
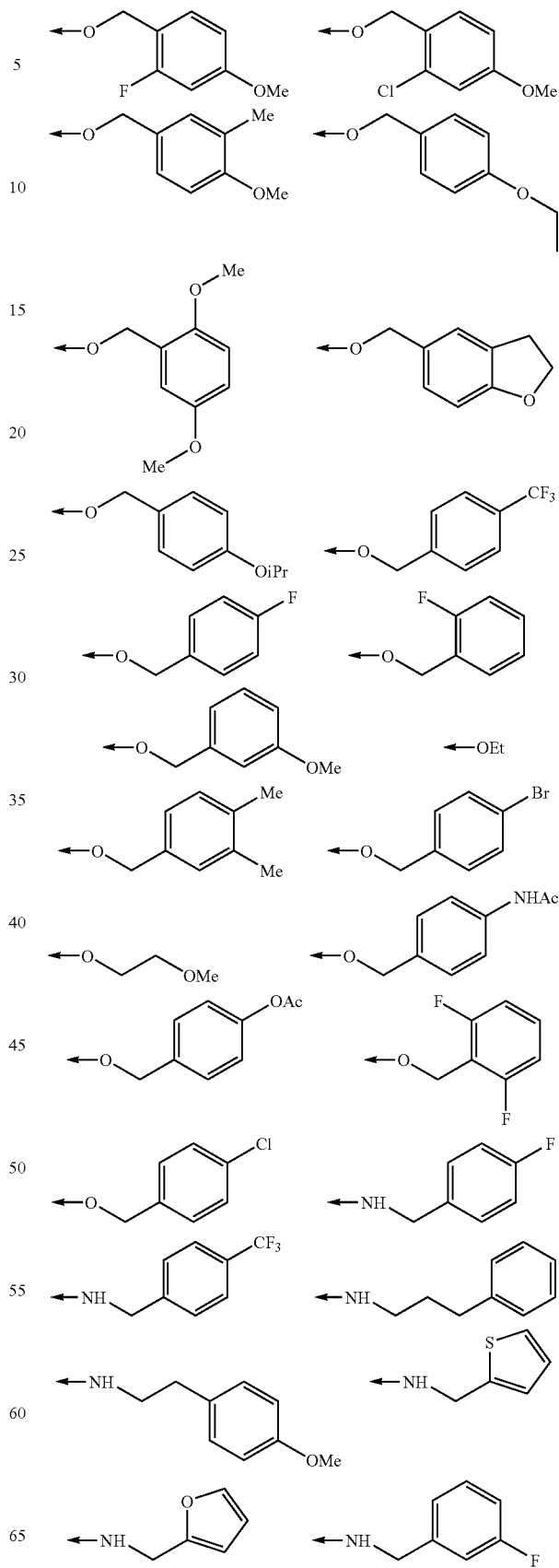

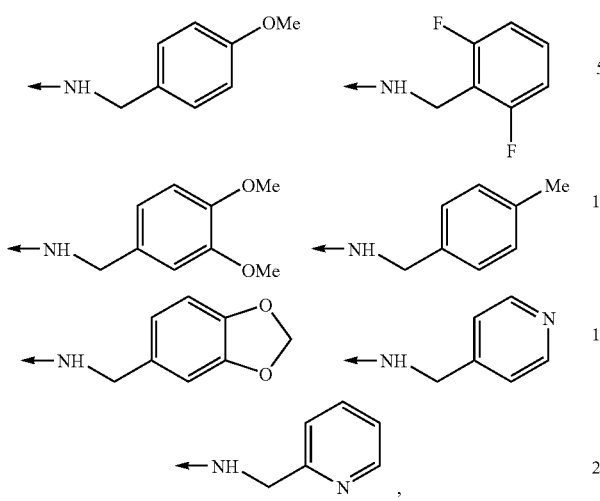
and —NR$_3$R$_4$ is a group selected from
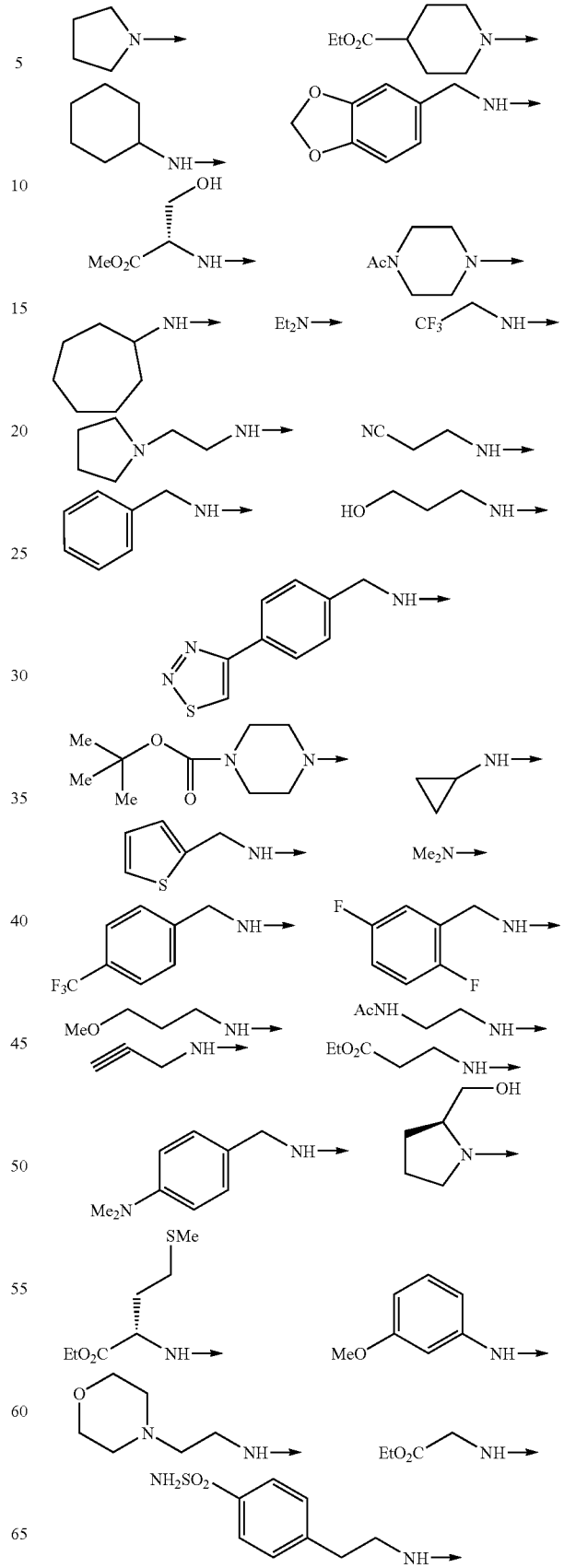

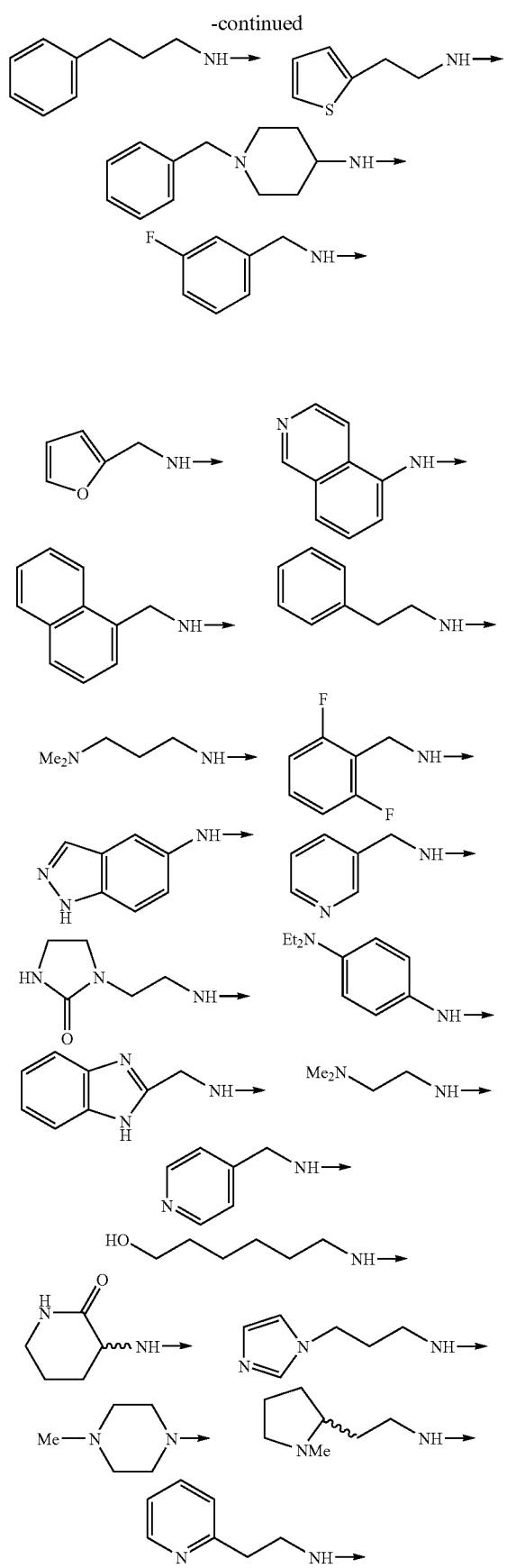
[20] the compound of [1], wherein $R_1$ is a group selected from
—X—Y—$R_2$ is a group selected from -continued

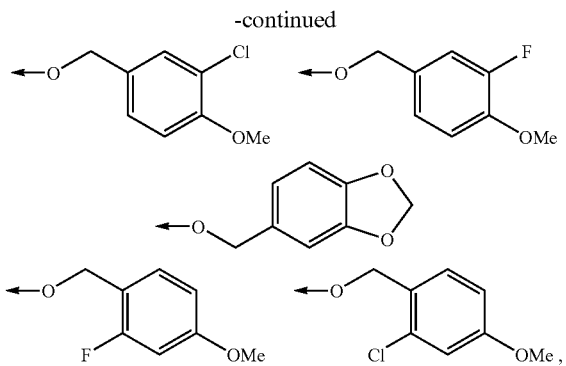

and —NR₃R₄ is a group selected from

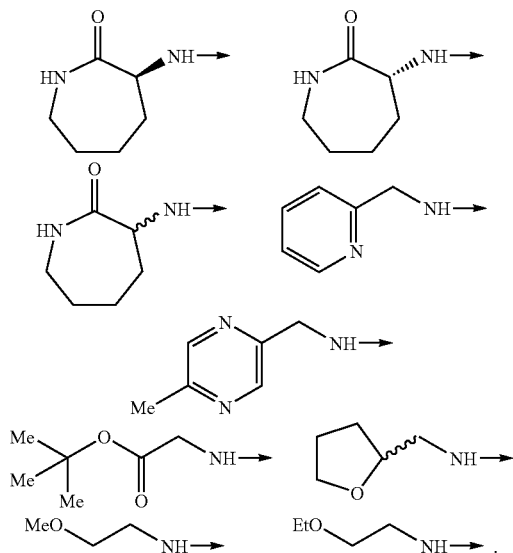

[21] the compound of [1], wherein R₁ is a group selected from the group consisting of

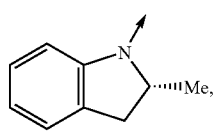

—X—Y—R₂ is a group selected from the group consisting of

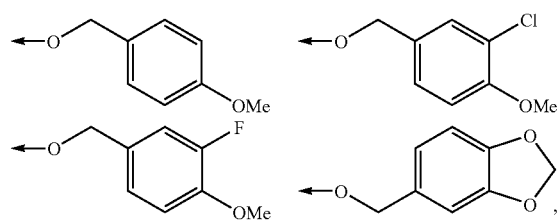

and —NR₃R₄ is a group selected from the group consisting of

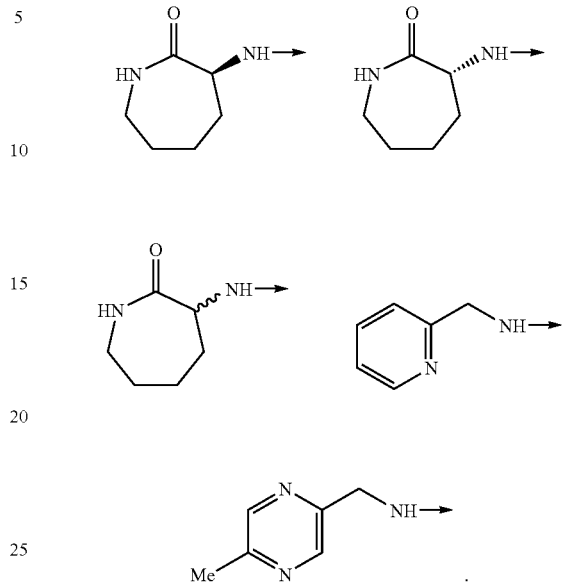

[22] (i) (RS)-2-(2,3-dihydro-1H-indol-1-yl)-4-[ (4-methoxybenzyl)oxy]-N-(2-oxo-3-azepanyl)-5-pyrimidinecarboxamide, (ii) 2-(2,3-dihydro-1H-indol-1-yl)-4-[ (4-methoxybenzyl)oxy]-N-[(5-methyl-2-pyrazinyl)methyl]-5-pyrimidinecarboxamide, (iii) 2-(2,3-dihydro-1H-indol-1-yl)-4-[(4-methoxybenzyl)oxy]-N-(2-pyridinylmethyl)-5-pyrimidinecarboxamide, (iv) (RS)-4-(1,3-benzodioxol-5-ylmethoxy)-2-(2,3-dihydro-1H-indol-1-yl)-N-(2-oxo-3-azepanyl)-5-pyrimidinecarboxamide, (v) 4-(1,3-benzodioxol-5-ylmethoxy)-2-(2,3-dihydro-1H-indol-1-yl)-N-(2-pyridinylmethyl)-5-pyrimidinecarboxamide, (vi) 2-(2,3-dihydro-1H-indol-1-yl)-4-[(3-fluoro-4-methoxybenzyl)oxy]-N-(2-pyridinylmethyl)-5-pyrimidinecarboxamide, (vii) 2-(2,3-dihydro-1H-indol-1-yl)-4-[(3-fluoro-4-methoxybenzyl)oxy]-N-(2-oxo-3-azepanyl)-5-pyrimidinecarboxamide, (viii) 2-(2,3-dihydro-1H-indol-1-yl)-4-[(3-fluoro-4-methoxybenzyl)oxy]-N-[(5-methyl-2-pyrazinyl)methyl]-5-pyrimidinecarboxamide, (ix) 4-[(3-chloro-4-methoxybenzyl)oxy]-2-(2,3-dihydro-1H-indol-1-yl)-N-(2-pyridinylmethyl)-5-pyrimidinecarboxamide, (x) 4-[(3-chloro-4-methoxybenzyl)oxy]-2-(2,3-dihydro-1H-indol-1-yl)-N-(2-oxo-3-azepanyl)-5-pyrimidinecarboxamide, (xi) 4-[(3-chloro-4-methoxybenzyl)oxy]-2-(2,3-dihydro-1H-indol-1-yl)-N-[(5-methyl-2-pyrazinyl)methyl]-5-pyrimidinecarboxamide, (xii) (rac)-4-[(4-methoxybenzyl)oxy]-2-(2-methyl-2,3-dihydro-1H-indol-1-yl)-N-(2-oxo-3-azepanyl)-5-pyrimidinecarboxamide, (xiii) 2-(2,3-dihydro-1H-indol-1-yl)-4-[(4-methoxybenzyl)oxy]-N-[(3S)-2-oxoazepanyl]-5-pyrimidinecarboxamide, (xiv) 2-(2,3-dihydro-1H-indol-1-yl)-4-[(4-methoxybenzyl)oxy]-N-[(3R)-2-oxoazepanyl]-5-pyrimidinecarboxamide, (xv) 4-(1,3-benzodioxol-5-ylmethoxy)-2-(2,3-dihydro-1H-indol-1-yl)-4-[(4-methoxybenzyl)oxy]-N-[(3S)-2-oxoazepanyl]-5-pyrimidinecarboxamide, (xvi) 2-(2,3-dihydro-1H-indol-1-yl)-4-[(3-fluoro-4-methoxybenzyl)oxy]-N-[(3S)-2-oxoazepanyl]-5-pyrimidinecarboxamide, (xvii) 4-[(3-chloro-4-methoxybenzyl)oxy]-2-(2,3-dihydro-1H-indol-1-yl)-N-[(3S)-2-oxoazepanyl]-5-pyrimidinecarboxamide, (xviii) 4-[(4-methoxybenzyl)oxy]-2-[(2RS)-2-methyl-2,3- dihydro-1H-indol-1-yl]-N-[(3S)-2-oxoazepanyl]-5-pyrimidinecarboxamide, (xix) 4-[(4-methoxybenzyl)oxy]-2-[(2RS)-2-methyl-2,3-dihydro-1H-indol-1-yl]-N-[(3R)-2-oxoazepanyl]-5-pyrimidinecarboxamide, (xx) 4-[(4-methoxybenzyl)oxy]-2-[(2R)-2-methyl-2,3-dihydro-1H-indol-1-yl]-N-[(3S)-2-oxoazepanyl]-5-pyrimidinecarboxamide, (xxi) 4-[(4-methoxybenzyl)oxy]-2-[(2R)-2-methyl-2,3-dihydro-1H-indol-1-yl]-N-[(3R)-2-oxoazepanyl]-5-pyrimidinecarboxamide, (xxii) 2-[(2R)-2-methyl-2,3-dihydro-1H-indol-1-yl]-4-[(3-fluoro-4-methoxybenzyl)oxy]-N-[(3S)-2-oxoazepanyl]-5-pyrimidinecarboxamide, (xxiii) 4-[(3-chloro-4-methoxybenzyl)oxy]-2-[(2R)-2-methyl-2,3-dihydro-1H-indol-1-yl]-N-[(3S)-2-oxoazepanyl]-5-pyrimidinecarboxamide, (xxiv) 4-[(4-methoxybenzyl)oxy]-2-[(2S)-2-methyl-2,3-dihydro-1H-indol-1-yl]-N-[(3S)-2-oxoazepanyl]-5-pyrimidinecarboxamide or (xxv) 4-[(4-methoxybenzyl)oxy]-2-[(2S)-2-methyl-2,3-dihydro-1H-indol-1-yl]-N-[(3R)-2-oxoazepanyl]-5-pyrimidinecarboxamide,

[23] a prodrug of the compound of [1],

[24] a production method of the compound of [1], which comprises reacting a compound of the formula

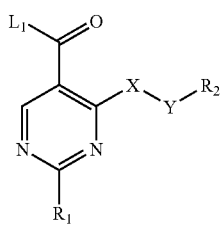

(II)

wherein $L_1$ is a leaving group and other symbols are as defined in [1], or a salt thereof, with an amine compound of the formula

wherein $R_3$ and $R_4$ are as defined in [1],

[25] a production method of the compound of [1], which comprises reacting a compound of the formula

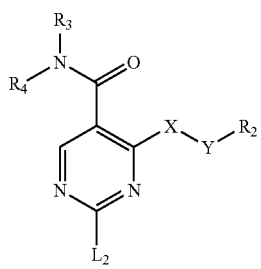

(III)

wherein $L_2$ is a leaving group and other symbols are as defined in [1], or a salt thereof, with a compound of the formula

wherein $R_1$ is as defined in [1],

[26] a production method of the compound of [1], which comprises reacting a compound of the formula

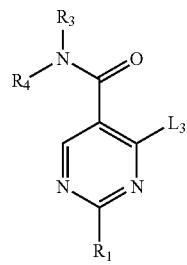

(IV)

wherein $L_3$ is a leaving group and other symbols are as defined in [1], or a salt thereof, with a compound of the formula

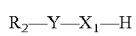

wherein $R_2$ and Y are as defined in [1] and $X_1$ is an oxygen atom, a nitrogen atom optionally substituted by a hydrocarbon group having 1 to 5 carbon atom(s) or a sulfur atom, and if desired, subjecting the resulting compound to oxidation,

[27] a production method of the compound of [1], which comprises reacting a compound of the formula

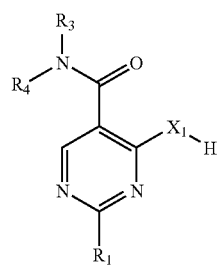

(V)

wherein symbols are as defined in [1], $X_1$ is an oxygen atom, a nitrogen atom optionally substituted by a hydrocarbon group having 1 to 5 carbon atom(s) or a sulfur atom, or a salt thereof, with a compound of the formula

wherein $R_2$ and Y are as defined in [1] and $L_4$ is a leaving group, and if desired, subjecting the resulting compound to oxidation,

[28] a pharmaceutical composition comprising a compound of the formula

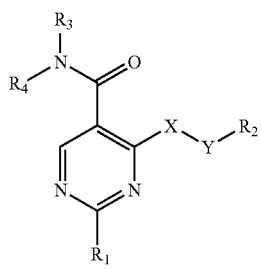

(I)

wherein symbols are as defined in [1], or a salt thereof or a prodrug thereof,

[29] the pharmaceutical composition of [28], which is a cyclic guanosine-3',5'-monophosphoric acid phosphodiesterase (particularly, cyclic guanosine-3',5'-monophosphoric acid phosphodiesterase V) inhibitor,

[30] the pharmaceutical composition of [28], which is a composition for the prophylaxis or treatment of angina pectoris, heart failure, cardiac infarction, hypertension, pulmonary hypertension, arteriosclerosis, allergic diseases, asthma, renal diseases, cerebral function disorders, immunodeficiency, ophthalmic diseases or disorders of male or female genital function,

[31] a method for inhibiting cyclic guanosine-3',5'-monophosphoric acid phosphodiesterase, which comprises administering an effective amount of the compound of [1] or a prodrug thereof to a mammal,

[32] a method for the prophylaxis or treatment of angina pectoris, heart failure, cardiac infarction, hypertension, pulmonary hypertension, arteriosclerosis, allergic diseases, asthma, renal diseases, cerebral function disorders, immunodeficiency, ophthalmic diseases or disorders of male or female genital function in a mammal, which comprises administering an effective amount of the compound of [1] or a prodrug thereof to the mammal,

[33] use of the compound of [1] or a prodrug thereof for the production of a cyclic guanosine-3',5'-monophosphoric acid phosphodiesterase inhibitor,

[34] use of the compound of [1] or a prodrug thereof for the production of an agent for the prophylaxis or treatment of angina pectoris, heart failure, cardiac infarction, hypertension, pulmonary hypertension, arteriosclerosis, allergic diseases, asthma, renal diseases, cerebral function disorders, immunodeficiency, ophthalmic diseases or disorders of male or female genital function,

[35] a compound of the formula

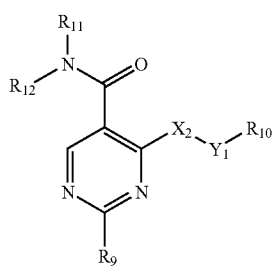

(I')

wherein
$R_9$ is a heterocycle having a skeleton consisting of 3 to 15 atoms including 1 to 5 nitrogen atom(s), and optionally having substituent(s), which heterocycle is attached by a secondary nitrogen atom forming the heterocycle,
$X_2$ is an oxygen atom, a nitrogen atom optionally substituted by a hydrocarbon group having 1 to 5 carbon atom(s) or a sulfur atom optionally oxidized with 1 or 2 oxygen,
$Y_1$ is a bond or a $C_{1-5}$ alkylene group,
$R_{10}$ is (1) a hydrogen atom, (2) a hydroxy group, (3) a $C_{1-5}$ alkoxy group, (4) a $C_{1-5}$ alkylthio group, (5) a $C_{3-15}$ carbocycle optionally having substituent(s) or (6) a heterocycle having a skeleton consisting of 3 to 15 atoms including 1 to 5 heteroatom(s) and optionally having substituent(s), one of $R_{11}$ and $R_{12}$ is a hydrogen atom or a group of the formula: —$Z_1$—$R_{13}$ ($Z_1$ is a bond or a $C_{1-10}$ alkylene group optionally having substituent (s)) $R_{13}$ is (1) a hydrogen atom, (2) a hydroxy group, (3) a $C_{1-5}$ alkoxy group, (4) a nitrile group, (5) a $C_{1-5}$ alkoxycarbonyl group, (6) a carboxyl group, (7) a carbamoyl group, (8) a (mono or di-$C_{1-5}$ alkyl)carbamoyl group, (9) an amino group, (10) a (di or mono-$C_{1-5}$ alkyl)amino group, (11) a ($C_{1-5}$ alkoxy-carbonyl)amino group, (12) a $C_{1-5}$ alkylthio group, (13) a $C_{3-15}$ carbocycle optionally having substituent(s) or (14) a heterocycle having a skeleton consisting of 3 to 15 atoms including 1 to 5 heteroatom(s) and optionally having substituent(s),
the other is a group of the formula: —$Z_1$—$R_{13}$ ($Z_1$ and $R_{13}$ are as defined above); and
$R_{11}$ and $R_{12}$ may form, together with the adjacent nitrogen atom, a heterocycle having a skeleton consisting of 3 to 15 atoms and optionally having substituent(s) and attached by a secondary nitrogen atom forming its ring], or a salt thereof, and

[36] a prodrug of the compound of [35].

BEST MODE FOR EMBODYING THE INVENTION

In the above-mentioned formula, the heterocycle group, represented by $R_1$ or $R_9$, has a skeleton consisting of 3 to 15 atoms including 1 to 5 nitrogen atom(s), and may be a monocyclic or fused ring and may be saturated or unsaturated. It is limited to a ring having a structure wherein a nitrogen atom constituting the heterocycle can have a bond, which is a ring having a secondary nitrogen atom.

As such heterocycle, (1) monocyclic heterocycles such as (a) aziridine, azetidine, pyrrole, 2- or 3-pyrroline, pyrrolidine, pyrazole, 2-, 3- or 4-pyrazoline, pyrazolidine, imidazole, 2-, 3- or 4-imidazoline, imidazolidine or (b) structurally possible hydrides of oxazole, isoxazole, thiazole, isothiazole, various oxadiazoles, various thiadiazoles, pyridine, pyridazine, pyrimidine or pyrazine; monocyclic heterocycle such as morpholine, thiomorpholine and the like, (2) fused heterocycles such as (a) indole, isoindole, indazole or purine and structurally possible hydrides thereof, (b) structurally possible hydrides of quinoline, isoquinoline, phthalazine, naphthyridine, quinoxaline, quinazoline, cinnoline or pteridine, (c) carbazole or carboline and structurally possible hydrides thereof, (d) structurally possible hydrides of phenanthridine, acridine, phenanthroline or phenazine, (e) phenothiazine or phenoxazine and structurally possible hydrides thereof and the like, and the like are used. Of these, pyrrole, pyrrolidine, pyrazole, pyrazolidine, imidazole, 1,2,3-triazole, 1,2,4-triazole, tetrazole, piperidine, piperazine, morpholine, thiomorpholine, indole, indoline, isoindole, isoindoline, indazole, 2,3-dihydroindazole, purine, 1,2,3,4-tetrahydroquinoline and the like are preferable, particularly indoline is preferable.

The heterocycle group represented by $R_1$ or $R_9$, which has a skeleton consisting of 3 to 15 atoms including 1 to 5 nitrogen atom(s), may be substituted by 1 to 5 the same or different substituent(s), as long as it is structurally possible. As such substituent(s), for example, $C_{1-8}$ alkyl (e.g., methyl, ethyl, propyl, isopropyl, butyl, sec-butyl, t-butyl, pentyl, hexyl, heptyl, octyl and the like, preferably $C_{1-6}$ alkyl), $C_{2-8}$ alkenyl (e.g., ethenyl, propenyl, butenyl, pentenyl and the like, preferably $C_{2-6}$ alkenyl), $C_{2-8}$ alkynyl (e.g., ethynyl, propinyl, butyryl, pentinyl and the like, preferably $C_{2-6}$ alkynyl), $C_{7-16}$ aralkyl (e.g., benzyl, phenethyl and the like), $C_{3-8}$ cycloalkyl (e.g., cyclopropyl, cyclobutyl, cyclopentyl, cyclohexyl, cycloheptyl, cyclooctyl and the like, preferably $C_{3-6}$ cycloalkyl), $C_{3-8}$ cycloalkenyl (e.g., cyclopentenyl, cyclohexenyl, cycloheptenyl, cyclooctenyl and the like, preferably $C_{3-6}$ cycloalkenyl), $C_{6-14}$ aryl (e.g., phenyl, naphthyl and the like), $C_{1-8}$ alkoxy (e.g., methoxy, ethoxy, propoxy, butoxy, t-butoxy, pentoxy and the like, preferably $C_{1-6}$ alkoxy), $C_{1-3}$ alkylenedioxy (e.g., methylenedioxy, ethylenedioxy and the like, preferably methylenedioxy), hydroxy, halogen atom (fluorine, chlorine, bromine, iodine), amino, (di or mono-$C_{1-5}$ alkyl)amino (e.g., methylamino, dimethylamino, ethylamino, diethylamino and the like), ($C_{1-5}$ alkoxy-carbonyl)amino (e.g., methoxycarbonylamino, ethoxycarbonylamino, propoxycarbonylamino and the like), ($C_{1-3}$ acyl)amino (e.g., formylamino, acetylamino, ethylcarbonylamino and the like), ($C_{1-5}$ acyl)($C_{1-5}$ alkyl)amino (e.g., formylmethylamino, acetylmethylamino, formylethylamino, acetylethylamino and the like), $C_{1-5}$ alkylthio (e.g., methylthio, ethylthio and the like), nitrile, nitro, $C_{1-5}$ alkoxycarbonyl (e.g., methoxycarbonyl, ethoxycarbonyl, propoxycarbonyl and the like), carboxyl, $C_{1-5}$ alkyl-carbonyloxy (e.g., methylcarbonyloxy, ethylcarbonyloxy and the like), oxo, thioxo, $C_{1-6}$ acyl group (e.g., $C_{1-5}$ alkyl-carbonyl group such as acetyl, ethylcarbonyl, propylcarbonyl and the like, and the like), sulfamoyl, (di or mono-$C_{1-5}$ alkyl)sulfamoyl (e.g., methylsulfamoyl, ethylsulfamoyl, dimethylsulfamoyl and the like) and the like are used.

The above-mentioned $C_{1-8}$ alkyl and $C_{1-8}$ alkoxy may be further substituted by 1 to 5 the same or different substituent(s) selected from the above-mentioned $C_{1-8}$ alkoxy, hydroxy, halogen atom, amino, (di or mono-$C_{1-5}$ alkyl)amino, ($C_{1-5}$ alkoxy-carbonyl)amino, ($C_{1-5}$ acyl) amino, ($C_{1-5}$ acyl)($C_{1-5}$ alkyl)amino, $C_{1-5}$ alkylthio, nitrile, nitro, $C_{1-5}$ alkoxy-carbonyl, carboxyl, $C_{1-5}$ alkyl-carbonyloxy, oxo, thioxo and the like, as long as it is structurally possible.

Of the above-mentioned substituents, optionally halogenated $C_{1-5}$ alkyl (e.g., methyl, ethyl, propyl, isopropyl, butyl, sec-butyl, t-butyl, trifluoromethyl and the like), $C_{1-3}$ alkoxy (e.g., methoxy, ethoxy, propoxy and the like), $C_{1-2}$ alkylenedioxy, halogen atom and the like are preferable, particularly, optionally halogenated $C_{1-3}$ alkyl such as methyl, ethyl, trifluoromethyl and the like, and halogen atom such as fluorine, chlorine, bromine and the like are more preferable.

In the above-mentioned formula, X and $X_2$ are oxygen atom, nitrogen atom optionally substituted by $C_{1-5}$ alkyl (e.g., methyl, ethyl, propyl, butyl and the like) or a sulfur atom optionally oxidized with 1 or 2 oxygen (S, SO, $SO_2$).

As X and $X_2$, oxygen atom and NH are preferable, particularly oxygen atom is preferable.

In the above-mentioned formula, Y and $Y_1$ represent a bond or $C_{1-5}$ alkylene group (e.g., methylene, ethylene, propylene, butylene and the like).

As Y and $Y_1$, $C_{1-3}$ alkylene group such as methylene, ethylene, propylene and the like are preferable, particularly methylene is preferable.

In the above-mentioned formula, $R_{10}$ represents (1) hydrogen atom, (2) hydroxy group, (3) ($C_{1-5}$ alkoxy group, (4) $C_{1-5}$ alkylthio group, (5) carbocycle having 3 to 15 carbon atoms or (6) heterocycle having a skeleton consisting of 3 to 15 atoms including 1 to 5 heteroatom(s).

In the above-mentioned formula, $R_2$ is (1) hydrogen atom, (2) hydroxy group, (3) $C_{1-5}$ alkoxy group, (4) $C_{1-5}$ alkylthio group, (5) carbocycle having 3 to 15 carbon atoms or (6) heterocycle having a skeleton consisting of 3 to 15 atoms including 1 to 5 heteroatom(s) (provided that when Y is a bond, $R_2$ is a carbocycle having 3 to 15 carbon atoms or a heterocycle having a skeleton consisting of 3 to 15 atoms including 1 to 5 heteroatom(s)).

As the $C_{1-5}$ alkoxy group represented by $R_2$ or $R_{10}$, for example, methoxy, ethoxy, propoxy, butoxy, t-butoxy, pentoxy and the like are used, with preference given to $C_{1-3}$ alkoxy such as methoxy, ethoxy, propoxy and the like, and the like.

As the $C_{1-5}$ alkylthio group represented by $R_2$ or $R_{10}$, for example, methylthio, ethylthio, propylthio and the like are used, with preference given to $C_{1-3}$ alkylthio group and the like.

As the carbocycle group having 3 to 15 carbon atoms, which is represented by $R_2$ or $R_{10}$, for example, (1) saturated or unsaturated monocyclic aliphatic hydrocarbon group such as $C_{3-8}$ cycloalkyl group (e.g., cyclopropyl, cyclobutyl, cyclopentyl, cyclohexyl, cycloheptyl, cyclooctyl), $C_{5-8}$ cycloalkenyl group (e.g., cyclopentenyl, cyclohexenyl, cycloheptenyl, cyclooctenyl) and the like, (2) saturated or unsaturated fused ring aliphatic hydrocarbon group having 9 to 15 carbon atoms or (3) monocyclic or polycyclic aryl group having 6 to 15 carbon atoms (e.g., phenyl, naphthyl, indenyl, phenanthrenyl, indenyl, indanyl, tetralinyl and the like) and the like are used. Of these, cyclopentyl, cyclohexyl, cycloheptenyl, 2-cyclopenten-1-yl, 3-cyclopenten-1-yl, 3-cyclohexen-1-yl, phenyl, naphthyl, indenyl, phenanthrenyl indanyl, tetralinyl and the like are preferable, particularly, phenyl is preferable.

As the heterocycle group having a skeleton consisting of 3 to 15 atoms including 1 to 5 heteroatom(s), which is represented by $R_2$ or $R_{10}$, for example, an aromatic heterocycle group or saturated or unsaturated non-aromatic heterocycle group having a skeleton consisting of 3 to 15 atoms including 1 to 5, the same or different nitrogen atom(s), oxygen atom(s) and/or sulfur atom(s), and the like are used.

As the above-mentioned aromatic heterocycle group, for example, furyl, thienyl, pyrrolyl, imidazolyl, pyrazolyl, thiazolyl, isothiazolyl, oxazolyl, isooxazolyl, 1,2,4-oxadiazolyl, 1,2,5-oxadiazolyl, pyridyl, pyrazinyl, pyrimidinyl, pyridazinyl, 1,3,5-triazinyl, 1,2,4-triazinyl, indolizinyl, isoindolyl, indolyl, indazolyl, purinyl, isoquinolyl, quinolyl, phthalazinyl, naphtyridinyl, quinoxalinyl, quinazolinyl, cinnolinyl, puteridinyl, carbazolyl, carbolinyl, phenanthridinyl, acrydinyl, phenanthrolinyl, phenazinyl, phenothiazinyl, phenoxadinyl and the like, and if structurally possible, a group wherein these are fused with a benzene ring, and the like are used. Particularly, an aromatic heterocycle group having a skeleton consisting of 5 or 6 atoms including 1 to 3 (preferably 1 or 2) heteroatom(s) such as nitrogen atom(s), oxygen atom(s) and sulfur atom(s), such as furyl, thienyl, pyridyl and the like, and the like are preferable.

As the above-mentioned saturated or unsaturated non-aromatic heterocycle group, for example, structurally possible partial or complete hydrides of the above-mentioned aromatic heterocycle group, aziridinyl, azetidinyl, oxetanyl, pyranyl, azepinyl, 1,3-diazepinyl, 1,4-diazepinyl, 1,3-oxazepinyl, 1,4-oxazepinyl, azocinyl, chromenyl and the like, and structurally possible hydrides thereof and the like are used.

The carbocycle having 3 to 15 carbon atoms and the heterocycle group having a skeleton consisting of 3 to 15 atoms including 1 to 5 heteroatom(s), which are represented by $R_2$ or $R_{10}$, may be substituted by 1 to 5 the same or different substituent(s) as long as it is structurally possible. As these substituents, those similar to the substituents of the aforementioned heterocycle group represented by $R_1$ are used.

Of these substituents, optionally halogenated $C_{1-8}$ alkyl (particularly, optionally halogenated $C_{1-6}$ alkyl such as methyl, ethyl, propyl, isopropyl, butyl, sec-butyl, t-butyl, trifluoromethyl and the like, particularly, optionally halogenated $C_{1-3}$ alkyl), $C_{1-8}$ alkoxy (preferably $C_{1-6}$ alkoxy such as methoxy, ethoxy and the like, particularly $C_{1-3}$ alkoxy), halogen atom such as fluorine, chlorine, bromine and the like, and the like are preferable.

As $R_{10}$, hydrogen atom, hydroxy group, $C_{1-5}$ alkoxy group, $C_{1-5}$ alkylthio group, the above-mentioned carbocycle having 3 to 15 carbon atoms or a heterocycle having a skeleton consisting of 3 to 15 atoms including 1 to 5 heteroatom(s) and the like are preferable.

As $R_2$, the above-mentioned carbocycle having 3 to 15 carbon atoms or a heterocycle having a skeleton consisting of 3 to 15 atoms including 1 to 5 heteroatom(s) and the like are preferable.

When Y is $C_{1-5}$ alkylene group, hydrogen atom, hydroxy group, $C_{1-5}$ alkoxy group, $C_{1-5}$ alkylthio group and the like are also preferable as $R_2$, and particularly when Y is methylene group, hydrogen atom, $C_{1-5}$ alkoxy group, $C_{1-5}$ alkylthio group and the like are also preferable as $R_2$.

In the above-mentioned formula, $R_3$ and $R_4$ are the same or different and each is hydrogen atom or a group of the formula:

—Z—$R_5$.

In the above-mentioned formula, $R_{11}$ and $R_{12}$ are the same or different and each is hydrogen atom or a group of the formula: —$Z_1$—$R_{13}$.

Z and $Z_1$ show a bond or $C_{1-10}$ alkylene group (e.g., methylene, ethylene, propylene, butylene, pentylene, hexylene, heptylene, octylene and the like, preferably $C_{1-6}$ alkylene group).

The $C_{1-10}$ alkylene group represented by Z or $Z_1$ may be substituted by 1 to 5 substituent(s) as long as it is structurally possible. As such substituents, those similar to the substituents of the aforementioned heterocycle group represented by $R_1$ are used.

As Z and $Z_1$, for example, a bond, $C_{1-4}$ alkylene (e.g., methylene, ethylene, propylene, butylene) and the like are preferable.

As (1) a carbocycle having 3 to 15 carbon atoms and (2) a heterocycle having a skeleton consisting of 3 to 15 atoms including 1 to 5 heteroatom(s), which are represented by $R_5$ or $R_{13}$, those similar to (1) a carbocycle having 3 to 15 carbon atoms and (2) a heterocycle having a skeleton consisting of 3 to 15 atoms including 1 to 5 heteroatom(s), which are represented by $R_2$, are used.

Particularly, as a carbocycle group having 3 to 15 carbon atoms represented by $R_5$ or $R_{13}$, for example, a non-aromatic carbocyclic ring group having 3 to 7 carbon atoms such as cyclopropyl, cyclobutyl, cyclopentyl, cyclohexyl, cycloheptenyl, 2-cyclopenten-1-yl, 3-cyclopenten-1-yl, 3-cyclohexen-1-yl and the like, and an aromatic carbocyclic ring group having 6 to 15 carbon atoms such as phenyl, naphthyl, indenyl, phenanthrenyl indanyl, tetralinyl and the like are preferable, which is particularly preferably $C_{6-14}$ aryl group such as phenyl and the like.

As the heterocycle group having a skeleton consisting of 3 to 15 atoms including 1 to 5 heteroatom(s) represented by $R_5$ or $R_{13}$, for example, non-aromatic heterocycle group such as azetidinyl, pyrrolizinyl, piperidinyl, piperazinyl, perhydroazepinyl, morphonyl, tetrahydrofuranyl, tetrahydrothienyl and the like, and an aromatic heterocycle group such as pyridin-2-yl, pyridin-3-yl, pyrazin-2-yl, perhydroazepin-3-yl and the like are preferable.

As long as structurally possible, (1) a carbocycle having 3 to 15 carbon atoms and (2) a heterocycle having a skeleton consisting of 3 to 15 atoms including 1 to 5 heteroatom(s), which are represented by $R_5$ or $R_{13}$, may have substituent(s) such as those similar to the substituent(s) of the aforementioned heterocycle group represented by $R_1$.

Of these substituents, optionally halogenated $C_{1-8}$ alkyl (particularly optionally halogenated $C_{1-6}$ alkyl such as methyl, ethyl, propyl, isopropyl, trifluoromethyl and the like), $C_{1-8}$ alkoxy (particularly $C_{1-6}$ alkoxy such as methoxy, ethoxy, propoxy, isopropyloxy, butoxy, sec-butoxy, t-butoxy and the like), halogen atom (fluorine, chlorine, bromine, iodine), oxo, thioxo, hydroxy, nitrile, $C_{1-5}$ alkylthio (particularly $C_{1-3}$ alkylthio such as methylthio, ethylthio and the like), carbamoyl, $C_{1-5}$ alkoxy-carbonyl group (particularly, methoxycarbonyl, ethoxycarbonyl and the like), $C_{1-6}$ acyl group (particularly $C_{1-5}$ alkyl-carbonyl group such as acetyl, ethylcarbonyl, propylcarbonyl and the like), and the like, sulfamoyl and the like are preferably, particularly $C_{1-8}$ alkyl, $C_{1-8}$ alkoxy, halogen atom such as fluorine, chlorine, bromine and the like, oxo, thioxo and the like are preferable.

Furthermore, $R_5$ and $R_{13}$ respectively show hydrogen atom; hydroxy group; $C_{1-5}$ alkoxy group such as methoxy, ethoxy and the like; nitrile group; $C_{1-5}$ alkoxy-carbonyl group such as methoxycarbonyl, ethoxycarbonyl, propoxycarbonyl, butoxycarbonyl, t-butoxycarbonyl and the like; carboxyl group; carbamoyl group; (mono or di-$C_{1-5}$ alkyl) carbamoyl group such as methylaminocarbonyl, diethylaminocarbonyl and the like; amino group; (di or mono-($C_{1-5}$ alkyl)amino group such as methylamino, diethylamino and the like; methoxycarbonylamino; ethoxycarbonylamino; propoxycarbonylamino; butoxycarbonylamino; $C_{1-5}$ alkylthio group such as methylthio and the like, and are respectively bonded to the adjacent Z and $Z_1$ at a substitutable position.

Particularly when Z is optionally substituted $C_{2-10}$ alkylene group, preferably the aforementioned carbocyclic ring or heterocycle, hydrogen atom, hydroxy group, $C_{1-5}$ alkoxy group such as methoxy, ethoxy and the like, nitrile group, $C_{1-5}$ alkoxy-carbonyl group such as methoxycarbonyl, ethoxycarbonyl, propoxycarbonyl, butoxycarbonyl, t-butoxycarbonyl and the like, carboxyl group, carbamoyl group, (mono or di-($C_{1-5}$ alkyl)carbamoyl group such as methylaminocarbonyl, diethylaminocarbonyl and the like, amino group, (di or mono-$C_{1-5}$ alkyl)amino group such as methylamino, diethylamino and the like, methoxycarbonylamino, ethoxycarbonylamino, propoxycarbonylamino, butoxycarbonylamino, $C_{1-5}$ alkylthio group such as methylthio and the like, and the like are also preferable as $R_5$. Particularly, hydroxy group, nitrile group, $C_{1-5}$ alkoxy-carbonylamino group such as t-butoxycarbonylamino and the like, $C_{1-5}$ alkoxy-carbonyl group such as methoxycarbonyl, t-butoxycarbonyl and the like, and the like are preferable.

When Z is optionally substituted methylene group, $R_5$ is, besides the aforementioned carbocyclic ring and heterocycle, nitrile group, $C_{1-5}$ alkoxy-carbonyl group such as methoxycarbonyl, t-butoxycarbonyl and the like, carboxyl group, carbamoyl group, (mono or di-($C_{1-5}$ alkyl)carbamoyl such as methylaminocarbonyl, diethylaminocarbonyl and the like, and the like are preferable, particularly nitrile group is preferable.

As $R_{13}$, besides the aforementioned carbocyclic ring and heterocycle, hydroxy group, nitrile group, $C_{1-5}$ alkoxy-carbonylamino group such as t-butoxycarbonylamino and the like, $C_{1-5}$ alkoxy-carbonyl group such as methoxycarbonyl, t-butoxycarbonyl and the like, and the like are also preferable.

As the combination of $R_3$ and $R_4$, that wherein $R_3$ is a hydrogen atom and $R_4$ is a group of the formula: —Z—$R_5$ is preferable.

As the combination of $R_{11}$ and $R_{12}$, that wherein $R_{11}$ is a hydrogen atom and $R_{12}$ is a group of the formula: —$Z_1$—$R_{13}$ is preferable.

As the group which is a heterocycle having a skeleton consisting of 3 to 15 atoms and formed by $R_3$ and $R_4$, or $R_{11}$ and $R_{12}$, together with the adjacent nitrogen atom, and which is attached by a secondary nitrogen atom forming the heterocycle, a group attached by a secondary nitrogen atom constituting a heterocycle having a skeleton consisting of 3 to 15 atoms including atoms such as carbon atom(s), oxygen atom(s), sulfur atom(s) and the like, besides at least one nitrogen atom, is used, which is, for example, aziridin-1-yl, azetidin-1-yl, pyrrolidin-1-yl, piperidino, piperazin-1-yl, morpholino, indolin-1-yl and the like. Particularly, a heterocycle having a skeleton consisting of 5 or 6 atoms including atoms such as carbon atom(s), oxygen atom(s), sulfur atom(s) and the like, besides at least one nitrogen atom, and attached by a secondary nitrogen atom is preferable, such as pyrrolidin-1-yl, piperidino, piperazin-1-yl, morpholino and the like.

The heterocycle having a skeleton consisting of 3 to 15 atoms and attached by a secondary nitrogen atom forming its ring, which is formed by $R_3$ and $R_4$, or $R_{11}$ and $R_{12}$ together with the adjacent nitrogen atom, may have substituents such as those similar to the substituents of the aforementioned heterocycle group represented by $R_1$.

Of these substituents, hydroxy group, nitrile group, $C_{1-5}$ alkoxy-carbonyl group such as methoxycarbonyl, t-butoxycarbonyl and the like, and the like are preferable.

As the compound (I') of the present invention, the compound (I) of the present invention, and the like are preferable.

As the compound (I) of the present invention, for example, the following compound and the like are also preferable.

(1) Compound (I) wherein X is a nitrogen atom optionally substituted by a hydrocarbon group having 1 to 5 carbon atom(s) or a sulfur atom optionally oxidized with 1 or 2 oxygen.

(2) Compound (I) wherein Y is $C_{1-5}$ alkylene group.

(3) Compound (I) wherein Y is $C_{1-5}$ alkylene group, and $R_2$ is hydroxy group, $C_{1-5}$ alkoxy group or $C_{1-5}$ alkylthio group.

(4) Compound (I) wherein $R_5$ is (a) a non-aromatic carbocycle having 3 to 15 carbon atoms or (b) a non-aromatic heterocycle having a skeleton consisting of 3 to 15 atoms including 1 to 5 heteroatom(s).

(5) Compound (I) wherein Z is $C_{2-10}$ alkylene group optionally having substituent(s), $R_5$ is hydroxy group, nitrile group, $C_{1-5}$ alkoxy-carbonyl, carboxyl group, carbamoyl group, (mono or di-$C_{1-5}$ alkyl)carbamoyl group, ($C_{1-5}$ alkoxy-carbonyl)amino group or $C_{1-5}$ alkylthio group.

(6) Compound (I) wherein Z is methylene group optionally having substituent(s), and $R_5$ is nitrile group, ($C_{1-5}$ alkoxy-carbonyl group, carboxyl group, carbamoyl group or (mono or di-$C_{1-5}$ alkyl)carbamoyl group.

(7) Compound (I) wherein the substituent(s) of heterocycle and a carbocycle having 3 to 15 carbon atoms are selected from the group consisting of $C_{2-8}$ alkenyl, $C_{2-8}$ alkynyl, $C_{7-16}$ aralkyl, $C_{3-8}$ cycloalkyl, $C_{3-8}$ cycloalkenyl, $C_{6-14}$ aryl, $C_{1-3}$ alkylenedioxy, hydroxy, ($C_{1-5}$ alkoxy-carbonyl)amino, ($C_{1-5}$ acyl)amino, ($C_{1-5}$ acyl) ($C_{1-5}$ alkyl)amino, $C_{1-5}$ alkylthio, nitrile, $C_{1-5}$ alkoxy-carbonyl, carboxyl, $C_{1-5}$ alkyl-carbonyloxy, oxo and thioxo.

(8) Compound (I) wherein $R_1$ is a heterocycle having a skeleton consisting of 5 to 12 atoms including 1 or 2 nitrogen atom(s), which is optionally substituted by substituent(s) selected from the group consisting of $C_{1-8}$ alkyl, $C_{2-8}$ alkenyl, $C_{2-8}$ alkynyl, $C_{7-16}$ aralkyl, $C_{3-8}$ cycloalkyl, $C_{3-8}$ cycloalkenyl, $C_{6-14}$ aryl, $C_{1-8}$ alkoxy, $C_{1-3}$ alkylenedioxy, hydroxy, halogen atom, amino, (di or mono-$C_{1-5}$ alkyl)amino, ($C_{1-5}$ alkoxy-carbonyl)amino, ($C_{1-5}$ acyl)amino, ($C_{1-5}$ acyl)($C_{1-5}$ alkyl)amino, $C_{1-5}$ alkylthio, nitrile, nitro, $C_{1-5}$ alkoxy-carbonyl, carboxyl, $C_{1-5}$ alkyl-carbonyloxy, oxo and thioxo.

(9) Compound (I) wherein $R_1$ is a heterocycle having a skeleton consisting of 8 to 12 atoms including a nitrogen atom, which is optionally substituted by substituent(s) selected from the group consisting of $C_{1-8}$ alkyl, $C_{2-8}$ alkenyl, $C_{2-8}$ alkynyl, $C_{7-16}$ aralkyl, $C_{3-8}$ cycloalkyl, $C_{3-8}$ cycloalkenyl, $C_{6-14}$ aryl, $C_{1-8}$ alkoxy, $C_{1-3}$ alkylenedioxy, hydroxy, halogen atom, amino, (di or mono-$C_{1-5}$ alkyl) amino, ($C_{1-5}$ alkoxy-carbonyl)amino, ($C_{1-5}$ acyl)amino, ($C_{1-5}$ acyl)($C_{1-5}$ alkyl)amino, $C_{1-5}$ alkylthio, nitrile, nitro, $C_{1-5}$ alkoxy-carbonyl, carboxyl, $C_{1-5}$ alkyl-carbonyloxy, oxo and thioxo.

(10) Compound (I) wherein $R_1$ is 1-indolinyl optionally substituted by substituent(s) selected from the group consisting of $C_{1-8}$ alkyl, $C_{2-8}$ alkenyl, $C_{2-8}$ alkynyl, $C_{7-16}$ aralkyl, $C_{3-8}$ cycloalkyl, $C_{3-8}$ cycloalkenyl, $C_{6-14}$ aryl, $C_{1-8}$ alkoxy, $C_{1-3}$ alkylenedioxy, hydroxy, halogen atom, amino, (di or mono-$C_{1-5}$ alkyl)amino, ($C_{1-5}$ alkoxy-carbonyl)amino, ($C_{1-5}$ acyl)amino, ($C_{1-5}$ acyl)($C_{1-5}$ alkyl)amino, $C_{1-5}$ alkylthio, nitrile, nitro, $C_{1-5}$ alkoxy-carbonyl, carboxyl, $C_{1-5}$ alkyl-carbonyloxy, oxo and thioxo.

(11) Compound (I) wherein $R_2$ is a carbocycle having 5 to 7 carbon atoms or a heterocycle having a skeleton consisting of 5 to 7 atoms including 1 or 2 heteroatom(s), which is optionally substituted by substituent(s) selected from the group consisting of $C_{1-8}$ alkyl, $C_{2-8}$ alkenyl, $C_{2-8}$ alkynyl, $C_{7-16}$ aralkyl, $C_{3-8}$ cycloalkyl, $C_{3-8}$ cycloalkenyl, $C_{6-14}$ aryl, $C_{1-8}$ alkoxy, $C_{1-3}$ alkylenedioxy, hydroxy, halogen atom, amino, (di or mono-($C_{1-5}$ alkyl)amino, ($C_{1-5}$ alkoxy-carbonyl)amino, ($C_{1-5}$ acyl)amino, ($C_{1-5}$ acyl)($C_{1-5}$ alkyl)amino, $C_{1-5}$ alkylthio, nitrile, nitro, $C_{1-5}$ alkoxy-carbonyl, carboxyl, $C_{1-5}$ alkyl-carbonyloxy, oxo and thioxo.

(12) Compound (I) wherein $R_2$ is phenyl optionally substituted by substituent(s) selected from the group consisting of $C_{1-8}$ alkyl, $C_{2-8}$ alkenyl, $C_{2-8}$ alkynyl, $C_{7-16}$ aralkyl, $C_{3-8}$ cycloalkyl, $C_{3-8}$ cycloalkenyl, $C_{6-14}$ aryl, $C_{1-8}$ alkoxy, $C_{1-3}$ alkylenedioxy, hydroxy, halogen atom, amino, (di or mono-$C_{1-5}$ alkyl)amino, ($C_{1-5}$ alkoxy-carbonyl)amino, ($C_{1-5}$ acyl) amino, ($C_{1-5}$ acyl)($C_{1-5}$ alkyl)amino, $C_{1-5}$ alkylthio, nitrile, nitro, ($C_{1-5}$ alkoxy-carbonyl, carboxyl, ($C_{1-5}$ alkyl-carbonyloxy, oxo, thioxo, $C_{1-6}$ acyl group, sulfamoyl and (di or mono-$C_{1-5}$ alkyl)sulfamoyl.

(13) Compound (I) wherein X is oxygen atom or NH, and Y is $C_{1-3}$ alkylene group.

(14) Compound (I) wherein X is oxygen atom, and Y is methylene group.

(15) Compound (I) wherein $R_3$ is hydrogen atom, and $R_4$ is a group of the formula: —Z—$R_5$.

(16) Compound (I) wherein Z is a bond or $C_{1-4}$ alkylene group, and $R_5$ is a carbocycle having 5 to 8 carbon atoms or a heterocycle having a skeleton consisting of 5 to 11 atoms including 1 to 5 hetero atom(s), which is optionally substituted by substituent(s) selected from the group consisting of $C_{1-8}$ alkyl, $C_{2-8}$ alkenyl, $C_{2-8}$ alkynyl, $C_{7-16}$ aralkyl, $C_{3-8}$ cycloalkyl, $C_{3-8}$ cycloalkenyl, $C_{6-14}$ aryl, $C_{1-8}$ alkoxy, $C_{1-3}$ alkylenedioxy, hydroxy, halogen atom, amino, (di or mono-$C_{1-5}$ alkyl)amino, ($C_{1-5}$ alkoxy-carbonyl)amino, ($C_{1-5}$ acyl)amino, ($C_{1-5}$ acyl)($C_{1-5}$ alkyl)amino, $C_{1-5}$ alkylthio, nitrile, nitro, $C_{1-5}$ alkoxy-carbonyl, carboxyl, $C_{1-5}$ alkyl-carbonyloxy, oxo, thioxo, $C_{1-6}$ acyl group, sulfamoyl and (di or mono-$C_{1-5}$ alkyl)sulfamoyl.

(17) Compound (I) wherein $R_1$ is a group selected from the group consisting of

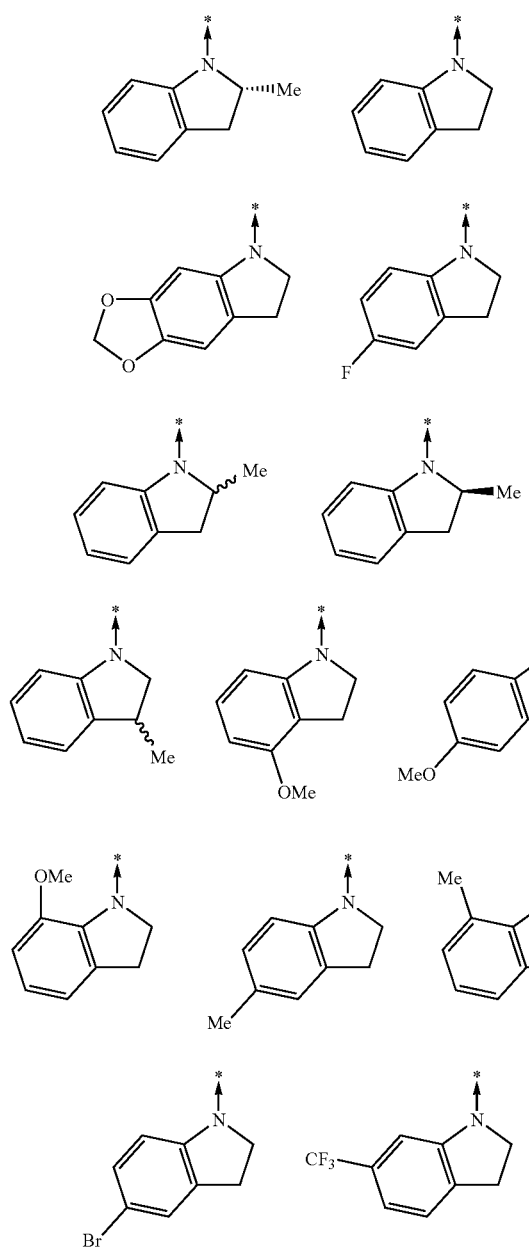

—X—Y—$R_2$ is a group selected from the group consisting of

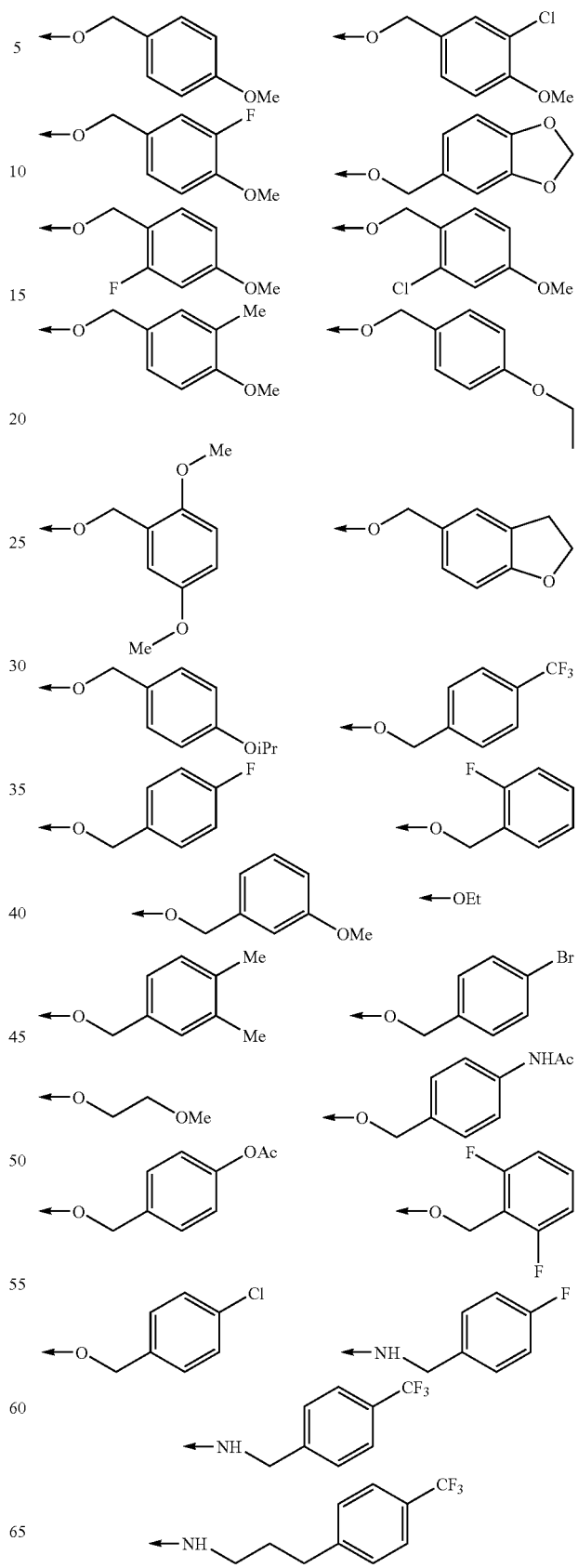

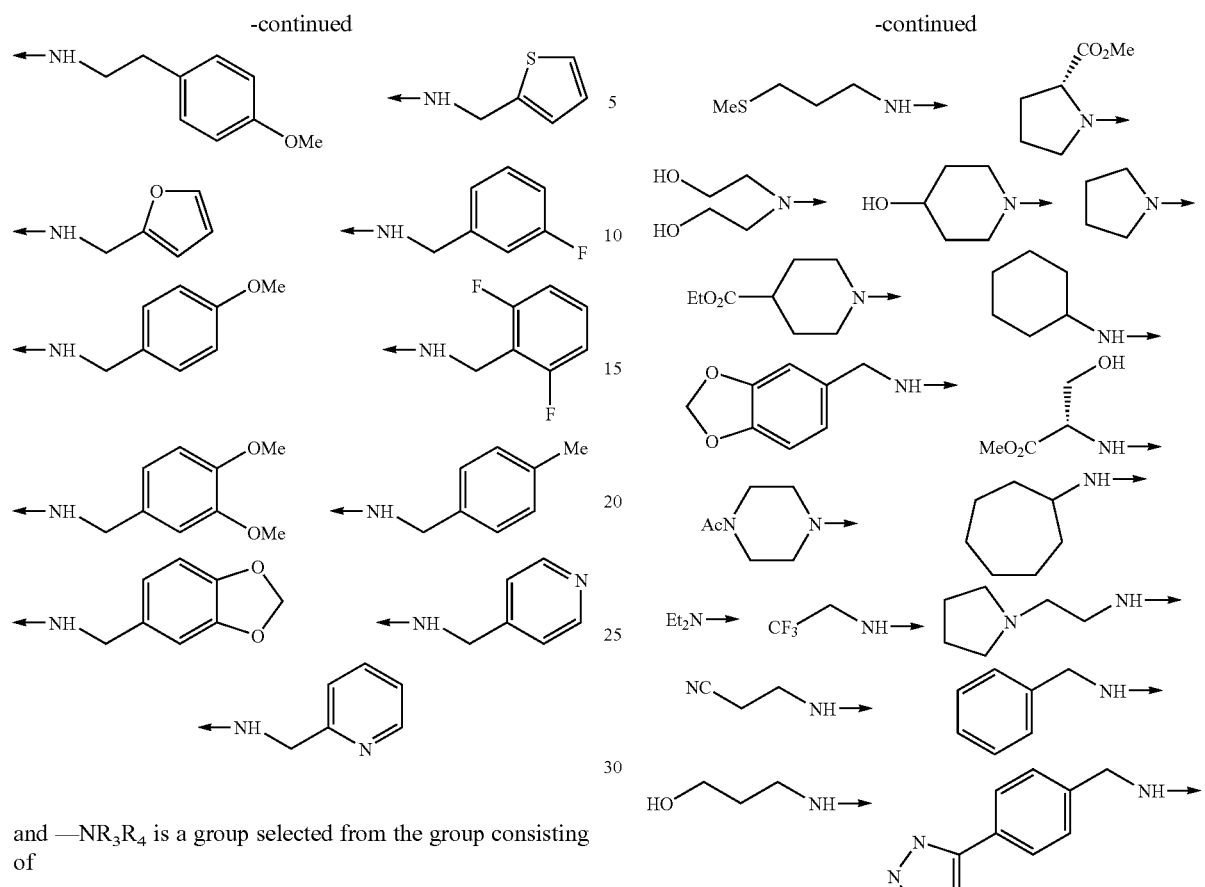
and —NR₃R₄ is a group selected from the group consisting of
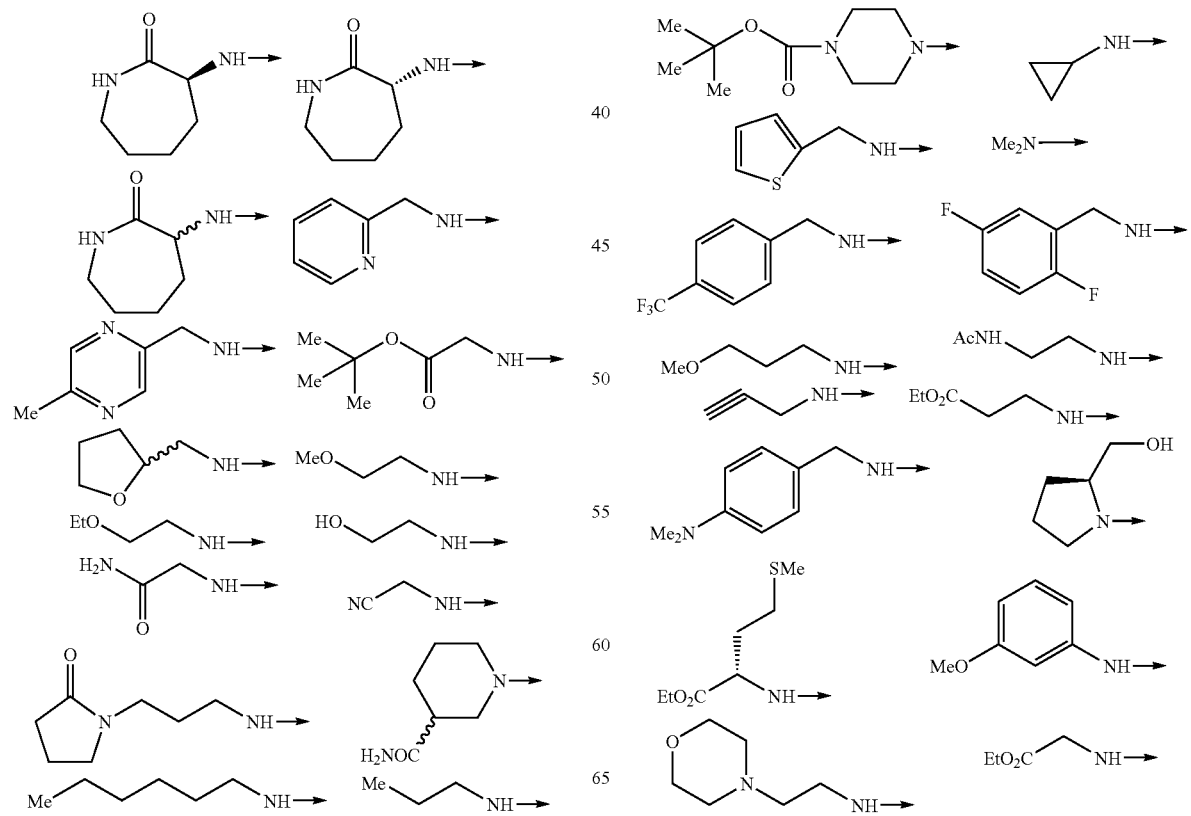

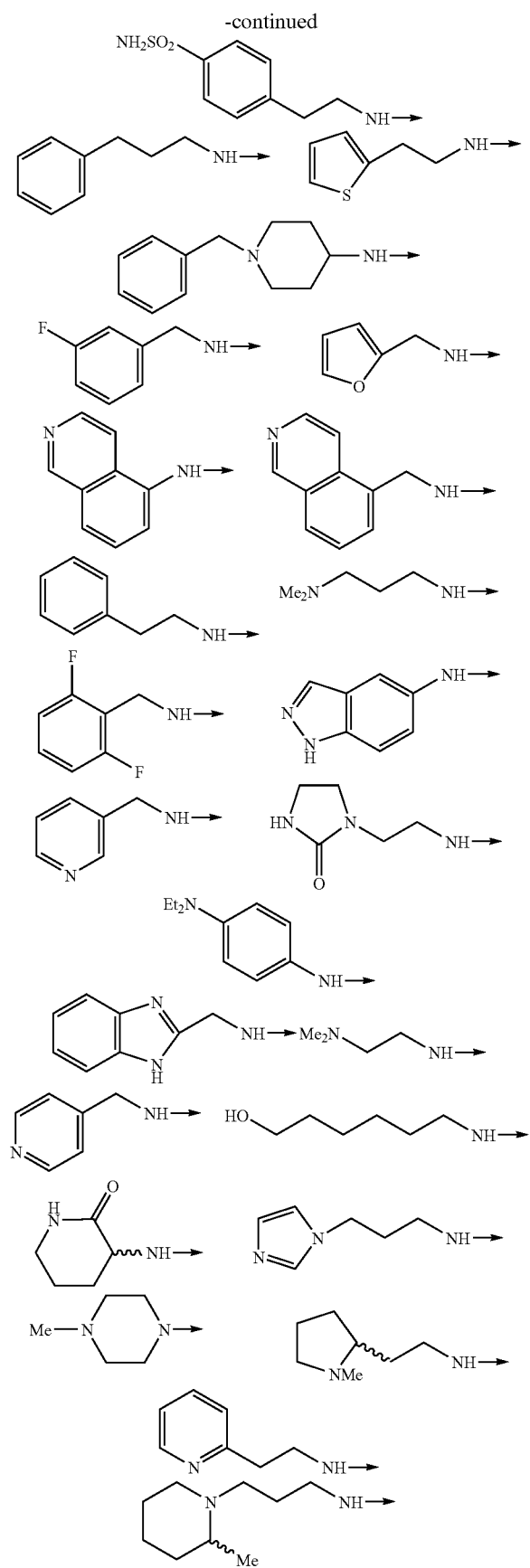
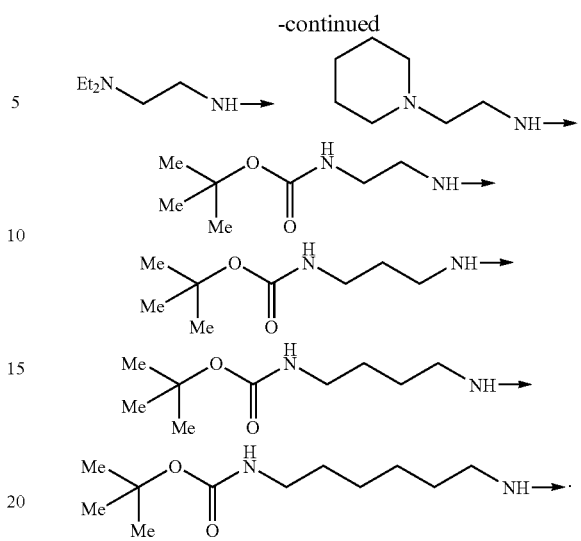
(18) Compound (I) wherein $R_1$ is a group selected from the group consisting of
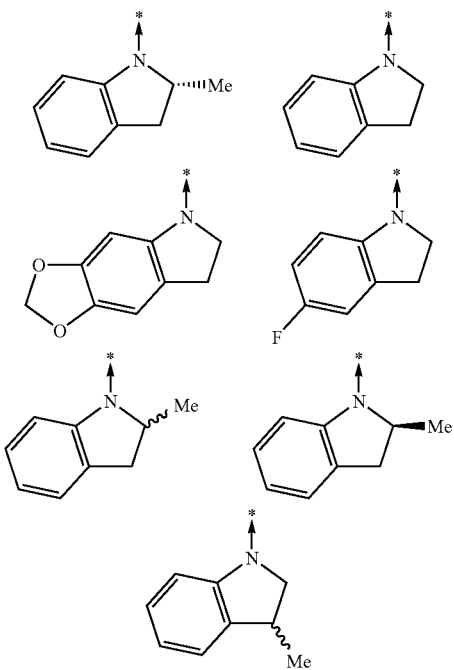
—X—Y—$R_2$ is a group selected from the group consisting of
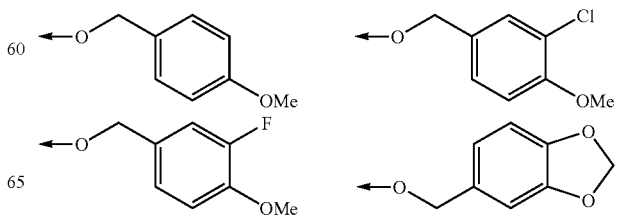

-continued

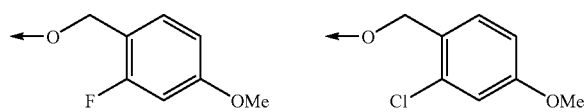

and —NR₃R₄ is a group selected from the group consisting of

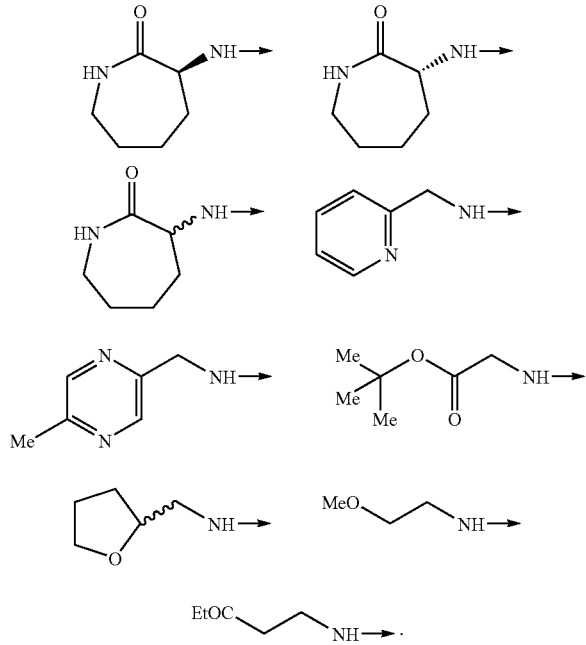

(19) Compound (I) wherein R₁ is a group selected from the group consisting of

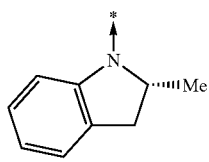

—X—Y—R₂ is a group selected from the group consisting of

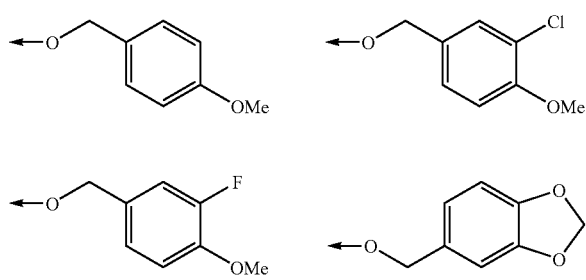

and —NR₃R₄ is a group selected from the group consisting of

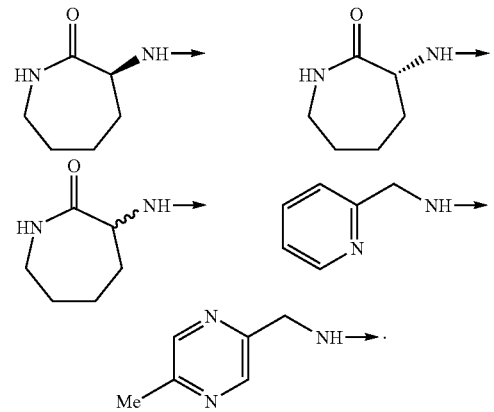

(20) Any compound produced in the Examples to be mentioned below.

(21) The following Example compounds:
Example 23-6: (RS)-2-(2,3-dihydro-1H-indol-1-yl)-4-[(4-methoxybenzyl)oxy]-N-(2-oxo-3-azepanyl)-5-pyrimidinecarboxamide,
Example 23-11: 2-(2,3-dihydro-1H-indol-1-yl)-4-[(4-methoxybenzyl)oxy]-N-[(5-methyl-2-pyrazinyl)methyl]-5-pyrimidinecarboxamide,
Example 23-16: 2-(2,3-dihydro-1H-indol-1-yl)-4-[(4-methoxybenzyl)oxy]-N-(2-pyridinylmethyl)-5-pyrimidinecarboxamide,
Example 27-1: (RS)-4-(1,3-benzodioxol-5-ylmethoxy)-2-(2,3-dihydro-1H-indol-1-yl)-N-(2-oxo-3-azepanyl)-5-pyrimidinecarboxamide,
Example 27-4: 4-(1,3-benzodioxol-5-ylmethoxy)-2-(2,3-dihydro-1H-indol-1-yl)-N-(2-pyridinylmethyl)-5-pyrimidinecarboxamide,
Example 31-3: 2-(2,3-dihydro-1H-indol-1-yl)-4-[(3-fluoro-4-methoxybenzyl)oxy]-N-(2-pyridinylmethyl)-5-pyrimidinecarboxamide,
Example 31-5: 2-(2,3-dihydro-1H-indol-1-yl)-4-[(3-fluoro-4-methoxybenzyl)oxy]-N-(2-oxo-3-azepanyl)-5-pyrimidinecarboxamide,
Example 31-6: 2-(2,3-dihydro-1H-indol-1-yl)-4-[(3-fluoro-4-methoxybenzyl)oxy]-N-[(5-methyl-2-pyrazinyl)methyl]-5-pyrimidinecarboxamide,
Example 33-3: 4-[(3-chloro-4-methoxybenzyl)oxy]-2-(2,3-dihydro-1H-indol-1-yl)-N-(2-pyridinylmethyl)-5-pyrimidinecarboxamide,
Example 33-5: 4-[(3-chloro-4-methoxybenzyl)oxy]-2-(2,3-dihydro-1H-indol-1-yl)-N-(2-oxo-3-azepanyl)-5-pyrimidinecarboxamide,
Example 33-6: 4-[(3-chloro-4-methoxybenzyl)oxy]-2-(2,3-dihydro-1H-indol-1-yl)-N-[(5-methyl-2-pyrazinyl)methyl]-5-pyrimidinecarboxamide,
Example 47-3: (rac)-4-[(4-methoxybenzyl)oxy]-2-(2-methyl-2,3-dihydro-1H-indol-1-yl)-N-(2-oxo-3-azepanyl)-5-pyrimidinecarboxamide,
Example 66-1: 2-(2,3-dihydro-1H-indol-1-yl)-4-[(4-methoxybenzyl)oxy]-N-[(3S)-2-oxoazepanyl]-5-pyrimidinecarboxamide,
Example 66-2: 2-(2,3-dihydro-1H-indol-1-yl)-4-[(4-methoxybenzyl)oxy]-N-[(3R)-2-oxoazepanyl]-5-pyrimidinecarboxamide, Example 66-3: 4-(1,3-benzodioxol-5-ylmethoxy)-2-(2,3-dihydro-1H-indol-1-yl)-4-[(4-methoxybenzyl)oxy]-N-[(3S)-2-oxoazepanyl]-5-pyrimidinecarboxamide, Example 66-6: 2-(2,3-dihydro-1H-indol-1-yl)-4-[(3-fluoro-4-methoxybenzyl)oxy]-N-[(3S)-2-oxoazepanyl]-5-pyrimidinecarboxamide, Example 66-8: 4-[(3-chloro-4-methoxybenzyl)oxy]-2-(2,3-dihydro-1H-indol-1-yl)-N-[(3S)-2-oxoazepanyl]-5-pyrimidinecarboxamide, Example 66-11: 4-[(4-methoxybenzyl)oxy]-2-[(2RS)-2-methyl-2,3-dihydro-1H-indol-1-yl]-N-[(3S)-2-oxoazepanyl]-5-pyrimidinecarboxamide, Example 66-12: 4-[(4-methoxybenzyl)oxy]-2-[(2RS)-2-methyl-2,3-dihydro-1H-indol-1-yl]-N-[(3R)-2-oxoazepanyl]-5-pyrimidinecarboxamide, Example 66-14: 4-[(4-methoxybenzyl)oxy]-2-[(2R)-2-methyl-2,3-dihydro-1H-indol-1-yl]-N-[(3S)-2-oxoazepanyl]-5-pyrimidinecarboxamide, Example 66-15: 4-[(4-methoxybenzyl)oxy]-2-[(2R)-2-methyl-2,3-dihydro-1H-indol-1-yl]-N-[(3R)-2-oxoazepanyl]-5-pyrimidinecarboxamide, Example 66-16: 2-[(2R)-2-methyl-2,3-dihydro-1H-indol-1-yl]-4-[(3-fluoro-4-methoxybenzyl)oxy]-N-[(3S)-2-oxoazepanyl]-5-pyrimidinecarboxamide, Example 66-17: 4-[(3-chloro-4-methoxybenzyl)oxy]-2-[(2R)-2-methyl-2,3-dihydro-1H-indol-1-yl]-N-[(3S)-2-oxoazepanyl]-5-pyrimidinecarboxamide, Example 66-20: 4-[(4-methoxybenzyl)oxy]-2-[(2S)-2-methyl-2,3-dihydro-1H-indol-1-yl]-N-[(3S)-2-oxoazepanyl]-5-pyrimidinecarboxamide, Example 66-21: 4-[(4-methoxybenzyl)oxy]-2-[(2S)-2-methyl-2,3-dihydro-1H-indol-1-yl]-N-[(3R)-2-oxoazepanyl]-5-pyrimidinecarboxamide, and salts thereof.

The compound (I) of the present invention and a salt thereof can be produced according to a known method or a similar method. For example, compound (I) or a salt thereof can be produced by reacting a compound of the formula

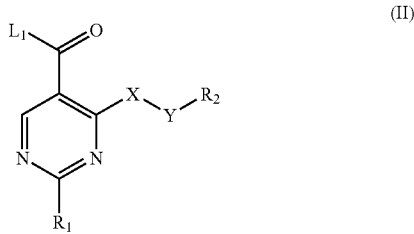

(II)

wherein $L_1$ is a leaving group and other symbols are as defined above, or a salt thereof, with an amine compound represented by $R_3R_4NH$ ($R_3$ and $R_4$ are as defined above).

As the leaving group usable for $L_1$, a suitable group capable of leaving, which is generally used in the field of organic synthetic chemistry, can be employed [e.g., groups capable of leaving, as described in Compendium of Organic Synthetic Methods, vols. 1–7, John Wiley & Sons Inc. New York (1971–1992), and R. C. Larock, Comprehensive Organic Transformation, VCH, New York (1989) and the like].

Specific examples of $L_1$ include hydroxy, substituted hydroxy (e.g., $C_{1-6}$ alkyloxy or $C_{6-10}$ aryloxy, $C_{1-6}$ alkylcarbonyloxy or $C_{6-10}$ aryl-carbonyloxy, $C_{1-6}$ alkyloxy-carbonyloxy or $C_{6-10}$ aryloxy-carbonyloxy, (di-$C_{1-6}$ alkyl or di-$C_{6-10}$ aryl)phosphonoxy, 4 to 8-membered heteroaryloxy optionally having 1 to 3 heteroatom(s) or dicarboxylic imidoxy and the like, wherein these alkyl group and aryl group are optionally substituted by 1 to 5 halogen atom, nitro, cyano and the like), substituted mercapto group (e.g., $C_{1-6}$ alkylthio, $C_{6-10}$ arylthio or 4 to 8-membered heteroarylthio having 1 to 3 heteroatom(s) or $C_{1-6}$ alkylcarbonylthio), halogen atom (fluorine, chlorine, bromine and the like), azide or cyano and the like, wherein the above-mentioned $C_{1-6}$ alkyl and $C_{6-10}$ aryl are optionally substituted by 1 to 5 halogen atom(s) (fluorine, chlorine, bromine and the like).

When reactive groups, such as amino, carboxy, hydroxy and the like, are contained, besides reaction points, in the structural formulas of compound (II) and $R_3R_4NH$, these groups may be protected by a suitable protecting group according to a conventional method. After reaction, these protecting groups may be removed according to a conventional method.

As such protecting groups, for example, those generally used in this field, which are described in T. W. Green and P. G. M. Wuts, Protective Groups in Organic Synthesis, $2^{nd}$ edition, John Wiley & Sons Inc. New York (1991) and the like, can be employed.

For a so-called amide bond forming reaction of compound (II) or a salt thereof and an amine compound represented by $R_3R_4NH$, a reaction known per se can be employed [for example, Izumiya et al., Peputidogousei no Kiso to Jikken (Basic and Experiment of Peptide Synthesis), Maruzen (1985) and R. C. Larock, Comprehensive Organic Transformation, VCH, New York (1989) and the like]. Some examples are given in the following. When $L_1$ is hydroxy, a so-called coupling reagent is preferably used.

As such reagent, for example, N,N'-dicyclohexylcarbodiimide (DCC), N,N'-diisopropylcarbodiimide (DIPCI), water-soluble carbodiimide (WSC, e.g., 1-ethyl-3-(3-dimethylaminopropyl)carbodiimide hydrochloride), carbonyldiimidazole, benzotriazolyl-N-hydroxytrisdimethylamino phosphonium hexafluorophosphorylate (Bop), diphenylphosphoryl azide (DPPA) and the like are used.

When carbodiimide is used as a coupling reagent, N-hydroxysuccinimide, 1-hydroxybenzotriazole and the like may be used as an additive. In addition, when $L_1$ is hydroxy, activated ester method with p-nitrophenyl ester, N-hydroxysuccinimide ester and the like, carboxylic acid activation methods such as mixed acid anhydride method using various carboxylic acids, various carbonic acids or various phosphoric acids or azide method and the like can be beneficially used.

The reaction between compound (II) or a salt thereof and an amine compound represented by $R_3R_4NH$ is generally carried out by agitation in an inert solvent.

The inert solvent to be used for the reaction is free of any particular limitation as long as the reaction is not adversely influenced. For example, aromatic hydrocarbons such as benzene, toluene, xylene and the like; ethers such as dioxane, diethoxyethane, tetrahydrofuran and the like; halogenated hydrocarbons such as dichloromethane, chloroform and the like; alkylnitriles such as acetonitrile, propionitrile and the like; nitroalkanes such as nitromethane, nitroethane and the like; and amides such as dimethylformamide, dimethylacetamide and the like are preferable.

A small amount of reeactable solvent (e.g., water, alcohol and the like) may be added depending on the property of the reactive group. While the reaction temperature varies depending on the starting material compound (II), amine compound represented by $R_3R_4NH$, the kind of additives, the kind of solvent and the like, it is generally from about −40° C. to about 100° C., preferably from about −30° C. to about 50° C. The reaction time is generally from about 1 minute to about 48 hours, preferably from about 15 minutes to about 24 hours.

The compound (II) and a salt thereof can be produced easily according to a known reaction or a similar reaction [e.g., Katritzky et al. ed., Comprehensive Heterocyclic Chemistry, vol. 3, and Brown et al. ed., The Pyrimidines, The Chemistry of Heterocyclic Compounds, vols. 16 and 52, John Wiley & Sons Inc., New York (1962 and 1994) and the like]. The compound represented by $R_3R_4NH$ may be a commercially available compound as it is or can be produced easily according to a known reaction or a similar reaction.

The compound (I) of the present invention or a salt thereof can be also produced by reacting a compound of the formula

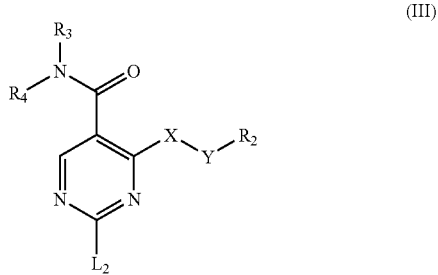

(III)

wherein $L_2$ is a leaving group and other symbols are as defined above, or a salt thereof, with a compound of the formula: $R_1$—H ($R_1$ is as defined above).

As the leaving group usable for $L_2$, a suitable group capable of leaving, which is generally used in the field of organic synthetic chemistry, can be employed [e.g., groups capable of leaving, as described in Compendium of Organic Synthetic Methods, vols. 1–7, John Wiley & Sons Inc. New York (1971–1992), and R. C. Larock, Comprehensive Organic Transformation, VCH, New York (1989) and the like].

As the preferable $L_2$, the leaving group used for introducing an amino group into the 2-position of pyrimidine, as described in Brown et al. ed., The Pyrimidines, The Chemistry of Heterocyclic Compounds, vol. 52, John Wiley & Sons Inc., New York (1994) and the like can be used.

Specific examples of $L_2$ to be used include halogen atom such as fluorine, chlorine, bromine and the like, mercapto, $C_{1-6}$ alkylthio, $C_{6-10}$ arylthio or 4 to 8-membered heteroarylthio optionally having 1 to 3 heteroatom(s), hydroxy, $C_{1-6}$ alkyloxy, $C_{6-10}$ aryloxy, $C_{1-6}$ alkylsulfonyl, $C_{6-10}$ arylsulfonyl, $C_{1-6}$ alkylsulfinyl, $C_{6-10}$ arylsulfinyl, thiocyanate, cyano, $C_{1-6}$ alkylcarbonyloxy, $C_{6-10}$arylcarbonyloxy, or amino optionally mono or di-substituted with $C_{1-6}$ alkyl or $C_{6-10}$ aryl, and the like, wherein the above-mentioned $C_{1-6}$ alkyl and $C_{6-10}$ aryl are optionally substituted by 1 to 5 halogen atom(s) (fluorine, chlorine, bromine and the like).

When reactive groups, such as amino, carboxy, hydroxy and the like, are contained, besides reaction points, in the structural formulas of compound (III) and $R_1$—H, these groups may be protected by a suitable protecting group according to a conventional method. After reaction, these protecting groups may be removed according to a conventional method.

As such protecting groups, for example, those generally used in this field, which are described in T. W. Green and P. G. M. Wuts, Protective Groups in Organic Synthesis, $2^{nd}$ edition, John Wiley & Sons Inc. New York (1991) and the like, can be employed.

For a so-called aromatic nucleophilic substitution reaction of compound (III) or a salt thereof and a secondary amine compound represented by $R_1$—H, a reaction known per se can be employed [for example, The Pyrimidines, The Chemistry of Heterocyclic Compounds, vol. 52, John Wiley & Sons Inc., New York (1994) and the like]. This reaction is generally carried out by agitation in or without a solvent.

The solvent to be used for the reaction is free of any particular limitation as long as the reaction is not adversely influenced. For example, aromatic hydrocarbons such as benzene, toluene, xylene and the like; ethers such as dioxane, diethoxyethane, tetrahydrofuran and the like; halogenated hydrocarbons such as dichloromethane, chloroform and the like; alkylnitriles such as acetonitrile, propionitrile and the like; nitroalkanes such as nitromethane, nitroethane and the like; amides such as dimethylformamide, dimethylacetamide and the like; alcohols such as methanol, ethanol and the like or water are preferable.

The reaction can be also carried out in the presence of a base, if necessary. Examples of the base include organic amines such as triethylamine, diisopropylethylamine and the like; basic inorganic salt such as sodium hydrogencarbonate, potassium carbonate and the like, and the like. This reaction can be also accelerated by the use of an acid catalyst. As such acid catalyst, for example, mineral acids such as hydrochloric acid, sulfuric acid and the like; organic acids such as trifluoroacetic acid, trifluoromethanesulfonic acid and the like; Lewis acids such as boron trifluoride, lanthanoide triflate and the like, and the like are used.

Particularly when $L_2$ is halogen, this reaction can be also accelerated by the use of palladium phosphine complex [e.g., combination of $Pd(dba)_2$ and tri-$C_{1-6}$ alkylphosphine or tri-$C_{6-10}$ arylphosphine and the like] as a catalyst.

While the reaction temperature varies depending on the starting material compound (III), a salt thereof, a secondary amine compound represented by $R_1$—H, the kind of additives, the kind of solvent and the like, it is generally from about 0° C. to about 200° C., preferably from about 20° C. to about 150° C. The reaction time is generally from about 1 minute to about 120 hours, preferably from about 15 minutes to about 72 hours.

The compound (III) and a salt thereof can be produced easily according to a known reaction or a similar reaction [e.g., Katritzky et al. ed., Comprehensive Heterocyclic Chemistry, vol. 3, and Brown et al. ed., The Pyrimidines, The Chemistry of Heterocyclic Compounds, vols. 16 and 52, John Wiley & Sons Inc., New York (1962 and 1994) and the like]. The compound represented by $R_1$—H may be a commercially available compound as it is or can be produced easily according to a known reaction or a similar reaction.

The compound (I) of the present invention or a salt thereof can be also produced by reacting a compound of the formula

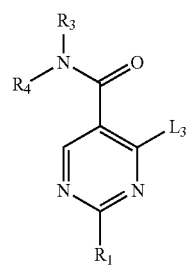

(IV)

wherein $L_3$ is a leaving group and other symbols are as defined above, or a salt thereof, with a compound of the formula: $R_2$—Y—$X_1$—H ($R_2$, Y and $X_1$ are as defined above), and if desired, subjecting the resulting compound to oxidation.

As the leaving group usable for $L_3$, those similar to the leaving groups mentioned with regard to $L_2$ can be employed.

When reactive groups, such as amino, carboxy, hydroxy and the like, are contained, besides reaction points, in the structural formulas of compound (IV) and $R_2$—Y—$X_1$—H, these groups may be protected by a suitable protecting group according to a conventional method. After reaction, these protecting groups may be removed according to a conventional method.

As such protecting groups, for example, those generally used in this field, which are described in T. W. Green and P. G. M. Wuts, Protective Groups in Organic Synthesis, $2^{nd}$ edition, John Wiley & Sons Inc. New York (1991) and the like, can be employed.

For a so-called aromatic nucleophilic substitution reaction of compound (IV) or a salt thereof and a compound represented by $R_2$—Y—$X_1$—H, a reaction known per se can be employed [for example, The Pyrimidines, The Chemistry of Heterocyclic Compounds, vol. 52, John Wiley & Sons Inc., New York (1994) and the like]. This reaction is generally carried out by agitation in or without a solvent.

The solvent to be used for the reaction is free of any particular limitation as long as the reaction is not adversely influenced. For example, aromatic hydrocarbons such as benzene, toluene, xylene and the like; ethers such as dioxane, diethoxyethane, tetrahydrofuran and the like; halogenated hydrocarbons such as dichloromethane, chloroform and the like; alkylnitriles such as acetonitrile, propionitrile and the like; nitroalkanes such as nitromethane, nitroethane and the like; amides such as dimethylformamide, dimethylacetamide and the like; alcohols such as methanol, ethanol and the like or water are preferable.

The reaction can be also carried out in the presence of a base, if necessary. Examples of the base include organic amines such as triethylamine, diisopropylethylamine and the like; basic inorganic salt such as sodium hydrogencarbonate, potassium carbonate and the like; metal hydrides such as sodium hydride, lithium hydride and the like, and the like.

This reaction can be also accelerated by the use of an acid catalyst. As such acid catalyst, for example, mineral acids such as hydrochloric acid, sulfuric acid and the like; organic acids such as trifluoroacetic acid, trifluoromethanesulfonic acid and the like; Lewis acids such as boron trifluoride, lanthanide triflate and the like, and the like are used.

While the reaction temperature varies depending on the starting material compound (IV), a compound represented by $R_2$—Y—$X_1$—H, the kind of additives, the kind of solvent and the like, it is generally from about 0° C. to about 200° C., preferably from about 20° C. to about 150° C. The reaction time is generally from about 1 minute to about 120 hours, preferably from about 15 minutes to about 72 hours.

When $X_1$ is sulfur atom, a compound (I) wherein X is sulfone or sulfoxide, or a salt thereof, can be produced by producing compound (I) or a salt thereof under the above-mentioned conditions and the like, and oxidizing the compound.

As the oxidation used for this reaction, a reaction known per se [e.g., reaction described in Hudlicky, Oxidations in Organic Chemistry, The American Chemical Society (1990) and the like] can be used. Preferably, for example, it is a reaction using organic peracids such as perbenzoic acid, m-chloroperbenzoic acid and the like, peroxides such as hydrogen peroxide, t-butyl hydroperoxide and the like, and the like.

The compound (IV) and a salt thereof can be produced easily according to a known reaction or a similar reaction [e.g., Katritzky et al. ed., Comprehensive Heterocyclic Chemistry, vol. 3, and Brown et al. ed., The Pyrimidines, The Chemistry of Heterocyclic Compounds, vols. 16 and 52, John Wiley & Sons Inc., New York (1962 and 1994) and the like]. The compound represented by $R_2$—Y—$X_1$—H may be a commercially available compound as it is or can be produced easily according to a known reaction or a similar reaction.

The compound (I) of the present invention can be also produced by reacting a compound of the formula

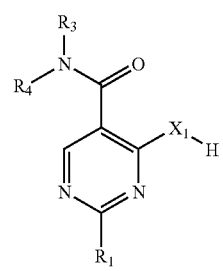

(V)

wherein $X_1$ is an oxygen atom, a nitrogen atom optionally substituted by a hydrocarbon group having 1 to 5 carbon atom(s) or a sulfur atom and other symbols are as defined above, or a salt thereof, with a compound represented by $R_2$-Y-$L_4$ ($L_4$ is leaving group and $R_2$ and Y are as defined above), and if desired, subjecting the resulting compound to oxidation.

As the leaving group usable for $L_4$, a suitable group capable of leaving, which is generally used in the field of organic synthetic chemistry, can be employed [e.g., groups capable of leaving, as described in Compendium of Organic Synthetic Methods, vols. 1–7, John Wiley & Sons Inc. New York (1971–1992), and R. C. Larock, Comprehensive Organic Transformation, VCH, New York (1989) and the like].

As $L_4$, for example, hydroxy, halogen atom (fluorine, chlorine, bromine and the like), substituted sulfonyloxy such as $C_{1-6}$ alkanesulfonyloxy, $C_{6-10}$ arenesulfonyloxy and the like are preferable, wherein $C_{1-6}$ alkane and $C_{6-10}$ arene are optionally substituted by 1 to 5 halogen atom(s) (fluorine, chlorine, bromine and the like).

When reactive groups, such as amino, carboxy, hydroxy and the like, are contained, besides reaction points, in the structural formulas of compound (V) and $R_2$—Y-$L_4$, these groups may be protected by a suitable protecting group according to a conventional method.

After reaction, these protecting groups may be removed according to a conventional method. As such protecting group, for example, those generally used in this field, which are described in T. W. Green and P. G. M. Wuts, Protective Groups in Organic Synthesis, $2^{nd}$ edition, John Wiley & Sons Inc. New York (1991) and the like, can be employed.

For a so-called nucleophilic substitution reaction of compound (V) or a salt thereof and a compound represented by $R_2$—Y-$L_4$, a reaction known per se can be employed [for example, reactions described in Comprehensive Organic Transformations, VCH, New York (1989) and the like]. To be specific, when, for example, $L_4$ is hydroxy, the conditions using a so-called Mitsunobu reagent (e.g., combination of diethyl azobiscarboxylate and triphenylphosphine and the like), and the like can be employed. When $L_4$ is halogen or substituted sulfonyloxy and the like, the reaction beneficially proceeds in the presence of a base.

As such base, organic amines such as triethylamine, diisopropylethylamine and the like; basic inorganic salt such as sodium hydrogencarbonate, potassium carbonate and the like; metal hydrides such as sodium hydride, lithium hydride and the like, and the like are used.

A so-called nucleophilic substitution reaction of compound (V) or a salt thereof and a compound represented by $R_2$—Y-$L_4$ is generally carried out by agitation in an inert solvent.

The inert solvent to be used for the reaction is free of any particular limitation as long as the reaction is not adversely influenced. For example, aromatic hydrocarbons such as benzene, toluene, xylene and the like; ethers such as dioxane, diethoxyethane, tetrahydrofuran and the like; halogenated hydrocarbons such as dichloromethane, chloroform and the like; alkylnitriles such as acetonitrile, propionitrile and the like; nitroalkanes such as nitromethane, nitroethane and the like; amides such as dimethylformamide, dimethylacetamide and the like; and mixed solvents thereof are preferable.

While the reaction temperature varies depending on the starting material compound (V), a compound represented by $R_2$—Y-$L_4$, the kind of additives, the kind of solvent and the like, it is generally from about −80° C. to about 150° C., preferably from about −30° C. to about 100° C. The reaction time is generally from about 1 minute to about 48 hours, preferably from about 15 minutes to about 24 hours.

The compound (V) and a salt thereof can be produced easily according to a known reaction or a similar reaction [e.g., Katritzky et al. ed., Comprehensive Heterocyclic Chemistry, vol. 3, and Brown et al. ed., The Pyrimidines, The Chemistry of Heterocyclic Compounds, vols. 16 and 52, John Wiley & Sons Inc., New York (1962 and 1994) and the like]. The compound represented by $R_2$—Y-$L_4$ may be a commercially available compound as it is or can be produced easily according to a known reaction or a similar reaction.

The compound (I) of the present invention and a salt thereof can be produced by converting the substituents represented by $R_1$, X, Y, $R_2$, $R_3$ and $R_4$ of compound (I) to those represented by $R_1$, X, Y, $R_2$, $R_3$ and $R_4$, which are respectively different chemically. For such conversion of the substituents, a reaction known per se can be used. For example, reactions described in Comprehensive Organic Transformations, VCH, New York (1989) and the like can be employed.

The starting material compounds (II), (III), (IV) and (V) and salts thereof to be used in the present invention can be produced according to the above-mentioned known method or a method analogous thereto.

To be specific, for example, compounds (II'), (II") and (V') and salts thereof can be produced according to the method represented by the scheme 1 or a method analogous thereto.

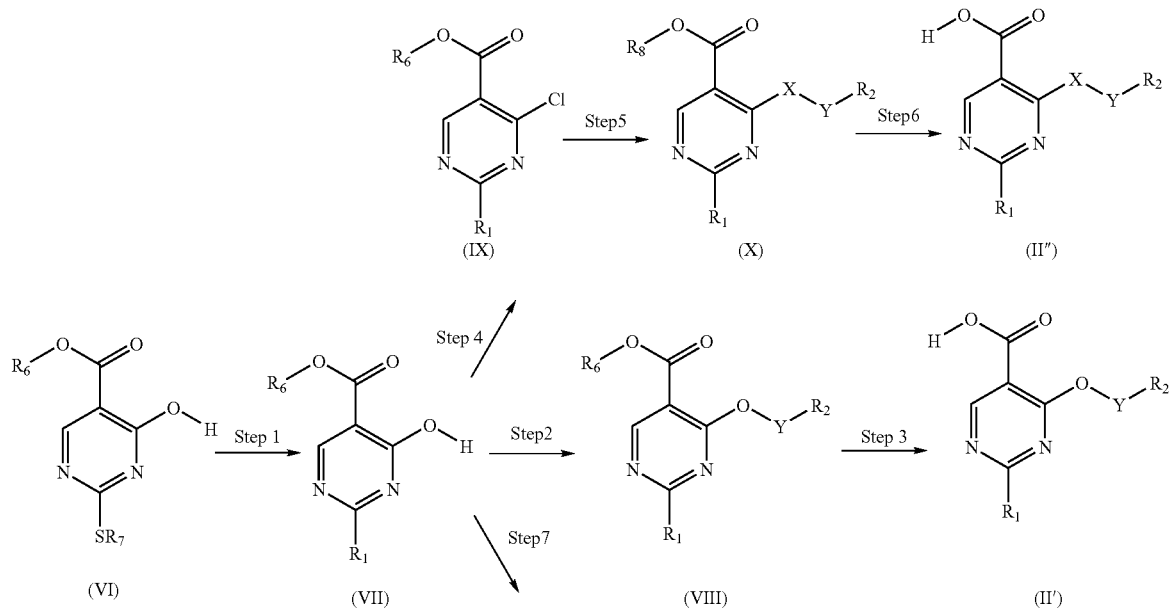

Scheme 1

-continued

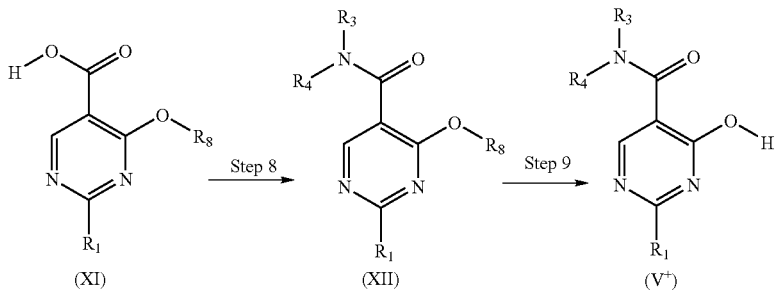

Step 1:

A compound of the formula

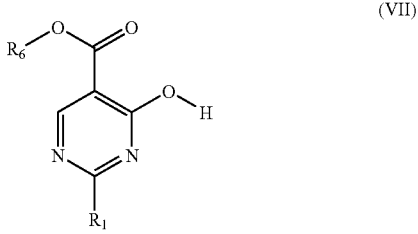

wherein $R_6$ is a carboxyl-protecting group and $R_1$ is as defined above, can be produced by subjecting a compound of the formula (VI)

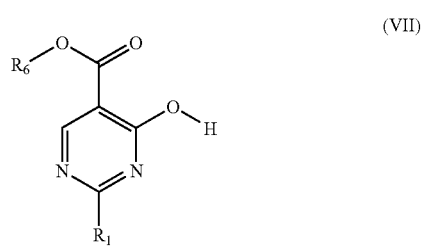

wherein $R_7$ is $C_{1-6}$ alkyl, $C_{6-10}$ aryl or a 4 to 8-membered heteroaryl optionally having 1 to 3 heteroatom(s), wherein $C_{1-6}$ alkyl and $C_{6-10}$ aryl are optionally substituted by 1 to 5 halogen atom(s) (fluorine, chlorine, bromine and the like) and $R_6$ is as defined above, and a compound represented by $R_1$—H ($R_1$ is as defined above) to a method described in Production Method 2 or a method analogous thereto.

Particularly preferable reaction conditions are alcohols such as methanol, ethanol and the like as a solvent, reaction temperature of about 30 –about 120° C., and reaction time of from about 1 hour to about 48 hours.

In the formula (VI), as the carboxyl-protecting group represented by $R_6$, a protecting group generally used in the field of organic synthesis chemistry can be used [e.g., protecting groups described in Green and Wuts, Protective Groups in Organic Synthesis, 2$^{nd}$ ed., John Wiley & Sons Inc., New York (1991) and the like].

As particularly preferable carboxyl-protecting group represented by $R_6$, for example, an ester-forming protecting groups, such as methyl, ethyl, methoxymethyl, methoxyethoxymethyl, benzyloxymethyl, tert-butyl, benzyl, p-methoxybenzyl, p-nitrobenzyl, o-nitrobenzyl, benzhydrile, trityl, 2,2,2-trichloroethyl, 2-trimethylsilylethyl, allyl and the like, are used.

In the formula (VI), as a group represented by $R_7$, $C_{1-6}$ alkyl and $C_{6-10}$ aryl are particularly preferable.

The compound (VI) and a salt thereof can be produced according to the method described in C. W. Todd et al., the Journal of The American Chemical Society, vol. 65, p. 350 (1943) or a method similar thereto.

Step 2:

A compound represented by the formula

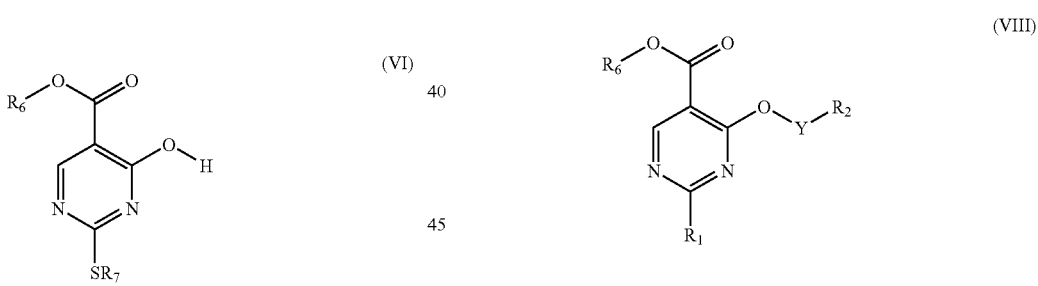

wherein each symbol is as defined above, can be produced by subjecting a compound represented by the formula (VII)

wherein $R_1$ and $R_6$ are as defined above, and a compound represented by $R_2$—Y-$L_4$ (each symbol is as defined above) to the method described in Production Method 4 or a method similar thereto.

When $L_4$ is a halogen atom such as chlorine, bromine and the like, particularly preferable reaction conditions are the use of aromatic hydrocarbons such as benzene, toluene, xylene and the like, ethers such as diethoxyethane, tetrahydrofuran and the like or amides such as dimethylformamide, dimethylacetamide and the like as a solvent in the presence of basic inorganic salts such as sodium hydrogencarbonate, potassium carbonate and the like or metal hydrides such as sodium hydride, lithium hydride and the like, and the like at a reaction temperature of about −30 –about 100° C., and the reaction time of from about 0.5 hour to about 48 hours.

Step 3:

A compound represented by the formula

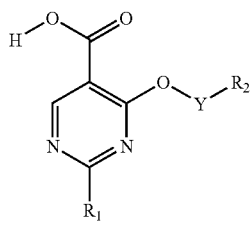

(II')

wherein the symbols in the formula are as defined above, can be produced by deprotecting the carboxylate residue (—COOR$_6$) of the compound represented by the formula

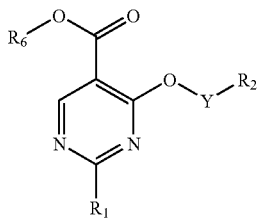

(VIII)

wherein each symbol is as defined above.

The carboxyl-protecting group represented by $R_6$ can be removed under deprotection conditions generally employed in the field of organic synthesis chemistry [e.g., deprotection method described in Green and (Wuts), Protective Groups in Organic Synthesis, 2$^{nd}$ ed., John Wiley & Sons Inc., New York (1991) and the like]. For example, a method using an acid, a method using a base, a method using reduction, a method using UV light, a method using a palladium complex, a method using a Lewis acid and the like can be mentioned.

Examples of preferable acid include organic acids such as formic acid, trifluoroacetic acid, benzenesulfonic acid, p-toluenesulfonic acid and the like; inorganic acids such as hydrochloric acid, hydrobromic acid, sulfuric acid and the like, and the like, with which tert-butyl, p-methoxybenzyl, benzhydrile and the like are hydrolyzed.

Examples of preferable base include alkali metal hydroxides such as lithium hydroxide, sodium hydroxide, potassium hydroxide and the like; alkaline earth metal hydroxides such as magnesium hydroxide, calcium hydroxide and the like; alkali metal carbonates such as sodium carbonate, potassium carbonate and the like; alkaline earth metal carbonates such as magnesium carbonate, calcium carbonate and the like; alkali metal hydrogencarbonates such as sodium hydrogencarbonate, potassium hydrogencarbonate and the like; alkali metal acetates such as sodium acetate, potassium acetate and the like; alkaline earth metal phosphates such as calcium phosphate, magnesium phosphate and the like; alkali metal hydrogenphosphate such as disodium hydrogenphosphate, dipotassium hydrogenphosphate and the like, inorganic base such as aqueous ammonia and the like; organic base such as trimethylamine, triethylamine, diisopropylethylamine, pyridine, picoline, N-methylpyrrolidine, N-methylpiperidine, N-methylmorpholine, 1,5-diazabicyclo[4.3.0]non-5-en, 1,4-diazabicyclo[2.2.2]octane, 1,8-diazabicyclo[5.4.0]-7-undecene and the like, and the like, with which methyl, ethyl and the like are hydrolyzed.

Examples of preferable reduction include reduction with sodium borohydride, reduction with zinc/acetic acid, catalytic reduction and the like, by which 2,2,2-trichloroethyl, benzyl, p-nitrobenzyl, benzhydrile and the like can be deprotected.

By the method using UV light, o-nitrobenzyl and the like can be deprotected.

By the method using palladium complex, allyl and the like can be deprotected.

Examples of preferable Lewis acid include zinc chloride, zinc bromide, titanium tetrachloride, trimethylsilyl triflate and the like, with which methoxymethyl, 2-methoxyethoxymethyl, benzhydryl and the like can be deprotected.

The solvent for such deprotection is not particularly limited as long as it has no possibility of causing anything other than the objective reaction. For example, aromatic hydrocarbons such as benzene, toluene, xylene and the like; ethers such as dioxane, diethoxyethane, tetrahydrofuran and the like; alcohols such as methanol, ethanol and the like; halogenated hydrocarbons such as dichloromethane, chloroform and the like; alkylnitriles such as acetonitrile, propionitrile and the like; nitroalkanes such as nitromethane, nitroethane and the like; amides such as dimethylformamide, dimethylacetamide and the like; water or mixed solvents thereof are preferable.

While the reaction temperature varies depending on the starting material compound (VIII), deprotection conditions, the kind of solvent and the like, it is generally from about −80° C. to about 150° C., preferably from about −30° C. to about 100° C. The reaction time is generally from about 1 minute to about 72 hours, preferably from about 15 minutes to about 24 hours.

Step 4:

A compound represented by the formula

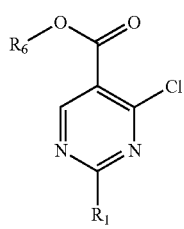

(IX)

wherein each symbol is as defined above, can be produced by converting hydroxy of a compound represented by the formula

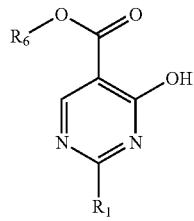
(VII)

wherein each symbol is as defined above, to chlorine.

Such conversion reaction is described in detail in, for example, The Chemistry of Heterocyclic Compounds, vols. 16 and 52, John Wiley & Sons Inc., New York (1962 and 1994) and the like, and such methods or similar reactions can be employed.

It is preferable to carry out the reaction using phosphorus oxychloride as a chlorinating agent, without solvent at room temperature to boiling point temperature. The reaction time is generally from about 1 hour to about 24 hours.

In this Step, an example wherein hydroxy was converted to chlorine is shown. However, this Step is not particularly limited to the conversion to chlorine and a different leaving group may be employed for the next reaction. As such leaving group, a leaving group represented by $L_3$ can be employed, and a synthetic method thereof may be one described in the above-mentioned publications and the like.

Step 5:

A compound represented by the formula

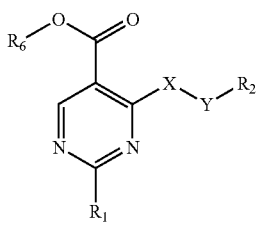
(X)

wherein the symbols in the formula are as defined above, can be produced by reacting a compound represented by

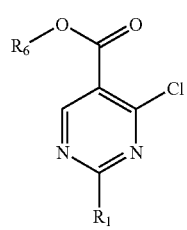
(IX)

wherein each symbol is as defined above, with a compound represented by $R_2$—Y—$X_1$—H ($R_2$, Y and $X_1$ are as defined above) under the conditions described in Production Method 3, whereafter subjecting the resulting compound to oxidation if necessary.

Preferable reaction conditions are reaction in the presence of basic inorganic salts such as sodium hydrogencarbonate, potassium carbonate and the like or metal hydrides such as sodium hydride, lithium hydride and the like, and the like, in aromatic hydrocarbons such as benzene, toluene, xylene and the like; ethers such as diethoxyethane, tetrahydrofuran and the like; amides such as dimethylformamide, dimethylacetamide and the like; alcohols such as methanol, ethanol, isopropanol and the like as a solvent, reaction temperature of from about −30° C. to about 100° C., and the reaction time of from about 0.5 hour to about 48 hours.

Step 6:

A compound represented by the formula

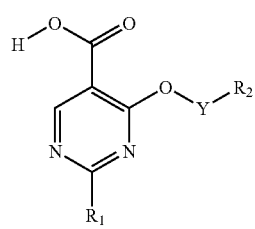
(II″)

wherein each symbol is as defined above, can be produced by deprotecting a carboxylic acid ester residue (—$COOR_6$) of the compound represented by the formula

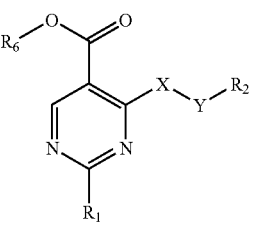
(X)

wherein each symbol is as defined above, under the same reaction conditions as in Step 3.

Step 7:

A compound represented by the formula

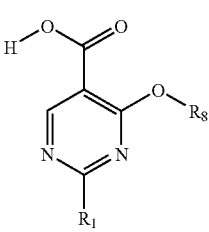
(XI)

wherein each symbol is as defined above, can be produced by protecting hydroxy of a compound represented by the formula Step 9:
A compound represented by the formula

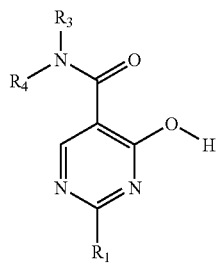

(V')

wherein each symbol is as defined above, can be produced by deprotecting a hydroxy-protecting group $R_8$ of a compound represented by the formula

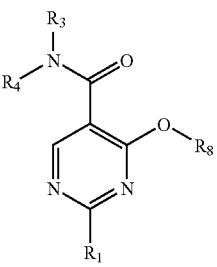

(XII)

wherein each symbol is as defined above.

The hydroxy-protecting group $R_8$, can be removed under the deprotection conditions generally employed in the field of organic synthesis chemistry [for example, deprotection methods described in Green and Wuts, Protective Groups in Organic Synthesis, $2^{nd}$ ed., John Wiley & Sons Inc., New York (1991) and the like].

The compound (II) other than the above-mentioned compound (II') and (II"), compound (III), (IV) and compound (V) other than compound (V') can be produced according to a method similar to the above-mentioned or a combination of methods described in The Chemistry of Heterocyclic Compounds, vols. 16 and 52, John Wiley & Sons Inc., New York (1962 and 1994) and Comprehensive Organic Synthesis, vols. 1–9, Pergamon Press, Oxford (1991) and the like.

The compound (I) and a salt thereof of the present invention thus obtained can be isolated and purified by a known means, such as solvent extraction, solvent exchange, phase transfer, salting out, crystallization, recrystallization, chromatography and the like. When a protecting group is contained in the reaction product, the protecting group is removed if necessary by a typical method to give compound (I) or a salt thereof. In the field of organic synthesis chemistry, the protecting groups of amino, hydroxy and carboxy have been conventionally studied and methods of protection and deprotection have been established. These methods can be used for the production of the compound (I) of the present invention and synthetic intermediates thereof.

A reaction product obtained by the above-mentioned method, which contains the objective compound (I) or reaction product (I) obtained by other known methods may be obtained as an enantiomer or diastereomer mixture in

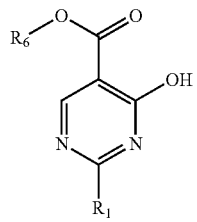

(VII)

wherein each symbol is as defined above, by a protecting group $R_8$, and deprotecting the carboxylic acid residue (—COOR$_6$) under the same reaction conditions as in step 3.

As the hydroxy-protecting group represented by $R_8$, a protecting group generally used in the field of organic synthesis chemistry can be used [for example, protecting group described in Green and Wuts, Protective Groups in Organic Synthesis, $2^{nd}$ ed., John Wiley & Sons Inc., New York (1991) and the like]. Preferably, ether type protecting group such as benzyl, p-methoxybenzyl, p-nitrobenzyl, o-nitrobenzyl, benzhydrile, trityl, 2,2,2-trichloroethyl, 2-trimethylsilyl ethyl, allyl and the like; silyl ether type protecting group such as trimethylsilyl, tert-butyldimethylsilyl, diphenyl tert-butylsilyl and the like, and the like are used.

The method of introducing these protecting groups is described in detail in the above-mentioned publications and the like. Carboxylic acid ester residue (—COOR$_6$) can be deprotected under the same reaction conditions as in Step 3.

Step 8:
A compound represented by the formula

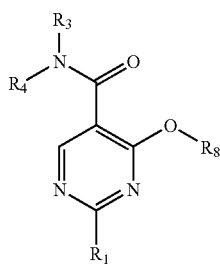

(XII)

wherein each symbol is as defined above, can be produced by reacting a compound represented by the formula

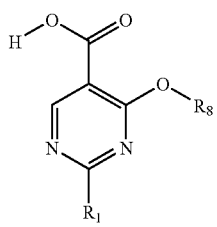

(XI)

wherein each symbol is as defined above, with an amine compound represented by R$_3$R$_4$NH wherein each symbol is as defined above, under the conditions described in Production Method 1.

some cases. Such mixture can be separated by fractional recrystallization, column chromatography and the like.

The compound (I') and a salt thereof of the present invention can be produced according to the above-mentioned production method of compound (I) of the present invention or a salt thereof.

The salts of compound (I) or (I') of the present invention are preferably pharmacologically acceptable. For example, salts with inorganic base, salts with organic base, salts with inorganic acid, salts with organic acid, salts with basic or acidic amino acid and the like are used.

Examples of preferable salts with inorganic base include alkali metal salts such as sodium salt, potassium salt and the like; alkaline earth metal salts such as calcium salt, magnesium salt and the like; aluminum salt, ammonium salt and the like.

Examples of preferable salts with organic base include trimethylamine, triethylamine, pyridine, picoline, ethanolamine, diethanolamine, triethanolamine, dicyclohexylamine, N,N'-dibenzylethylenediamine and the like.

Examples of preferable salts with inorganic acid include salts with hydrochloric acid, hydrobromic acid, nitric acid, sulfuric acid, phosphoric acid and the like.

Examples of preferable salts with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Examples of preferable salts with basic amino acid include salts with arginine, lysin, ornithine and the like, examples of preferable salts with acidic amino acid include salts with aspartic acid, glutamic acid and the like.

It is also possible to convert compounds (I), (I') and salts thereof of the present invention to hydrate thereof according to a known method.

As the salts of the above-mentioned starting material compounds used for the production of compounds (I), (I') and salts thereof of the present invention, the same salts with the salts of compounds (I) and (I') are used.

The prodrug of compound (I), (I') or a salt thereof of the present invention may be a compound that converts to compound (I), (I') or a salt thereof due to the reaction of enzyme, gastric acid and the like under the physiological conditions in the body. That is, a compound that converts to compound (I), (I') or a salt thereof by enzymatic oxidation, reduction, hydrolysis and the like, and a compound that converts to compound (I), (I') or a salt thereof by hydrolysis and the like by gastric acid and the like.

A prodrug of compound (I), (I') or a salt thereof of the present invention is exemplified by a compound wherein an amino group of compound (I) or (I') is acylated, alkylated, phosphorylated (e.g., compound where amino group of compound (I) or (I') is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, tert-butylated and the like); compound wherein a hydroxy group of compound (I) or (I') is acylated, alkylated, phosphorinated, borated (e.g., compound where hydroxy group of compound (I) or (I') is acetylated, palmitoylated, propanoylated, pivaloylated, succinilated, fumarilated, alanilated, dimethylaminomethylcarbonylated and the like); compound wherein a carboxyl group of compound (I) or (I') is esterified or amidated (e.g., compound where carboxyl group of compound (I) or (I') is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonyethyl esterified, methylamidated and the like) and the like. These compounds can be produced from compound (I) or (I') by a method known per se.

A prodrug of compound (I) or (I') may be a compound that converts to compound (I) or (I') under physiological conditions as described in Iyakuhin no Kaihatsu (Development of pharmaceutical products), vol. 7, Molecule Design, 163–198, Hirokawa Shoten (1990).

The compound (I), (I'), a salt thereof and a prodrug thereof (hereinafter sometimes to be simply referred to as the compound of the present invention) can be used safely as an agent for the prophylaxis or treatment of the diseases induced by promoted metabolism of cGMP.

The compound of the present invention can be admixed with a pharmaceutically acceptable carrier and orally or parenterally administered as a solid preparation such as tablet, capsule, granule, powder and the like; or a liquid preparation such as syrup, injection and the like.

Various organic or inorganic carriers conventionally used as materials for pharmaceutical preparations are used as a pharmacologically acceptable carrier, which is added as excipient, lubricant, binder, disintegrant for solid preparations; and solvent, dissolution aids, suspending agent, isotonicity agent, buffer, soothing agent and the like for liquid preparations. If necessary, additive for pharmaceutical preparations, such as preservative, antioxidant, coloring agent, sweetening agent and the like, can be also used.

Examples of preferable excipient include lactose, sucrose, D-mannitol, starch, crystalline cellulose, light silicic anhydride and the like.

Examples of preferable lubricant include magnesium stearate, calcium stearate, talc, colloidal silica and the like.

Examples of preferable binder include crystalline cellulose, sucrose, D-mannitol, dextrin, hydroxypropyl cellulose, hydroxypropylmethylcellulose, polyvinylpyrrolidone and the like.

Examples of preferable disintegrant include starch, carboxymethylcellulose, calcium carboxymethylcellulose, sodium crosscarmellose, sodium carboxymethyl starch, and the like.

Examples of preferable solvent include water for injection, alcohol, propylene glycol, macrogol, sesame oil, corn oil, and the like.

Examples of preferable dissolution aids include polyethylene glycol, propylene glycol, D-mannitol, benzyl benzoate, ethanol, Tris aminomethane, cholesterol, triethanolamine, sodium carbonate, sodium citrate, and the like.

Examples of preferable suspending agent include surfactants such as stearyltriethanolamine, sodium lauryl sulfate, lauryl aminopropionate, lecithin, benzalkonium chloride, benzethonium chloride, monostearic glyceride and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like.

Examples of preferable isotonicity agent include sodium chloride, glycerol, D-mannitol, and the like.

Examples of preferable buffer include phosphate buffer, acetate buffer, carbonate buffer, citrate buffer, and the like.

Examples of preferable soothing agent include benzyl alcohol and the like.

Examples of preferable preservative include p-oxybenzoic acid esters, chlorobutanol, benzyl alcohol, phenethyl alcohol, dehydroacetic acid, sorbic acid and the like.

Examples of preferable antioxidant include sulfite, ascorbic acid and the like.

The compound of the present invention can prevent or treat diseases induced by promoted metabolism of cGMP, in human and other mammals, such as angina pectoris, heart failure, cardiac infarction, hypertension, pulmonary hypertension, arteriosclerosis, allergic diseases, asthma, renal diseases, cerebral function disorders, immunodeficiency, ophthalmic diseases, disorders of male or female genital function and the like, by inhibiting the action of cGMP-PDE, particularly cGMP-PDE V. While the dose of the compound of the present invention varies depending on the condition and body weight of administration subject, administration route and the like, the compound of the present invention as an active ingredient is generally given by intravenous, muscular injection and the like once to 3 times a day in a single dose of about 0.1–80 mg/kg body weight, preferably 1–25 mg/kg body weight, in the case of, for example, parenteral administration to an adult. In the case of oral or nasal administration, the dose is given at once or divided in three doses, wherein a single dose of the compound of the present invention as an active ingredient is about 1–100 mg/kg body weight, preferably 2–50 mg/kg body weight.

The present invention is explained in more detail by the following Reference Examples and Examples. These are mere examples and do not limit the present invention in any way.

The extraction by column chromatography in the following Reference Examples and Examples was performed under observation by TLC (thin-layer chromatography). In the TLC observation, 60F$_{254}$ (Merck) was used as a TLC plate, the solvent used as an elution solvent in the column chromatography was used as a solvent and UV detector was used for detection. As silica gel for column, Kieselgel 60 (70–230 or 230–400 mesh) manufactured by Merck was used.

The NMR spectrum was measured with Varian Gemini 200 (200 MHz) type spectrometer using tetramethylsilane as an internal or external standard, and all δ values are shown in ppm. For mass analysis, cation was measured by atmospheric pressure chemical ionization (APCI) using platform II spectrometer (MICROMASS). The figures in parentheses for mixed solvents are mixing volume ratios of respective solvents and % of the mixed solvent means percent by volume. The abbreviations in Examples and Reference Examples mean the following.

s: singlet
d: doublet
t: triplet
q: quartet
dd: double doublet
m: multiplet
br broad
J: coupling constant

EXAMPLES

Reference Example 1 ethyl 2-methylthio-4-hydroxypyrimidine-5-carboxylate

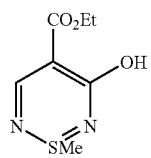

To a 4N sodium hydroxide solution (200 mL) was added S-methylisothioureasulfate (55.6 g, 0.2 mol), and after stirring for 30 min, at room temperature a solution of diethyl ethoxymethylenemalonate (80.8 mL, 0.35 mol) in ethanol (100 mL) was dropwise added slowly over 1 h. After stirring for 18 h, the precipitated crystals were collected by filtration, washed several times with cold ethanol and the obtained crystals were added to 1N hydrochloric acid (300 mL). The mixture was stirred for 30 min and the precipitated crystals were collected by filtration, washed several times with cold water and dried with heating under vacuum to give the title compound (26 g, 61%) as crystals.

$^1$H-NMR (δ ppm, CDCl$_3$): 1.42 (3H, t, J=7.0 Hz), 2.60 (3H, s), 4.44 (2H, q, J=7.0 Hz), 8.76 (1H, s), 13.25 (1H, br)

Reference Example 2-1 ethyl 4-hydroxy-2-(2,3-dihydro-1H-indol-1-yl)-5-pyrimidinecarboxylate

To a solution of indoline (3.58 g, 30 mmol) in ethanol (50 mL) was added ethyl 2-methylthio-4-hydroxypyrimidine-5-carboxylate (5.35 g, 25 mmol) and the mixture was heated under reflux for 18 h. The reaction mixture was allowed to cool to room temperature and the precipitated crystals were collected by filtration. The crystals were washed several times with cold ethanol and dried to give the title compound (5.5 g, 77%) as crystals.

In the same manner as in Reference Example 2-1, compounds of Reference Examples 2-2 to 2-14 were synthesized.

Reference Example 2-2: ethyl 2-(5-fluoro-2,3-dihydro-1H-indol-1-yl)-4-hydroxy-5-pyrimidinecarboxylate Reference Example 2-3: ethyl 2-(6,7-dihydro-5H-[1,3]dioxolo[4,5-f]indol-5-yl)-4-hydroxy-5-pyrimidinecarboxylate Reference Example 2-4: ethyl 4-hydroxy-2-(5-methoxy-2,3-dihydro-1H-indol-1-yl)-5-pyrimidinecarboxylate Reference Example 2-5: ethyl 2-(5-bromo-2,3-dihydro-1H-indol-1-yl)-4-hydroxy-5-pyrimidinecarboxylate Reference Example 2-6: ethyl 4-hydroxy-2-(6-nitro-2,3-dihydro-1H-indol-1-yl)-5-pyrimidinecarboxylate Reference Example 2-7: ethyl 4-hydroxy-2-(4-methoxy-2,3-dihydro-1H-indol-1-yl)-5-pyrimidinecarboxylate Reference Example 2-8: ethyl 4-hydroxy-2-(5-methyl-2,3-dihydro-1H-indol-1-yl)-5-pyrimidinecarboxylate Reference Example 2-9: ethyl (RS)-4-hydroxy-2-(3-methoxy-2,3-dihydro-1H-indol-1-yl)-5-pyrimidinecarboxylate Reference Example 2-10: ethyl 4-hydroxy-2-(7-methoxy-2,3-dihydro-1H-indol-1-yl)-5-pyrimidinecarboxylate Reference Example 2-11: ethyl (RS)-4-hydroxy-2-(2-methyl-2,3-dihydro-1H-indol-1-yl)-5-pyrimidinecarboxylate Reference Example 2-12: ethyl 4-hydroxy-2-(7-methyl-2,3-dihydro-1H-indol-1-yl)-5-pyrimidinecarboxylate Reference Example 2-13: ethyl (R)-4-hydroxy-2-(2-methyl-2,3-dihydro-1H-indol-1-yl)-5-pyrimidinecarboxylate Reference Example 2-14: ethyl (S)-4-hydroxy-2-(2-methyl-2,3-dihydro-1H-indol-1-yl)-5-pyrimidinecarboxylate Respective structural formulas and NMR data are shown in the following Table.

TABLE 1

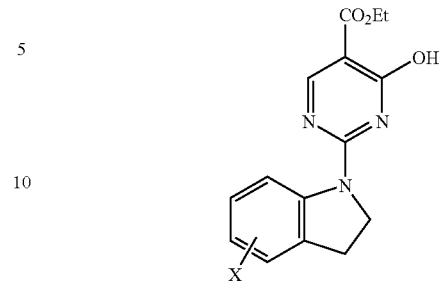

| Reference Example No. | X | yield (%) | ¹H-NMR (δ ppm, CDCl₃) |
|---|---|---|---|
| 2-1 | H | 77 | 1.42(3H, t, J=7.0Hz), 3.21(2H, t, J=7.6Hz), 4.32(2H, t, J=7.6 Hz), 4.42(2H, q, J=7.2Hz), 7.02 (1H, t, J=7.0Hz), 7.20–7.30(2H, m), 8.50(1H, d, J=7.0Hz), 8.84 (1H, s) |
| 2-2 | 5-F | 55 | 1.42(3H, t, J=7.6Hz), 3.19(2H, t, J=8.4Hz), 4.33(2H, t, J=8.4 Hz), 4.42(2H, q, J=7.0Hz), 6.86–6.98(2H, m), 8.39–8.50(1H, br), 8.82(1H, s) |
| 2-3 | 5,6-OCH₂O | 72 | 1.42(3H, t, J=7.4Hz), 3.10(2H, t, J=8.8Hz), 4.31(2H, t, J=8.0 Hz), 4.41(2H, q, J=7.4Hz), 5.96 (2H, s), 6.70(1H, s), 8.20(1H, br s), 8.79(1H, s) |
| 2-4 | 5-MeO | 82 | 1.42(3H, t, J=7.6Hz), 3.18(2H, t, J=8.4Hz), 3.81(3H, s), 4.30 (2H, t, J=8.4Hz), 4.41(2H, q, J=7.6Hz), 6.72–6.81(2H, m), 8.40 (1H, d, J=7.5Hz), 8.81(1H, s) |
| 2-5 | 5-Br | 65 | 1.42(3H, t, J=7.6Hz), 3.19(2H, t, J=8.4Hz), 4.32(2H, t, J=8.4Hz), 4.42(2H, q, J=7.0Hz), 7.30–7.38 (2H, m), 8.38(1H, d, J=7.5Hz), 8.83(1H, s) |
| 2-6 | 6-NO₂ | 45 | 1.44(3H, t, J=7.0Hz), 3.29(2H, t, J=8.4Hz), 4.37–4.50(4H, m), 7.31(1H, d, J=8.2Hz), 7.90(1H, dd, J=8.0, 2.2Hz), 8.94(1H, br s), 9.31(1H, d, J=2.2Hz) |
| 2-7 | 4-MeO | 78 | 1.42(3H, t, J=7.0Hz), 3.12(2H, t, J=8.4Hz), 3.86(3H, s), 4.34 (2H, t, J=8.4Hz), 4.42(2H, q, J=7.0Hz), 6.70(1H, d, J=8.2Hz), 7.18–7.28(2H, m), 8.14(1H, d, J=8.0Hz), 8.83(1H, s) |
| 2-8 | 5-Me | 76 | 1.42(3H, t, J=7.4Hz), 2.33(3H, s), 3.17(2H, t, J=8.8Hz), 4.29 (2H, t, J=8.8Hz), 4.42(2H, q, J=6.8Hz), 7.00–7.08(2H, m), 8.36 (1H, d, J=8.8Hz), 8.83(1H, s) |
| 2-9 | (RS)-3-Me | 84 | 1.32–1.47(6H, m), 3.40–3.60(1H, m), 3.84(1H, dd, J=12.2, 6.6Hz), 4.37–4.56(4H, m), 7.05(1H, t, J=7.2Hz), 7.19–7.30(2H, m), 8.46 (1H, br d, J=7.2Hz), 8.84(1H, s) |
| 2-10 | 7-MeO | 29 | 1.37(3H, t, J=7.0Hz), 3.13(2H, t, J=8.2Hz), 4.04(3H, s), 4.34 (2H, q, J=7.0Hz), 4.51(2H, t, J=8.2Hz), 6.89–7.00(2H, m), 7.21 (1H, t, J=8.0Hz), 8.66(1H, s) |
| 2-11 | (RS)-2-Me | 46 | 1.30–1.48(6H, m), 2.70(1H, d, J=16.2Hz), 3.42(1H, dd, J=16.2, 9.2Hz), 4.41(2H, q, J=7.4Hz), 4.98–5.13(1H, m), 7.03(1H, t, J=6.6Hz), 7.20–7.30(2H, m), 8.43 (1H, d, J=8.2Hz), 8.82(1H, s) |

TABLE 1-continued

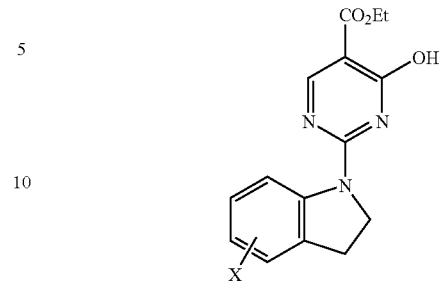

| Reference Example No. | X | yield (%) | ¹H-NMR (δ ppm, CDCl₃) |
|---|---|---|---|
| 2-12 | 7-Me | 41 | 1.41(3H, t, J=7.4Hz), 2.26(3H, s), 3.06(2H, t, J=8.2Hz), 4.31–4.48(4H, m), 6.95–7.20(3H, m), 8.77(2H, s) |
| 2-13 | (R)-2-Me | 85 | 1.30–1.48(6H, m), 2.70(1H, d, J=16.2Hz), 3.42(1H, dd, J=16.2, 9.2Hz), 4.41(2H, q, J=7.4Hz), 4.98–5.13(1H, m), 7.03(1H, t, J=6.6Hz), 7.20–7.30(2H, m), 8.43 (1H, d, J=8.2Hz), 8.82(1H, s) |
| 2-14 | (S)-2-Me | 57 | 1.30–1.48(6H, m), 2.70(1H, d, J=16.2Hz), 3.42(1H, dd, J=16.2, 9.2Hz), 4.41(2H, q, J=7.4Hz), 4.98–5.13(1H, m), 7.03(1H, t, J=6.6Hz), 7.20–7.30(2H, m), 8.43 (1H, d, J=8.2Hz), 8.82(1H, s) |

Reference Example 3-1 ethyl 2-(2,3-dihydro-1H-indol-1-yl)-4-[(4-fluorobenzyl)oxy]-5-pyrimidinecarboxylate To a solution of ethyl 4-hydroxy-2-(2,3-dihydro-1H-indol-1-yl)-5-pyrimidinecarboxylate (7.1 g, 27.6 mmol) in N,N-dimethylformamide (100 ml) were added potassium carbonate (7.8 g, 60 mmol) and 4-fluorobenzylbromide (3.74 ml, 30 mmol) and the mixture was stirred at 80° C. for 18 h. The reaction mixture was allowed to cool to room temperature and water was added. The precipitated crystals were collected by filtration, washed several times with cold water and cold ether and dried to give the title compound (8.6 g, 79%).

In the same manner as in Reference Example 3-1, compounds of Reference Examples 3-2 to 3-22 were synthesized.

Reference Example 3-2: ethyl 2-(2,3-dihydro-1H-indol-1-yl)-4-[(2-fluorobenzyl)oxy]-5-pyrimidinecarboxylate Reference Example 3-3: ethyl 2-(2,3-dihydro-1H-indol-1-yl)-4-{[4-(trifluoromethyl)benzyl]oxy}-5-pyrimidinecarboxylate Reference Example 3-4: ethyl 2-(2,3-dihydro-1H-indol-1-yl)-4-[(3-methoxybenzyl)oxy]-5-pyrimidinecarboxylate Reference Example 3-5: ethyl 2-(2,3-dihydro-1H-indol-1-yl)-4-ethoxy-5-pyrimidinecarboxylate Reference Example 3-6: ethyl 4-[(4-bromobenzyl)oxy]-2-(2,3-dihydro-1H-indol-1-yl)-5-pyrimidinecarboxylate Reference Example 3-7: ethyl 2-(2,3-dihydro-1H-indol-1-yl)-4-(2-methoxyethoxy)-5-pyrimidinecarboxylate Reference Example 3-8: ethyl 4-[(4-fluorobenzyl)oxy]-2-(5-fluoro-2,3-dihydro-1H-indol-1-yl)-5-pyrimidinecarboxylate Reference Example 3-9: ethyl 2-(5-fluoro-2,3-dihydro-1H-indol-1-yl)-4-[(3-methoxybenzyl)oxy]-5-pyrimidinecarboxylate Reference Example 3-10: ethyl (RS)-4-[(4-fluorobenzyl)oxy]-2-(2-methyl-2,3-dihydro-1H-indol-1-yl)-5-pyrimidinecarboxylate Reference Example 3-11: ethyl (RS)-4-[(3-methoxybenzyl)oxy]-2-(2-methyl-2,3-dihydro-1H-indol-1-yl)-5-pyrimidinecarboxylate Reference Example 3-12: ethyl 2-(6,7-dihydro-5H-[1,3]dioxolo[4,5-f]indol-5-yl)-4-[(4-fluorobenzyl)oxy]-5-pyrimidinecarboxylate Reference Example 3-13: ethyl 2-(5-bromo-2,3-dihydro-1H-indol-1-yl)-4-[(4-fluorobenzyl)oxy]-5-pyrimidinecarboxylate Reference Example 3-14: ethyl 2-(5-bromo-2,3-dihydro-1H-indol-1-yl)-4-[(3-methoxybenzyl)oxy]-5-pyrimidinecarboxylate Reference Example 3-15: ethyl 2-(5-bromo-2,3-dihydro-1H-indol-1-yl)-4-ethoxy-5-pyrimidinecarboxylate Reference Example 3-16: ethyl 4-[(4-bromobenzyl)oxy]-2-(5-bromo-2,3-dihydro-1H-indol-1-yl)-5-pyrimidinecarboxylate Reference Example 3-17: ethyl 4-[(4-fluorobenzyl)oxy]-2-(5-methoxy-2,3-dihydro-1H-indol-1-yl)-5-pyrimidinecarboxylate Reference Example 3-18: ethyl 4-[(3-methoxybenzyl)oxy]-2-(5-methoxy-2,3-dihydro-1H-indol-1-yl)-5-pyrimidinecarboxylate Reference Example 3-19: ethyl 4-ethoxy-2-(4-methoxy-2,3-dihydro-1H-indol-1-yl)-5-pyrimidinecarboxylate Reference Example 3-20: ethyl 4-[(4-bromobenzyl)oxy]-2-(4-methoxy-2,3-dihydro-1H-indol-1-yl)-5-pyrimidinecarboxylate Reference Example 3-21: ethyl 4-ethoxy-2-(5-methyl-2,3-dihydro-1H-indol-1-yl)-5-pyrimidinecarboxylate Reference Example 3-22: ethyl 4-[(4-bromobenzyl)oxy]-2-(5-methyl-2,3-dihydro-1H-indol-1-yl)-5-pyrimidinecarboxylate Respective structural formulas and NMR data are shown in the following Tables.

TABLE 2

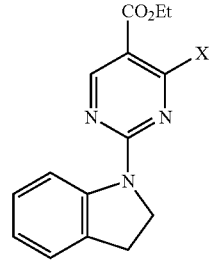

| Reference Example No. | X | Yield (%) | $^1$H-NMR ($\delta$ ppm, CDCl$_3$) |
|---|---|---|---|
| 3-1 | 4-F-C$_6$H$_4$-CH$_2$-O- | 79 | 1.35(3H, t, J=7.0Hz), 3.22 (2H, t, J=8.4Hz), 4.23–4.40 (4H, m), 5.56(2H, s), 6.96–7.16(3H, m), 7.17–7.28(2H, m), 7.46–7.58(2H, m), 8.20–8.50(1H, br s), 8.93(1H, s) |
| 3-2 | 2-F-C$_6$H$_4$-CH$_2$-O- | 77 | 1.36(3H, t, J=7.0Hz), 3.21 (2H, t, J=8.4Hz), 4.22–4.40 (4H, m), 5.67(2H, s), 6.95–7.38(6H, m), 7.66(1H, t, J=6.6Hz), 8.20–8.50(1H, br), 8.94(1H, s) |
| 3-3 | 4-CF$_3$-C$_6$H$_4$-CH$_2$-O- | 93 | 1.38(3H, t, J=7.0Hz), 3.21 (2H, t, J=8.4Hz), 4.18–4.42 (4H, m), 5.64(2H, s), 7.01 (1H, t, J=7.0Hz), 7.18–7.29 (2H, m), 7.66(4H, s), 8.10–8.50(1H, br), 8.95(1H, s) |
| 3-4 | 3-OMe-C$_6$H$_4$-CH$_2$-O- | 82 | 1.35(3H, t, J=7.0Hz), 3.20 (2H, t, J=8.8Hz), 3.82(3H, s), 4.25–4.42(4H, m), 5.54 (2H, s), 6.95–7.40(6H, m), 7.35(1H, t, J=8.6Hz), 8.20–8.55(1H, br), 8.91(1H, s) |

TABLE 2-continued

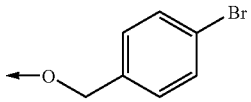

| Reference Example No. | X | Yield (%) | $^1$H-NMR (δ ppm, CDCl$_3$) |
|---|---|---|---|
| 3-5 | ←—OEt | 99 | 1.37(3H, t, J=7.4Hz), 1.52 (3H, t, J=7.0Hz), 3.21(2H, t, J=8.4Hz), 4.23–4.38(4H, m), 4.59(2H, q, J=7.2Hz), 7.00(1H, t, J=6.6Hz), 7.19–7.28(2H, m), 8.32–8.42(1H, br), 8.89(1H, s) |
| 3-6 | ←—O—C$_6$H$_4$—Br | 94 | 1.37(3H, t, J=7.0Hz), 3.21 (2H, t, J=8.8Hz), 4.21–4.40 (4H, m), 5.54(2H, s), 7.01 (1H, t, J=7.0Hz), 7.18–7.28 (2H, m), 7.41(2H, d, J=8.0 Hz), 7.52(2H, d, J=8.0Hz), 8.17–8.50(1H, br), 8.93(1H, s) |
| 3-7 | ←—O—CH$_2$CH$_2$—OMe | 98 | 1.37(3H, t, J=7.0Hz), 3.21 (2H, t, J=8.0Hz), 3.49(3H, s), 3.86(2H, t, J=4.4Hz), 4.22–4.40(4H, m), 4.65(2H, t, J=5.2Hz), 7.00(1H, t, J=7.2Hz), 7.18–7.29(2H, m), 8.23–8.42(1H, br), 8.90(1H, s) |

TABLE 3

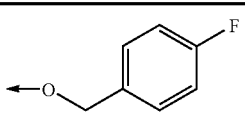

| Reference Example No. | X | yield (%) | $^1$H-NMR (δ ppm, CDCl$_3$) |
|---|---|---|---|
| 3-8 | ←—O—CH$_2$—C$_6$H$_4$—F | 86 | 1.35(3H, t, J=7.0Hz), 3.20 (2H, t, J=8.8Hz), 4.25–4.40 (4H, m), 5.53(2H, s), 6.85–6.98(2H, m), 7.08(2H, t, J=8.8Hz), 7.50(2H, dd, J=5.4, 8.4Hz), 8.15–8.43 (1H, br), 8.92(1H, s) |

TABLE 3-continued
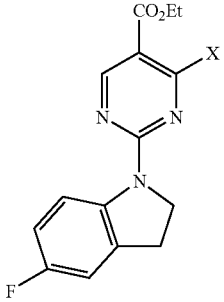
| Reference Example No. | X | yield (%) | ¹H-NMR (δ ppm, CDCl₃) |
|---|---|---|---|
| 3-9 | (3-methoxybenzyloxy) | 81 | 1.36(3H, t, J=7.0Hz), 3.19 (2H, t, J=8.8Hz), 3.82(3H, s), 4.23–4.40(4H, m), 5.56 (2H, s), 6.80–6.95(3H, m), 7.07–7.12(2H, m), 7.30(1H, t, J=8.4Hz), 8.00–8.42(1H, br), 8.91(1H, s) |
TABLE 4
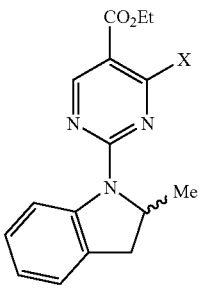
| Reference Example No. | X | yield (%) | ¹H-NMR (δ ppm, CDCl₃) |
|---|---|---|---|
| 3-10 | (4-fluorobenzyloxy) | 95 | 1.29–1.42(6H, m), 2.62(1H, d, J=16.0Hz), 3.44(1H, dd, J=9.2, 15.8Hz), 4.33(2H, q, J=9.4Hz), 5.02(1H, quintet, J=7.0Hz), 5.54 (2H, s), 6.97–7.14(3H, m), 7.19–7.28(2H, m), 7.51(2H, dd, J=5.4, 8.8Hz), 8.29 (1H, d, J=7.0Hz), 8.93(1H, s) |
| 3-11 | (3-methoxybenzyloxy) | 99 | 1.30–1.44(6H, m), 2.70(1H, d, J=15.2Hz), 3.43(1H, dd, J=8.2, 15.2Hz), 3.81(3H, s), 4.34(2H, q, J=7.0Hz), 4.92–5.12(1H, br), 5.56 (2H, s), 6.80–7.14(4H, m), 7.18–7.35(3H, m), 8.20–8.35 (1H, br), 8.92(1H, s) |

TABLE 5

[Structure: Ethyl pyrimidine-5-carboxylate with X substituent at 4-position and 2-(methylenedioxy-indolin-1-yl) at 2-position]

| Reference Example No. | X | yield (%) | ¹H-NMR (δ ppm, CDCl₃) |
|---|---|---|---|
| 3-12 | -O-CH₂-(4-F-C₆H₄) | 95 | 1.35(3H, t, J=7.0Hz), 3.11(2H, t, J=8.4Hz), 4.20–4.38(4H, m), 5.53(2H, s), 5.96(2H, s), 6.71 (1H, s), 7.07(2H, t, J=8.8Hz), 7.44–7.53(2H, m), 7.70–8.20(1H, br), 8.89(1H, s) |

TABLE 6

[Structure: Ethyl pyrimidine-5-carboxylate with X substituent at 4-position and 2-(5-bromo-indolin-1-yl) at 2-position]

| Reference Example No. | X | yield (%) | ¹H-NMR (δ ppm, CDCl₃) |
|---|---|---|---|
| 3-13 | -O-CH₂-(4-F-C₆H₄) | 80 | 1.35(3H, t, J=7.0Hz), 3.20 (2H, t, J=8.8Hz), 4.22–4.38 (4H, m), 5.53(2H, s), 7.08 (2H, t, J=8.4Hz), 7.29–7.39 (2H, m), 7.49(2H, dd, J=5.6, 8.8Hz), 8.08–8.30(1H, br), 8.92(1H, s) |
| 3-14 | -O-CH₂-(3-OMe-C₆H₄) | 83 | 1.36(3H, t, J=7.0Hz), 3.18(2H, t, J=8.4Hz), 3.82(3H, s), 4.22–4.41 (4H, m), 5.55(2H, s), 6.85(1H, dd, J=3.0, 8.0 Hz), 7.05–7.12(2H, m), 7.27–7.35(3H, m), 8.00–8.30(1H, br), 8.91(1H, s) |
| 3-15 | -OEt | 94 | 1.37(3H, t, J=7.0Hz), 1.51(3H, t, J=6.8Hz), 3.19(2H, t, J=8.6Hz), 4.22–4.39(4H, m), 4.55 (2H, q, J=7.0Hz), 7.30–7.39(2H, m), 8.17–8.33 (1H, br), 8.88(1H, s) |

TABLE 6-continued

| Reference Example No. | X | yield (%) | $^1$H-NMR (δ ppm, CDCl$_3$) |
|---|---|---|---|
| 3-16 | (4-bromobenzyloxy) | 73 | 1.37(3H, t, J=7.2Hz), 3.20(2H, t, J=8.4Hz), 4.22–4.40(4H, m), 5.52 (2H, s), 7.29–7.43(4H, m), 7.52(2H, d, J=8.8 Hz), 8.00–8.30(1H, br), 8.93(1H, s) |

TABLE 7

| Reference Example No. | X | yield (%) | $^1$H-NMR (δ ppm, CDCl$_3$) |
|---|---|---|---|
| 3-17 | (4-fluorobenzyloxy) | 92 | 1.35(3H, t, J=7.0Hz), 3.19 (2H, t, J=8.4Hz), 3.81(3H, s), 4.20–4.38(4H, m), 5.54(2H, s), 6.71–6.82(2H, m), 7.08(2H, t, J=8.8Hz), 7.43–7.53(2H, m), 8.00–8.40(1H, br), 8.90 (1H, s) |
| 3-18 | (3-methoxybenzyloxy) | 77 | 1.36(3H, t, J=7.0Hz), 3.18 (2H, t, J=8.4Hz), 3.81(6H, s), 4.15–4.41(4H, m), 5.56 (2H, s), 6.68–6.88(3H, m), 7.02–7.20(2H, m), 7.20–7.38 (1H, m), 8.00–8.40(1H, br), 8.90(1H, s) |

TABLE 8

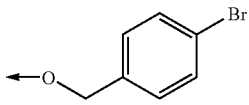

| Reference Example No. | X | yield (%) | ¹H-NMR (δ ppm, CDCl₃) |
|---|---|---|---|
| 3-19 | ←OEt | 87 | 1.37(3H, t, J=7.4Hz), 1.51(3H, t, J=7.2Hz), 3.12(2H, t, J=8.8 Hz), 3.87(3H, s), 4.25–4.40(4H, m), 4.58(2H, q, J=7.0Hz), 6.58 (1H, d, J=8.0Hz), 7.22(1H, d, J=8.2Hz), 8.00(1H, br d, J=8.2 Hz), 8.88(1H, s) |
| 3-20 | ←O-CH₂-C₆H₄-Br (4-bromobenzyloxy) | 83 | 1.37(3H, t, J=6.6Hz), 3.12 (2H, t, J=9.2Hz), 3.87(3H, s), 4.23–4.40(4H, m), 5.53 (2H, s), 6.59(1H, d, J=8.4 Hz), 7.19(1H, d, J=8.2Hz), 7.41(2H, d, J=8.4Hz), 7.52 (2H, d, J=8.4Hz), 7.80–8.05 (1H, br), 8.92(1H, s) |

TABLE 9

| Reference Example No. | X | yield (%) | ¹H-NMR (δ ppm, CDCl₃) |
|---|---|---|---|
| 3-21 | ←OEt | 81 | 1.36(3H, t, J=6.8Hz), 1.51(3H, t, J=7.2Hz), 2.33(3H, s), 3.17(2H, t, J=8.4Hz), 4.20–4.38(4H, m), 4.57 (2H, q, J=7.2Hz), 7.00–7.08(2H, m), 8.14–8.30(1H, br), 8.88(1H, s) |

TABLE 9-continued

| Reference Example No. | X | yield (%) | ¹H-NMR (δ ppm, CDCl₃) |
|---|---|---|---|
| 3-22 | ←O-CH₂-C₆H₄-Br | 89 | 1.36(3H, t, J=7.0Hz), 2.33(3H, s), 3.17(2H, t, J=8.6Hz), 4.20–4.40(4H, m), 5.53 (2H, s), 6.99–7.08 (2H, m), 7.41(2H, d, J=8.4Hz), 7.52(2H, d, J=8.4Hz), 8.00–8.35(1H, br), 8.92 (1H, s) |

Reference Example 4-1

Ethyl 2-(2,3-dihydro-1H-indol-1-yl)-4-[(4-methoxybenzyl)oxy]-5-pyrimidinecarboxylate To a solution of ethyl 4-hydroxy-2-(2,3-dihydro-1H-indol-1-yl)-5-pyrimidinecarboxylate (500 mg, 1.75 mmol) in N,N-dimethylformamide (10 mL) were added potassium carbonate (500 g, 4 mmol), sodium iodide (300 mg, 2 mmol) and 4-methoxybenzyl chloride (0.29 mL, 2 mmol), and the mixture was stirred at 80° C. for 18 h. The reaction mixture was allowed to cool to room temperature and water was added. The precipitated crystals were collected by filtration, washed several times with cold water and cold ether, and dried to give the title compound (550 mg, 78%).

In the same manner as in Reference Example 4-1, compounds of Reference Examples 4-2 to 4-32 were synthesized.

Reference Example 4-2: ethyl 4-[(2,6-difluorobenzyl)oxy]-2-(2,3-dihydro-1H-indol-1-yl)-5-pyrimidinecarboxylate Reference Example 4-3: ethyl 4-[(4-chlorobenzyl)oxy]-2-(2,3-dihydro-1H-indol-1-yl)-5-pyrimidinecarboxylate Reference Example 4-4: ethyl 2-(2,3-dihydro-1H-indol-1-yl)-4-[(3,4-dimethylbenzyl)oxy]-5-pyrimidinecarboxylate Reference Example 4-5: ethyl 4-(1,3-benzodioxol-5-ylmethoxy)-2-(2,3-dihydro-1H-indol-1-yl)-5-pyrimidinecarboxylate Reference Example 4-6: ethyl 2-(2,3-dihydro-1H-indol-1-yl)-4-[(2,5-dimethoxybenzyl)oxy]-5-pyrimidinecarboxylate Reference Example 4-7: ethyl 2-(2,3-dihydro-1H-indol-1-yl)-4-[(4-isopropoxybenzyl)oxy]-5-pyrimidinecarboxylate Reference Example 4-8: ethyl 2-(2,3-dihydro-1H-indol-1-yl)-4-[(4-ethoxybenzyl)oxy]-5-pyrimidinecarboxylate Reference Example 4-9: ethyl 2-(2,3-dihydro-1H-indol-1-yl)-4-[(3-fluoro-4-methoxybenzyl)oxy]-5-pyrimidinecarboxylate Reference Example 4-10: ethyl 2-(2,3-dihydro-1H-indol-1-yl)-4-[(4-methoxy-3-methylbenzyl)oxy]-5-pyrimidinecarboxylate Reference Example 4-11: ethyl 4-[(3-chloro-4-methoxybenzyl)oxy]-2-(2,3-dihydro-1H-indol-1-yl)-5-pyrimidinecarboxylate Reference Example 4-12: ethyl 4-(2,3-dihydro-1-benzofuran-5-ylmethoxy)-2-(2,3-dihydro-1H-indol-1-yl)-5-pyrimidinecarboxylate Reference Example 4-13: ethyl 4-(1,3-benzodioxol-5-ylmethoxy)-2-(5-fluoro-2,3-dihydro-1H-indol-1-yl)-5-pyrimidinecarboxylate Reference Example 4-14: ethyl 2-(5-fluoro-2,3-dihydro-1H-indol-1-yl)-4-[(4-methoxybenzyl)oxy]-5-pyrimidinecarboxylate Reference Example 4-15: ethyl 2-(6,7-dihydro-5H-[1,3]dioxolo[4,5-f]indol-5-yl)-4-[(4-methoxybenzyl)oxy]-5-pyrimidinecarboxylate Reference Example 4-16: ethyl 2-(5-bromo-2,3-dihydro-1H-indol-1-yl)-4-[(4-methoxybenzyl)oxy]-5-pyrimidinecarboxylate Reference Example 4-17: ethyl 2-(5-bromo-2,3-dihydro-1H-indol-1-yl)-4-[(2,5-dimethoxybenzyl)oxy]-5-pyrimidinecarboxylate Reference Example 4-18: ethyl 4-(1,3-benzodioxol-5-ylmethoxy)-2-(5-bromo-2,3-dihydro-1H-indol-1-yl)-5-pyrimidinecarboxylate Reference Example 4-19: ethyl 4-(1,3-benzodioxol-5-ylmethoxy)-2-(5-methoxy-2,3-dihydro-1H-indol-1-yl)-5-pyrimidinecarboxylate Reference Example 4-20: ethyl 4-[(4-methoxybenzyl)oxy]-2-(5-methoxy-2,3-dihydro-1H-indol-1-yl)-5-pyrimidinecarboxylate Reference Example 4-21: ethyl 4-[(2,5-dimethoxybenzyl)oxy]-2-(4-methoxy-2,3-dihydro-1H-indol-1-yl)-5-pyrimidinecarboxylate Reference Example 4-22: ethyl 4-[(4-methoxybenzyl)oxy]-2-(4-methoxy-2,3-dihydro-1H-indol-1-yl)-5-pyrimidinecarboxylate Reference Example 4-23: ethyl 4-[(4-methoxybenzyl)oxy]-2-(5-methyl-2,3-dihydro-1H-indol-1-yl)-5-pyrimidinecarboxylate Reference Example 4-24: ethyl 4-[(2,5-dimethoxybenzyl)oxy]-2-(5-methyl-2,3-dihydro-1H-indol-1-yl)-5-pyrimidinecarboxylate Reference Example 4-25: ethyl (RS)-4-[(4-methoxybenzyl)oxy]-2-(2-methyl-2,3-dihydro-1H-indol-1-yl)-5-pyrimidinecarboxylate Reference Example 4-26: ethyl (RS)-4-[(4-methoxybenzyl)oxy]-2-(3-methyl-2,3-dihydro-1H-indol-1-yl)-5-pyrimidinecarboxylate Reference Example 4-27: ethyl 4-[(4-methoxybenzyl)oxy]-2-(7-methyl-2,3-dihydro-1H-indol-1-yl)-5-pyrimidinecarboxylate Reference Example 4-28: ethyl (R)-4-[(4-methoxybenzyl)oxy]-2-(2-methyl-2,3-dihydro-1H-indol-1-yl)-5-pyrimidinecarboxylate Reference Example 4-29: ethyl (R)-4-[(3-fluoro-4-methoxybenzyl)oxy]-2-(2-methyl-2,3-dihydro-1H-indol-1-yl)-5-pyrimidinecarboxylate Reference Example 4-30: ethyl (R)-4-[(3-chloro-4-methoxybenzyl)oxy]-2-(2-methyl-2,3-dihydro-1H-indol-1-yl)-5-pyrimidinecarboxylate Reference Example 4-31: ethyl (R)-4-[(2-fluoro-4-methoxybenzyl)oxy]-2-(2-methyl-2,3-dihydro-1H-indol-1-yl)-5-pyrimidinecarboxylate Reference Example 4-32: ethyl (R)-4-[(2-chloro-4-methoxybenzyl)oxy]-2-(2-methyl-2,3-dihydro-1H-indol-1-yl)-5-pyrimidinecarboxylate Reference Example 4-33: ethyl (S)-4-[(4-methoxybenzyl)oxy]-2-(2-methyl-2,3-dihydro-1H-indol-1-yl)-5-pyrimidinecarboxylate

TABLE 10

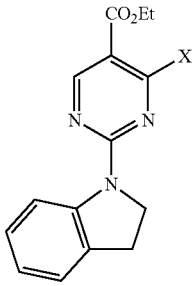

| Reference Example No. | X | yield (%) | $^1$H-NMR ($\delta$ ppm, CDCl$_3$) |
|---|---|---|---|
| 4-1 | (4-methoxybenzyl)oxy | 78 | 1.34(3H, t, J=7.0Hz), 3.22 (2H, t, J=8.4Hz), 3.81(3H, s), 4.32(2H, q, J=6.8Hz), 5.53 (2H, s), 6.88–7.08(3H, m), 7.18–7.30(2H, m), 7.45(2H, d, J=8.8Hz), 8.38(1H, br d, J=8.0 Hz), 8.92(1H, s) |
| 4-2 | (2,6-difluorobenzyl)oxy | 92 | 1.24(3H, t, J=7.0Hz), 3.23 (2H, t, J=8.8Hz), 4.19–4.20 (2H, m), 5.65(2H, s), 6.88– 7.06(3H, m), 7.20–7.42(3H, m), 8.42(1H, d, J=7.4Hz), 8.91(1H, s) |
| 4-3 | (4-chlorobenzyl)oxy | 91 | 1.36(3H, t, J=7.0Hz), 3.21 (2H, t, J=8.6Hz), 4.20–4.40 (2H, m), 5.56(2H, s), 7.01 (1H, t, J=7.4Hz), 7.18–7.28 (2H, m), 7.36(2H, d, J=8.4 Hz), 7.48(2H, d, J=8.4Hz), 8.20–8.50(1H, br), 8.93 (1H, s) |
| 4-4 | (3,4-dimethylbenzyl)oxy | 73 | 1.36(3H, t, J=7.4Hz), 2.26 (3H, s), 2.34(3H, s), 3.22 (2H, t, J=8.4Hz), 4.24–4.40 (4H, m), 5.54(2H, s), 7.01 (1H, t, J=8.0Hz), 7.08–7.30 (4H, m), 8.29–8.45(1H, br), 8.92(1H, s) |
| 4-5 | (1,3-benzodioxol-5-yl)methoxy | 98 | 1.36(3H, t, J=7.4Hz), 3.22 (2H, t, J=8.0Hz), 4.25–4.38 (4H, m), 5.50(2H, s), 5.96 (2H, s), 6.81(1H, d, J=8.0 Hz), 6.93–7.04(3H, m), 7.19–7.28(2H, m), 8.24–8.45 (1H, br), 8.92(1H, s) |
| 4-6 | (2,5-dimethoxybenzyl)oxy | 80 | 1.37(3H, t, J=6.8Hz), 3.20 (2H, t, J=9.2Hz), 3.77(3H, s), 3.86(3H, s), 4.24–4.41 (4H, m), 5.62(2H, s), 6.78– 6.86(2H, m), 6.99(1H, t, J=7.4Hz), 7.17–7.29(3H, m), 8.20–8.40(1H, br), 8.93 (1H, s) |

TABLE 10-continued

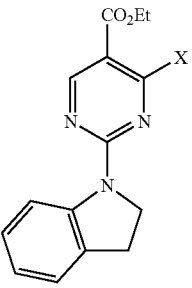

| Reference Example No. | X | yield (%) | $^1$H-NMR ($\delta$ ppm, CDCl$_3$) |
|---|---|---|---|
| 4-7 | 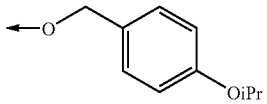 | 61 | 1.25(6H, d, J=6.0Hz), 3.19 (2H, t, J=8.0Hz), 4.26(2H, t, J=8.6Hz), 4.61(1H, sevenplet, J=6.0Hz), 5.50 (2H, s), 6.92(2H, d, J=8.8 Hz), 7.02(1H, d, J=7.6Hz), 7.18–7.32(2H, m), 7.42(2H, d, J=8.6Hz), 8.31(1H, br s), 8.80(1H, s) |
| 4-8 | 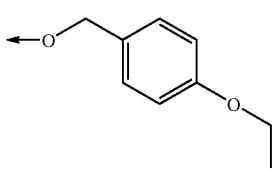 | 74 | 1.34(3H, t, J=7.4Hz), 1.41 (3H, t, J=7.0Hz), 3.21(2H, t, J=8.4Hz), 4.03(2H, q, J=7.0Hz), 4.25–4.39(4H, m), 5.53(2H, s), 6.90(2H, d, J=9.4Hz), 7.00(1H, t, J=6.6Hz), 7.18–7.30(2H, m), 7.44(2H, d, J=8.8Hz), 8.36(1H, br d, J=9.2Hz), 8.91(1H, s) |
| 4-9 | 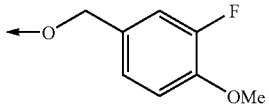 | 81 | 1.36(3H, t, J=7.4Hz), 3.22 (2H, t, J=8.8Hz), 3.90(3H, s), 4.24–4.40(4H, m), 5.51 (2H, s), 6.90–7.07(2H, m), 7.20–7.32(4H, m), 8.35(1H, br s), 8.93(1H, s) |
| 4-10 | 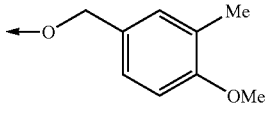 | 80 | 1.34(3H, t, J=7.2Hz), 2.23 (2H, t, J=8.8Hz), 3.22(2H, t, J=8.8Hz), 3.83(3H, s), 4.25–4.39(4H, m), 5.51(2H, s), 6.82(1H, d, J=8.0Hz), 7.00(1H, t, J=7.0Hz), 7.00–7.38(4H, m), 8.40(1H, br s), 8.91(1H, s) |
| 4-11 | 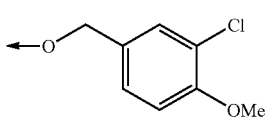 | 81 | 1.37(3H, t, J=7.0Hz), 3.22 (2H, t, J=8.8Hz), 3.91(3H, s), 4.25–4.40(4H, m), 5.50 (2H, s), 6.90–7.08(2H, m), 7.20–7.30(2H, m), 7.41(1H, dd, J=2.2, 8.4Hz), 7.56 (1H, d, J=2.2Hz), 8.20–8.45 (1H, br), 8.93(1H, s) |
| 4-12 | 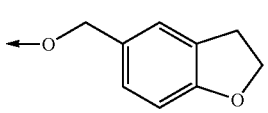 | 60 | 1.34(3H, t, J=7.0Hz), 3.22 (4H, t, J=8.8Hz), 4.26–4.39 (4H, m), 4.58(2H, t, J=8.8 Hz), 5.52(2H, s), 6.78(1H, d, J=8.2Hz), 7.01(1H, t, J=7.8Hz), 7.20–7.31(3H, m), 7.38(1H, s), 8.37(1H, br s), 8.92(1H, s) |

TABLE 11

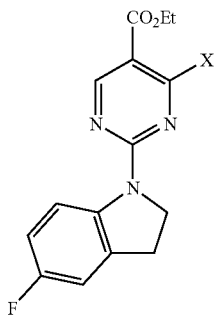

| Reference Example No. | X | yield (%) | ¹H-NMR (δ ppm, CDCl₃) |
|---|---|---|---|
| 4-13 | (benzodioxole-CH₂-O-) | 86 | 1.36(3H, t, J=7.4Hz), 3.20 (2H, t, J=8.0Hz), 4.27–4.39 (4H, m), 5.48(2H, s), 5.97(2H, s), 6.79–7.04(5H, m), 8.10–8.43(1H, br), 8.90(1H, s) |
| 4-14 | (4-MeO-C₆H₄-CH₂-O-) | 92 | 1.34(3H, t, J=8.0Hz), 3.21(2H, t, J=8.4Hz), 3.81(3H, s), 4.24–4.38 (4H, m), 5.51(2H, s), 6.84– |

TABLE 12

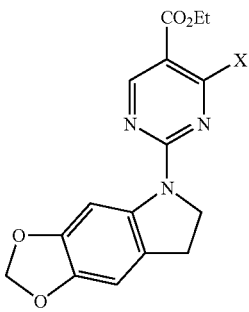

| Reference Example No. | X | yield (%) | ¹H-NMR (δ ppm, CDCl₃) |
|---|---|---|---|
| 4-15 | (4-MeO-C₆H₄-CH₂-O-) | 100 | 1.34(3H, t, J=7.4Hz), 3.12(2H, t, J=8.4Hz), 3.81(3H, s), 4.24–4.37(4H, m), 5.50(2H, s), 5.96(2H, s), 6.71 (1H, s), 6.91(2H, d, J=8.8Hz), 7.45(2H, d, J=8.8Hz), 7.90–8.25(1H, br), 8.87 (1H, s) |

TABLE 13

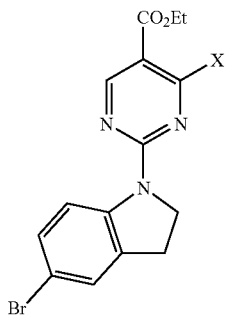

| Reference Example No. | X | yield (%) | ¹H-NMR (δ ppm, CDCl₃) |
|---|---|---|---|
| 4-16 | (4-MeO-C₆H₄-CH₂-O-) | 81 | 1.34(3H, t, J=7.0Hz), 3.20(2H, t, J=8.4Hz), 3.81(3H, s), 4.24–4.38(4H, m), 5.51(2H, s), 6.91(2H, d, J=8.6Hz), 7.29–7.36 (2H, m), 7.44(2H, d, J=8.6Hz), 8.16–8.32(1H, br), 8.90 (1H, s) |

TABLE 13-continued

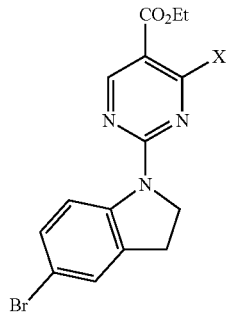

| Reference Example No. | X | yield (%) | ¹H-NMR (δ ppm, CDCl₃) |
|---|---|---|---|
| 4-17 | 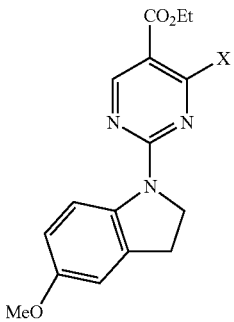 | 81 | 1.37(3H, t, J=7.0Hz), 3.18(2H, t, J=8.4Hz), 3.77(3H, s), 3.86(3H, s), 4.23–4.41(4H, m), 5.59(2H, s), 6.79–6.85(2H, m), 7.21–7.33(3H, m), 8.05–8.30(1H, br), 8.92(1H, s) |
| 4-18 | 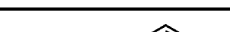 | 78 | 1.40(3H, t, J=7.4Hz), 3.20(2H, t, J=8.8Hz), 4.23–4.39(4H, m), 5.47(2H, s), 5.97(2H, s), 6.81(1H, d, J=7.8Hz), 6.90–7.05(2H, m), 7.28–7.38(2H, m), 8.10–8.35(1H, br), 8.91(1H, s) |

TABLE 14

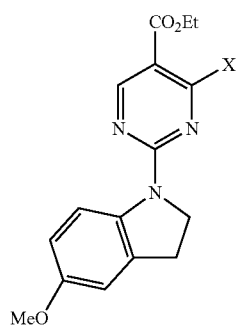

| Reference Example No. | X | yield (%) | ¹H-NMR (δ ppm, CDCl₃) |
|---|---|---|---|
| 4-19 | | 84 | 1.35(3H, t, J=7.0Hz), 3.19(2H, t, J=8.6Hz), 3.81(3H, s), 4.22–4.37(4H, m), 5.48(2H, br s), 5.96(2H, s), 6.72–6.84(3H, m), 6.95–7.05(2H, m), 8.00–8.23(1H, br), 8.90(1H, s) |

TABLE 14-continued

| Reference Example No. | X | yield (%) | ¹H-NMR (δ ppm, CDCl₃) |
|---|---|---|---|
| 4-20 | | 63 | 1.34(3H, t, J=7.0Hz), 3.19(2H, t, J=8.0Hz), 3.81(6H, s), 4.25–4.36(4H, m), 5.52(2H, s), 6.72–6.83(2H, m), 6.91(2H, d, J=8.8Hz), 7.46(2H, d, J=8.8Hz), 8.10–8.45(1H, br), 8.89(1H, s) |

TABLE 15

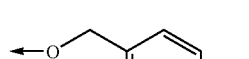

| Reference Example No. | X | yield (%) | ¹H-NMR (δ ppm, CDCl₃) |
|---|---|---|---|
| 4-21 | 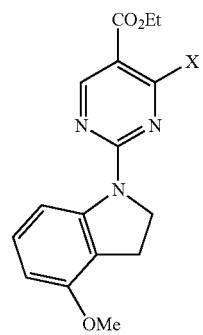 | 84 | 1.37(3H, t, J=7.0Hz), 3.11(2H, t, J=8.8Hz), 3.77(3H, s), 3.85(6H, s), 4.24–4.40(4H, m), 5.61(2H, s), 6.57(2H, d, J=8.0Hz), 6.80–6.83(2H, m), 7.13–7.24(2H, m), 7.90–8.05(1H, br), 8.92(1H, s) |

TABLE 15-continued

| Reference Example No. | X | yield (%) | ¹H-NMR (δ ppm, CDCl₃) |
|---|---|---|---|
| 4-22 | (4-methoxybenzyloxy) | 84 | 1.34(3H, t, J=7.4Hz), 3.13(2H, t, J=8.4Hz), 3.81(3H, s), 3.87(3H, s), 4.25–4.37(4H, m), 5.53(2H, s), 6.59 (1H, d, J=8.4Hz), 6.91(2H, d, J=8.8Hz), 7.22(1H, t, J=8.2Hz), 7.45(2H, d, J=8.8Hz), 7.95–8.09(1H, br), 8.90 (1H, s) |

TABLE 16

| Reference Example No. | X | yield (%) | ¹H-NMR (δ ppm, CDCl₃) |
|---|---|---|---|
| 4-23 | (4-methoxybenzyloxy) | 86 | 1.34(3H, t, J=7.4Hz), 2.33(3H, s), 3.17(2H, t, J=8.4Hz), 3.81(3H, s), 4.23–4.38(4H, m), 5.53(2H, s), 6.91 (2H, d, J=8.8Hz), 6.99–7.08(2H, m), 7.45(2H, d, J=8.8Hz), 8.15–8.29 (1H, br), 8.90(1H, s) |

TABLE 16-continued

| Reference Example No. | X | yield (%) | ¹H-NMR (δ ppm, CDCl₃) |
|---|---|---|---|
| 4-24 | (2,5-dimethoxybenzyloxy) | 90 | 1.37(3H, t, J=7.0Hz), 2.33(3H, s), 3.16(2H, t, J=8.4Hz), 3.77(3H, s), 3.86(3H, s), 4.20–4.40(4H, m), 5.61 (2H, s), 6.80–6.85 (2H, m), 6.96–7.06 (3H, m), 8.00–8.40 (1H, br), 8.92(1H, s) |

TABLE 17

| Reference Example No. | X | yield (%) | ¹H-NMR (δ ppm, CDCl₃) |
|---|---|---|---|
| 4-25 | (4-methoxybenzyloxy) | 100 | 1.36(3H, d, J=7.0Hz), 2.71(1H, d, J=16.8Hz), 3.44(1H, dd, J=7.0, 15.6Hz), 3.82(3H, s), 4.32 (2H, q, J=7.0Hz), 4.95–5.09(1H, m), 5.52(2H, s), 6.92 (2H, d, J=8.8Hz), 7.02(1H, t, J=8.0Hz), 7.20–7.30 (2H, m), 7.45(2H, d, J=8.4Hz), 8.31 (1H, d, J=8.4Hz), 8.91(1H, s) |

TABLE 18

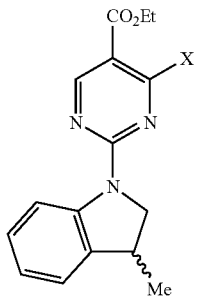

| Reference Example No. | X | yield (%) | $^1$H-NMR ($\delta$ ppm, CDCl$_3$) |
|---|---|---|---|
| 4-26 | 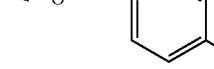 | 72 | 1.34(3H, t, J=7.2Hz), 3.43–3.58 (1H, m), 3.73–3.88 (4H, m), 4.32(2H, q, J=7.0Hz), 4.50 (1H, dd, J=9.8, 12.0Hz), 5.54(2H, s), 6.92(2H, d, J=8.8Hz), 7.04(1H, t, J=6.6Hz), 7.19–7.28(2H, m), 7.46 (2H, d, J=8.4Hz), 8.28–8.39(1H, br), 8.91(1H, s) |

TABLE 19

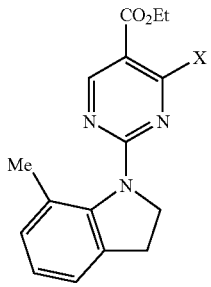

| Reference Example No. | X | yield (%) | $^1$H-NMR ($\delta$ ppm, CDCl$_3$) |
|---|---|---|---|
| 4-27 |  | 46 | 1.33(3H, t, J=7.0Hz), 2.25(3H, s), 3.05(2H, t, J=7.4Hz), 3.80(3H, s), 4.30(2H, q, J=6.8Hz), 4.43(2H, t, J=7.8Hz), 5.42(2H, s), 6.85(2H, d, J=8.8Hz), 7.00–7.15 (3H, m), 7.35(2H, d, J=8.8Hz), 8.83 (1H, s) |

TABLE 20

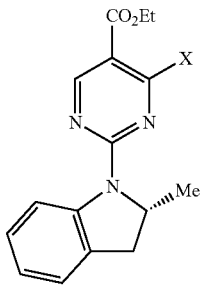

| Reference Example No. | X | yield (%) | $^1$H-NMR ($\delta$ ppm, CDCl$_3$) |
|---|---|---|---|
| 4-28 | 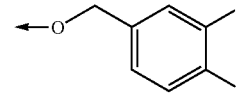 | 96 | 1.36(3H, d, J=7.0Hz), 2.71(1H, d, J=16.8Hz), 3.44(1H, dd, J=7.0, 15.6Hz), 3.82(3H, s), 4.32 (2H, q, J=7.0Hz), 4.95–5.09(1H, m), 5.52(2H, s), 6.92 (2H, d, J=8.8Hz), 7.02(1H, t, J=8.0Hz), 7.20–7.30 (2H, m), 7.45(2H, d, J=8.4Hz), 8.31 (1H, d, J=8.4Hz), 8.91(1H, s) |
| 4-29 | 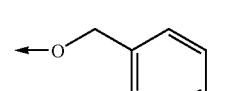 | 97 | 1.30–1.40(6H, m), 2.72(1H, d, J=16.4Hz), 3.44(1H, dd, J=9.2, 15.4Hz), 3.90(3H, s), 4.34 (2H, q, J=7.4Hz), 4.95–5.13(1H, m), 5.50(2H, s), 6.90–7.15(2H, m), 7.20–7.32(4H, m), 8.28 (1H, d, J=9.2Hz), 8.92(1H, s) |
| 4-30 | | 94 | 1.30–1.42(6H, m), 2.72(1H, d, J=15.8Hz), 3.43(1H, dd, J=9.4, 14.0Hz), 3.91(3H, s), 4.34 (2H, q, J=7.0Hz), 4.95–5.08(1H, m), 5.49(2H, s), 6.88–7.08(2H, m), 7.20–7.35(1H, m), 7.37–7.44(2H, m), 7.55 (1H, d, J=2.2Hz), 8.29(1H, d, J=7.0Hz), 8.92(1H, s) |
| 4-31 | | 98 | 1.28–1.40(6H, m), 2.72(1H, d, J=16.6Hz), 3.44(1H, dd, J=9.6, 15.8Hz), 3.80(3H, s), 4.32 (2H, q, J=7.0Hz), 4.95–5.12(1H, m), 5.57(2H, s), 6.62–6.77(2H, m), 7.02 (1H, t, J=7.4Hz), 7.20–7.35(2H, m), 7.52(1H, t, J=8.4Hz), 8.32(1H, d, J=8.6Hz), 8.92(1H, s) |

TABLE 20-continued

Structure: pyrimidine with CO₂Et at 5-position, X at 4-position, and 2-(2-methylindolin-1-yl) substituent.

| Reference Example No. | X | yield (%) | ¹H-NMR (δ ppm, CDCl₃) |
|---|---|---|---|
| 4-32 | –O–CH₂–(2-Cl, 4-OMe-phenyl) | 100 | 1.30–1.41(6H, m), 2.72(1H, d, J=16.4Hz), 3.44(1H, dd, J=9.6, 16.2Hz), 3.81(3H, s), 4.35(2H, q, J=7.4Hz), 4.95–5.10(1H, m), 5.62(2H, s), 6.85(1H, dd, J=2.2, 8.4Hz), 6.97(1H, d, J=2.4Hz), 7.04(1H, d, J=6.8Hz), 7.19–7.28(2H, m), 7.62(1H, d, J=8.8Hz), 8.29(1H, d, J=7.0Hz), 8.93(1H, s) |

TABLE 21

Structure: pyrimidine with CO₂Et at 5-position, X at 4-position, and 2-(2-methylindolin-1-yl) substituent.

| Reference Example No. | X | yield (%) | ¹H-NMR (δ ppm, CDCl₃) |
|---|---|---|---|
| 4-33 | –O–CH₂–(4-OMe-phenyl) | 66 | 1.36(3H, d, J=7.0Hz), 2.71(1H, d, J=16.8Hz), 3.44(1H, dd, J=7.0, 15.6Hz), 3.82(3H, s), 4.32(2H, q, J=7.0Hz), 4.95–5.09(1H, m), 5.52(2H, s), 6.92(2H, d, J=8.8Hz), 7.02(1H, t, J=8.0Hz), 7.20–7.30(2H, m), 7.45(2H, d, J=8.4Hz), 8.31(1H, d, J=8.4Hz), 8.91(1H, s) |

Reference Example 5-1 ethyl 4-chloro-2-(2,3-dihydro-1H-indol-1-yl)-5-pyrimidinecarboxylate

To ethyl 4-hydroxy-2-(2,3-dihydro-1H-indol-1-yl)-5-pyrimidinecarboxylate (2.85 g, 10 mmol) was added phosphorus oxychloride (10 mL, 2 mmol) and the mixture was stirred at 120° C. for 15 h. The reaction mixture was concentrated under reduced pressure. The obtained residue was dissolved in ethyl acetate, washed with saturated aqueous sodium hydrogencarbonate solution (×3) and saturated brine (×1) and dried over anhydrous sodium sulfate. The solvent was concentrated under reduced pressure to give the title compound (2.9 g, 100%).

In the same manner as in Reference Example 5-1, a compound of Reference Example 5-2 was synthesized.

Reference Example 5-2: (RS)-ethyl 4-chloro-2-(2-methyl-2,3-dihydro-1H-indol-1-yl)-5-pyrimidinecarboxylate Respective structural formulas and NMR data are shown in the following Table.

TABLE 22

Structure: pyrimidine with CO₂Et at 5-position, Cl at 4-position, and 2-(2-X-indolin-1-yl) substituent.

| Reference Example No. | X | yield (%) | ¹H-NMR(δ ppm, CDCl₃) |
|---|---|---|---|
| 5-1 | H | 100 | 1.42(3H, t, J=7.2Hz), 3.21(2H, t, J=7.6Hz), 4.31(2H, t, J=7.6Hz), 4.42(2H, q, J=7.2Hz), 7.03(1H, t, J=7.2Hz), 7.20–7.30(2H, m), 8.50(1H, d, J=7.6Hz), 8.84(1H, s) |
| 5-2 | Me | 100 | 1.34–1.43(6H, m), 2.74(1H, d, J=15.8Hz), 3.45(1H, dd, J=9.0, 15.6Hz), 4.38(2H, q, J=7.4Hz), 4.97–5.13(1H, m), 7.07(1H, t, J=7.2Hz), 7.22–7.32(2H, m), 8.36(1H, d, J=8.2Hz), 8.98(1H, s) |

Reference Example 6 ethyl 2-(2,3-dihydro-1H-indol-1-yl)-4-{[4-(trifluoromethoxy)benzyl]oxy}-5-pyrimidinecarboxylate

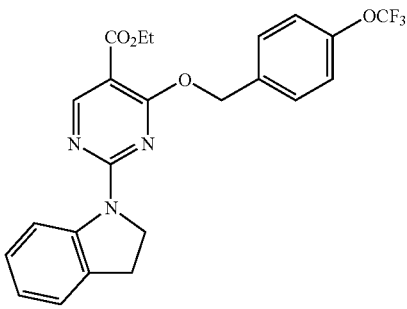

To a solution of ethyl 4-chloro-2-(2,3-dihydro-1H-indol-1-yl)-5-pyrimidinecarboxylate (520 mg, 1.72 mmol) in N,N-dimethylformamide (5 mL) was added potassium carbonate (829 mg, 6 mmol) and 4-(trifluoromethoxy)benzyl alcohol (384 mg, 2 mmol) and the mixture was stirred at 100° C. for 18 h. The reaction mixture was allowed to cool to room temperature and water was added, which was followed by extraction with ethyl acetate. The organic layer was washed with saturated brine and dried over anhydrous sodium sulfate. The solvent was concentrated under reduced pressure and the residue was applied to silica gel column chromatography and eluted with hexane-ethyl acetate (4:1) to give the title compound (420 mg, 53%).

$^1$H-NMR (δ ppm, CDCl$_3$): 1.36 (3H, t, J=7.0 Hz), 3.22 (2H, t, J=8.8 Hz), 4.20–4.40 (4H, m), 5.59 (2H, s), 7.01 (1H, t, J=7.8 Hz), 7.18–7.28 (3H, m), 7.57 (2H, d, J=8.8 Hz), 8.20–8.40 (1H, br), 8.94 (1H, s)

Reference Example 7-1 ethyl 2-(2,3-dihydro-1H-indol-1-yl)-4-[(4-fluorobenzyl)amino]-5-pyrimidinecarboxylate To a solution of ethyl 4-chloro-2-(2,3-dihydro-1H-indol-1-yl)-5-pyrimidinecarboxylate (607 mg, 2.0 mmol) in isopropanol (5 mL) were added sodium carbonate (424 mg, 4 mmol) and 4-fluorobenzylamine (313 mg, 4 mmol) and the mixture was heated under reflux for 18 h. The reaction mixture was allowed to cool to room temperature and water was added. The precipitated crystals were collected by filtration, washed several times with cold water and cold ether and dried to give the title compound (637 mg, 81%).

In the same manner as in Reference Example 7-1, compounds of Reference Examples 7-2 to 7-16 were synthesized.

Reference Example 7-2: ethyl 2-(2,3-dihydro-1H-indol-1-yl)-4 {[4-(trifluoromethyl)benzyl]amino}-5-pyrimidinecarboxylate Reference Example 7-3: ethyl 4-[(1,3-benzodioxol-5-ylmethyl)amino]-2-(2,3-dihydro-1H-indol-1-yl)-5-pyrimidinecarboxylate Reference Example 7-4: ethyl 2-(2,3-dihydro-1H-indol-1-yl)-4-[(3-phenylpropyl)amino]-5-pyrimidinecarboxylate Reference Example 7-5: ethyl 2-(2,3-dihydro-1H-indol-1-yl)-4-[(4-methoxyphenethyl)amino]-5-pyrimidinecarboxylate Reference Example 7-6: ethyl 2-(2,3-dihydro-1H-indol-1-yl)-4-[(2-thienylmethyl)amino]-5-pyrimidinecarboxylate Reference Example 7-7: ethyl 2-(2,3-dihydro-1H-indol-1-yl)-4-[(2-furylmethyl)amino]-5-pyrimidinecarboxylate Reference Example 7-8: ethyl 2-(2,3-dihydro-1H-indol-1-yl)-4-[(3-fluorobenzyl)amino]-5-pyrimidinecarboxylate Reference Example 7-9: ethyl 2-(2,3-dihydro-1H-indol-1-yl)-4-[(4-methoxybenzyl)amino]-5-pyrimidinecarboxylate Reference Example 7-10: ethyl 4-[(2,6-difluorobenzyl)amino]-2-(2,3-dihydro-1H-indol-1-yl)-5-pyrimidinecarboxylate Reference Example 7-11: ethyl 2-(2,3-dihydro-1H-indol-1-yl)-4-[(3,4-dimethoxybenzyl)amino]-5-pyrimidinecarboxylate Reference Example 7-12: ethyl 2-(2,3-dihydro-1H-indol-1-yl)-4-[(4-methylbenzyl)amino]-5-pyrimidinecarboxylate Reference Example 7-13: ethyl 2-(2,3-dihydro-1H-indol-1-yl)-4-[(2-pyridinylmethyl)amino]-5-pyrimidinecarboxylate Reference Example 7-14: ethyl 2-(2,3-dihydro-1H-indol-1-yl)-4-[(4-pyridinylmethyl)amino]-5-pyrimidinecarboxylate Reference Example 7-15: ethyl (RS)-4-[(4-methoxybenzyl)amino]-2-(2-methyl-2,3-dihydro-1H-indol-1-yl)-5-pyrimidinecarboxylate Reference Example 7-16: ethyl (RS)-4-[(1,3-benzodioxol-5-ylmethyl)amino]-2-(2-methyl-2,3-dihydro-1H-indol-1-yl)-5-pyrimidinecarboxylate Respective structural formulas and NMR data are shown in the following Table.

TABLE 23

| Reference Example No. | X | yield (%) | $^1$H-NMR(δ ppm, CDCl$_3$) |
|---|---|---|---|
| 7-1 | ←NH-CH$_2$-C$_6$H$_4$-F (4-fluorobenzylamino) | 81 | 1.37(3H, t, J=7.0Hz), 3.17(2H, d, J=8.0Hz), 4.20–4.35(4H, m), 4.75 (2H, d, J=5.6Hz), 6.90–7.24(5H, m), 7.35(2H, dd, J=4.0, 7.0Hz), 8.21–8.33(1H, br), 8.51–8.62 (1H, br), 8.78(1H, s) |

TABLE 23-continued
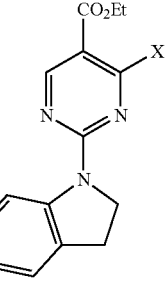
| Reference Example No. | X | yield (%) | ¹H-NMR(δ ppm, CDCl₃) |
|---|---|---|---|
| 7-2 | 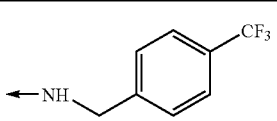 | 99 | 1.38(3H, t, J=7.2Hz), 3.14(2H, t, J=8.4Hz), 4.13–4.36(4H, m), 4.85 (2H, d, J=6.0Hz), 6.93 (1H, t, J=8.0Hz), 7.00–7.14(1H, br), 7.18(1H, d, J=8.0Hz), 7.49(2H, d, J=8.0Hz), 7.60(2H, d, J=8.0Hz), 8.00–8.35 (1H, br), 8.68(1H, br s), 8.79(1H, s) |
| 7-3 | 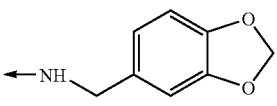 | 85 | 1.36(3H, t, J=7.2Hz), 3.17(2H, t, J=8.4Hz), 4.20–4.35(4H, m), 4.69 (2H, d, J=5.4Hz), 5.94 (2H, s), 6.74–6.98(4H, m), 7.10–7.24(2H, m), 7.32(1H, d, J=8.8Hz), 8.51(1H, br s), 8.77 (1H, s) |
| 7-4 | 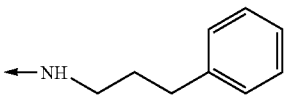 | 100 | 1.37(3H, t, J=7.0Hz), 2.04(2H, quintet, J=7.6Hz), 2.76(2H, t, J=8.0Hz), 3.16(2H, t, J=8.8Hz), 3.59(2H, q, J=6.2Hz), 4.16–4.36(4H, m), 6.96(1H, t, J=7.4Hz), 7.12–7.32(7H, m), 8.25 (1H, br s), 8.40(1H, d, J=8.4Hz), 8.74(1H, s) |
| 7-5 | 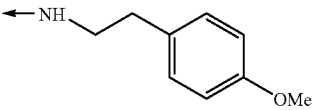 | 91 | 1.35(3H, t, J=7.0Hz), 2.94(2H, t, J=6.8Hz), 3.19(2H, t, J=8.4Hz), 3.69–3.83(5H, m), 4.23–4.34(4H, m), 6.87(2H, d, J=8.4Hz), 6.96(1H, t, J=7.2Hz), 7.14–7.25 (4H, m), 8.28(1H, br s), 8.45(1H, d, J=8.0Hz), 8.74(1H, s) |

TABLE 23-continued
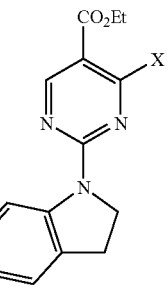
| Reference Example No. | X | yield (%) | $^1$H-NMR($\delta$ ppm, CDCl$_3$) |
|---|---|---|---|
| 7-6 | 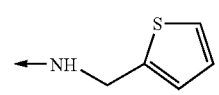 | 100 | 1.36(3H, t, J=7.4Hz), 3.18(2H, t, J=8.4Hz), 4.23–4.34(4H, m), 4.95 (2H, d, J=5.2Hz), 6.91–7.08(3H, m), 7.13–7.23 (2H, m), 8.39(1H, d, J=8.2Hz), 8.48–8.62(1H, br), 8.77(1H, s) |
| 7-7 | 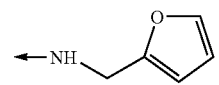 | 92 | 1.36(3H, t, J=6.8Hz), 3.15(2H, t, J=8.4Hz), 4.22–4.35(4H, m), 4.77 (2H, d, J=5.2Hz), 6.25–6.34(2H, m), 6.96(1H, t, J=8.0Hz), 7.16–7.25 (2H, m), 7.39(1H, s), 8.39(1H, d, J=8.2Hz), 8.40–8.55(1H, br s), 8.76(1H, s) |
| 7-8 | 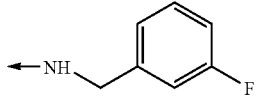 | 92 | 1.38(3H, t, J=6.8Hz), 3.15(2H, t, J=8.4Hz), 4.18–4.37(4H, m), 4.78 (2H, d, J=5.8Hz), 6.88–7.02(2H, m), 7.04–7.23 (3H, m), 7.24–7.36(1H, m), 8.10–8.33(1H, br), 8.62(1H, br s), 8.79 (1H, s) |
| 7-9 | 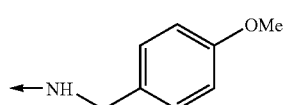 | 95 | 1.36(3H, t, J=7.0Hz), 3.17(2H, t, J=8.4Hz), 3.80(3H, s), 4.22–4.34 (4H, m), 4.72(2H, d, J=5.6Hz), 6.84–6.98(3H, m), 7.09–7.21(2H, m), 7.31(2H, d, J=9.4Hz), 8.33(1H, d, J=8.0Hz), 8.50(1H, br s), 8.77 (1H, s) |
| 7-10 | 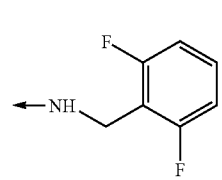 | 100 | 1.35(3H, t, J=7.0Hz), 3.19(2H, t, J=8.4Hz), 4.21–4.37(4H, m), 4.90 (2H, d, J=5.2Hz), 6.85–7.00(3H, m), 7.16–7.29 (3H, m), 8.42–8.57(2H, m), 8.76(1H, s) |

TABLE 23-continued

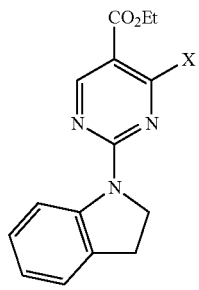

| Reference Example No. | X | yield (%) | $^1$H-NMR($\delta$ ppm, CDCl$_3$) |
|---|---|---|---|
| 7-11 | ←NH—CH₂—C₆H₃(OMe)₂ (3,4-dimethoxybenzyl) | 100 | 1.36(3H, t, J=7.4Hz), 3.16(2H, t, J=8.4Hz), 3.85(3H, s), 3.87(3H, s), 4.22–4.34(4H, m), 4.72(2H, d, J=5.4Hz), 6.80–6.98(4H, m), 7.09–7.22(2H, m), 8.34(1H, d, J=8.0Hz), 8.50(1H, br s), 8.77(1H, s) |
| 7-12 | ←NH—CH₂—C₆H₄—Me (4-methylbenzyl) | 100 | 1.36(3H, t, J=7.4Hz), 2.33(3H, s), 3.16(2H, t, J=8.4Hz), 4.20–4.35(4H, m), 4.75(2H, d, J=5.6Hz), 6.93(1H, t, J=8.0Hz), 7.09–7.31(5H, m), 8.31(1H, d, J=8.0Hz), 8.53(1H, br s), 8.77(1H, s) |
| 7-13 | ←NH—CH₂-(2-pyridyl) | 86 | 1.39(3H, t, J=7.0Hz), 3.14(2H, t, J=8.6Hz), 4.22(2H, t, J=8.8Hz), 4.34(2H, q, J=7.2Hz), 4.92(2H, d, J=5.6Hz), 6.92(1H, t, J=8.4Hz), 7.08–7.23(3H, m), 7.33(1H, d, J=7.6Hz), 7.64(1H, dt, J=1.8, 7.6Hz), 8.17–8.31(1H, br), 8.63(1H, d, J=4.8Hz), 8.79(1H, s), 8.94(1H, br t, J=5.0Hz) |
| 7-14 | ←NH—CH₂-(4-pyridyl) | 72 | 1.39(3H, t, J=6.8Hz), 3.13(2H, t, J=8.6Hz), 4.00–4.40(4H, m), 4.80(2H, d, J=5.8Hz), 6.92(1H, t, J=8.2Hz), 6.97–7.12(1H, br), 7.18(1H, d, J=8.0Hz), 7.29(2H, d, J=6.2Hz), 7.90–8.30(1H, br), 8.55(2H, d, J=4.6Hz), 8.62–8.74(1H, br), 8.80(1H, s) |

TABLE 24

[Structure: pyrimidine with CO2Et group at 5-position, X at 4-position, and N-linked indoline with Me substituent]

| Reference Example No. | X | yield (%) | ¹H-NMR (δ ppm, CDCl₃) |
|---|---|---|---|
| 7-15 | —NH—CH₂—C₆H₄—OMe (para) | 83 | 1.29–1.40(6H, m), 2.66(1H, d, J=15.8Hz), 3.39 (1H, dd, J=9.4, 16.0Hz), 3.80 (3H, s), 4.28(2H, q, J=7.2Hz), 4.70 (2H, d, J=5.6Hz), 4.90–5.08(1H, m), 6.82–7.00 (3H, m), 7.10–7.32(3H, m), 8.27 (1H, d, J=7.8Hz), 8.40(1H, br t, J=7.0Hz), 8.76 (1H, s) |
| 7-16 | —NH—CH₂—(benzo[1,3]dioxole) | 90 | 1.28–1.40(6H, m), 2.66(1H, d, J=16.4Hz), 3.39 (1H, dd, J=9.4, 15.6Hz), 4.29 (2H, q, J=7.0Hz), 4.67(2H, d, J=6.0Hz), 4.94–5.08 (1H, m), 5.94(2H, s), 6.77–6.90(3H, m), 6.95(1H, t, J=7.6Hz), 7.10–7.30 (2H, m), 8.25(1H, d, J=8.2Hz), 8.48 (1H, br t, J=7.0Hz), 8.76(1H, s) |

Reference Example 8-1

5-methoxy-2,3-dihydro-1H-indole

To a solution of 5-methoxyindole (528 mg, 3.6 mmol) in acetic acid (5 mL) was added sodium cyanoborohydride (452 mg, 7.2 mmol) by small portions at room temperature and the mixture was stirred for 18 h in situ. The solvent was evaporated under reduced pressure and the obtained residue was dissolved in ethyl acetate. The organic layer was washed with saturated aqueous sodium hydrogencarbonate solution (×3) and saturated brine, and dried over anhydrous sodium sulfate. The solvent was evaporated under reduced pressure to give almost pure title compound (503 mg, 94%).

In the same manner as in Reference Example 8-1, compounds of Reference Examples 8-2 to 8-9 were synthesized.
Reference Example 8-2: 6,7-dihydro-5H-[1,3]dioxolo[4,5-f]indole
Reference Example 8-3: 5-fluoro-2,3-dihydro-1H-indole
Reference Example 8-4: 5-methyl-2,3-dihydro-1H-indole
Reference Example 8-5: 4-methoxy-2,3-dihydro-1H-indole
Reference Example 8-6: 7-methoxy-2,3-dihydro-1H-indole
Reference Example 8-7: (RS)-3-methyl-2,3-dihydro-1H-indole
Reference Example 8-8: 7-methyl-2,3-dihydro-1H-indole
Reference Example 8-9: 6-(trifluoromethyl)-2,3-dihydro-1H-indole Respective structural formulas and NMR data are shown in the following Table.

TABLE 25

| Reference Example No. | Structural Formula | yield (%) | ¹H-NMR(δ ppm, CDCl₃) |
|---|---|---|---|
| 8-1 | 5-methoxy-2,3-dihydro-1H-indole | 94 | 2.94(2H, t, J=8.0Hz), 3.81(3H, s), 4.30(2H, t, J=8.4Hz), 6.73–6.82 (2H, m), 8.39(1H, br d, J=8.0Hz), 8.81(1H, s) |
| 8-2 | 6,7-dihydro-5H-[1,3]dioxolo[4,5-f]indole | 80 | 2.94(2H, t, J=8.4Hz), 3.56(2H, t, J=8.4Hz), 5.86(2H, s), 6.32(1H, s), 6.65(1H, s) |
| 8-3 | 5-fluoro-2,3-dihydro-1H-indole | 100 | 3.02(2H, t, J=8.4Hz), 3.57(2H, t, J=8.0Hz), 6.55(1H, dd, J=4.8, 8.4Hz), 6.71(1H, dt, J=2.6, 8.8Hz), 6.84(1H, d, J=8.8Hz) |
| 8-4 | 5-methyl-2,3-dihydro-1H-indole | 100 | 2.28(3H, s), 3.04(2H, t, J=8.0Hz), 3.61(2H, t, J=8.0Hz), 6.25(1H, d, J=7.6Hz), 6.90(1H, d, J=8.0Hz), 7.01(1H, s) |
| 8-5 | 4-methoxy-2,3-dihydro-1H-indole | 100 | 2.99(2H, t, J=8.4Hz), 3.58(2H, t, J=8.0Hz), 3.82(3H, s), 6.35(2H, t, J=8.0Hz), 7.02(1H, t, J=7.8Hz) |
| 8-6 | 7-methoxy-2,3-dihydro-1H-indole | 100 | 3.06(2H, t, J=8.2Hz), 3.59(2H, t, J=8.2Hz), 3.82(3H, s), 6.64–6.84 (3H, m) |
| 8-7 | (RS)-3-methyl-2,3-dihydro-1H-indole | 100 | 1.32(3H, d, J=6.8Hz), 3.11(1H, t, J=8.4Hz), 3.37(1H, q, J=7.8Hz), 3.70(1H, t, J=8.4Hz), 6.65(1H, d, J=7.6Hz), 6.74(1H, t, J=7.4Hz), 6.98–7.13(2H, m) |

TABLE 25-continued

| Reference Example No. | Structural Formula | yield (%) | $^1$H-NMR($\delta$ ppm, CDCl$_3$) |
|---|---|---|---|
| 8-8 | Me-indoline | 100 | 2.15(3H, s), 3.06(2H, t, J=8.4Hz), 3.58(2H, t, J=8.4Hz), 6.68(1H, t, J=7.2Hz), 6.87(1H, d, J=7.0Hz), 6.99(1H, d, J=7.6Hz) |
| 8-9 | CF$_3$-indoline | 100 | 3.26(2H, t, J=8.8Hz), 4.14(2H, J=8.6Hz), 7.26 (2H, s), 8.48(1H, s) |

Reference Example 9-1

(RS)-2-hydroxymethylindoline

To a solution of (RS)-indoline-2-carboxylic acid (8.16 g, 50 mmol) in tetrahydrofuran (50 ml) was added under ice-cooling lithium aluminum hydride (5.7 g, 150 mmol) and the mixture was stirred at 60° C. for 18 h. The reaction mixture was stirred under ice-cooling and ethanol and 1N hydrochloric acid were added. The precipitate was filtered off and the mother liquor was washed with saturated brine and dried over anhydrous sodium sulfate. The solvent was evaporated under reduced pressure and the obtained residue was applied to silica gel column chromatography and eluted with ethyl acetate-hexane (1:4-1:1) to give the title compound (4.8 g, 64%).

In the same manner as in Reference Example 9-1, a compound of Reference Example 9-2 was synthesized from (S)-indoline-2-carboxylic acid.

Reference Example 9-2: (S)-2-hydroxymethylindoline

Respective structural formulas and NMR data are shown in the following Table.

TABLE 26

| Reference Example No. | Structural Formula | Yield (%) | $^1$H-NMR ($\delta$ ppm, CDCl$_3$) |
|---|---|---|---|
| 9-1 | indoline-OH (racemic) | 64 | 1.83(1H, dd, J=7.8, 15.8Hz), 3.12(1H, dd, J=9.0, 15.6Hz), 3.58(1H, dd, J=6.2, 10.6Hz), 3.73(1H, dd, J=3.6, 10.6Hz), 3.98–4.15(1H, m), 6.60–6.77(2H, m), 6.95–7.13(2H, m) |
| 9-2 | (S)-indoline-OH | 100 (crude) | |

Reference Example 10

(R)-2-hydroxymethylindoline

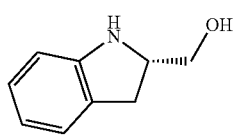

To a solution of (R)-mandelic acid (8.72 g, 58 mmol) in ether (100 ml) was added (RS)-2-hydroxymethylindoline (4.27 g, 28.6 mmol), and the mixture was stirred for a while and concentrated under reduced pressure until the amount of the solvent became 50 ml. The precipitated crystals were collected by filtration and washed with cold ether. This operation was repeated twice to give (R)-2-hydroxymethylindoline (R)-dimandelate (5.3 g). To the thus-obtained mandelate (5.3 g) was added 0.5N aqueous sodium hydroxide solution and the mixture was extracted with ethyl acetate. The organic layer was washed with saturated brine and dried over anhydrous sodium sulfate. The solvent was evaporated under reduced pressure to give the title compound (1.5 g, 72%).

$^1$H-NMR ($\delta$ ppm, CDCl$_3$): 1.83 (1H, dd, J=7.8, 15.8 Hz), 3.12 (1H, dd, J=9.0, 15.6 Hz), 3.58 (1H, dd, J=6.2, 10.6 Hz), 3.73 (1H, dd, J=3.6, 10.6 Hz), 3.98–4.15 (1H, m), 6.60–6.77 (2H, m), 6.95–7.13 (2H, m)

Reference Example 11-1

(R)-1-p-tosyl-2-p-tosyloxymethylindoline

To a solution of (R)-2-hydroxymethylindoline (2.4 g, 16.1 mmol) in pyridine (25 mL) was added under ice-cooling p-toluenesulfonyl chloride (6.9 g, 36.2 mmol) and the mixture was stirred at room temperature for 18 h. The solvent was concentrated under reduced pressure and to the obtained residue were added ethyl acetate and 1N hydrochloric acid. The organic layer was washed with saturated brine and dried over anhydrous sodium sulfate. The solvent was evaporated under reduced pressure and the obtained residue was applied to silica gel column chromatography and eluted with ethyl acetate-hexane (1:4-1:1) to give the title compound (10.5 g, 70%).

In the same manner as in Reference Example 11-1, a compound of Reference Example 11-2 was synthesized from (S)-2-hydroxymethylindoline.

Reference Example 11-2: (S)-1-p-tosyl-2-p-tosyloxymethylindoline

Respective structural formulas and NMR data are shown in the following Table.

TABLE 27

| Reference Example No. | Structural Formula | yield (%) | $^1$H-NMR ($\delta$ ppm, CDCl$_3$) |
|---|---|---|---|
| 11-1 | NTs-indoline-OTs (R) | 79 | 2.35(3H, s), 2.47(3H, s), 2.80–3.09(2H, m), 4.01(1H, dd, J=8.4, 9.6Hz), 4.24–4.44(2H, m), 7.03(2H, d, J=4.4Hz), 7.12–7.28(3H, m), 7.36(2H, d, J=8.4Hz), 7.48(2H, d, J=8.4Hz), 7.58(1H, d, J=7.6Hz), 7.78(2H, d, J=6.6Hz) |
| 11-2 | NTs-indoline-OTs (S) | 70 | |

Reference Example 12-1

(S)-2-methylindoline

To a solution of (R)-1-p-tosyl-2-p-tosyloxymethylindoline (5.8 g, 12.7 mmol) in tetrahydrofuran (50 mL) was added under ice-cooling lithium aluminum hydride (2.4 g, 63.5 mmol) and the mixture was stirred at 60° C. for 3 days. The reaction mixture was stirred under ice-cooling and ethanol and 1N aqueous sodium hydroxide solution were added. The precipitate was filtered off and the mother liquor was washed with saturated brine and dried over anhydrous sodium sulfate. The solvent was evaporated under reduced pressure and the obtained residue was applied to silica gel column chromatography and eluted with ethyl acetate-hexane (1:4) to give the title compound (1.5 g, 90%).

In the same manner as in Reference Example 12-1, a compound of Reference Example 12-2 was synthesized from (S)-1-p-tosyl-2-p-tosyloxymethylindoline.

Reference Example 12-2

(R)-2-methylindoline

Respective structural formulas and NMR data are shown in the following Table. Optical purity was determined by measuring the amide, which is obtained by reacting (S)-2-methylindoline and (R)-2-methylindoline respectively with (S)-α-methoxy-α-trifluoromethylphenylacetyl chloride in pyridine, for $^1$H-NMR and calculating the integral ratio of the 2-position methyl group.

TABLE 28

| Reference Example No. | Structural Formula | yield (%) | Optical purity (ee, %) | $^1$H-NMR (δ ppm, CDCl$_3$) |
|---|---|---|---|---|
| 12-1 | | 90 | 80 | 1.29(3H, d, J=6.2Hz), 2.63(1H, dd, J=7.6, 15.4Hz), 3.14(1H, dd, J=8.4, 15.4Hz), 3.90–4.08 (1H, m), 6.57–6.73 (2H, m), 6.94–7.08 (2H, m) |
| 12-2 | | 89 | >95 | |

Reference Example 13-1

(2,3-dihydrobenzo[b]furan-5-yl)methanol

To a solution of 2,3-dihydrobenzo[b]furan-5-carboxylic acid (1.64 g, 10 mmol) in tetrahydrofuran (10 mL) was added under ice-cooling lithium aluminum hydride (949 mg, 25 mmol) and the mixture was stirred at 60° C. for 1 h. The reaction mixture was stirred under ice-cooling and methanol and 1N hydrochloric acid were added. The precipitate was filtered off and the mother liquor was washed with saturated brine and dried over anhydrous sodium sulfate. The solvent was evaporated under reduced pressure to give an almost pure title compound (1.5 g, 100%).

In the same manner as in Reference Example 13-1, a compound of Reference Example 13-2 was synthesized from 4-isopropoxybenzoic acid.

Reference Example 13-2

4-isopropoxybenzyl alcohol

Respective structural formulas and NMR data are shown in the following Table.

TABLE 29

| Reference Example No. | Structural Formula | yield (%) | $^1$H-NMR (δ ppm, CDCl$_3$) |
|---|---|---|---|
| 13-1 | | 100 | 1.52(1H, br t, J=8.0Hz), 3.21(2H, t, J=8.8Hz), 4.52–4.63(4H, m), 6.76 (1H, d, J=8.0Hz), 7.10(1H, d, J=8.2Hz), 7.22(1H, s) |
| 13-2 | | 100 | 1.33(6H, d, J=5.8Hz), 1.52(1H, br t, J=5.6Hz), 4.55(1H, sevenplet, J=6.0Hz), 4.61(2H, d, J=5.4Hz), 6.87 (2H, d, J=6.6Hz), 7.27(2H, d, J=6.6Hz) |

Reference Example 14-1

(2,3-dihydrobenzo[b]furan-5-yl)methyl chloride

To a solution of (2,3-dihydrobenzo[b]furan-5-yl)methanol (1.5 g, 10 mmol) in dichloromethane (10 mL) were added under ice-cooling triethylamine (1.67 mL, 12 mmol) and methanesulfonyl chloride (0.85 mL, 10 mmol) and the mixture was stirred at room temperature for 1 h. The solvent was evaporated under reduced pressure and the obtained residue was dissolved in ethyl acetate. The organic layer was washed with saturated brine and dried over anhydrous sodium sulfate. The solvent was evaporated under reduced pressure to give an almost pure title compound (1.6 g, 100%).

In the same manner as in Reference Example 14-1, a compound of Reference Example 14-2 was synthesized from 4-isopropoxybenzyl alcohol.

Reference Example 14-2

4-isopropoxybenzyl chloride

Respective structural formulas and NMR data are shown in the following Table.

TABLE 30

| Reference Example No. | Structural Formula | yield (%) | $^1$H-NMR (δ ppm, CDCl$_3$) |
|---|---|---|---|
| 14-1 | | 100 | 3.21(2H, t, J=8.4Hz), 4.50–4.62 (4H, m), 6.75(1H, d, J=8.0Hz), 7.08 (1H, d, J=8.0Hz), 7.23(1H, s) |
| 14-2 | | 100 | 1.33(6H, d, J=5.0Hz), 4.45–4.62 (3H, m), 6.85(2H, d, J=6.6Hz), 7.29 (2H, d, J=6.6Hz) |

Reference Example 15 methyl 3-chloro-4-methoxybenzoate

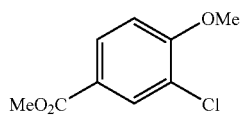

To a solution of 3-chloro-4-hydroxybenzoic acid (3.45 g, 20 mmol) in N,N-dimethylformamide (10 mL) were added potassium carbonate (6.9 g, 50 mmol) and methyl iodide (large excess) and the mixture was stirred at 60° C. for 2 h. Water was added to the reaction mixture and the mixture was extracted with ethyl acetate. The organic layer was washed with saturated brine and dried over anhydrous sodium sulfate. The solvent was evaporated under reduced pressure to give an almost pure title compound (4.0 g, 100%).

$^1$H-NMR (δ ppm, CDCl$_3$): 3.90 (3H, s), 3.97 (3H, s), 6.95 (1H, d, J=8.8 Hz), 7.95 (1H, dd, J=2.2, 8.8 Hz), 8.06 (1H, d, J=2.2 Hz)

Reference Example 16

3-chloro-4-methoxybenzyl alcohol

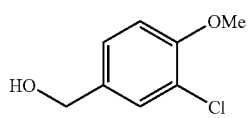

To a solution of methyl 3-chloro-4-methoxybenzoate (1.2 g, 6 mmol) in tetrahydrofuran (10 ml) was added under ice-cooling lithium aluminum hydride (455 mg, 12 mmol) and the mixture was stirred at room temperature for 1 h. The reaction mixture was stirred under ice-cooling and 0.1N hydrochloric acid was added. The mixture was extracted with ethyl acetate. The organic layer was washed with saturated brine and dried over anhydrous sodium sulfate. The solvent was evaporated under reduced pressure to give an almost pure title compound (1.1 g, 100%).

$^1$H-NMR (δ ppm, CDCl$_3$): 1.69 (1H, br t, J=6.0 Hz), 3.91 (3H, s) 4.61 (2H, d, J=5.4 Hz), 6.91 (1H, d, J=8.4 Hz), 7.22 (1H, dd, J=2.2, 8.4 Hz), 7.39 (1H, d, J=2.2 Hz)

Reference Example 17

3-chloro-4-methoxybenzyl chloride

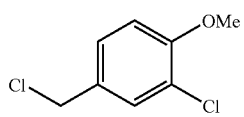

To a solution of 3-chloro-4-methoxybenzyl alcohol (1.1 g, 6 mmol) in tetrahydrofuran (5 mL) were added under ice-cooling triethylamine (1.67 mL, 12 mmol) and methanesulfonyl chloride (0.51 ml, 6 mmol) and the mixture was stirred at room temperature for 18 h. The solvent was evaporated under reduced pressure and the obtained residue was dissolved in ethyl acetate. The organic layer was washed with saturated brine and dried over anhydrous sodium sulfate. The solvent was evaporated under reduced pressure to give an almost pure title compound (700 mg, 61%).

$^1$H-NMR (δ ppm, CDCl$_3$): 3.91 (3H, s), 4.52 (2H, s), 6.90 (1H, d, J=8.4 Hz), 7.25 (1H, dd, J=2.2, 8.8 Hz), 7.42 (1H, d, J=2.2 Hz)

Reference Example 18-1

3-fluoro-4-methoxybenzyl alcohol

To a solution of 3-fluoro-4-methoxybenzaldehyde (1 g, 6.5 mmol) in methanol (15 mL) was added under ice-cooling sodium borohydride (378 mg, 10 mmol) and the mixture was stirred at room temperature for 1 h. The solvent was evaporated under reduced pressure and the obtained residue was dissolved in ethyl acetate. The organic layer was washed with saturated brine and dried over anhydrous sodium sulfate. The solvent was evaporated under reduced pressure to give an almost pure title compound (1 g, 100%).

In the same manner as in Reference Example 18-1, a compound of Reference Example 18-2 was synthesized from 2-fluoro-4-methoxybenzaldehyde.

Reference Example 18-2

2-fluoro-4-methoxybenzyl alcohol

Respective structural formulas and NMR data are shown in the following Table.

TABLE 31

| Reference Example No. | Structural Formula | yield (%) | $^1$H-NMR (δ ppm, CDCl$_3$) |
|---|---|---|---|
| 18-1 | ![structure] | 100 | 1.64(1H, br t, J=5.8Hz), 3.89(3H, s), 4.62(2H, d, J=5.8Hz), 6.94(1H, t, J=8.8Hz), 7.00–7.15(2H, m) |
| 18-2 | ![structure] | 47 | 1.69(1H, t, J=5.6Hz), 3.80(3H, s), 4.67(2H, d, J=5.8Hz), 6.58–6.72(2H, m), 7.30(1H, t, J=8.8Hz) |

Reference Example 19-1

3-fluoro-4-methoxybenzyl chloride

To a solution of 3-fluoro-4-methoxybenzyl alcohol (1 g, 6.5 mmol) in dichloromethane (10 mL) were added under ice-cooling triethylamine (1.8 mL, 13 mmol) and methanesulfonyl chloride (0.60 mL, 7 mmol) and the mixture was stirred at room temperature for 30 min. The solvent was evaporated under reduced pressure and the obtained residue was dissolved in ethyl acetate. The organic layer was washed with saturated brine and dried over anhydrous sodium sulfate. The solvent was evaporated under reduced pressure to give an almost pure title compound (1.1 g, 100%).

In the same manner as in Reference Example 19-1, a compound of Reference Example 17-2 was synthesized from 2-fluoro-4-methoxybenzyl alcohol.

Reference Example 19-2

2-fluoro-4-methoxybenzyl chloride

Respective structural formulas and NMR data are shown in the following Table.

TABLE 32

| Reference Example No. | Structural Formula | yield (%) | $^1$H-NMR (δ ppm, CDCl$_3$) |
|---|---|---|---|
| 19-1 | 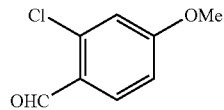 | 100 | 3.89(3H, s), 4.53(2H, s), 6.92(1H, t, J=9.2Hz), 7.00–7.15(2H, m) |
| 19-2 | 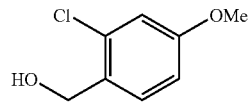 | 82 | 3.80(3H, s), 4.61(2H, s), 6.58–6.71(2H, m), 7.30(1H, t, J=8.4Hz) |

Reference Example 20

2-chloro-4-methoxybenzaldehyde

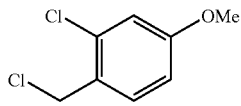

To a solution of 2-chloro-4-hydroxybenzaldehyde (2 g, 12.8 mmol) in N,N-dimethylformamide (25 mL) were added potassium carbonate (3.46 g, 25 mmol) and methyl iodide (large excess) and the mixture was stirred at room temperature for 18 h. Water was added to the reaction mixture and the mixture was extracted with ethyl acetate. The organic layer was washed with saturated brine and dried over anhydrous sodium sulfate. The solvent was evaporated under reduced pressure to give an almost pure title compound (1.55 g, 70%).

$^1$H-NMR (δ ppm, CDCl$_3$): 3.89 (3H, s), 6.84–6.95 (2H, m), 7.90 (1H, d, J=8.8 Hz), 10.33 (1H, s)

Reference Example 21

2-chloro-4-methoxybenzyl alcohol

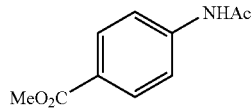

To a solution of 2-chloro-4-methoxybenzaldehyde (1.55 g, 9 mmol) in methanol (20 mL) was added under ice-cooling sodium borohydride (378 mg, 10 mmol) and the mixture was stirred at room temperature for 30 min. The solvent was evaporated under reduced pressure and the obtained residue was dissolved in ethyl acetate. The organic layer was washed with saturated brine and dried over anhydrous sodium sulfate. The solvent was evaporated under reduced pressure to give an almost pure title compound (1.5 g, 97%).

$^1$H-NMR (δ ppm, CDCl$_3$): 1.87 (1H, br t, J=6.2 Hz), 3.80 (3H, s) 4.71 (2H, d, J=5.8 Hz), 6.81 (1H, dd, J=2.6, 8.6 Hz), 6.93 (1H, d, J=2.6 Hz), 7.35 (1H, d, J=8.4 Hz)

Reference Example 22

2-chloro-4-methoxybenzyl chloride

To a solution of 2-chloro-4-methoxybenzyl alcohol (1.5 g, 8.7 mmol) in dichloromethane (10 mL) were added under ice-cooling triethylamine (2.4 mL, 17.4 mmol) and methanesulfonyl chloride (0.74 mL, 9.5 mmol) and the mixture was stirred at room temperature for 2 h. The solvent was evaporated under reduced pressure and the obtained residue was dissolved in ethyl acetate. The organic layer was washed with saturated brine and dried over anhydrous sodium sulfate. The solvent was evaporated under reduced pressure to give an almost pure title compound (1.01 g, 61%).

$^1$H-NMR (δ ppm, CDCl$_3$): 3.80 (3H, s), 4.67 (2H, s), 6.80 (1H, dd, J=2.6, 8.8 Hz), 6.95 (1H, d, J=2.6 Hz), 7.35 (1H, d, J=8.4 Hz)

Reference Example 23 methyl 4-acetamidebenzoate

To a solution of methyl 4-aminobenzoate (7.56 g, 50 mmol) in tetrahydrofuran (50 mL) were added under ice-cooling triethylamine (10 mL, 73 mmol) and acetyl chloride (3.91 mL, 55 mmol) and the mixture was stirred at room temperature for 2 h. The solvent was evaporated under reduced pressure and the obtained residue was dissolved in ethyl acetate. The organic layer was washed with saturated brine and dried over anhydrous sodium sulfate. The solvent was evaporated under reduced pressure and the obtained crystals were recrystallized from dichloromethane-isopropyl ether to give the title compound (6.4 g, 76%).

$^1$H-NMR (δ ppm, CDCl$_3$): 2.21 (3H, s), 3.90 (3H, s), 7.40–7.52 (1H, br), 7.59 (2h, d, J=8.8 Hz), 8.00 (2H, d, J=8.8 Hz)

Reference Example 24

4-hydroxymethylacetanilide

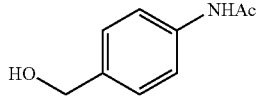

To a solution of methyl 4-acetamidebenzoate (483 mg, 2.5 mmol) in tetrahydrofuran (10 mL) was added under ice-cooling lithium aluminum hydride (190 mg, 5 mmol) and the mixture was stirred at room temperature for 1 h. The reaction mixture was stirred under ice-cooling and 1N hydrochloric acid was added. The mixture was extracted with ethyl acetate, and the organic layer was washed with saturated brine and dried over anhydrous sodium sulfate. The solvent was evaporated under reduced pressure to give an almost pure title compound (230 mg, 56%).

$^1$H-NMR (δ ppm, CDCl$_3$): 2.02 (3H, s), 4.42 (2H, br s), 5.00–5.15 (1H, br), 6.53 (1H, br s), 7.22 (2H, d, J=8.8 Hz), 7.51 (2H, d, J=8.4 Hz)

Reference Example 25

4-chloromethylacetanilide

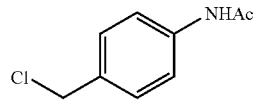

To a solution of 4-hydroxymethylacetanilide (230 mg, 1.4 mmol) in tetrahydrofuran (5 mL) were added under ice-cooling triethylamine (0.39 mL, 2.8 mmol) and methanesulfonyl chloride (0.17 mL, 2 mmol) and the mixture was stirred at room temperature for 2 h. The solvent was evaporated under reduced pressure and the obtained residue was dissolved in ethyl acetate. The organic layer was washed with saturated brine and dried over anhydrous sodium sulfate. The solvent was evaporated under reduced pressure to give an almost pure title compound (200 mg, 78%).

$^1$H-NMR (δ ppm, CDCl$_3$): 2.18 (3H, s), 4.56 (2H, s), 7.28–7.38 (3H, m), 7.50 (2H, d, J=8.6 Hz)

Reference Example 26 ethyl 2-(2,3-dihydro-1H-indol-1-yl)-4-[(RS)-1-phenylethoxy]-5-pyrimidinecarboxylate

Reference Example 27 ethyl 2-[(R)-2-methyl-2,3-dihydro-1H-indol-1-yl]-4-[(RS)-1-phenylethoxy]-5-pyrimidinecarboxylate In the same manner as in Reference Example 3-1 using ethyl 4-hydroxy-2-(2,3-dihydro-1H-indol-1-yl)-5-pyrimidinecarboxylate and ethyl 4-hydroxy-2-[(R)-2-methyl-2,3-dihydro-1H-indol-1-yl]-5-pyrimidinecarboxylate as starting materials, compounds of Reference Examples 26 and 27 were synthesized.

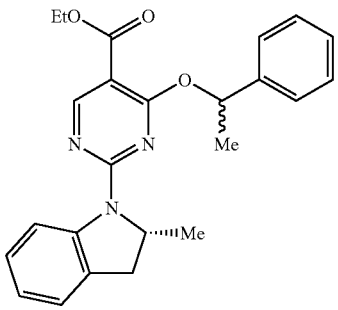

Respective NMR data are shown in the following Table.

| Reference Example No. | yield (%) | $^1$H-NMR(δ ppm, CDCl$_3$) |
|---|---|---|
| 26 | 77 | 1.41(3H, t, J=7.0Hz), 1.73(3H, d, J=8.8Hz), 3.17(2H, t, J=8.8Hz), 4.22 (2H, t, J=8.4Hz), 4.37(2H, q, J=7.2 Hz), 6.34(1H, q, J=6.2Hz), 6.98(1H, t, J=7.2Hz), 7.16–7.40(4H, m), 7.50 (2H, d, J=7.0Hz), 8.00–8.40(1H, br), 8.90(1H, s) |
| 27 | 94 | 1.30–1.52(6H, m), 1.67–1.77(3H, m), 2.67(1H, d, J=15.0Hz), 3.29–3.48(1H, m), 4.37(2H, q, J=7.0Hz), 4.80–5.02 (1H, m), 6.32(1H, t, J=6.0Hz), 7.00 (1H, t, J=7.6Hz), 7.13–7.53(7H, m), 8.00–8.30(1H, m), 8.89(1H, s) |

Example 1-1 t-butyl 2-[({2-(2,3-dihydro-1H-indol-1-yl)-4-[(4-fluorobenzyl)oxy]-5-pyrimidinyl}carbonyl)amino] acetate To a suspension of ethyl 2-(2,3-dihydro-1H-indol-1-yl)-4-[(4-fluorobenzyl)oxy]-5-pyrimidinecarboxylate (5.0 g, 13 mmol) in ethanol (25 mL) were added 10% aqueous sodium hydroxide solution (15 mL) and tetrahydrofuran (15 mL) and the mixture was heated under reflux for 30 min. The reaction mixture was allowed to cool to room temperature and 1N hydrochloric acid was added to adjust the reaction mixture to pH 5. The precipitated crystals were collected by filtration, washed several times with water, dried with heating under vacuum to give 2-(2,3-dihydro-1H-indol-1-yl)-4-[(4-fluorobenzyl)oxy]-5-pyrimidinecarboxylic acid (4.8 g, 100%) as crystals. To the obtained suspension of the obtained carboxylic acid (183 mg, 0.5 mmol), t-butyl glycine (89 mg, 0.53 mmol) and 1-ethyl-3-(3-dimethylaminopropyl)carbodiimide hydrochloride (102 mg, 0.53 mmol) in dichloromethane (2 mL) was added triethylamine (0.21 mL, 1.5 mmol) and the mixture was stirred at room temperature for 18 h. Water and ethyl acetate were added to the reaction mixture and the organic layer was concentrated under reduced pressure. The obtained residue was subjected to silica gel chromatography and eluted with ethyl acetate to give the title compound (210 mg, 88%).

In the same manner as in Example 1-1, compounds of Examples 1-2 to 1-46 were synthesized.

Example 1-2: N-benzyl-2-(2,3-dihydro-1H-indol-1-yl)-4-[(4-fluorobenzyl)oxy]-5-pyrimidinecarboxamide Example 1-3: 2-(2,3-dihydro-1H-indol-1-yl)-4-[(4-fluorobenzyl)oxy]-N-(3-methoxypropyl)-5-pyrimidinecarboxamide Example 1-4: N-(2-cyanoethyl)-2-(2,3-dihydro-1H-indol-1-yl)-4-[(4-fluorobenzyl)oxy]-5-pyrimidinecarboxamide Example 1-5: N-(2-cyanomethyl)-2-(2,3-dihydro-1H-indol-1-yl)-4-[(4-fluorobenzyl)oxy]-5-pyrimidinecarboxamide Example 1-6: 2-(2,3-dihydro-1H-indol-1-yl)-4-[(4-fluorobenzyl)oxy]-N-propyl-5-pyrimidinecarboxamide Example 1-7: N-(2-amino-2-oxoethyl)-2-(2,3-dihydro-1H-indol-1-yl)-4-[(4-fluorobenzyl)oxy]-5-pyrimidinecarboxamide Example 1-8: (RS)-2-(2,3-dihydro-1H-indol-1-yl)-4-[(4-fluorobenzyl)oxy]-N-(2-oxo-3-azepanyl)-5-pyrimidinecarboxamide Example 1-9: (RS)-1-({2-(2,3-dihydro-1H-indol-1-yl)-4-[(4-fluorobenzyl)oxy]-5-pyrimidinyl}carbonyl)-3-piperidinecarboxamide Example 1-10: N-cyclohexyl-2-(2,3-dihydro-1H-indol-1-yl)-4-[(4-fluorobenzyl)oxy]-5-pyrimidinecarboxamide Example 1-11: 2-(2,3-dihydro-1H-indol-1-yl)-N,N-diethyl-4-[(4-fluorobenzyl)oxy]-5-pyrimidinecarboxamide Example 1-12: 2-(2,3-dihydro-1H-indol-1-yl)-4-[(4-fluorobenzyl)oxy]-N-[3-(2-oxo-1-pyrrolizinyl)propyl]-5-pyrimidinecarboxamide Example 1-13: methyl (2S)-1-({2-(2,3-dihydro-1H-indol-1-yl)-4-[(4-fluorobenzyl)oxy]-5-pyrimidinyl}carbonyl)-2-pyrrolidinecarboxylate Example 1-14: 2-(2,3-dihydro-1H-indol-1-yl)-4-[(4-fluorobenzyl)oxy]-N-hexyl-5-pyrimidinecarboxamide Example 1-15: (RS)-2-(2,3-dihydro-1H-indol-1-yl)-4-[(4-fluorobenzyl)oxy]-N-(tetrahydro-2-furanylmethyl)-5-pyrimidinecarboxamide Example 1-16: 2-(2,3-dihydro-1H-indol-1-yl)-N-(2-ethoxyethyl)-4-[(4-fluorobenzyl)oxy]-5-pyrimidinecarboxamide Example 1-17: 2-(2,3-dihydro-1H-indol-1-yl)-4-[(4-fluorobenzyl)oxy]-N,N-bis(2-hydroxyethyl)-5-pyrimidinecarboxamide Example 1-18: {2-(2,3-dihydro-1H-indol-1-yl)-4-[(4-fluorobenzyl)oxy]-5-pyrimidinyl}(4-hydroxy-1-piperidinyl)methanone Example 1-19: {2-(2,3-dihydro-1H-indol-1-yl)-4-[(4-fluorobenzyl)oxy]-5-pyrimidinyl}(1-pyrrolizinyl)methanone Example 1-20: ethyl 1-({2-(2,3-dihydro-1H-indol-1-yl)-4-[(4-fluorobenzyl)oxy]-5-pyrimidinyl}carbonyl)-4-piperidinecarboxylate Example 1-21: N-(1,3-benzodioxol-5-ylmethyl)-2-(2,3-dihydro-1H-indol-1-yl)-4-[(4-fluorobenzyl)oxy]-5-pyrimidinecarboxamide Example 1-22: methyl (2S)-2-[({2-(2,3-dihydro-1H-indol-1-yl)-4-[(4-fluorobenzyl)oxy]-5-pyrimidinyl}carbonyl)amino]-3-hydroxypropanoate Example 1-23: 1-[4-({2-(2,3-dihydro-1H-indol-1-yl)-4-[(4-fluorobenzyl)oxy]-5-pyrimidinyl}carbonyl)-1-piperazinyl]-1-ethanone Example 1-24: 2-(2,3-dihydro-1H-indol-1-yl)-4-[(4-fluorobenzyl)oxy]-N-(2-hydroxyethyl)-5-pyrimidinecarboxamide Example 1-25: N-(2,5-difluorobenzyl)-2-(2,3-dihydro-1H-indol-1-yl)-4-[(4-fluorobenzyl)oxy]-5-pyrimidinecarboxamide Example 1-26: t-butyl 4-({2-(2,3-dihydro-1H-indol-1-yl)-4-[(4-fluorobenzyl)oxy]-5-pyrimidinyl}carbonyl)-1-piperazinecarboxylate Example 1-27: 2-(2,3-dihydro-1H-indol-1-yl)-4-[(4-fluorobenzyl)oxy]-N-[4-(trifluoromethyl)benzyl]-5-pyrimidinecarboxamide Example 1-28: 2-(2,3-dihydro-1H-indol-1-yl)-4-[(4-fluorobenzyl)oxy]-N-(2-thienylmethyl)-5-pyrimidinecarboxamide Example 1-29: 2-(2,3-dihydro-1H-indol-1-yl)-4-[(4-fluorobenzyl)oxy]-N-(2,2,2-trifluoroethyl)-5-pyrimidinecarboxamide Example 1-30: N-[2-(acetylamino)ethyl]-2-(2,3-dihydro-1H-indol-1-yl)-4-[(4-fluorobenzyl)oxy]-5-pyrimidinecarboxamide Example 1-31: ethyl 3-[({2-(2,3-dihydro-1H-indol-1-yl)-4-[(4-fluorobenzyl)oxy]-5-pyrimidinyl}carbonyl)amino]propanoate Example 1-32: 2-(2,3-dihydro-1H-indol-1-yl)-4-[(4-fluorobenzyl)oxy]-N,N-dimethyl-5-pyrimidinecarboxamide Example 1-33: {2-(2,3-dihydro-1H-indol-1-yl)-4-[(4-fluorobenzyl)oxy]-5-pyrimidinyl}[(2S)-2-(hydroxymethyl)-pyrrolizinyl]methanone Example 1-34: ethyl (2S)-2-[({2-(2,3-dihydro-1H-indol-1-yl)-4-[(4-fluorobenzyl)oxy]-5-pyrimidinyl}carbonyl)amino]-4-(methylsulfanyl)butanoate Example 1-35: {2-(2,3-dihydro-1H-indol-1-yl)-4-[(4-fluorobenzyl)oxy]-5-pyrimidinyl}(4-methyl-1-piperazinyl)methanone Example 1-36: 2-(2,3-dihydro-1H-indol-1-yl)-4-[(4-fluorobenzyl)oxy]-N-(3-methoxyphenyl)-5-pyrimidinecarboxamide Example 1-37: 2-(2,3-dihydro-1H-indol-1-yl)-4-[(4-fluorobenzyl)oxy]-N-[2-(4-morpholinyl)ethyl]-5-pyrimidinecarboxamide Example 1-38: ethyl 2-[({2-(2,3-dihydro-1H-indol-1-yl)-4-[(4-fluorobenzyl)oxy]-5-pyrimidinyl}carbonyl)amino]acetate Example 1-39: N-[4-(aminosulfonyl)phenethyl]-2-(2,3-dihydro-1H-indol-1-yl)-4-[(4-fluorobenzyl)oxy]-5-pyrimidinecarboxamide Example 1-40: 2-(2,3-dihydro-1H-indol-1-yl)-4-[(4-fluorobenzyl)oxy]-N-(2-pyridinylmethyl)-5-pyrimidinecarboxamide Example 1-41: 2-(2,3-dihydro-1H-indol-1-yl)-4-[(4-fluorobenzyl)oxy]-N-(3-phenylpropyl)-5-pyrimidinecarboxamide Example 1-42: 2-(2,3-dihydro-1H-indol-1-yl)-4-[(4-fluorobenzyl)oxy]-N-phenethyl-5-pyrimidinecarboxamide Example 1-43: 2-(2,3-dihydro-1H-indol-1-yl)-4-[(4-fluorobenzyl)oxy]-N-(2-furylmethyl)-5-pyrimidinecarboxamide Example 1-44: 2-(2,3-dihydro-1H-indol-1-yl)-4-[(4-fluorobenzyl)oxy]-N-(1-naphthylmethyl)-5-pyrimidinecarboxamide Example 1-45: 2-(2,3-dihydro-1H-indol-1-yl)-N-(3-fluorobenzyl)-4-[(4-fluorobenzyl)oxy]-5-pyrimidinecarboxamide Example 1-46: 2-(2,3-dihydro-1H-indol-1-yl)-N-(2,6-difluorobenzyl)-4-[(4-fluorobenzyl)oxy]-5-pyrimidinecarboxamide Respective structural formulas, MASS spectrum data and NMR data are shown in the following Tables.

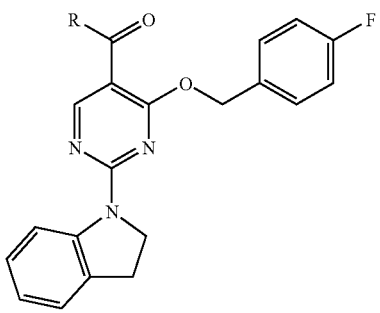

| Example No. | R | yield (%) | MASS spectrum (APCIMS, m/z) $^1$H-NMR($\delta$ ppm, CDCl$_3$) |
|---|---|---|---|
| 1-1 | Me-C(Me)(Me)-O-C(=O)-CH$_2$-NH— | 88 | 479(M+H)$^+$ 1.47(9H, s), 3.22(2H, t, J=8.8Hz), 4.08(2H, d, J=4.6Hz), 4.30(2H, t, J=7.8Hz), 5.63(2H, s), 6.95–7.30(5H, m), 7.53(2H, dd, J=5.8, 8.2Hz) |
| 1-2 | Ph-CH$_2$-NH— | 83 | 455(M+H)$^+$ 3.23(2H, t, J=8.6Hz), 4.32 (2H, t, J=8.0Hz), 4.55(2H, d, J=5.2Hz), 5.49(2H, s), 6.90–7.07(3H, m), 7.10–7.32 (9H, m), 7.50–7.63(1H, br), 8.20–8.45(1H, br), 9.17(1H, s) |
| 1-3 | MeO-CH$_2$CH$_2$CH$_2$-NH— | 91 | 437(M+H)$^+$ 1.77(2H, quintet, J=6.6Hz), 3.17–3.26(5H, m), 3.36 (2H, t, J=5.8Hz), 3.48(2H, q, J=5.4Hz), 4.30(2H, t, J=8.0Hz), 5.59(2H, s), 6.94–7.13(5H, m), 7.19–7.64 (3H, m), 8.20–8.40(1H, br), 9.13(1H, s) |
| 1-4 | NC-CH$_2$CH$_2$-NH— | 96 | 418(M+H)$^+$ |
| 1-5 | NC-CH$_2$-NH— | 82 | 404(M+H)$^+$ |
| 1-6 | Me-CH$_2$CH$_2$-NH— | 82 | 407(M+H)$^+$ 0.79(3H, t, J=7.8Hz), 1.45 (2H, sextet, J=7.0Hz), 3.17–3.38(4H, m), 4.31(2H, t, J=8.8Hz), 5.55(2H, s), 6.95–8.50(8H, m), 8.24–8.43 (1H, br), 9.14(1H, s) |
| 1-7 | H$_2$N-C(=O)-CH$_2$-NH— | 19 | 422(M+H)$^+$ 3.23(2H, t, J=8.4Hz), 4.10 (2H, d, J=5.2Hz), 4.31(2H, t, J=10.8Hz), 5.66(2H, s), 6.00–6.10(1H, br), 6.95–7.28(5H, m), 7.50–7.60(2H, m), 8.09(1H, t, J=8.0Hz), 8.20–8.42(1H, br), 9.07(1H, s) |

-continued
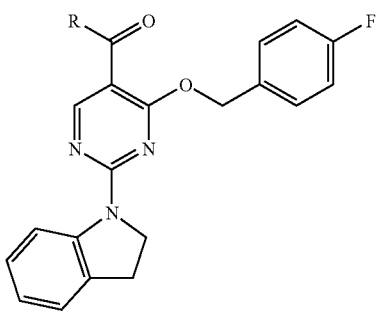
| Example No. | R | yield (%) | MASS spectrum (APCIMS, m/z) ¹H-NMR(δ ppm, CDCl₃) |
|---|---|---|---|
| 1-8 | 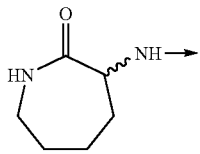 | 28 | 476(M+H)⁺ |
| 1-9 | 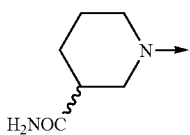 | 23 | 476(M+H)⁺ |
| 1-10 | 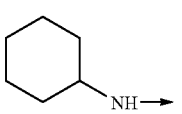 | 35 | 447(M+H)⁺ |
| 1-11 |  | 33 | 421(M+H)⁺ 0.08–1.20(6H, m), 3.10–3.25 (4H, m), 3.40–3.62(2H, m), 4.27(2H, t, J=9.0Hz), 5.48 (2H, s), 6.93–7.13(3H, m), 7.14–7.27(2H, m), 7.41(2H, dd, J=5.2, 10.4Hz), 8.24–8.34(2H, m) |
| 1-12 | 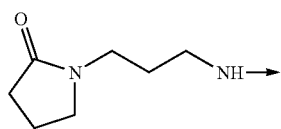 | 49 | 490(M+H)⁺ |
| 1-13 | 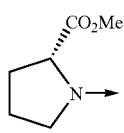 | 76 | 477(M+H)⁺ |
| 1-14 | 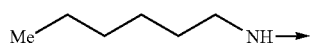 | 42 | 449(M+H)⁺ |
| 1-15 | 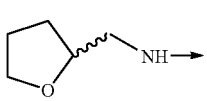 | 33 | 449(M+H)⁺ |

TABLE 34

| | | | |
|---|---|---|---|
| 1-16 | 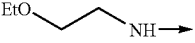 | 54 | 437(M+H)+ 1.10(3H, t, J=7.0Hz), 3.21(2H, t, J=8.4Hz), 3.40(2H, q, J=7.0Hz), 3.47–3.64(4H, m), 4.29 (2H, t, J=8.4Hz), 5.59(2H, s), 6.93–7.30(5H, m), 7.46 (2H, dd, J=5.0, 8.6Hz), 7.70(1H, br s), 8.20–8.45(1H, br), 9.14(1H, s) |
| 1-17 |  | 19 | 453(M+H)+ |
| 1-18 | 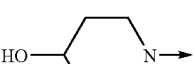 | 27 | 449(M+H)+ |
| 1-19 | 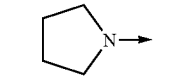 | 43 | 419(M+H)+ |
| 1-20 | 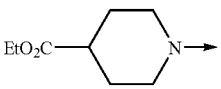 | 56 | 505(M+H)+ 1.25(3H, t, J=7.2Hz), 1.40–2.05 (4H, m), 2.38–2.58 (1H, m), 2.83–3.12 (2H, m), 3.21(2H, t, J=8.0Hz), 3.40–3.75 (1H, m), 4.13(2H, q, J=7.0Hz), 4.27 (2H, t, J=9.2Hz), 4.35–4.60(1H, m), 5.49(2H, s), 6.92–7.14(3H, m), 7.14–7.25(2H, m), 7.41 (2H, dd, J=5.0, 8.8Hz), 8.29(1H, d, J=8.8Hz), 8.35(1H, s) |
| 1-21 | 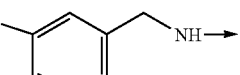 | 28 | 499(M+H)+ |
| 1-22 | 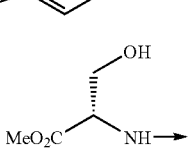 | 55 | 467(M+H)+ |
| 1-23 | 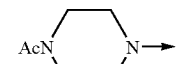 | 58 | 476(M+H)+ 2.09(3H, s), 3.00–3.80(10H, m), 4.28 (2H, t, J=8.8Hz), 5.49(2H, s), 6.92–7.28(5H, m), 7.40 (2H, dd, J=5.2, 9.0Hz), 8.25(1H, d, J=9.0Hz), 8.40(1H, s) |
| 1-24 |  | 27 | 409(M+H)+ |
| 1-25 | 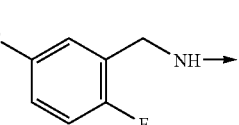 | 48 | 491(M+H)+ |

TABLE 34-continued

| | | | |
|---|---|---|---|
| 1-26 | 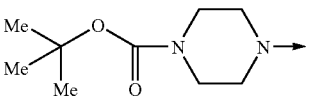 | 40 | 534(M+H)+ |
| 1-27 | 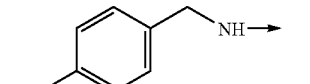 | 54 | 523(M+H)+ 3.23(2H, t, J=8.0Hz), 4.33(2H, t, J=8.2Hz), 4.60(2H, d, J=8.8Hz), 5.52 (2H, s), 6.95–7.07 (4H, m), 7.20–7.35 (5H, m), 7.49–7.68 (3H, m), 8.20–8.45 (1H, br), 9.17(1H, s) |
| 1-28 | 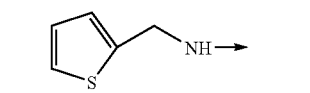 | 47 | 461(M+H)+ |
| 1-29 | 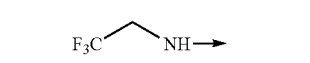 | 40 | 447(M+H)+ |
| 1-30 | 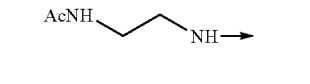 | 94 | 450(M+H)+ 1.94(3H, s), 3.21 (2H, t, J=8.4Hz), 3.35–3.60(4H, m), 4.28(2H, t, J=8.4Hz), 5.62(2H, s), 6.30–6.45(1H, br), 6.95–7.30(5H, m), 7.47(2H, dd, J=3.0, 8.4Hz), 7.60–7.72 (1H, br), 8.15–8.45 (1H, br), 9.10(1H, s) |
| 1-31 | 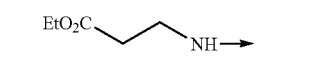 | 71 | 465(M+H)+ |
| 1-32 | Me$_2$N— | 71 | 393(M+H)+ |
| 1-33 | 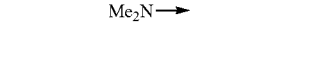 | 35 | 449(M+H)+ |
| 1-34 | 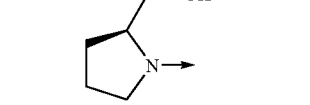 | 69 | 524(M+H)+ |
| 1-35 |  | 25 | 448(M+H)+ |

TABLE 35

| | | | |
|---|---|---|---|
| 1-36 | 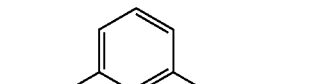 | 17 | 471(M+H)+ |

TABLE 35-continued

| 1-37 | [morpholinoethylamine structure] | 21 | 478(M+H)⁺ |
| 1-38 | EtO₂C-CH₂-NH— | 91 | 451(M+H)⁺ |
| 1-39 | NH₂SO₂-C₆H₄-CH₂CH₂-NH— | 61 | 548(M+H)⁺ |
| 1-40 | 2-pyridylmethyl-NH— | 28 | 456(M+H)⁺ 3.22(2H, t, J=8.8Hz), 4.32(2H, t, J=8.4Hz), 4.73(2H, d, J=4.8Hz), 5.62 (2H, s), 6.97–7.10 (1H, m), 7.12–7.28 (5H, m), 7.49(2H, dd, J=5.6, 8.8Hz), 7.64(1H, dt, J=1.8, 7.8Hz), 8.29–8.50 (3H, m), 9.17(1H, s) |
| 1-41 | Ph-(CH₂)₃-NH— | 52 | 483(M+H)⁺ |
| 1-42 | Ph-CH₂CH₂-NH— | 51 | 469(M+H)⁺ |
| 1-43 | 2-furylmethyl-NH— | 59 | 445(M+H)⁺ |
| 1-44 | 1-naphthylmethyl-NH— | 70 | 505(M+H)⁺ |
| 1-45 | 3-F-C₆H₄-CH₂-NH— | 58 | 473(M+H)⁺ |
| 1-46 | 2,6-diF-C₆H₃-CH₂-NH— | 59 | 491(M+H)⁺ |

Example 2

In the same manner as in Example 1-1 using ethyl 2-(2,3-dihydro-1H-indol-1-yl)-4-[(2-fluorobenzyl)oxy]-5-pyrimidinecarboxylate as a starting material, compounds of Examples 2-1 to 2-5 were synthesized.

Example 2-1: ethyl 2-[({2-(2,3-dihydro-1H-indol-1-yl)-4-[(2-fluorobenzyl)oxy]-5-pyrimidinyl}carbonyl)amino] acetate Example 2-2: (RS)-2-(2,3-dihydro-1H-indol-1-yl)-4-[(2-fluorobenzyl)oxy]-N-(tetrahydro-2-furanylmethyl)-5-pyrimidinecarboxamide Example 2-3: 2-(2,3-dihydro-1H-indol-1-yl)-4-[(2-fluorobenzyl)oxy]-N-[3-(2-oxo-1-pyrrolizinyl)propyl]-5-pyrimidinecarboxamide Example 2-4: N-benzyl-2-(2,3-dihydro-1H-indol-1-yl)-4-[(2-fluorobenzyl)oxy]-5-pyrimidinecarboxamide Example 2-5: t-butyl 2-[({2-(2,3-dihydro-1H-indol-1-yl)-4-[(2-fluorobenzyl)oxy]-5-pyrimidinyl}carbonyl)amino] acetate Respective structural formulas, MASS spectrum data and NMR data are shown in the following Table.

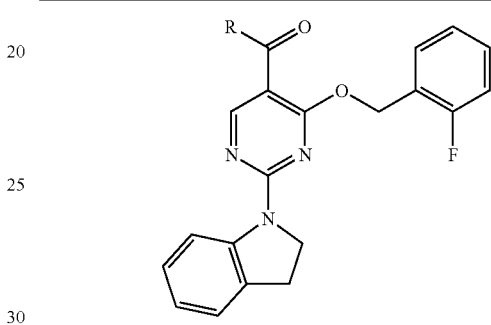

| Example No. | R | yield (%) | MASS spectrum (APCIMS, m/z) ¹H-NMR (δ ppm, CDCl₃) |
|---|---|---|---|
| 2-1 | EtO₂C-CH₂-NH— | 51 | 450(M+H)⁺ 1.28(3H, t, J=7.0Hz), 3.22(2H, t, J=8.4Hz), 4.15–4.35 (6H, m), 5.76(2H, s), 7.00(1H, t, J=7.0Hz), 7.08–7.45 (5H, m), 7.53(1H, t, J=7.0Hz), 7.92(1H, t, J=7.0Hz), 8.20–8.50(1H, br), 9.13 (1H, s) |
| 2-2 | tetrahydrofuran-2-ylmethyl-NH— | 55 | 449(M+H)⁺ |
| 2-3 | 2-oxo-pyrrolidin-1-yl-(CH₂)₃-NH— | 37 | 490(M+H)⁺ |
| 2-4 | PhCH₂-NH— | 22 | 455(M+H)⁺ |
| 2-5 | Me₃C-O-C(O)-CH₂-NH— | 77 | 479(M+H)⁺ |

Example 3

In the same manner as in Example 1-1 using ethyl 2-(2,3-dihydro-1H-indol-1-yl)-4-{[4-(trifluoromethyl)benzyl]oxy}-5-pyrimidinecarboxylate as a starting material, compounds of Examples 3-1 to 3-6 were synthesized.

Example 3-1: (RS)-2-(2,3-dihydro-1H-indol-1-yl)-N-(tetrahydro-2-furanylmethyl)-4-{[4-(trifluoromethyl)benzyl]oxy}-5-pyrimidinecarboxamide Example 3-2: 2-(2,3-dihydro-1H-indol-1-yl)-N-[3-(2-oxo-1-pyrrolizinyl)propyl]-4-{[4-(trifluoromethyl)benzyl]oxy)-5-pyrimidinecarboxamide Example 3-3: N-benzyl-2-(2,3-dihydro-1H-indol-1-yl)-4-{[4-(trifluoromethyl)benzyl]oxy}-5-pyrimidinecarboxamide Example 3-4: t-butyl 2-{[(2-(2,3-dihydro-1H-indol-1-yl)-4-([4-(trifluoromethyl)benzyl]oxy)-5-pyrimidinyl)carbonyl]-amino}acetate Example 3-5: N-(cyanomethyl)-2-(2,3-dihydro-1H-indol-1-yl)-4-{[4-(trifluoromethyl)benzyl]oxy}-5-pyrimidinecarboxamide Example 3-6: ethyl 2-{[(2-(2,3-dihydro-1H-indol-1-yl)-4-{[4-(trifluoromethyl)benzyl]oxy}-5-pyrimidinyl)carbonyl]-amino}acetate Respective structural formulas, MASS spectrum data and NMR data are shown in the following Table.

TABLE 37

| Example No. | R | yield (%) | MASS spectrum (APCIMS, m/z) $^1$H-NMR (δ ppm, CDCl$_3$) |
|---|---|---|---|
| 3-1 | tetrahydrofurfuryl-NH– | 36 | 499(M+H)$^+$ 1.50–2.10(4H, m), 3.15–3.40(3H, m), 3.59–3.80(3H, m), 3.90–4.10(1H, m), 4.29(2H, t, J=8.0Hz), 5.68(2H, s), 7.00(1H, t, J=8.0Hz), 7.15–7.30 (3H, m), 7.60–7.75 (4H, m), 8.20–8.45 (1H, br), 9.16(1H, s) |
| 3-2 | 2-oxo-1-pyrrolidinyl-propyl-NH– | 26 | 540(M+H)$^+$ |
| 3-3 | benzyl-NH– | 28 | 505(M+H)$^+$ |
| 3-4 | Me$_3$C-O-C(O)-CH$_2$-NH– | 57 | 529(M+H)$^+$ |
| 3-5 | NC-CH$_2$-NH– | 57 | 454(M+H)$^+$ |
| 3-6 | EtO$_2$C-CH$_2$-NH– | 20 | 501(M+H)$^+$ |

Example 4

In the same manner as in Example 1-1 using ethyl 2-(2,3-dihydro-1H-indol-1-yl)-4-[(3-methoxybenzyl)oxy]-5-pyrimidinecarboxylate as a starting material, compounds of Examples 4-1 to 4-6 were synthesized.

Example 4-1: t-butyl 2-[({2-(2,3-dihydro-1H-indol-1-yl)-4-[(3-methoxybenzyl)oxy]-5-pyrimidinyl}carbonyl)amino]acetate Example 4-2: (RS)-2-(2,3-dihydro-1H-indol-1-yl)-4-[(3-methoxybenzyl)oxy]-N-(tetrahydro-2-furanylmethyl)-5-pyrimidinecarboxamide Example 4-3: (RS)-2-(2,3-dihydro-1H-indol-1-yl)-4-[(3-methoxybenzyl)oxy]-N-(2-oxo-3-azepanyl)-5-pyrimidinecarboxamide Example 4-4: 2-(2,3-dihydro-1H-indol-1-yl)-4-[(3-methoxybenzyl)oxy]-N-(2-pyridinylmethyl)-5-pyrimidinecarboxamide Example 4-5: 2-(2,3-dihydro-1H-indol-1-yl)-4-[(3-methoxybenzyl)oxy]-N-(3-pyridinylmethyl)-5-pyrimidinecarboxamide Example 4-6: N-(1H-benzimidazol-2-ylmethyl)-2-(2,3-dihydro-1H-indol-1-yl)-4-[(3-methoxybenzyl)oxy]-5-pyrimidinecarboxamide Respective structural formulas and MASS spectrum data are shown in the following Table.

TABLE 38

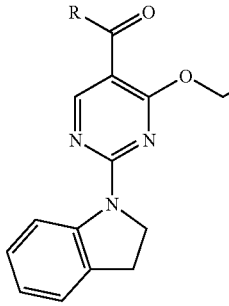

| Example No. | R | yield (%) | MASS spectrum (APCIMS, m/z) |
|---|---|---|---|
| 4-1 | Me₃C-O-C(O)-CH₂-NH— | 75 | 491(M+H)⁺ |
| 4-2 | (tetrahydrofuran-2-yl)CH₂-NH— | 70 | 461(M+H)⁺ |
| 4-3 | (2-oxo-azepan-3-yl)-NH— | 49 | 488(M+H)⁺ |
| 4-4 | (pyridin-2-yl)CH₂-NH— | 69 | 468(M+H)⁺ |
| 4-5 | (pyridin-3-yl)CH₂-NH— | 34 | 467(M+H)⁺ |

TABLE 38-continued

| Example No. | R | yield (%) | MASS spectrum (APCIMS, m/z) |
|---|---|---|---|
| 4-6 | (1H-benzimidazol-2-yl)CH₂-NH— | 40 | 506(M+H)⁺ |

Example 5

In the same manner as in Example 1-1 using ethyl 2-(2,3-dihydro-1H-indol-1-yl)-4-ethoxy-5-pyrimidinecarboxylate as a starting material, compounds of Examples 5-1 to 5-5 were synthesized.

Example 5-1: t-butyl 2-({[2-(2,3-dihydro-1H-indol-1-yl)-4-ethoxy-5-pyrimidinyl]carbonyl}amino)acetate Example 5-2: 2-(2,3-dihydro-1H-indol-1-yl)-4-ethoxy-N-(2-oxo-3-azepanyl)-5-pyrimidinecarboxamide Example 5-3: t-butyl 3-({[2-(2,3-dihydro-1H-indol-1-yl)-4-ethoxy-5-pyrimidinyl]carbonyl}amino)propylcarbamate Example 5-4: 2-(2,3-dihydro-1H-indol-1-yl)-4-ethoxy-N-[(5-methyl-2-pyrazinyl)methyl]-5-pyrimidinecarboxamide Example 5-5: 2-(2,3-dihydro-1H-indol-1-yl)-4-ethoxy-N-(2-pyridinylmethyl)-5-pyrimidinecarboxamide Respective structural formulas, MASS spectrum data and NMR data are shown in the following Table.

TABLE 39

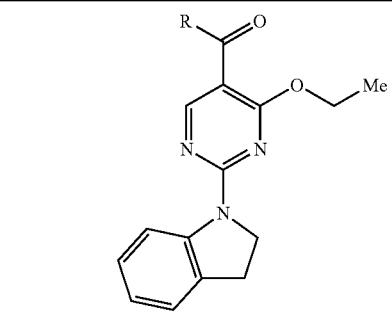

| Example No. | R | yield (%) | MASS spectrum (APCIMS, m/z) ¹H-NMR(δ ppm, CDCl₃) |
|---|---|---|---|
| 5-1 | Me₃C-O-C(O)-CH₂-NH— | 62 | 399(M+H)⁺ 1.50–1.63(12H, m), 3.21 (2H, t, J=8.0Hz), 4.13 (2H, d, J=4.8Hz), 4.31 (2H, t, J=8.0Hz), 4.67 (2H, q, J=6.8Hz), 7.00 (1H, t, J=6.8Hz), 7.20–7.28(2H, m), 8.05(1H, br t, J=7.0Hz), 8.10–8.42 (1H, br), 9.10(1H, s) |

TABLE 39-continued

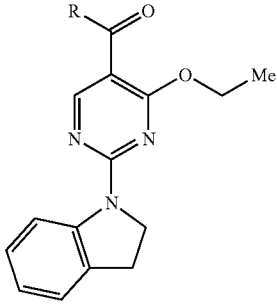

| Example No. | R | yield (%) | MASS spectrum (APCIMS, m/z) $^1$H-NMR(δ ppm, CDCl$_3$) |
|---|---|---|---|
| 5-2 | 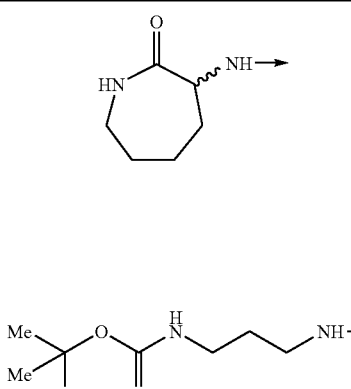 | 75 | 396(M+H)$^+$ |
| 5-3 | 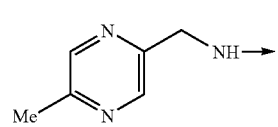 | 68 | 442(M+H)$^+$ |
| 5-4 | 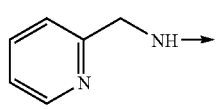 | 78 | 391(M+H)$^+$ |
| 5-5 |  | 87 | 376(M+H)$^+$ |

Example 6

In the same manner as in Example 1-1 using ethyl 4-[(4-bromobenzyl)oxy]-2-(2,3-dihydro-1H-indol-1-yl)-5-pyrimidinecarboxylate as a starting material, compounds of Examples 6-1 to 6-6 were synthesized.

Example 6-1: 2-(2,3-dihydro-1H-indol-1-yl)-N-(2-oxo-3-azepanyl)-5-pyrimidinecarboxamide Example 6-2: t-butyl 3-({[4-[(4-bromobenzyl)oxy]-2-(2,3-dihydro-1H-indol-1-yl)-5-pyrimidinyl]carbonyl}amino)-propylcarbamate Example 6-3: 4-[(4-bromobenzyl)oxy]-2-(2,3-dihydro-1H-indol-1-yl)-N-[(5-methyl-2-pyrazinyl)methyl]-5-pyrimidinecarboxamide Example 6-4: 4-[(4-bromobenzyl)oxy]-2-(2,3-dihydro-1H-indol-1-yl)-N-(2-pyridinylmethyl)-5-pyrimidinecarboxamide Example 6-5: 4-[(4-bromobenzyl)oxy]-2-(2,3-dihydro-1H-indol-1-yl)-N-(3-pyridinylmethyl)-5-pyrimidinecarboxamide Example 6-6: N-(1H-benzimidazol-2-ylmethyl)-4-[(4-bromobenzyl)oxy]-2-(2,3-dihydro-1H-indol-1-yl)-5-pyrimidinecarboxamide Respective structural formulas and MASS spectrum data are shown in the following Table.

TABLE 40

| Example No. | R | yield (%) | MASS spectrum (APCIMS, m/z) |
|---|---|---|---|
| 6-1 | (3-amino-2-oxoazepanyl group) | 34 | 537(M+H)+ |
| 6-2 | (3-(Boc-amino)propylamino group) | 48 | 583(M+H)+ |
| 6-3 | (5-methylpyrazin-2-ylmethylamino group) | 55 | 532(M+H)+ |
| 6-4 | (pyridin-2-ylmethylamino group) | 48 | 517(M+H)+ |
| 6-5 | (pyridin-3-ylmethylamino group) | 67 | 517(M+H)+ |
| 6-6 | (1H-benzimidazol-2-ylmethylamino group) | 92 | 556(M+H)+ |

Example 7

In the same manner as in Example 1-1 using ethyl 2-(2,3-dihydro-1H-indol-1-yl)-4-(2-methoxyethoxy)-5-pyrimidinecarboxylate as a starting material, compounds of Examples 7-1 to 7-3 were synthesized.

Example 7-1: 2-(2,3-dihydro-1H-indol-1-yl)-4-(2-methoxyethoxy)-N-(2-oxo-3-azepanyl)-5-pyrimidinecarboxamide Example 7-2: t-butyl 3-({[2-(2,3-dihydro-1H-indol-1-yl)-4-(2-methoxyethoxy)-5-pyrimidinyl]carbonyl}amino)propylcarbamate Example 7-3: 2-(2,3-dihydro-1H-indol-1-yl)-4-(2-methoxyethoxy)-N-(2-pyridinylmethyl)-5-pyrimidinecarboxamide Respective structural formulas and MASS spectrum data are shown in the following Table.

TABLE 41

[Structure: pyrimidine with R-C(=O)- at 5-position, -O-CH2CH2-OMe at 4-position, and 2,3-dihydroindol-1-yl at 2-position]

| Example No. | R | yield (%) | MASS spectrum (APCIMS, m/z) |
|---|---|---|---|
| 7-1 | [3-amino-2-oxo-azepanyl-NH–] | 66 | 426(M+H)⁺ |
| 7-2 | [Me₃C-O-C(=O)-NH-CH₂CH₂CH₂-NH–] | 50 | 472(M+H)⁺ |
| 7-3 | [(pyridin-2-yl)methyl-NH–] | 57 | 406(M+H)⁺ |

Example 8

In the same manner as in Example 1-1 using ethyl 4-[(4-fluorobenzyl)oxy]-2-(5-fluoro-2,3-dihydro-1H-indol-1-yl)-5-pyrimidinecarboxylate as a starting material, compounds of Examples 8-1 to 8-5 were synthesized.

Example 8-1: t-butyl 2-({[4-[(4-fluorobenzyl)oxy]-2-(5-fluoro-2,3-dihydro-1H-indol-1-yl)-5-pyrimidinyl]carbonyl}amino)acetate Example 8-2: (RS)-4-[(4-fluorobenzyl)oxy]-2-(5-fluoro-2,3-dihydro-1H-indol-1-yl)-N-(tetrahydro-2-furanylmethyl)-5-pyrimidinecarboxamide Example 8-3: 4-[(4-fluorobenzyl)oxy]-2-(5-fluoro-2,3-dihydro-1H-indol-1-yl)-N-(2-oxo-3-azepanyl)-5-pyrimidinecarboxamide Example 8-4: 4-[(4-fluorobenzyl)oxy]-2-(5-fluoro-2,3-dihydro-1H-indol-1-yl)-N-(2-pyridinylmethyl)-5-pyrimidinecarboxamide Example 8-5: 4-[(4-fluorobenzyl)oxy]-2-(5-fluoro-2,3-dihydro-1H-indol-1-yl)-N-(3-pyridinylmethyl)-5-pyrimidinecarboxamide Respective structural formulas and MASS spectrum data are shown in the following Table.

TABLE 42

[Structure: pyrimidine with R-C(=O)- at 5-position, -O-CH2-(4-fluorophenyl) at 4-position, and 5-fluoro-2,3-dihydroindol-1-yl at 2-position]

| Example No. | R | yield (%) | MASS spectrum (APCIMS, m/z) |
|---|---|---|---|
| 8-1 | [Me₃C-O-C(=O)-CH₂-NH–] | 82 | 497(M+H)⁺ |
| 8-2 | [(tetrahydrofuran-2-yl)methyl-NH–] | 53 | 467(M+H)⁺ |

TABLE 42-continued

Structure: pyrimidine with R-C(=O)- at position 5, 4-[(4-fluorobenzyl)oxy], 2-(5-fluoro-2,3-dihydro-1H-indol-1-yl)

| Example No. | R | yield (%) | MASS spectrum (APCIMS, m/z) |
|---|---|---|---|
| 8-3 | 3-amino-2-oxo-azepanyl (HN-C(=O)-CH(NH–)-(CH2)4-) | 76 | 494(M+H)+ |
| 8-4 | 2-pyridinylmethyl-NH– | 76 | 474(M+H)+ |
| 8-5 | 3-pyridinylmethyl-NH– | 67 | 474(M+H)+ |

Example 9

In the same manner as in Example 1-1 using ethyl 2-(5-fluoro-2,3-dihydro-1H-indol-1-yl)-4-[(3-methoxybenzyl)oxy]-5-pyrimidinecarboxylate as a starting material, compounds of Examples 9-1 to 9-5 were synthesized.

Example 9-1: t-butyl 2-[({2-(5-fluoro-2,3-dihydro-1H-indol-1-yl)-4-[(3-methoxybenzyl)oxy]-5-pyrimidinyl}carbonyl)-amino]acetate Example 9-2: (RS)-2-(5-fluoro-2,3-dihydro-1H-indol-1-yl)-4-[(3-methoxybenzyl)oxy]-N-(tetrahydro-2-furanylmethyl)-5-pyrimidinecarboxamide Example 9-3: 2-(5-fluoro-2,3-dihydro-1H-indol-1-yl)-4-[(3-methoxybenzyl)oxy]-N-(2-oxo-3-azepanyl)-5-pyrimidinecarboxamide Example 9-4: 2-(5-fluoro-2,3-dihydro-1H-indol-1-yl)-4-[(3-methoxybenzyl)oxy]-N-(2-pyridinylmethyl)-5-pyrimidinecarboxamide Example 9-5: 2-(5-fluoro-2,3-dihydro-1H-indol-1-yl)-4-[(3-methoxybenzyl)oxy]-N-(3-pyridinylmethyl)-5-pyrimidinecarboxamide Respective structural formulas, MASS spectrum data and NMR data are shown in the following Table.

TABLE 43

Structure: pyrimidine with R-C(=O)- at position 5, 4-[(3-methoxybenzyl)oxy], 2-(5-fluoro-2,3-dihydro-1H-indol-1-yl)

| Example No. | R | yield (%) | MASS spectrum (APCIMS, m/z) / $^1$H-NMR (δ ppm, CDCl$_3$) |
|---|---|---|---|
| 9-1 | Me$_3$C-O-C(=O)-CH$_2$-NH– | 85 | 509(M+H)+ |
| 9-2 | (tetrahydrofuran-2-yl)-CH$_2$-NH– | 55 | 479(M+H)+; 1.50–2.00(4H, m), 3.20(2H, t, J=8.0Hz), 3.30–3.50 (1H, m), 3.60–3.70 (3H, m), 3.83(3H, s), 3.90–4.05(1H, m), 4.33(2H, t, J=8.0Hz), 5.70(2H, d, J=2.2Hz), 6.85–7.12(4H, m), 7.20–7.35(2H, m), 7.65–7.80(1H, br), 8.20–8.40(1H, br), 9.13 (1H, s) |
| 9-3 | 2-oxo-3-azepanyl-NH– | 74 | 506(M+H)+ |
| 9-4 | 2-pyridinylmethyl-NH– | 70 | 486(M+H)+ |
| 9-5 | 3-pyridinylmethyl-NH– | 70 | 486(M+H)+ |

Example 10

In the same manner as in Example 1-1 using ethyl (RS)-4-[(4-fluorobenzyl)oxy]-2-(2-methyl-2,3-dihydro-1H-indol-1-yl)-5-pyrimidinecarboxylate as a starting material, compounds of Examples 10-1 to 10-5 were synthesized.

Example 10-1: t-butyl (RS)-2-({[4-[(4-fluorobenzyl)oxy]-2-(2-methyl-2,3-dihydro-1H-indol-1-yl)-5-pyrimidinyl]carbonyl}-amino)acetate Example 10-2: (RS)-4-[(4-fluorobenzyl)oxy]-2-(2-methyl-2,3-dihydro-1H-indol-1-yl)-N-(tetrahydro-2-furanylmethyl)-5-pyrimidinecarboxamide Example 10-3: (RS)-4-[(4-fluorobenzyl)oxy]-2-(2-methyl-2,3-dihydro-1H-indol-1-yl)-N-(2-oxo-3-azepanyl)-5-pyrimidinecarboxamide Example 10-4: (RS)-4-[(4-fluorobenzyl)oxy]-2-(2-methyl-2,3-dihydro-1H-indol-1-yl)-N-(2-pyridinylmethyl)-5-pyrimidinecarboxamide Example 10-5: (RS)-4-[(4-fluorobenzyl)oxy]-2-(2-methyl-2,3-dihydro-1H-indol-1-yl)-N-(3-pyridinylmethyl)-5-pyrimidinecarboxamide Respective structural formulas and MASS spectrum data are shown in the following Table.

TABLE 44

| Example No. | R | yield (%) | MASS spectrum (APCIMS, m/z) |
|---|---|---|---|
| 10-1 | Me₃C-O-C(=O)-CH₂-NH— | 83 | 493(M+H)⁺ |
| 10-2 | (tetrahydrofuran-2-yl)methyl-NH— | 87 | 463(M+H)⁺ |
| 10-3 | (2-oxo-3-azepanyl)-NH— | 73 | 490(M+H)⁺ |
| 10-4 | (pyridin-2-yl)methyl-NH— | 55 | 470(M+H)⁺ |
| 10-5 | (pyridin-3-yl)methyl-NH— | 39 | 470(M+H)⁺ |

Example 11-4: (RS)-4-[(3-methoxybenzyl)oxy]-2-(2-methyl-2,3-dihydro-1H-indol-1-yl)-N-(2-pyridinylmethyl)-5-pyrimidinecarboxamide Respective structural formulas, MASS spectrum data and NMR data are shown in the following Table.

TABLE 45

| Example No. | R | yield (%) | MASS spectrum (APCIMS, m/z) ¹H-NMR(δ ppm, CDCl₃) |
|---|---|---|---|
| 11-1 | Me₃C-O-C(=O)-CH₂-NH— | 92 | 505(M+H)⁺ |
| 11-2 | (tetrahydrofuran-2-yl)methyl-NH— | 80 | 575(M+H)⁺ |
| 11-3 | (2-oxo-3-azepanyl)-NH— | 59 | 502(M+H)⁺ |
| 11-4 | (pyridin-2-yl)methyl-NH— | 82 | 482(M+H)⁺ 1.35(3H, d, J=6.2Hz), 2.72(1H, d, J=15.6Hz), 3.44(1H, dd, J=9.8, 16.2Hz), 3.73(3H, s), 4.74(2H, d, J=4.6Hz), 4.95–5.10 (1H, m), 5.62(2H, s), 6.83–7.32(8H, m), 7.62(1H, dt, J=2.0, 7.6Hz), 8.24–8.32(2H, m), 8.53(1H, br t, J=7.0Hz), 9.17(1H, s) |

Example 11

In the same manner as in Example 1-1 using ethyl (RS)-4-[(3-methoxybenzyl)oxy]-2-(2-methyl-2,3-dihydro-1H-indol-1-yl)-5-pyrimidinecarboxylate as a starting material, compounds of Examples 11-1 to 11-5 were synthesized.

Example 11-1: t-butyl (RS)-2-({[4-[(3-methoxybenzyl)oxy]-2-(2-methyl-2,3-dihydro-1H-indol-1-yl)-5-pyrimidinyl]carbonyl}-amino)acetate Example 11-2: (RS)-4-[(3-methoxybenzyl)oxy]-2-(2-methyl-2,3-dihydro-1H-indol-1-yl)-N-(tetrahydro-2-furanylmethyl)-5-pyrimidinecarboxamide Example 11-3: (RS)-4-[(3-methoxybenzyl)oxy]-2-(2-methyl-2,3-dihydro-1H-indol-1-yl)-N-(2-oxo-3-azepanyl)-5-pyrimidinecarboxamide Example 12

In the same manner as in Example 1-1 using ethyl 2-(6,7-dihydro-5H-[1,3]dioxolo[4,5-f]indol-5-yl)-4-[(4-fluorobenzyl)-oxy]-5-pyrimidinecarboxylate as a starting material, compounds of Examples 12-1 to 12-6 were synthesized Example 12-1: t-butyl [({2-(6,7-dihydro-5H-[1,3]dioxolo[4,5-f]indol-5-yl)-4-[(4-fluorobenzyl)oxy]-5-pyrimidinyl}carbonyl)-amino]acetate Example 12-2: (RS)-2-(6,7-dihydro-5H-[1,3]dioxolo[4,5-f]indol-5-yl)-4-[(4-fluorobenzyl)oxy]-N-(2-oxo-3-azepanyl)-5-pyrimidinecarboxamide Example 12-3: (RS)-2-(6,7-dihydro-5H-[1,3]dioxolo[4,5-f]indol-5-yl)-4-[(4-fluorobenzyl)oxy]-N-(tetrahydro-2-furanylmethyl)-5-pyrimidinecarboxamide Example 12-4: 2-(6,7-dihydro-5H-[1,3]dioxolo[4,5-f]indol-5-yl)-4-[(4-fluorobenzyl)oxy]-N-(2-pyridinylmethyl)-5-pyrimidinecarboxamide Example 12-5: 2-(6,7-dihydro-5H-[1,3]dioxolo[4,5-f]indol-5-yl)-4-[(4-fluorobenzyl)oxy]-N-(3-pyridinylmethyl)-5-pyrimidinecarboxamide Respective structural formulas and MASS spectrum data are shown in the following Table.

TABLE 46

| Example No. | R | yield (%) | MASS spectrum (APCIMS, m/z) |
|---|---|---|---|
| 12-1 | Me₃C-O-CH₂-C(=O)-NH— (t-butyl acetate group) | 54 | 523(M+H)⁺ |
| 12-2 | 3-amino-2-oxo-azepanyl | 39 | 520(M+H)⁺ |
| 12-3 | tetrahydro-2-furanylmethyl-NH— | 12 | 493(M+H)⁺ |
| 12-4 | 2-pyridinylmethyl-NH— | 40 | 500(M+H)⁺ |
| 12-5 | 3-pyridinylmethyl-NH— | 49 | 500(M+H)⁺ |

Example 13

In the same manner as in Example 1-1 using ethyl 2-(5-bromo-2,3-dihydro-1H-indol-1-yl)-4-[(4-fluorobenzyl)oxy]-5-pyrimidinecarboxylate as a starting material, compounds of Examples 13-1 to 13-5 were synthesized.

Example 13-1: t-butyl 2-[({2-(5-bromo-2,3-dihydro-1H-indol-1-yl)-4-[(4-fluorobenzyl)oxy]-5-pyrimidinyl}carbonyl)-amino]acetate Example 13-2: (RS)-2-(5-bromo-2,3-dihydro-1H-indol-1-yl)-4-[(4-fluorobenzyl)oxy]-N-(tetrahydro-2-furanylmethyl)-5-pyrimidinecarboxamide Example 13-3: (RS)-2-(5-bromo-2,3-dihydro-1H-indol-1-yl)-4-[(4-fluorobenzyl)oxy]-N-(2-oxo-3-azepanyl)-5-pyrimidinecarboxamide Example 13-4: 2-(5-bromo-2,3-dihydro-1H-indol-1-yl)-4-[(4-fluorobenzyl)oxy]-N-(2-pyridinylmethyl)-5-pyrimidinecarboxamide Example 13-5: 2-(5-bromo-2,3-dihydro-1H-indol-1-yl)-4-[(4-fluorobenzyl)oxy]-N-(3-pyridinylmethyl)-5-pyrimidinecarboxamide Respective structural formulas, MASS spectrum data and NMR data are shown in the following Table.

TABLE 47

| Example No. | R | yield (%) | MASS spectrum (APCIMS, m/z) ¹H-NMR(δ ppm, CDCl₃) |
|---|---|---|---|
| 13-1 | Me₃C-O-CH₂-C(=O)-NH— | 62 | 558(M+H)⁺ |
| 13-2 | tetrahydro-2-furanylmethyl-NH— | 44 | 528(M+H)⁺ 1.50–2.60(4H, m), 3.15–3.40(3H, m), 3.62–3.75(3H, m), 3.75–4.02(1H, m), 4.32(2H, t, J=8.4Hz), 5.50(2H, s), 7.12(2H, t, J=8.8Hz), 7.30–7.40 (2H, m), 7.47(2H, dd, J=6.0, 9.0Hz), 7.60–7.75(1H, m), 8.10–8.30(1H, br), 9.14(1H, s) |
| 13-3 | 3-amino-2-oxo-azepanyl | 49 | 555(M+H)⁺ |
| 13-4 | 2-pyridinylmethyl-NH— | 46 | 535(M+H)⁺ |
| 13-5 | 3-pyridinylmethyl-NH— | 62 | 535(M+H)⁺ |

Example 14

In the same manner as in Example 1-1 using ethyl 2-(5-bromo-2,3-dihydro-1H-indol-1-yl)-4-[(3-methoxybenzyl)oxy]-5-pyrimidinecarboxylate as a starting material, compounds of Examples 14-1 to 14-6 were synthesized.

Example 14-1: t-butyl 2-[({2-(5-bromo-2,3-dihydro-1H-indol-1-yl)-4-[(3-methoxybenzyl)oxy]-5-pyrimidinyl}carbonyl)-amino]acetate Example 14-2: (RS)-2-(5-bromo-2,3-dihydro-1H-indol-1-yl)-4-[(3-methoxybenzyl)oxy]-N-(tetrahydro-2-furanylmethyl)-5-pyrimidinecarboxamide Example 14-3: (RS)-2-(5-bromo-2,3-dihydro-1H-indol-1-yl)-4-[(3-methoxybenzyl)oxy]-N-(2-oxo-3-azepanyl)-5-pyrimidinecarboxamide Example 14-4: 2-(5-bromo-2,3-dihydro-1H-indol-1-yl)-N-[2-(dimethylamino)ethyl]-4-[(3-methoxybenzyl)oxy]-5-pyrimidinecarboxamide Example 14-5: 2-(5-bromo-2,3-dihydro-1H-indol-1-yl)-4-[(3-methoxybenzyl)oxy]-N-(2-pyridinylmethyl)-5-pyrimidinecarboxamide Example 14-6: 2-(5-bromo-2,3-dihydro-1H-indol-1-yl)-4-[(3-methoxybenzyl)oxy]-N-(3-pyridinylmethyl)-5-pyrimidinecarboxamide Respective structural formulas, MASS spectrum data and NMR data are shown in the following Table.

Example 15

In the same manner as in Example 1-1 using ethyl 2-(5-bromo-2,3-dihydro-1H-indol-1-yl)-4-ethoxy-5-pyrimidinecarboxylate as a starting material, compounds of Examples 15-1 to 15-4 were synthesized.

Example 15-1: (RS)-2-(5-bromo-2,3-dihydro-1H-indol-1-yl)-4-ethoxy-N-(2-oxo-3-azepanyl)-5-pyrimidinecarboxamide Example 15-2: t-butyl 2-({[2-(5-bromo-2,3-dihydro-1H-indol-1-yl)-4-ethoxy-5-pyrimidinyl]carbonyl}amino)propylcarbamate Example 15-3: N-(1,3-benzodioxol-5-ylmethyl)-2-(5-bromo-2,3-dihydro-1H-indol-1-yl)-4-ethoxy-5-pyrimidinecarboxamide Example 15-4: 2-(5-bromo-2,3-dihydro-1H-indol-1-yl)-4-ethoxy-N-(2-pyridinylmethyl)-5-pyrimidinecarboxamide Respective structural formulas and MASS spectrum data are shown in the following Table.

TABLE 48

| Example No. | R | yield (%) | MASS spectrum (APCIMS, m/z) $^1$H-NMR(δ ppm, CDCl$_3$) |
|---|---|---|---|
| 14-1 | Me$_3$C-O-C(O)-CH$_2$-NH— | 60 | 570(M+H)$^+$ |
| 14-2 | (tetrahydrofuran-2-yl)-CH$_2$-NH— | 50 | 540(M+H)$^+$ |
| 14-3 | (2-oxo-azepan-3-yl)-NH— | 28 | 567(M+H)$^+$<br>1.50–2.26(6H, m), 3.14–3.40(4H, m), 3.79(3H, s), 4.29(2H, t, J=8.8Hz), 4.70–4.80(1H, m), 5.68(2H, s), 5.97(1H, t, J=7.0Hz), 6.82–6.90(1H, m), 7.08–7.14(2H, m), 7.23–7.35(3H, m), 8.00–8.35(1H, br), 8.83(1H, d, J=6.2Hz), 9.09(1H, s) |
| 14-4 | Me$_2$N-CH$_2$CH$_2$-NH— | 33 | 527(M+H)$^+$ |
| 14-5 | (pyridin-2-yl)-CH$_2$-NH— | 50 | 547(M+H)$^+$ |
| 14-6 | (pyridin-3-yl)-CH$_2$-NH— | 64 | 547(M+H)$^+$ |

TABLE 49

| Example No. | R | yield (%) | MASS spectrum (APCIMS, m/z) |
|---|---|---|---|
| 15-1 | (2-oxo-azepan-3-yl)-NH— | 25 | 475(M+H)$^+$ |
| 15-2 | Me$_3$C-O-C(O)-CH$_2$-NH— | 46 | 521(M+H)$^+$ |
| 15-3 | (1,3-benzodioxol-5-yl)-CH$_2$-NH— | 56 | 498(M+H)$^+$ |
| 15-4 | (pyridin-2-yl)-CH$_2$-NH— | 63 | 455(M+H)$^+$ |

Example 16

In the same manner as in Example 1-1 using ethyl 4-[(4-bromobenzyl)oxy]-2-(5-bromo-2,3-dihydro-1H-indol-1-yl)-5-pyrimidinecarboxylate as a starting material, compounds of Examples 16-1 to 16-5 were synthesized.

Example 16-1: (RS)-4-[(4-bromobenzyl)oxy]-2-(5-bromo-2,3-dihydro-1H-indol-1-yl)-N-(2-oxo-3-azepanyl)-5-pyrimidinecarboxamide Example 16-2: t-butyl 3-({[4-[(4-bromobenzyl)oxy]-2-(5-bromo-2,3-dihydro-1H-indol-1-yl)-5-pyrimidinyl]carbonyl}amino)-propylcarbamate Example 16-3: 4-[(4-bromobenzyl)oxy]-2-(5-bromo-2,3-dihydro-1H-indol-1-yl)-N-[(5-methyl-2-pyrazinyl)methyl]-5-pyrimidinecarboxamide Example 16-4: 4-[(4-bromobenzyl)oxy]-2-(5-bromo-2,3-dihydro-1H-indol-1-yl)-N-(2-pyridinylmethyl)-5-pyrimidinecarboxamide Example 16-5: 4-[(4-bromobenzyl)oxy]-2-(5-bromo-2,3-dihydro-1H-indol-1-yl)-N-(3-pyridinylmethyl)-5-pyrimidinecarboxamide Respective structural formulas, MASS spectrum data and NMR data are shown in the following Table.

TABLE 50

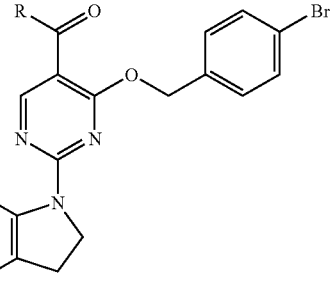

| Example No. | R | yield (%) | MASS spectrum (APCIMS, m/z) $^1$H-NMR (δ ppm, CDCl$_3$) |
|---|---|---|---|
| 16-1 | 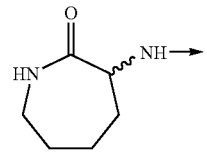 | 29 | 616(M+H)$^+$ 1.40–2.30(6H, m), 3.15–3.40(4H, m), 4.28(2H, t, J=8.4Hz), 4.68–4.80(1H, m), 5.64(2H, s), 5.86–6.00(1H, m), 7.20–7.38(6H, m), 8.00–8.30(1H, br), 8.76(1H, d, J=7.0Hz), 9.09(1H, s) |
| 16-2 | 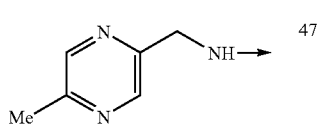 | 45 | 662(M+H)$^+$ |
| 16-3 | 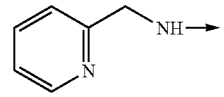 | 47 | 611(M+H)$^+$ |
| 16-4 | 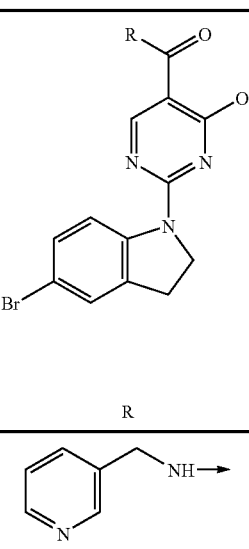 | 42 | 596(M+H)$^+$ |
| 16-5 | 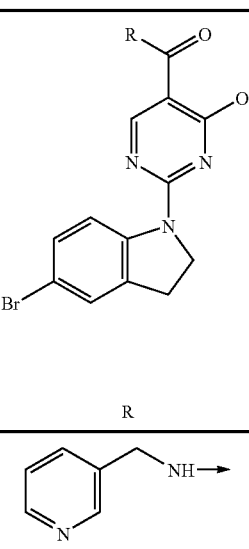 | 58 | 596(M+H)$^+$ |

Example 17

In the same manner as in Example 1-1 using ethyl 4-[(4-fluorobenzyl)oxy]-2-(5-methoxy-2,3-dihydro-1H-indol-1-yl)-5-pyrimidinecarboxylate as a starting material, compounds of Examples 17-1 to 17-4 were synthesized.

Example 17-1: t-butyl 2-({[4-[(4-fluorobenzyl)oxy]-2-(5-methoxy-2,3-dihydro-1H-indol-1-yl)-5-pyrimidinyl]carbonyl}-amino)acetate Example 17-2: (RS)-4-[(4-fluorobenzyl)oxy]-2-(5-methoxy-2,3-dihydro-1H-indol-1-yl)-N-(tetrahydro-2-furanylmethyl)-5-pyrimidinecarboxamide Example 17-3: (RS)-4-[(4-fluorobenzyl)oxy]-2-(5-methoxy-2,3-dihydro-1H-indol-1-yl)-N-(2-oxo-3-azepanyl)-5-pyrimidinecarboxamide Example 17-4: 4-[(4-fluorobenzyl)oxy]-2-(5-methoxy-2,3-dihydro-1H-indol-1-yl)-N-(2-pyridinylmethyl)-5-pyrimidinecarboxamide Respective structural formulas and MASS spectrum data are shown in the following Table.

TABLE 51

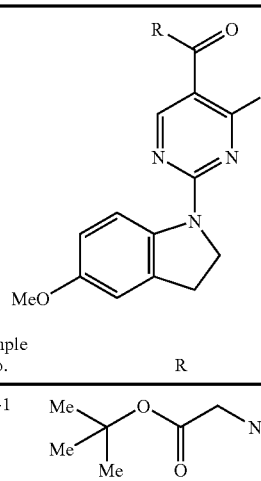

| Example No. | R | yield (%) | MASS spectrum (APCIMS, m/z) |
|---|---|---|---|
| 17-1 | 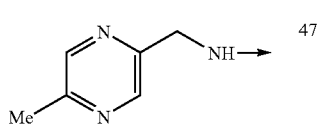 | 60 | 509(M+H)$^+$ |

TABLE 51-continued

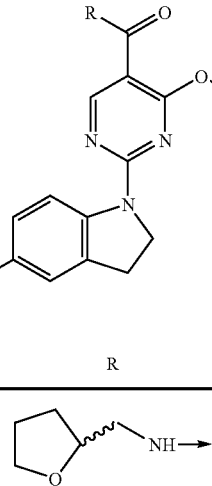

| Example No. | R | yield (%) | MASS spectrum (APCIMS, m/z) |
|---|---|---|---|
| 17-2 | 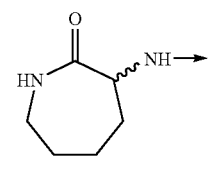 | 66 | 479(M+H)⁺ |
| 17-3 | 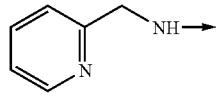 | 67 | 506(M+H)⁺ |
| 17-4 | 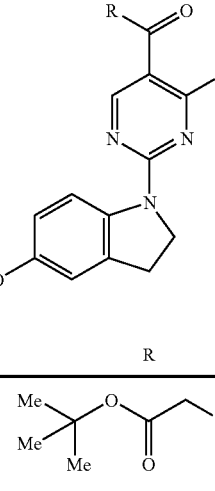 | 83 | 486(M+H)⁺ |

TABLE 52

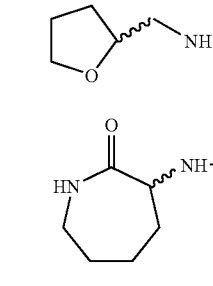

| Example No. | R | yield (%) | MASS spectrum (APCIMS, m/z) |
|---|---|---|---|
| 18-1 | 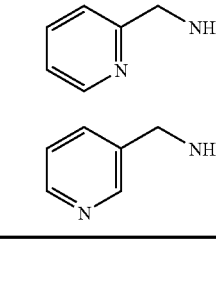 | 96 | 521(M+H)⁺ |
| 18-2 | 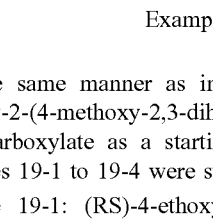 | 56 | 491(M+H)⁺ |
| 18-3 | 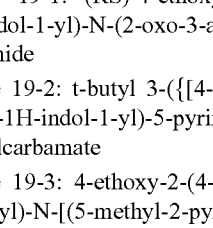 | 84 | 518(M+H)⁺ |
| 18-4 | | 50 | 498(M+H)⁺ |
| 18-5 | | 43 | 498(M+H)⁺ |

Example 18

In the same manner as in Example 1-1 using ethyl 4-[(3-methoxybenzyl)oxy]-2-(5-methoxy-2,3-dihydro-1H-indol-1-yl)-5-pyrimidinecarboxylate as a starting material, compounds of Examples 18-1 to 18-5 were synthesized.

Example 18-1: t-butyl 2-({[4-[(3-methoxybenzyl)oxy]-2-(5-methoxy-2,3-dihydro-1H-indol-1-yl)-5-pyrimidinyl]carbonyl}-amino)acetate Example 18-2: (RS)-4-[(3-methoxybenzyl)oxy]-2-(5-methoxy-2,3-dihydro-1H-indol-1-yl)-N-(tetrahydro-2-furanylmethyl)-5-pyrimidinecarboxamide Example 18-3: (RS)-4-[(3-methoxybenzyl)oxy]-2-(5-methoxy-2,3-dihydro-1H-indol-1-yl)-N-(2-oxo-3-azepanyl)-5-pyrimidinecarboxamide Example 18-4: 4-[(3-methoxybenzyl)oxy]-2-(5-methoxy-2,3-dihydro-1H-indol-1-yl)-N-(2-pyridinylmethyl)-5-pyrimidinecarboxamide Example 18-5: 4-[(3-methoxybenzyl)oxy]-2-(5-methoxy-2,3-dihydro-1H-indol-1-yl)-N-(3-pyridinylmethyl)-5-pyrimidinecarboxamide Respective structural formulas and MASS spectrum data are shown in the following Table.

Example 19

In the same manner as in Example 1-1 using ethyl 4-ethoxy-2-(4-methoxy-2,3-dihydro-1H-indol-1-yl)-5-pyrimidinecarboxylate as a starting material, compounds of Examples 19-1 to 19-4 were synthesized.

Example 19-1: (RS)-4-ethoxy-2-(4-methoxy-2,3-dihydro-1H-indol-1-yl)-N-(2-oxo-3-azepanyl)-5-pyrimidinecarboxamide Example 19-2: t-butyl 3-({[4-ethoxy-2-(4-methoxy-2,3-dihydro-1H-indol-1-yl)-5-pyrimidinyl]carbonyl}amino) propylcarbamate Example 19-3: 4-ethoxy-2-(4-methoxy-2,3-dihydro-1H-indol-1-yl)-N-[(5-methyl-2-pyrazinyl)methyl]-5-pyrimidinecarboxamide Example 19-4: 4-ethoxy-2-(4-methoxy-2,3-dihydro-1H-indol-1-yl)-N-(2-pyridinylmethyl)-5-pyrimidinecarboxamide Respective structural formulas and MASS spectrum data are shown in the following Table.

TABLE 53

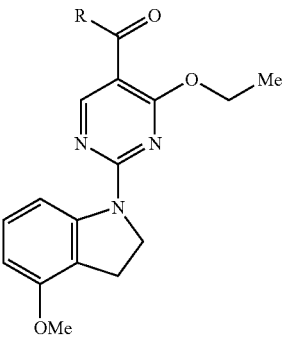

| Example No. | R | yield (%) | MASS spectrum (APCIMS, m/z) |
|---|---|---|---|
| 19-1 | 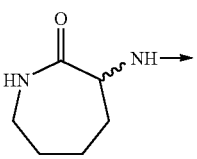 | 75 | 426(M+H)⁺ |
| 19-2 | 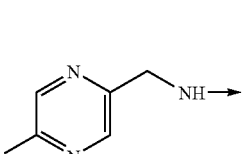 | 69 | 472(M+H)⁺ |
| 19-3 | 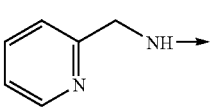 | 88 | 421(M+H)⁺ |
| 19-4 |  | 89 | 406(M+H)⁺ |

Example 20

In the same manner as in Example 1-1 using ethyl 4-[(4-bromobenzyl)oxy]-2-(4-methoxy-2,3-dihydro-1H-indol-1-yl)-5-pyrimidinecarboxylate as a starting material, compounds of Examples 20-1 to 20-4 were synthesized.

Example 20-1: (RS)-4-[(4-bromobenzyl)oxy]-2-(4-methoxy-2,3-dihydro-1H-indol-1-yl)-N-(2-oxo-3-azepanyl)-5-pyrimidinecarboxamide Example 20-2: t-butyl 3-({[4-[(4-bromobenzyl)oxy]-2-(4-methoxy-2,3-dihydro-1H-indol-1-yl)-5-pyrimidinyl]carbonyl}amino)-propylcarbamate Example 20-3: 4-[(4-bromobenzyl)oxy]-2-(4-methoxy-2,3-dihydro-1H-indol-1-yl)-N-[(5-methyl-2-pyrazinyl)methyl]-5-pyrimidinecarboxamide Example 20-4: 4-[(4-bromobenzyl)oxy]-2-(4-methoxy-2,3-dihydro-1H-indol-1-yl)-N-(2-pyridinylmethyl)-5-pyrimidinecarboxamide Respective structural formulas, MASS spectrum data and NMR data are shown in the following Table.

TABLE 54

| Example No. | R | yield (%) | MASS spectrum (APCIMS, m/z) ¹H-NMR (δ ppm, CDCl₃) |
|---|---|---|---|
| 20-1 | (3-amino-2-oxo-azepanyl group) | 44 | 567(M+H)⁺ |
| 20-2 | (Boc-NH-CH₂CH₂CH₂-NH−) | 50 | 613(M+H)⁺ |
| 20-3 | (5-methyl-2-pyrazinyl)methyl-NH− | 68 | 562(M+H)⁺ 2.57(3H, s), 3.13(2H, t, J=8.0Hz), 3.87(3H, s), 4.31(2H, t, J=10.0Hz), 4.71(2H, d, J=4.8Hz), 5.55(2H, s), 6.58(1H, d, J=8.2Hz), 7.21(1H, t, J=8.0Hz), 7.35(2H, d, J=8.6Hz), 7.51(2H, d, J=8.4Hz), 7.80–8.05 (1H, br), 8.08(1H, s), 8.20–8.30(1H, br), 8.46(1H, s), 9.15(1H, s) |
| 20-4 | (2-pyridinyl)methyl-NH− | 66 | 547(M+H)⁺ |

Example 21

In the same manner as in Example 1-1 using ethyl 4-ethoxy-2-(5-methyl-2,3-dihydro-1H-indol-1-yl)-5-pyrimidinecarboxylate as a starting material, compounds of Examples 21-1 to 21-4 were synthesized.

Example 21-1: (RS)-4-ethoxy-2-(5-methyl-2,3-dihydro-1H-indol-1-yl)-N-(2-oxo-3-azepanyl)-5-pyrimidinecarboxamide Example 21-2: t-butyl 3-({[4-ethoxy-2-(5-methyl-2,3-dihydro-1H-indol-1-yl)-5-pyrimidinyl]carbonyl}amino)propylcarbamate Example 21-3: 4-ethoxy-2-(5-methyl-2,3-dihydro-1H-indol-1-yl)-N-[(5-methyl-2-pyrazinyl)methyl]-5-pyrimidinecarboxamide Example 21-4: 4-ethoxy-2-(5-methyl-2,3-dihydro-1H-indol-1-yl)-N-(2-pyridinylmethyl)-5-pyrimidinecarboxamide Respective structural formulas and MASS spectrum data are shown in the following Table.

TABLE 55

| Example No. | R | yield (%) | MASS spectrum (APCIMS, m/z) |
|---|---|---|---|
| 21-1 | (3-amino-2-oxo-azepanyl)-NH— | 68 | 410(M+H)⁺ |
| 21-2 | Boc-NH-CH₂CH₂CH₂-NH— | 57 | 456(M+H)⁺ |
| 21-3 | (5-methylpyrazin-2-yl)methyl-NH— | 85 | 405(M+H)⁺ |
| 21-4 | (pyridin-2-yl)methyl-NH— | 95 | 390(M+H)⁺ |

Example 22

In the same manner as in Example 1-1 using ethyl 4-[(4-bromobenzyl)oxy]-2-(5-methyl-2,3-dihydro-1H-indol-1-yl)-5-pyrimidinecarboxylate as a starting material, compounds of Examples 22-1 to 22-4 were synthesized.

Example 22-1: (RS)-4-[(4-bromobenzyl)oxy]-2-(5-methyl-2,3-dihydro-1H-indol-1-yl)-N-(2-oxo-3-azepanyl)-5-pyrimidinecarboxamide Example 22-2: t-butyl 3-({[4-[(4-bromobenzyl)oxy]-2-(5-methyl-2,3-dihydro-1H-indol-1-yl)-5-pyrimidinyl]carbonyl}amino)-propylcarbamate Example 22-3: 4-[(4-bromobenzyl)oxy]-2-(5-methyl-2,3-dihydro-1H-indol-1-yl)-N-[(5-methyl-2-pyrazinyl)methyl]-5-pyrimidinecarboxamide Example 22-4: 4-[(4-bromobenzyl)oxy]-2-(5-methyl-2,3-dihydro-1H-indol-1-yl)-N-(2-pyridinylmethyl)-5-pyrimidinecarboxamide Respective structural formulas and MASS spectrum data are shown in the following Table.

TABLE 56

[Structure: pyrimidine core with R-C(=O)- at position 5, 4-[(4-bromobenzyl)oxy], and 2-(5-methyl-2,3-dihydro-1H-indol-1-yl)]

| Example No. | R | yield (%) | MASS spectrum (APCIMS, m/z) |
|---|---|---|---|
| 22-1 | 3-amino-hexahydro-2-oxo-1H-azepin-3-yl (NH→ attached) | 33 | 551 (M + H)⁺ |
| 22-2 | t-butyl N-(3-aminopropyl)carbamate (NH→) | 63 | 597 (M + H)⁺ |
| 22-3 | (5-methylpyrazin-2-yl)methyl-NH→ | 75 | 546 (M + H)⁺ |
| 22-4 | (pyridin-2-yl)methyl-NH→ | 69 | 531 (M + H)⁺ |

Example 23

In the same manner as in Example 1-1 using ethyl 2-(2,3-dihydro-1H-indol-1-yl)-4-[(4-methoxybenzyl)oxy]-5-pyrimidinecarboxylate as a starting material, compounds of Examples 23-1 to 23-49 were synthesized.

Example 23-1: ethyl 2-[({2-(2,3-dihydro-1H-indol-1-yl)-4-[(4-methoxybenzyl)oxy]-5-pyrimidinyl}carbonyl)amino]acetate Example 23-2: (RS)-2-(2,3-dihydro-1H-indol-1-yl)-4-[(4-methoxybenzyl)oxy]-N-(tetrahydro-2-furanylmethyl)-5-pyrimidinecarboxamide Example 23-3: 2-(2,3-dihydro-1H-indol-1-yl)-4-[(4-methoxybenzyl)oxy]-N-[3-(2-oxo-1-pyrrolizinyl)propyl]-5-pyrimidinecarboxamide Example 23-4: N-benzyl-2-(2,3-dihydro-1H-indol-1-yl)-4-[(4-methoxybenzyl)oxy]-5-pyrimidinecarboxamide Example 23-5: t-butyl 2-[({2-(2,3-dihydro-1H-indol-1-yl)-4-[(4-methoxybenzyl)oxy]-5-pyrimidinyl}carbonyl)amino]acetate Example 23-6: (RS)-2-(2,3-dihydro-1H-indol-1-yl)-4-[(4-methoxybenzyl)oxy]-N-(2-oxo-3-azepanyl)-5-pyrimidinecarboxamide Example 23-7: 2-(2,3-dihydro-1H-indol-1-yl)-N-(2-ethoxyethyl)-4-[(4-methoxybenzyl)oxy]-5-pyrimidinecarboxamide Example 23-8: 2-(2,3-dihydro-1H-indol-1-yl)-4-[(4-methoxybenzyl)oxy]-N-(4-pyridinylmethyl)-5-pyrimidinecarboxamide Example 23-9: (RS)-2-(2,3-dihydro-1H-indol-1-yl)-4-[(4-methoxybenzyl)oxy]-N-(2-oxo-3-piperidinyl)-5-pyrimidinecarboxamide Example 23-10: 2-(2,3-dihydro-1H-indol-1-yl)-N-[3-(1H-imidazol-1-yl) propyl]-4-[(4-methoxybenzyl)oxy]-5-pyrimidinecarboxamide Example 23-11: 2-(2,3-dihydro-1H-indol-1-yl)-4-[(4-methoxybenzyl)oxy]-N-[(5-methyl-2-pyrazinyl)methyl]-5-pyrimidinecarboxamide Example 23-12: 2-(2,3-dihydro-1H-indol-1-yl)-4-[(4-ethoxybenzyl)oxy]-N-[2-(2-pyridinyl)ethyl]-5-pyrimidinecarboxamide Example 23-13: 2-(2,3-dihydro-1H-indol-1-yl)-N-(6-hydroxyhexyl)-4-[(4-methoxybenzyl)oxy]-5-pyrimidinecarboxamide Example 23-14: N-[2-(diethylamino)ethyl]-2-(2,3-dihydro-1H-indol-1-yl)-4-[(4-methoxybenzyl)oxy]-5-pyrimidinecarboxamide Example 23-15: 2-(2,3-dihydro-1H-indol-1-yl)-4-[(4-methoxybenzyl)oxy]-N-[1-(pyrrolizinyl)ethyl]-5-pyrimidinecarboxamide Example 23-16: 2-(2,3-dihydro-1H-indol-1-yl)-4-[(4-methoxybenzyl)oxy]-N-(2-pyridinylmethyl)-5-pyrimidinecarboxamide Example 23-17: 2-(2,3-dihydro-1H-indol-1-yl)-N-(3-hydroxypropyl)-4-[(4-methoxybenzyl)oxy]-5-pyrimidinecarboxamide Example 23-18: N-cyclopropyl-2-(2,3-dihydro-1H-indol-1-yl)-4-[(4-methoxybenzyl)oxy]-5-pyrimidinecarboxamide Example 23-19: 2-(2,3-dihydro-1H-indol-1-yl)-N-[2-(dimethylamino)ethyl]-4-[(4-methoxybenzyl)oxy]-5-pyrimidinecarboxamide Example 23-20: t-butyl 6-[({2-(2,3-dihydro-1H-indol-1-yl)-4-[(4-methoxybenzyl)oxy]-5-pyrimidinyl}carbonyl)amino]-hexylcarbamate Example 23-21: t-butyl 4-[({2-(2,3-dihydro-1H-indol-1-yl)-4-[(4-methoxybenzyl)oxy]-5-pyrimidinyl}carbonyl)amino]-butylcarbamate Example 23-22: t-butyl 3-[({2-(2,3-dihydro-1H-indol-1-yl)-4-[(4-methoxybenzyl)oxy]-5-pyrimidinyl}carbonyl)amino]-propylcarbamate Example 23-23: t-butyl 2-[({2-(2,3-dihydro-1H-indol-1-yl)-4-[(4-methoxybenzyl)oxy]-5-pyrimidinyl}carbonyl)amino]-ethylcarbamate Example 23-24: N-(1-benzyl-4-piperidinyl)-2-(2,3-dihydro-1H-indol-1-yl)-4-[(4-methoxybenzyl)oxy]-5-pyrimidinecarboxamide Example 23-25: (RS)-2-(2,3-dihydro-1H-indol-1-yl)-4-[(4-methoxybenzyl)oxy]-N-[3-(2-methyl-1-piperidinyl)propyl]-5-pyrimidinecarboxamide Example 23-26: 2-(2,3-dihydro-1H-indol-1-yl)-4-[(4-methoxybenzyl)oxy]-N-[2-(4-morpholinyl)ethyl]-5-pyrimidinecarboxamide Example 23-27: 2-(2,3-dihydro-1H-indol-1-yl)-4-[(4-methoxybenzyl)oxy]-N-[2-(1-piperidinyl)ethyl]-5-pyrimidinecarboxamide Example 23-28: 2-(2,3-dihydro-1H-indol-1-yl)-4-[(4-methoxybenzyl)oxy]-N-(2-propinyl)-5-pyrimidinecarboxamide Example 23-29: 2-(2,3-dihydro-1H-indol-1-yl)-N-[4-(dimethylamino)benzyl]-4-[(4-methoxybenzyl)oxy]-5-pyrimidinecarboxamide Example 23-30: 2-(2,3-dihydro-1H-indol-1-yl)-N-[3-(dimethylamino)propyl]-4-[(4-methoxybenzyl)oxy]-5-pyrimidinecarboxamide Example 23-31: N-(1,3-benzodioxol-5-ylmethyl)-2-(2,3-dihydro-1H-indol-1-yl)-4-[(4-methoxybenzyl)oxy]-5-pyrimidinecarboxamide Example 23-32: 2-(2,3-dihydro-1H-indol-1-yl)-4-[(4-methoxybenzyl)oxy]-N-(2-thienylmethyl)-5-pyrimidinecarboxamide Example 23-33: 2-(2,3-dihydro-1H-indol-1-yl)-4-[(4-methoxybenzyl)oxy]-N-(2,2,2-trifluoroethyl)-5-pyrimidinecarboxamide Example 23-34: 2-(2,3-dihydro-1H-indol-1-yl)-4-[(4-methoxybenzyl)oxy]-N-[3-(methylsulfanyl)propyl]-5-pyrimidinecarboxamide Example 23-35: N-(cyanomethyl)-2-(2,3-dihydro-1H-indol-1-yl)-4-[(4-methoxybenzyl)oxy]-5-pyrimidinecarboxamide Example 23-36: 2-(2,3-dihydro-1H-indol-1-yl)-4-[(4-methoxybenzyl)oxy]-N-(2-methoxyethyl)-5-pyrimidinecarboxamide Example 23-37: N-[4-(diethylamino)phenyl]-2-(2,3-dihydro-1H-indol-1-yl)-4-[(4-methoxybenzyl)oxy]-5-pyrimidinecarboxamide Example 23-38: (RS)-2-(2,3-dihydro-1H-indol-1-yl)-4-[(4-methoxybenzyl)oxy]-N-[2-(1-methyl-2-pyrrolizinyl)ethyl]-5-pyrimidinecarboxamide Example 23-39: 2-(2,3-dihydro-1H-indol-1-yl)-N-(5-isoquinolinyl)-4-[(4-methoxybenzyl)oxy]-5-pyrimidinecarboxamide Example 23-40: 2-(2,3-dihydro-1H-indol-1-yl)-N-(1H-indazol-5-yl)-4-[(4-methoxybenzyl)oxy]-5-pyrimidinecarboxamide Example 23-41: 2-(2,3-dihydro-1H-indol-1-yl)-4-[(4-methoxybenzyl)oxy]-N-[2-(2-oxo-1-imidazolidinyl)ethyl]-5-pyrimidinecarboxamide Example 23-42: N-[2-(acetylamino)ethyl]-2-(2,3-dihydro-1H-indol-1-yl)-4-[(4-methoxybenzyl)oxy]-5-pyrimidinecarboxamide Example 23-43: 2-(2,3-dihydro-1H-indol-1-yl)-4-[(4-methoxybenzyl)oxy]-N-(3-pyridinylmethyl)-5-pyrimidinecarboxamide Example 23-44: 2-(2,3-dihydro-1H-indol-1-yl)-N-(2-hydroxyethyl)-4-[(4-methoxybenzyl)oxy]-5-pyrimidinecarboxamide Example 23-45: N-(1H-benzimidazol-2-ylmethyl)-2-(2,3-dihydro-1H-indol-1-yl)-4-[(4-methoxybenzyl)oxy]-5-pyrimidinecarboxamide Example 23-46: 2-(2,3-dihydro-1H-indol-1-yl)-4-[(4-methoxybenzyl)oxy]-N-[4-(1,2,3-thiadiazol-4-yl)benzyl]-5-pyrimidinecarboxamide Example 23-47: 2-(2,3-dihydro-1H-indol-1-yl)-4-[(4-methoxybenzyl)oxy]-N-[2-(2-thienyl)ethyl]-5-pyrimidinecarboxamide Example 23-48: N-(2-amino-2-oxoethyl)-2-(2,3-dihydro-1H-indol-1-yl)-4-[(4-methoxybenzyl)oxy]-5-pyrimidinecarboxamide Example 23-49: N-(cycloheptyl)-2-(2,3-dihydro-1H-indol-1-yl)-4-[(4-methoxybenzyl)oxy]-5-pyrimidinecarboxamide Respective structural formulas, MASS spectrum data and NMR data are shown in the following Table.

TABLE 57

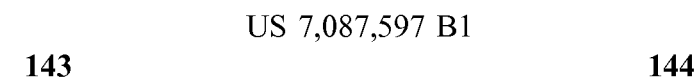

| Example No. | R | yield (%) | MASS spectrum (APCIMS, m/z) ¹H-NMR (δ ppm, CDCl₃) |
|---|---|---|---|
| 23-1 | EtO₂C–CH₂–NH→ | 47 | 463 (M + H)⁺ |
| 23-2 | (tetrahydrofuran-2-yl)–CH₂–NH→ | 48 | 461 (M + H)⁺ |
| 23-3 | (2-oxopyrrolidin-1-yl)–(CH₂)₃–NH→ | 32 | 502 (M + H)⁺ |
| 23-4 | Ph–CH₂–NH→ | 35 | 467 (M + H)⁺ 1.70(2H, quintet, J=6.6 Hz), 2.02(2H, quintet, J=7.6 Hz), 2.38(2H, t, J=8.0 Hz), 3.15–3.40(8H, m), 3.82(3H, s), 4.31 (2H, t, J=8.8 Hz), 5.60(2H, s), 6.87–7.04(3H, m), 7.22 (2H, dd, J=2.6, 6.8 Hz), 7.45(2H, d, J=8.6 Hz), 7.80(1H, br t, J=6.8 Hz), 8.37 (1H, d, J=8.0 Hz), 9.09(1H, s) |
| 23-5 | Me₃C–O–CO–CH₂–NH→ | 69 | 491 (M + H)⁺ |
| 23-6 | (2-oxoazepan-3-yl)–NH→ | 60 | 488 (M + H)⁺ |
| 23-7 | EtO–CH₂CH₂–NH→ | 62 | 449 (M + H)⁺ |
| 23-8 | (pyridin-3-yl)–CH₂–NH→ | 51 | 468 (M + H)⁺ |
| 23-9 | (2-oxopiperidin-3-yl)–NH→ | 28 | 474 (M + H)⁺ |

TABLE 57-continued
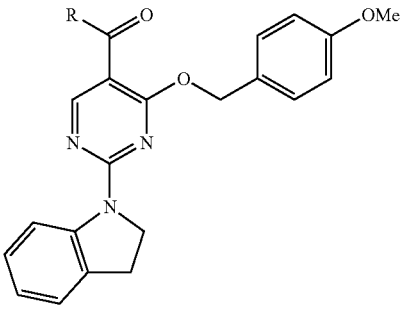
| Example No. | R | yield (%) | MASS spectrum (APCIMS, m/z) $^1$H-NMR (δ ppm, CDCl$_3$) |
|---|---|---|---|
| 23-10 | 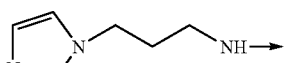 | 55 | 485 (M + H)$^+$ |
| 23-11 | 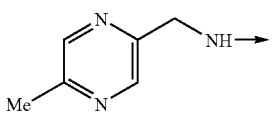 | 92 | 483 (M + H)$^+$ |
| 23-12 | 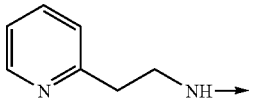 | 65 | 482 (M + H)$^+$ |
| 23-13 | 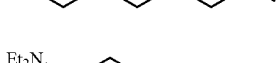 | 84 | 477 (M + H)$^+$ |
| 23-14 | 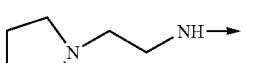 | 28 | 476 (M + H)$^+$ |
| 23-15 | 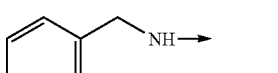 | 47 | 474 (M + H)$^+$ |
| 23-16 | 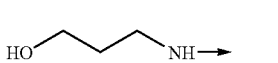 | 86 | 468 (M + H)$^+$ |
| 23-17 |  | 35 | 435 (M + H)$^+$ |
| 23-18 | 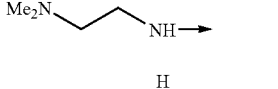 | 63 | 417 (M + H)$^+$ |
| 23-19 |  | 36 | 448 (M + H)$^+$ |
| 23-20 | 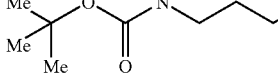 | 87 | 576 (M + H)$^+$ |
| 23-21 |  | 81 | 548 (M + H)$^+$ |

TABLE 57-continued

[Structure: pyrimidine core with R-C(=O)- at 5-position, 4-(4-methoxybenzyloxy), 2-(indolin-1-yl)]

| Example No. | R | yield (%) | MASS spectrum (APCIMS, m/z) ¹H-NMR (δ ppm, CDCl₃) |
|---|---|---|---|
| 23-22 | Me₃C-O-C(=O)-NH-CH₂CH₂CH₂-NH— | 95 | 534 (M + H)⁺ |
| 23-23 | Me₃C-O-C(=O)-NH-CH₂CH₂-NH— | 82 | 520 (M + H)⁺ |
| 23-24 | 1-benzylpiperidin-4-yl-NH— | 81 | 550 (M + H)⁺ |

TABLE 58

| Example No. | R | yield (%) | MASS spectrum (APCIMS, m/z) |
|---|---|---|---|
| 23-25 | (2-methylpiperidin-1-yl)-CH₂CH₂CH₂-NH— | 26 | 516 (M + H)⁺ |
| 23-26 | morpholin-4-yl-CH₂CH₂-NH— | 80 | 490 (M + H)⁺ |
| 23-27 | piperidin-1-yl-CH₂CH₂-NH— | 75 | 488 (M + H)⁺ |
| 23-28 | HC≡C-CH₂-NH— | 57 | 415 (M + H)⁺ |
| 23-29 | 4-(Me₂N)-C₆H₄-CH₂-NH— | 82 | 510 (M + H)⁺ |
| 23-30 | Me₂N-CH₂CH₂CH₂-NH— | 50 | 462 (M + H)⁺ |
| 23-31 | (1,3-benzodioxol-5-yl)-CH₂-NH— | 70 | 511 (M + H)⁺ |

TABLE 58-continued
| 23-32 | 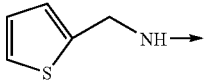 | 70 | 473 (M + H)+ |
|---|---|---|---|
| 23-33 | 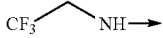 | 72 | 459 (M + H)+ |
| 23-34 |  | 54 | 465 (M + H)+ |
| 23-35 | 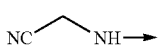 | 73 | 416 (M + H)+ |
| 23-36 |  | 61 | 435 (M + H)+ |
| 23-37 | 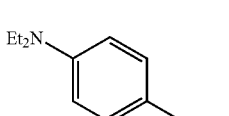 | 38 | 524 (M + H)+ |
| 23-38 |  | 27 | 488 (M + H)+ |
| 23-39 | 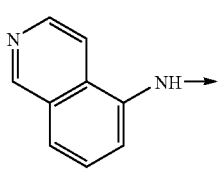 | 37 | 504 (M + H)+ |
| 23-40 | 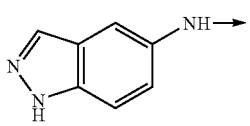 | 37 | 493 (M + H)+ |
| 23-41 | 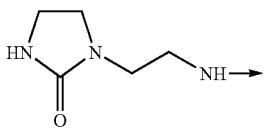 | 38 | 489 (M + H)+ |
| 23-42 | 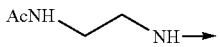 | 71 | 462 (M + H)+<br>1.92(3H, s), 3.22(2H, t, J=<br>8.6 Hz),3.30–3.43(2H, m),<br>3.44–3.53(2H, m), 3.84<br>(3H, s), 4.32(2H, t, J=8.0<br>Hz), 5.56(2H, s), 6.32–<br>6.43(1H, br), 6.90–7.07<br>(3H, s), 7.18–7.26(2H, m),<br>7.42(2H, d, J=8.8 Hz),<br>7.60–7.75(1H, br), 8.25–<br>8.47(1H, br), 9.09(1H, s) |

TABLE 58-continued

| | | | |
|---|---|---|---|
| 23-43 | 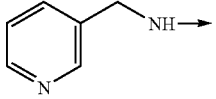 | 42 | 468 (M + H)⁺ |
| 23-44 | 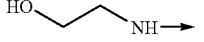 | 50 | 421 (M + H)⁺ |
| 23-45 | 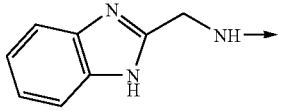 | 61 | 507 (M + H)⁺<br>3.21(2H, t, J=8.4 Hz), 3.81 (3H, s), 4.30(1H, t, J=8.8 Hz), 4.73(2H, d, J=5.8 Hz), 5.54(2H, s), 6.87(2H, d, J=8.4 Hz), 7.01(1H, t, J=8.0 Hz), 7.20–7.40(7H, m), 7.50–7.64(2H, m), 8.14(1H, t, J=7.0 Hz), 8.20–8.50(1H, br), 9.15 (1H, s) |
| 23-46 | 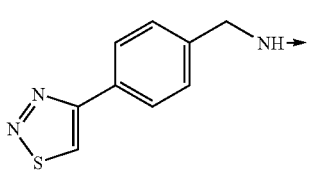 | 80 | 551 (M + H)⁺<br>3.23(2H, t, J=8.4 Hz), 3.72 (3H, s), 4.34(2H, t, J=8.4 Hz), 4.61(2H, d, J=5.0 Hz), 5.49(2H, s), 6.82(2H, d, J=8.8 Hz), 7.01(1H, t, J=7.4 Hz), 7.20–7.32(6H, m), 7.75(1H, t, J=7.0 Hz), 7.93(2H, d, J=8.0 Hz), 8.35–8.43(1H, m), 8.68 (1H, s), 9.17(1H, s) |
| 23-47 | 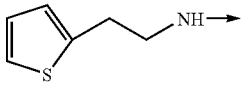 | 90 | 487 (M + H)⁺ |
| 23-48 | 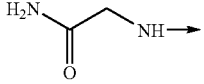 | 60 | 434 (M + H)⁺ |
| 23-49 | 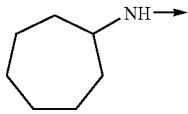 | 73 | 473 (M + H)⁺ |

Example 24

In the same manner as in Example 1-1 using ethyl 4-[(2,6-difluorobenzyl)oxy]-2-(2,3-dihydro-1H-indol-1-yl)-5-pyrimidinecarboxylate as a starting material, compounds of Examples 24-1 to 24-5 were synthesized.

Example 24-1: (RS)-4-[(2,6-difluorobenzyl)oxy]-2-(2,3-dihydro-1H-indol-1-yl)-N-(tetrahydro-2-furanylmethyl)-5-pyrimidinecarboxamide Example 24-2: 4-[(2,6-difluorobenzyl)oxy]-2-(2,3-dihydro-1H-indol-1-yl)-N-[3-(2-oxo-1-pyrrolizinyl)propyl]-5-pyrimidinecarboxamide Example 24-3: N-benzyl-4-[(2,6-difluorobenzyl)oxy]-2-(2,3-dihydro-1H-indol-1-yl)-5-pyrimidinecarboxamide Example 24-4: t-butyl 2-({[4-[(2,6-difluorobenzyl)oxy]-2-(2,3-dihydro-1H-indol-1-yl)-5-pyrimidinyl]carbonyl}amino)acetate Example 24-5: ethyl 2-({[4-[(2,6-difluorobenzyl)oxy]-2-(2,3-dihydro-1H-indol-1-yl)-5-pyrimidinyl]carbonyl}amino)acetate Respective structural formulas and MASS spectrum data are shown in the following Table.

TABLE 59

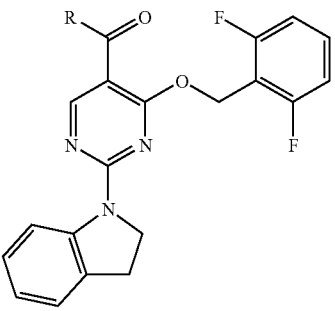

| Example No. | R | yield (%) | MASS spectrum (APCIMS, m/z) |
|---|---|---|---|
| 24-1 | (tetrahydrofuran-2-yl)methyl-NH— | 31 | 467 (M + H)⁺ |
| 24-2 | 3-(2-oxopyrrolidin-1-yl)propyl-NH— | 28 | 508 (M + H)⁺ |
| 24-3 | benzyl-NH— | 49 | 473 (M + H)⁺ |
| 24-4 | Me₃C-O-C(=O)-CH₂-NH— | 83 | 497 (M + H)⁺ |
| 24-5 | EtO₂C-CH₂-NH— | 60 | 469 (M + H)⁺ |

Example 25

In the same manner as in Example 1-1 using ethyl 4-[(4-chlorobenzyl)oxy]-2-(2,3-dihydro-1H-indol-1-yl)-5-pyrimidinecarboxylate as a starting material, compounds of Examples 25-1 to 25-7 were synthesized.

Example 25-1: 4-[(4-chlorobenzyl)oxy]-2-(2,3-dihydro-1H-indol-1-yl)-N-(2-ethoxyethyl)-5-pyrimidinecarboxamide Example 25-2: 4-[(4-chlorobenzyl)oxy]-N-(cyanomethyl)-2-(2,3-dihydro-1H-indol-1-yl)-5-pyrimidinecarboxamide Example 25-3: ethyl 2-({[4-[(4-chlorobenzyl)oxy]-2-(2,3-dihydro-1H-indol-1-yl)-5-pyrimidinyl]carbonyl}amino) acetate Example 25-4: (RS)-4-[(4-chlorobenzyl)oxy]-2-(2,3-dihydro-1H-indol-1-yl)-N-(tetrahydro-2-furanylmethyl)-5-pyrimidinecarboxamide Example 25-5: 4-[(4-chlorobenzyl)oxy]-2-(2,3-dihydro-1H-indol-1-yl)-N-[3-(2-oxo-1-pyrrolizinyl)propyl]-5-pyrimidinecarboxamide Example 25-6: N-benzyl-4-[(4-chlorobenzyl)oxy]-2-(2,3-dihydro-1H-indol-1-yl)-5-pyrimidinecarboxamide Example 25-7: t-butyl 2-({[4-[(4-chlorobenzyl)oxy]-2-(2,3-dihydro-1H-indol-1-yl)-5-pyrimidinyl]carbonyl}amino) acetate Respective structural formulas, MASS spectrum data and NMR data are shown in the following Table.

TABLE 60

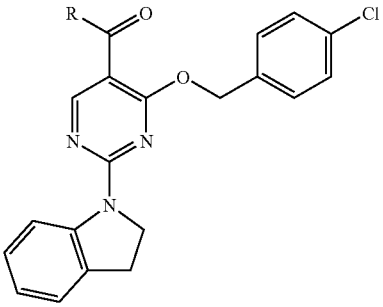

| Example No. | R | yield (%) | MASS spectrum (APCIMS, m/z) ¹H-NMR (δ ppm, CDCl₃) |
|---|---|---|---|
| 25-1 | 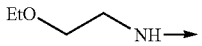 | 70 | 453 (M + H)⁺ 1.09(3H, t, J=7.0 Hz), 3.22(2H, t, J=8.4 Hz), 3.30–3.65(6H, m), 4.29 (2H, t, J=8.8 Hz), 5.60 (2H, s), 6.99(1H, t, J=7.2 Hz), 7.15–7.48 (6H, m), 7.70(1H, br s), 8.20–8.50(1H, br), 9.15(1H, s) |
| 25-2 | 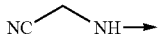 | 18 | 420 (M + H)⁺ |
| 25-3 | 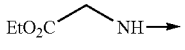 | 45 | 467 (M + H)⁺ |
| 25-4 |  | 39 | 465 (M + H)⁺ |
| 25-5 | 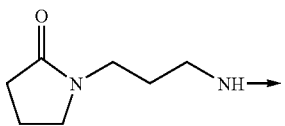 | 42 | 506 (M + H)⁺ |
| 25-6 | 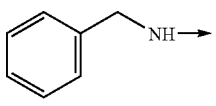 | 65 | 471 (M + H)⁺ |
| 25-7 | 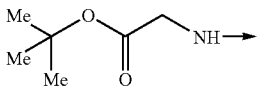 | 20 | 495 (M + H)⁺ |

Example 26

In the same manner as in Example 1-1 using ethyl 2-(2,3-dihydro-1H-indol-1-yl)-4-[(3,4-dimethylbenzyl) oxy]-5-pyrimidinecarboxylate as a starting material, compounds of Examples 26-1 to 26-5 were synthesized.

Example 26-1: t-butyl 2-[({2-(2,3-dihydro-1H-indol-1-yl)-4-[(3,4-dimethylbenzyl)oxy]-5-pyrimidinyl}carbonyl) amino]acetate Example 26-2: N-benzyl-2-(2,3-dihydro-1H-indol-1-yl)-4-[(3,4-dimethylbenzyl)oxy]-5-pyrimidinecarboxamide Example 26-3: (RS)-2-(2,3-dihydro-1H-indol-1-yl)-4-[(3,4-dimethylbenzyl)oxy]-N-(2-oxo-3-azepanyl)-5-pyrimidinecarboxamide Example 26-4: ethyl 2-[({2-(2,3-dihydro-1H-indol-1-yl)-4-[(3,4-dimethylbenzyl)oxy]-5-pyrimidinyl}carbonyl) amino]acetate Example 26-5: (RS)-2-(2,3-dihydro-1H-indol-1-yl)-4-[(3,4-dimethylbenzyl)oxy]-N-(2-oxo-3-piperidinyl)-5-pyrimidinecarboxamide Respective structural formulas and MASS spectrum data are shown in the following Table.

TABLE 61

| Example No. | R | yield (%) | MASS spectrum (APCIMS, m/z) |
|---|---|---|---|
| 26-1 | Me₂C(Me)-O-CH₂-C(O)-NH— (t-butyl ester glycine) | 51 | 489 (M + H)⁺ |
| 26-2 | benzyl-NH— | 30 | 465 (M + H)⁺ |
| 26-3 | (2-oxo-3-azepanyl)-NH— | 25 | 486 (M + H)⁺ |
| 26-4 | EtO₂C-CH₂-NH— | 65 | 461 (M + H)⁺ |
| 26-5 | (2-oxo-3-piperidinyl)-NH— | 37 | 472 (M + H)⁺ |

Example 27

In the same manner as in Example 1-1 using ethyl 4-(1,3-benzodioxol-5-ylmethoxy)-2-(2,3-dihydro-1H-indol-1-yl)-5-pyrimidinecarboxylate as a starting material, compounds of Examples 27-1 to 27-6 were synthesized.

Example 27-1: (RS)-4-(1,3-benzodioxol-5-ylmethoxy)-2-(2,3-dihydro-1H-indol-1-yl)-N-(2-oxo-3-azepanyl)-5-pyrimidinecarboxamide Example 27-2: (RS)-4-(1,3-benzodioxol-5-ylmethoxy)-2-(2,3-dihydro-1H-indol-1-yl)-N-(2-oxo-3-piperidinyl)-5-pyrimidinecarboxamide Example 27-3: t-butyl 2-({[4-(1,3-benzodioxol-5-ylmethoxy)-2-(2,3-dihydro-1H-indol-1-yl)-5-pyrimidinyl]carbonyl}-amino)acetate Example 27-4: 4-(1,3-benzodioxol-5-ylmethoxy)-2-(2,3-dihydro-1H-indol-1-yl)-N-(2-pyridinylmethyl)-5-pyrimidinecarboxamide Example 27-5: 4-(1,3-benzodioxol-5-ylmethoxy)-2-(2,3-dihydro-1H-indol-1-yl)-N-(3-pyridinylmethyl)-5-pyrimidinecarboxamide Respective structural formulas and MASS spectrum data are shown in the following Table.

TABLE 62

| Example No. | R | yield (%) | MASS spectrum (APCIMS, m/z) |
|---|---|---|---|
| 27-1 | (2-oxo-3-azepanyl)-NH— | 52 | 502 (M + H)⁺ |
| 27-2 | (2-oxo-3-piperidinyl)-NH— | 12 | 488 (M + H)⁺ |
| 27-3 | Me₂C(Me)-O-CH₂-C(O)-NH— (t-butyl ester glycine) | 35 | 505 (M + H)⁺ |
| 27-4 | (2-pyridinyl)methyl-NH— | 65 | 482 (M + H)⁺ |
| 27-5 | (3-pyridinyl)methyl-NH— | 67 | 482 (M + H)⁺ |

Example 28

In the same manner as in Example 1-1 using ethyl 2-(2,3-dihydro-1H-indol-1-yl)-4-[(2,5-dimethoxybenzyl)oxy]-5-pyrimidinecarboxylate as a starting material, compounds of Examples 28-1 to 28-4 were synthesized.

Example 28-1: (RS)-2-(2,3-dihydro-1H-indol-1-yl)-4-[(2,5-dimethoxybenzyl)oxy]-N-(2-oxo-3-azepanyl)-5-pyrimidinecarboxamide Example 28-2: t-butyl 3-[({2-(2,3-dihydro-1H-indol-1-yl)-4-[(2,5-dimethoxybenzyl)oxy]-5-pyrimidinyl}carbonyl)amino]-propylcarbamate Example 28-3: 2-(2,3-dihydro-1H-indol-1-yl)-4-[(2,5-dimethoxybenzyl)oxy]-N-[(5-methyl-2-pyrazinyl)methyl]-5-pyrimidinecarboxamide Example 28-4: 2-(2,3-dihydro-1H-indol-1-yl)-4-[(2,5-dimethoxybenzyl)oxy]-N-(2-pyridinylmethyl)-5-pyrimidinecarboxamide Respective structural formulas, MASS spectrum data and NMR data are shown in the following Table.

TABLE 63

| Example No. | R | yield (%) | MASS spectrum (APCIMS, m/z) ¹H-NMR (δ ppm, CDCl₃) |
|---|---|---|---|
| 28-1 | (3-amino-2-oxoazepanyl group: HN-C(=O)-cycloheptane with NH→) | 30 | 518 (M + H)⁺ |
| 28-2 | Me₃C-O-C(=O)-NH-CH₂CH₂CH₂-NH→ | 68 | 564 (M + H)⁺ 1.43(9H, s), 1.63 (2H, quintet, J=6.2 Hz), 3.07(2H, q, J=6.6 Hz), 3.22 (2H, t, J=8.4 Hz), 3.43(2H, q, J=6.2 Hz), 3.74(3H, s), 3.85(3H, s), 4.32 (2H, t, J=8.4 Hz), 5.00–5.15(1H, m), 5.62(2H, s), 6.83– 7.08(4H, m), 7.20– 7.25(1H, m), 7.40– 7.70(1H, br), 8.30–8.43(1H, br). 9.09(1H, s) |
| 28-3 | (5-methyl-2-pyrazinyl)methyl-NH→ | 80 | 513 (M + H)⁺ |
| 28-4 | (2-pyridinyl)methyl-NH→ | 50 | 498 (M + H)⁺ |

Example 29

In the same manner as in Example 1-1 using ethyl 2-(2,3-dihydro-1H-indol-1-yl)-4-[(4-isopropoxybenzyl)oxy]-5-pyrimidinecarboxylate as a starting material, compounds of Examples 29-1 to 29-6 were synthesized.

Example 29-1: 2-(2,3-dihydro-1H-indol-1-yl)-4-[(4-isopropoxybenzyl)oxy]-N-(4-pyridinylmethyl)-5-pyrimidinecarboxamide Example 29-2: 2-(2,3-dihydro-1H-indol-1-yl)-4-[(4-isopropoxybenzyl)oxy]-N-(3-pyridinylmethyl)-5-pyrimidinecarboxamide Example 29-3: 2-(2,3-dihydro-1H-indol-1-yl)-4-[(4-isopropoxybenzyl)oxy]-N-(2-pyridinylmethyl)-5-pyrimidinecarboxamide Example 29-4: N-(1H-benzimidazol-2-ylmethyl)-2-(2,3-dihydro-1H-indol-1-yl)-4-[(4-isopropoxybenzyl)oxy]-5-pyrimidinecarboxamide Example 29-5: (RS)-2-(2,3-dihydro-1H-indol-1-yl)-4-[(4-isopropoxybenzyl)oxy]-N-(2-oxo-3-azepanyl)-5-pyrimidinecarboxamide Example 29-6: 2-(2,3-dihydro-1H-indol-1-yl)-4-[(4-isopropoxybenzyl)oxy]-N-[(5-methyl-2-pyrazinyl)methyl]-5-pyrimidinecarboxamide Respective structural formulas and MASS spectrum data are shown in the following Table.

TABLE 64

[Structure: pyrimidine core with R-C(=O)- at position 5, 4-position has -O-CH2-C6H4-O-CH(Me)2 (4-isopropoxybenzyloxy), 2-position has 2,3-dihydro-1H-indol-1-yl]

| Example No. | R | yield (%) | MASS spectrum (APCIMS, m/z) |
|---|---|---|---|
| 29-1 | 4-pyridinyl-CH2-NH— | 51 | 496 (M + H)+ |
| 29-2 | 3-pyridinyl-CH2-NH— | 61 | 496 (M + H)+ |
| 29-3 | 2-pyridinyl-CH2-NH— | 65 | 496 (M + H)+ |
| 29-4 | 1H-benzimidazol-2-yl-CH2-NH— | 22 | 535 (M + H)+ |
| 29-5 | (2-oxo-3-azepanyl)-NH— | 47 | 516 (M + H)+ |
| 29-6 | (5-methyl-2-pyrazinyl)-CH2-NH— | 55 | 511 (M + H)+ |

Example 30

In the same manner as in Example 1-1 using ethyl 2-(2,3-dihydro-1H-indol-1-yl)-4-[(4-ethoxybenzyl)oxy]-5-pyrimidinecarboxylate as a starting material, compounds of Examples 30-1 to 30-6 were synthesized.

Example 30-1: 2-(2,3-dihydro-1H-indol-1-yl)-4-[(4-ethoxybenzyl)oxy]-N-(4-pyridinylmethyl)-5-pyrimidinecarboxamide Example 30-2: 2-(2,3-dihydro-1H-indol-1-yl)-4-[(4-ethoxybenzyl)oxy]-N-(3-pyridinylmethyl)-5-pyrimidinecarboxamide Example 30-3: 2-(2,3-dihydro-1H-indol-1-yl)-4-[(4-ethoxybenzyl)oxy]-N-(2-pyridinylmethyl)-5-pyrimidinecarboxamide Example 30-4: N-(1H-benzimidazol-2-ylmethyl)-2-(2,3-dihydro-1H-indol-1-yl)-4-[(4-ethoxybenzyl)oxy]-5-pyrimidinecarboxamide Example 30-5: 2-(2,3-dihydro-1H-indol-1-yl)-4-[(4-ethoxybenzyl)oxy]-N-(2-oxo-3-azepanyl)-5-pyrimidinecarboxamide Example 30-6: 2-(2,3-dihydro-1H-indol-1-yl)-4-[(4-ethoxybenzyl)oxy]-N-[(5-methyl-2-pyrazinyl)methyl]-5-pyrimidinecarboxamide Respective structural formulas and MASS spectrum data are shown in the following Table.

TABLE 65

[Structure: pyrimidine core with R-C(=O)- at position 5, 4-position has -O-CH2-C6H4-OEt (4-ethoxybenzyloxy), 2-position has 2,3-dihydro-1H-indol-1-yl]

| Example No. | R | yield (%) | MASS spectrum (APCIMS, m/z) |
|---|---|---|---|
| 30-1 | 4-pyridinyl-CH2-NH— | 93 | 482 (M + H)+ |
| 30-2 | 3-pyridinyl-CH2-NH— | 90 | 482 (M + H)+ |
| 30-3 | 2-pyridinyl-CH2-NH— | 83 | 482 (M + H)+ |
| 30-4 | 1H-benzimidazol-2-yl-CH2-NH— | 24 | 521 (M + H)+ |
| 30-5 | (2-oxo-3-azepanyl)-NH— | 70 | 502 (M + H)+ |
| 30-6 | (5-methyl-2-pyrazinyl)-CH2-NH— | 65 | 497 (M + H)+ |

Example 31

In the same manner as in Example 1-1 using ethyl 2-(2,3-dihydro-1H-indol-1-yl)-4-[(3-fluoro-4-methoxybenzyl)oxy]-5-pyrimidinecarboxylate as a starting material, compounds of Examples 31-1 to 31-8 were synthesized.

Example 31-1: 2-(2,3-dihydro-1H-indol-1-yl)-4-[(3-fluoro-4-methoxybenzyl)oxy]-N-(4-pyridinylmethyl)-5-pyrimidinecarboxamide Example 31-2: 2-(2,3-dihydro-1H-indol-1-yl)-4-[(3-fluoro-4-methoxybenzyl)oxy]-N-(3-pyridinylmethyl)-5-pyrimidinecarboxamide Example 31-3: 2-(2,3-dihydro-1H-indol-1-yl)-4-[(3-fluoro-4-methoxybenzyl)oxy]-N-(2-pyridinylmethyl)-5-pyrimidinecarboxamide Example 31-4: N-(1H-benzimidazol-2-ylmethyl)-2-(2,3-dihydro-1H-indol-1-yl)-4-[(3-fluoro-4-methoxybenzyl)oxy]-5-pyrimidinecarboxamide Example 31-5: 2-(2,3-dihydro-1H-indol-1-yl)-4-[(3-fluoro-4-methoxybenzyl)oxy]-N-(2-oxo-3-azepanyl)-5-pyrimidinecarboxamide Example 31-6: 2-(2,3-dihydro-1H-indol-1-yl)-4-[(3-fluoro-4-methoxybenzyl)oxy]-N-[(5-methyl-2-pyrazinyl)methyl]-5-pyrimidinecarboxamide Example 31-7: N-cycloheptyl-2-(2,3-dihydro-1H-indol-1-yl)-4-[(3-fluoro-4-methoxybenzyl)oxy]-5-pyrimidinecarboxamide Example 31-8: N-(2-amino-2-oxoethyl)-2-(2,3-dihydro-1H-indol-1-yl)-4-[(3-fluoro-4-methoxybenzyl)oxy]-5-pyrimidinecarboxamide Respective structural formulas and MASS spectrum data are shown in the following Table.

TABLE 66

| Example No. | R | yield (%) | MASS spectrum (APCIMS, m/z) |
|---|---|---|---|
| 31-1 | 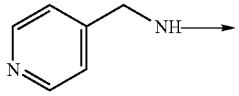 | 75 | 486 (M + H)+ |
| 31-2 | 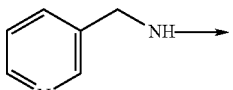 | 79 | 486 (M + H)+ |
| 31-3 | 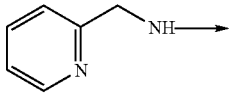 | 73 | 486 (M + H)+ |
| 31-4 | 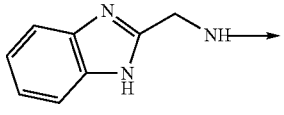 | 80 | 525 (M + H)+ |
| 31-5 | 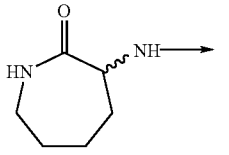 | 93 | 506 (M + H)+ |
| 31-6 | 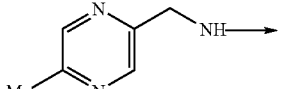 | 77 | 501 (M + H)+ |
| 31-7 | 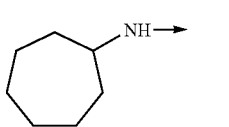 | 42 | 491 (M + H)+ |

TABLE 66-continued

| Example No. | R | yield (%) | MASS spectrum (APCIMS, m/z) |
|---|---|---|---|
| 31-8 | 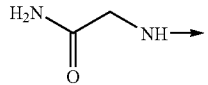 | 48 | 452 (M + H)+ |

Example 32

In the same manner as in Example 1-1 using ethyl 2-(2,3-dihydro-1H-indol-1-yl)-4-[(4-methoxy-3-methylbenzyl)oxy]-5-pyrimidinecarboxylate as a starting material, compounds of Examples 32-1 to 32-5 were synthesized.

Example 32-1: 2-(2,3-dihydro-1H-indol-1-yl)-4-[(4-methoxy-3-methylbenzyl)oxy]-N-(4-pyridinylmethyl)-5-pyrimidinecarboxamide Example 32-2: 2-(2,3-dihydro-1H-indol-1-yl)-4-[(4-methoxy-3-methylbenzyl)oxy]-N-(3-pyridinylmethyl)-5-pyrimidinecarboxamide Example 32-3: 2-(2,3-dihydro-1H-indol-1-yl)-4-[(4-methoxy-3-methylbenzyl)oxy]-N-(2-pyridinylmethyl)-5-pyrimidinecarboxamide Example 32-4: N-(1H-benzimidazol-2-ylmethyl)-2-(2,3-dihydro-1H-indol-1-yl)-4-[(4-methoxy-3-methylbenzyl)oxy]-5-pyrimidinecarboxamide Example 32-5: 2-(2,3-dihydro-1H-indol-1-yl)-4-[(4-methoxy-3-methylbenzyl)oxy]-N-(2-oxo-3-azepanyl)-5-pyrimidinecarboxamide Respective structural formulas and MASS spectrum data are shown in the following Table.

TABLE 67

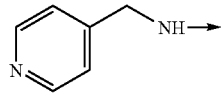

| Example No. | R | yield (%) | MASS spectrum (APCIMS, m/z) |
|---|---|---|---|
| 32-1 | 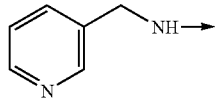 | 35 | 482 (M + H)+ |
| 32-2 |  | 61 | 482 (M + H)+ |

TABLE 67-continued

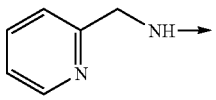

| Example No. | R | yield (%) | MASS spectrum (APCIMS, m/z) |
|---|---|---|---|
| 32-3 | 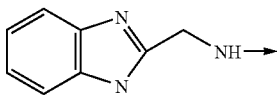 | 47 | 482 (M + H)+ |
| 32-4 | 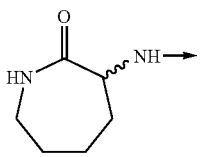 | 56 | 497 (M + H)+ |
| 32-5 | 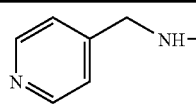 | 45 | 502 (M + H)+ |

Example 33

In the same manner as in Example 1-1 using ethyl 4-[(3-chloro-4-methoxybenzyl)oxy]-2-(2,3-dihydro-1H-indol-1-yl)-5-pyrimidinecarboxylate as a starting material, compounds of Examples 33-1 to 33-6 were synthesized.

Example 33-1: 4-[(3-chloro-4-methoxybenzyl)oxy]-2-(2,3-dihydro-1H-indol-1-yl)-N-(4-pyridinylmethyl)-5-pyrimidinecarboxamide Example 33-2: 4-[(3-chloro-4-methoxybenzyl)oxy]-2-(2,3-dihydro-1H-indol-1-yl)-N-(3-pyridinylmethyl)-5-pyrimidinecarboxamide Example 33-3: 4-[(3-chloro-4-methoxybenzyl)oxy]-2-(2,3-dihydro-1H-indol-1-yl)-N-(2-pyridinylmethyl)-5-pyrimidinecarboxamide Example 33-4: N-(1H-benzimidazol-2-ylmethyl)-4-[(3-chloro-4-methoxybenzyl)oxy]-2-(2,3-dihydro-1H-indol-1-yl)-5-pyrimidinecarboxamide Example 33-5: 4-[(3-chloro-4-methoxybenzyl)oxy]-2-(2,3-dihydro-1H-indol-1-yl)-N-(2-oxo-3-azepanyl)-5-pyrimidinecarboxamide Example 33-6: 4-[(3-chloro-4-methoxybenzyl)oxy]-2-(2,3-dihydro-1H-indol-1-yl)-N-[(5-methyl-2-pyrazinyl)methyl]-5-pyrimidinecarboxamide Respective structural formulas and MASS spectrum data are shown in the following Table.

TABLE 68

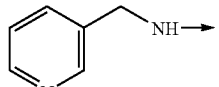

| Example No. | R | yield (%) | MASS spectrum (APCIMS, m/z) |
|---|---|---|---|
| 33-1 | 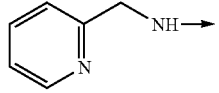 | 22 | 502 (M + H)+ |
| 33-2 | 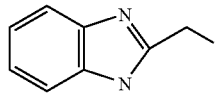 | 54 | 502 (M + H)+ |
| 33-3 | 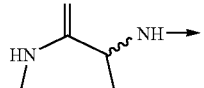 | 58 | 502 (M + H)+ |
| 33-4 | 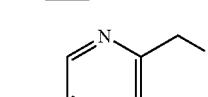 | 43 | 656 (M + H)+ |
| 33-5 | | 53 | 522 (M + H)+ |
| 33-6 | | 76 | 516 (M + H)+ |

Example 34

In the same manner as in Example 1-1 using ethyl 4-(2,3-dihydro-1-benzofuran-5-ylmethoxy)-2-(2,3-dihydro-1H-indol-1-yl)-5-pyrimidinecarboxylate as a starting material, compounds of Examples 34-1 to 34-7 were synthesized.

Example 34-1: 4-(2,3-dihydro-1-benzofuran-5-ylmethoxy)-2-(2,3-dihydro-1H-indol-1-yl)-N-(4-pyridinylmethyl)-5-pyrimidinecarboxamide Example 34-2: 4-(2,3-dihydro-1-benzofuran-5-ylmethoxy)-2-(2,3-dihydro-1H-indol-1-yl)-N-(3-pyridinylmethyl)-5-pyrimidinecarboxamide Example 34-3: 4-(2,3-dihydro-1-benzofuran-5-ylmethoxy)-2-(2,3-dihydro-1H-indol-1-yl)-N-(2-pyridinylmethyl)-5-pyrimidinecarboxamide Example 34-4: N-(1H-benzimidazole-2-ylmethyl)-4-(2,3-dihydro-1-benzofuran-5-ylmethoxy)-2-(2,3-dihydro-1H-indol-1-yl)-5-pyrimidinecarboxamide Example 34-5: 4-(2,3-dihydro-1-benzofuran-5-ylmethoxy)-2-(2,3-dihydro-1H-indol-1-yl)-N-(2-oxo-3-azepanyl)-5-pyrimidinecarboxamide Example 34-6: 4-(2,3-dihydro-1-benzofuran-5-ylmethoxy)-2-(2,3-dihydro-1H-indol-1-yl)-N-[(5-methyl-2-pyrazinyl)methyl]-5-pyrimidinecarboxamide Example 34-7: N-(2-amino-2-oxoethyl)-4-(2,3-dihydro-1-benzofuran-5 ylmethoxy)-2-(2,3-dihydro-1H-indol-1-yl)-5-pyrimidinecarboxamide Respective structural formulas and NMR data are shown in the following Table.

TABLE 69

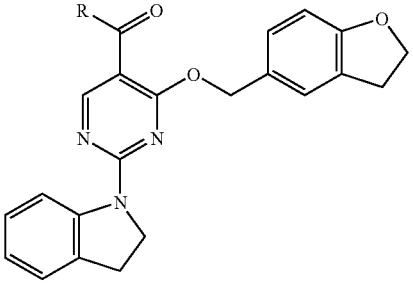

| Example No. | R | yield (%) | $^1$H-NMR (δ ppm, CDCl$_3$) |
|---|---|---|---|
| 34-1 | (4-pyridyl)CH$_2$NH— | 28 | 3.10–3.30(4H, m), 4.34(2H, t, J=8.0 Hz), 4.52–4.65(4H, m), 5.43(2H, s), 6.75(1H, d, J=7.6 Hz), 6.90–7.30(7H, m), 7.70–7.80(1H, br), 8.22–8.50(3H, m), 9.15(1H, s) |
| 34-2 | (3-pyridyl)CH$_2$NH— | 40 | 3.10–3.28(4H, m), 4.34 (2H, t, J=8.2 Hz), 4.54–4.66(4H, m), 5.46(2H, s), 6.73(1H, d, J=8.0 Hz), 6.95–7.25(6H, m), 7.49(1H, d, J=8.2 Hz), 7.73(1H, t, J=7.0 Hz), 8.30–8.52(3H, m), 9.15 (1H, s) |
| 34-3 | (2-pyridyl)CH$_2$NH— | 66 | 3.09–3.28(4H, m), 4.34 (2H, t, J=8.4 Hz), 4.58 (2H, t, J=8.4 Hz), 4.72 (2H, d, J=4.8 Hz), 5.57 (2H, s), 6.75(1H, d, J=8.0 Hz), 7.00(1H, t, J=7.8 Hz), 7.10–7.36(6H, m), 7.62(1H, dt, J=1.8, 7.6 Hz), 8.30–8.50(3H, m), 9.17(1H, s) |
| 34-4 | (benzimidazol-2-yl)CH$_2$NH— | 56 | 3.03(2H, t, J=8.4 Hz), 3.23(2H, t, J=8.4 Hz), 4.33(2H, t, J=8.8 Hz), 4.52(2H, t, J=8.4 Hz), 4.80(2H, d, J=5.4 Hz), 5.55(2H, s), 6.67(1H, d, J=5.4 Hz), 7.01(1H, t, J=8.4 Hz), 7.18–7.31(5H, m), 7.50–7.60(2H, m) |
| 34-5 | (2-oxo-3-azepanyl)NH— | 43 | 1.40–2.24(6H, m), 3.14–3.40(6H, m), 4.32(2H, t, J=8.4 Hz), 4.57(2H, t, J=8.8 Hz), 4.68–4.80(1H, m), 5.65(2H, s), 5.88–6.00(1H, m), 6.77(1H, d, J=7.6 Hz), 7.00(1H, t, J=6.8 Hz), 7.18–7.43(4H, m), 8.39(1H, d, J=8.8 Hz), 8.79(1H, d, J=9.0 Hz), 9.09(1H, s) |

TABLE 69-continued

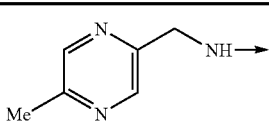

| Example No. | R | yield (%) | $^1$H-NMR (δ ppm, CDCl$_3$) |
|---|---|---|---|
| 34-6 | 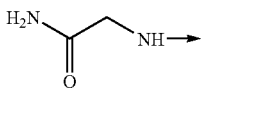 | 82 | 2.55(3H, s), 3.10–3.29 (4H, m), 4.33(2H, t, J=8.8 Hz), 4.60(2H, t, J=8.4 Hz), 4.69(2H, d, J=4.8 Hz), 5.53(2H, s), 6.76(1H, d, J=8.4 Hz), 7.00(1H, t, J=7.0 Hz), 7.18–7.30(4H, m), 8.15 (1H, s), 8.20–8.44(3H, m), 9.15(1H, s) |
| 34-7 | 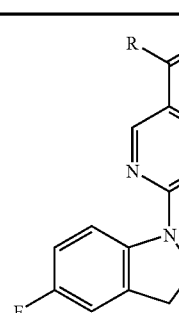 | 75 | 3.23(4H, t, J=8.4 Hz), 4.08(2H, d, J=5.4 Hz), 4.32(2H, t, J=8.0 Hz), 4.59(2H, t, J=8.4 Hz), 5.58(2H, s), 5.70–5.88 (1H, br), 6.60–6.81(2H, m), 7.00(1H, t, J=7.6 Hz), 7.20–7.40(3H, m), 8.06(1H, br t, J=6.8 Hz), 8.37(1H, d, J=8.0 Hz), 9.07(1H, s) |

Example 35

In the same manner as in Example 1-1 using ethyl 4-(1,3-benzodioxol-5-ylmethoxy)-2-(5-fluoro-2,3-dihydro-1H-indol-1-yl)-5-pyrimidinecarboxylate as a starting material, compounds of Examples 35-1 to 35-6 were synthesized.

Example 35-1: t-butyl 2-({[4-(1,3-benzodioxol-5-ylmethoxy)-2-(5-fluoro-2,3-dihydro-1H-indol-1-yl)-5-pyrimidinyl]carbonyl}-amino)acetate Example 35-2: (RS)-4-(1,3-benzodioxol-5-ylmethoxy)-2-(5-fluoro-2,3-dihydro-1H-indol-1-yl)-N-(tetrahydro-2-furanylmethyl)-5-pyrimidinecarboxamide Example 35-3: (RS)-4-(1,3-benzodioxol-5-ylmethoxy)-2-(5-fluoro-2,3-dihydro-1H-indol-1-yl)-N-(2-oxo-3-azepanyl)-5-pyrimidinecarboxamide Example 35-4: 4-(1,3-benzodioxol-5-ylmethoxy)-2-(5-fluoro-2,3-dihydro-1H-indol-1-yl)-N-(2-pyridinylmethyl)-5-pyrimidinecarboxamide Example 35-5: 4-(1,3-benzodioxol-5-ylmethoxy)-2-(5-fluoro-2,3-dihydro-1H-indol-1-yl)-N-(3-pyridinylmethyl)-5-pyrimidinecarboxamide Example 35-6: N-(1H-benzimidazole-2-ylmethyl)-4-(1,3-benzodioxol-5-ylmethoxy)-2-(5-fluoro-2,3-dihydro-1H-indol-1-yl)-5-pyrimidinecarboxamide Respective structural formulas and MASS spectrum data are shown in the following Table.

TABLE 70

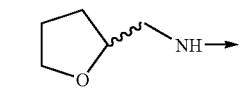

| Example No. | R | yield (%) | MASS spectrum (APCIMS, m/z) |
|---|---|---|---|
| 35-1 | Me, Me, Me — O — C(=O) — CH$_2$ — NH→ | 80 | 523(M + H)$^+$ |
| 35-2 | tetrahydrofuran-2-yl-CH$_2$-NH→ | 53 | 593(M + H)$^+$ |

TABLE 70-continued

[Structure: R-C(=O) attached to pyrimidine bearing 4-O-CH2-benzo[1,3]dioxole and 2-(5-fluoro-2,3-dihydro-1H-indol-1-yl)]

| Example No. | R | yield (%) | MASS spectrum (APCIMS, m/z) |
|---|---|---|---|
| 35-3 | 3-amino-2-oxo-azepanyl (HN-C(=O)-cycloheptyl-NH→) | 81 | 520(M + H)+ |
| 35-4 | (2-pyridinyl)methyl-NH→ | 68 | 500(M + H)+ |
| 35-5 | (3-pyridinyl)methyl-NH→ | 65 | 500(M + H)+ |
| 35-6 | (1H-benzimidazol-2-yl)methyl-NH→ | 71 | 539(M + H)+ |

Example 36

In the same manner as in Example 1-1 using ethyl 2-(5-fluoro-2,3-dihydro-1H-indol-1-yl)-4-[(4-methoxybenzyl)oxy]-5-pyrimidinecarboxylate as a starting material, compounds of Examples 36-1 to 36-5 were synthesized.

Example 36-1: t-butyl 2-[({2-(5-fluoro-2,3-dihydro-1H-indol-1-yl)-4-[(4-methoxybenzyl)oxy]-5-pyrimidinyl}carbonyl)amino]-acetate Example 36-2: (RS)-2-(5-fluoro-2,3-dihydro-1H-indol-1-yl)-4-[(4-methoxybenzyl)oxy]-N-(tetrahydro-2-furanylmethyl)-5-pyrimidinecarboxamide Example 36-3: (RS)-2-(5-fluoro-2,3-dihydro-1H-indol-1-yl)-4-[(4-methoxybenzyl)oxy]-N-(2-oxo-3-azepanyl)-5-pyrimidinecarboxamide Example 36-4: 2-(5-fluoro-2,3-dihydro-1H-indol-1-yl)-4-[(4-methoxybenzyl)oxy]-N-(2-pyridinylmethyl)-5-pyrimidinecarboxamide Example 36-5: 2-(5-fluoro-2,3-dihydro-1H-indol-1-yl)-4-[(4-methoxybenzyl)oxy]-N-(3-pyridinylmethyl)-5-pyrimidinecarboxamide Respective structural formulas and MASS spectrum data are shown in the following Table.

TABLE 71

[Structure: R-C(=O) attached to pyrimidine bearing 4-O-CH2-(4-methoxyphenyl) and 2-(5-fluoro-2,3-dihydro-1H-indol-1-yl)]

| Example No. | R | yield (%) | MASS spectrum (APCIMS, m/z) |
|---|---|---|---|
| 36-1 | Me3C-O-C(=O)-CH2-NH→ | 93 | 509(M+H)+ |
| 36-2 | (tetrahydrofuran-2-yl)methyl-NH→ | 60 | 479(M+H)+ |
| 36-3 | 3-amino-2-oxo-azepanyl (HN-C(=O)-cycloheptyl-NH→) | 84 | 506(M+H)+ |
| 36-4 | (2-pyridinyl)methyl-NH→ | 74 | 486(M+H)+ |
| 36-5 | (3-pyridinyl)methyl-NH→ | 62 | 486(M+H)+ |

Example 37

In the same manner as in Example 1-1 using ethyl 2-(6,7-dihydro-5H-[1,3]dioxolo[4,5-f]indol-5-yl)-4-[(4-methoxybenzyl)oxy]-5-pyrimidinecarboxylate as a starting material, compounds of Examples 37-1 to 37-6 were synthesized.

Example 37-1: t-butyl 2-[({2-(6,7-dihydro-5H-[1,3]dioxolo[4,5-f]indol-5-yl)-4-[(4-methoxybenzyl)oxy]-5-pyrimidinyl}carbonyl)-amino]acetate Example 37-2: (RS)-2-(6,7-dihydro-5H-[1,3]dioxolo[4,5-f]indol-5-yl)-4-[(4-methoxybenzyl)oxy]-N-(tetrahydro-2-furanylmethyl)-5-pyrimidinecarboxamide Example 37-3: (RS)-2-(6,7-dihydro-5H-[1,3]dioxolo[4,5-f]indol-5-yl)-4-[(4-methoxybenzyl)oxy]-N-(2-oxo-3-azepanyl)-5-pyrimidinecarboxamide Example 37-4: 2-(6,7-dihydro-5H-[1,3]dioxolo[4,5-f]indol-5-yl)-4-[(4-methoxybenzyl)oxy]-N-(2-pyridinylmethyl)-5-pyrimidinecarboxamide Example 37-5: 2-(6,7-dihydro-5H-[1,3]dioxolo[4,5-f]indol-5-yl)-4-[(4-methoxybenzyl)oxy]-N-(3-pyridinylmethyl)-5-pyrimidinecarboxamide Example 37-6: N-(1H-benzimidazole-2-ylmethyl)-2-(6,7-dihydro-5H-[1,3]dioxolo[4,5-f]indol-5-yl)-4-[(4-methoxybenzyl)oxy]-5-pyrimidinecarboxamide Respective structural formulas and MASS spectrum data are shown in the following Table.

TABLE 72

| Example No. | R | yield (%) | MASS spectrum (APCIMS, m/z) |
|---|---|---|---|
| 37-1 | Me₃C-O-C(=O)-CH₂-NH– | 83 | 535(M+H)⁺ |
| 37-2 | (tetrahydrofuran-2-yl)methyl-NH– | 66 | 505(M+H)⁺ |
| 37-3 | (3-oxo-azepan-2-yl)-NH– | 71 | 532(M+H)⁺ |
| 37-4 | (pyridin-2-yl)methyl-NH– | 66 | 512(M+H)⁺ |
| 37-5 | (pyridin-3-yl)methyl-NH– | 84 | 512(M+H)⁺ |
| 37-6 | (1H-benzimidazol-2-yl)methyl-NH– | 81 | 551(M+H)⁺ |

Example 38

In the same manner as in Example 1-1 using ethyl 2-(5-bromo-2,3-dihydro-1H-indol-1-yl)-4-[(4-methoxybenzyl)oxy]-5-pyrimidinecarboxylate as a starting material, compounds of Examples 38-1 to 38-6 were synthesized.

Example 38-1: t-butyl 2-[({2-(5-bromo-2,3-dihydro-1H-indol-1-yl)-4-[(4-methoxybenzyl)oxy]-5-pyrimidinyl}carbonyl)amino]-acetate Example 38-2: (RS)-2-(5-bromo-2,3-dihydro-1H-indol-1-yl)-4-[(4-methoxybenzyl)oxy]-N-(tetrahydro-2-furanylmethyl)-5-pyrimidinecarboxamide Example 38-3: (RS)-2-(5-bromo-2,3-dihydro-1H-indol-1-yl)-4-[(4-methoxybenzyl)oxy]-N-(2-oxo-3-azepanyl)-5-pyrimidinecarboxamide Example 38-4: 2-(5-bromo-2,3-dihydro-1H-indol-1-yl)-N-[2-(dimethylamino)ethyl]-4-[(4-methoxybenzyl)oxy]-5-pyrimidinecarboxamide Example 38-5: 2-(5-bromo-2,3-dihydro-1H-indol-1-yl)-4-[(4-methoxybenzyl)oxy]-N-(2-pyridinylmethyl)-5-pyrimidinecarboxamide Example 38-6: 2-(5-bromo-2,3-dihydro-1H-indol-1-yl)-4-[(4-methoxybenzyl)oxy]-N-(3-pyridinylmethyl)-5-pyrimidinecarboxamide Respective structural formulas and MASS spectrum data are shown in the following Table.

TABLE 73

| Example No. | R | yield (%) | MASS spectrum (APCIMS, m/z) |
|---|---|---|---|
| 38-1 | Me₃C-O-C(=O)-CH₂-NH– | 79 | 570(M+H)⁺ |
| 38-2 | (tetrahydrofuran-2-yl)methyl-NH– | 80 | 540(M+H)⁺ |
| 38-3 | (3-oxo-azepan-2-yl)-NH– | 55 | 567(M+H)⁺ |
| 38-4 | Me₂N-CH₂CH₂-NH– | 86 | 527(M+H)⁺ |
| 38-5 | (pyridin-2-yl)methyl-NH– | 89 | 547(M+H)⁺ |
| 38-6 | (pyridin-3-yl)methyl-NH– | 54 | 547(M+H)⁺ |

Example 39

In the same manner as in Example 1-1 using ethyl 2-(5-bromo-2,3-dihydro-1H-indol-1-yl)-4-[(2,5-dimethoxybenzyl)oxy]-5-pyrimidinecarboxylate as a starting material, compounds of Examples 39-1 to 39-4 were synthesized.

Example 39-1: (RS)-2-(5-bromo-2,3-dihydro-1H-indol-1-yl)-4-[(2,5-dimethoxybenzyl)oxy]-N-(2-oxo-3-azepanyl)-5-pyrimidinecarboxamide Example 39-2: t-butyl 3-[({2-(5-bromo-2,3-dihydro-1H-indol-1-yl)-4-[(2,5-dimethoxybenzyl)oxy]-5-pyrimidinyl}carbonyl)amino]-propylcarbamate Example 39-3: 2-(5-bromo-2,3-dihydro-1H-indol-1-yl)-4-[(2,5-dimethoxybenzyl)oxy]-N-[(5-methyl-2-pyrazinyl)methyl]-5-pyrimidinecarboxamide Example 39-4: 2-(5-bromo-2,3-dihydro-1H-indol-1-yl)-4-[(2,5-dimethoxybenzyl)oxy]-N-(2-pyridinylmethyl)-5-pyrimidinecarboxamide Respective structural formulas and MASS spectrum data are shown in the following Table.

Example 40

In the same manner as in Example 1-1 using ethyl 4-(1,3-benzodioxol-5-ylmethoxy)-2-(5-bromo-2,3-dihydro-1H-indol-1-yl)-5-pyrimidinecarboxylate as a starting material, compounds of Examples 40-1 to 40-4 were synthesized.

Example 40-1: t-butyl 2-({[4-(1,3-benzodioxol-5-ylmethoxy)-2-(5-bromo-2,3-dihydro-1H-indol-1-yl)-5-pyrimidinyl]carbonyl}-amino)acetate Example 40-2: (RS)-4-(1,3-benzodioxol-5-ylmethoxy)-2-(5-bromo-2,3-dihydro-1H-indol-1-yl)-N-(tetrahydro-2-furanylmethyl)-5-pyrimidinecarboxamide Example 40-3: (RS)-4-(1,3-benzodioxol-5-ylmethoxy)-2-(5-bromo-2,3-dihydro-1H-indol-1-yl)-N-(2-oxo-3-azepanyl)-5-pyrimidinecarboxamide Example 40-4: 4-(1,3-benzodioxol-5-ylmethoxy)-2-(5-bromo-2,3-dihydro-1H-indol-1-yl)-N-[2-(dimethylamino)ethyl]-5-pyrimidinecarboxamide Respective structural formulas and MASS spectrum data are shown in the following Table.

TABLE 74

| Example No. | R | yield (%) | MASS spectrum (APCIMS, m/z) |
|---|---|---|---|
| 39-1 | (3-amino-2-oxo-azepanyl) | 74 | 597(M+H)+ |
| 39-2 | Boc-NH-(CH2)3-NH– | 35 | 643(M+H)+ |
| 39-3 | (5-methyl-2-pyrazinyl)methyl-NH– | 55 | 592(M+H)+ |
| 39-4 | (2-pyridinyl)methyl-NH– | 68 | 577(M+H)+ |

TABLE 75

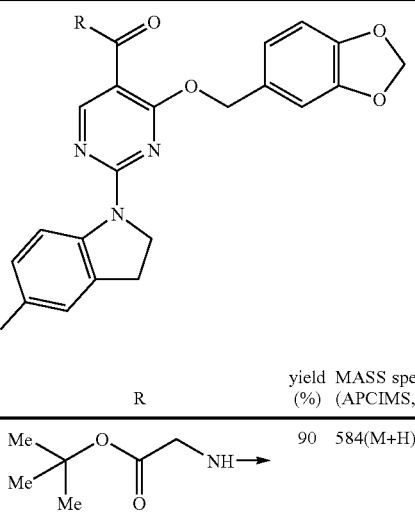

| Example No. | R | yield (%) | MASS spectrum (APCIMS, m/z) |
|---|---|---|---|
| 40-1 | 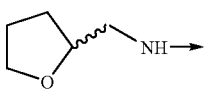 | 90 | 584(M+H)+ |
| 40-2 | 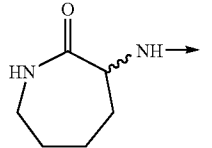 | 51 | 554(M+H)+ |
| 40-3 | 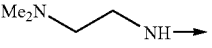 | 75 | 581(M+H)+ |
| 40-4 | Me₂N~~NH→ | 95 | 541(M+H)+ |

Example 41

In the same manner as in Example 1-1 using ethyl 4-(1,3-benzodioxol-5-ylmethoxy)-2-(5-methoxy-2,3-dihydro-1H-indol-1-yl)-5-pyrimidinecarboxylate as a starting material, compounds of Examples 41-1 to 41-4 were synthesized.

Example 41-1: t-butyl 2-({[4-(1,3-benzodioxol-5-ylmethoxy)-2-(5-methoxy-2,3-dihydro-1H-indol-1-yl)-5-pyrimidinyl]carbonyl}-amino)acetate Example 41-2: (RS)-4-(1,3-benzodioxol-5-ylmethoxy)-2-(5-methoxy-2,3-dihydro-1H-indol-1-yl)-N-(tetrahydro-2-furanylmethyl)-5-pyrimidinecarboxamide Example 41-3: (RS)-4-(1,3-benzodioxol-5-ylmethoxy)-2-(5-methoxy-2,3-dihydro-1H-indol-1-yl)-N-(2-oxo-3-azepanyl)-5-pyrimidinecarboxamide Example 41-4: 4-(1,3-benzodioxol-5-ylmethoxy)-2-(5-methoxy-2,3-dihydro-1H-indol-1-yl)-N-(2-pyridylmethyl)-5-pyrimidinecarboxamide Respective structural formulas, MASS spectrum data and NMR data are shown in the following Table.

TABLE 76

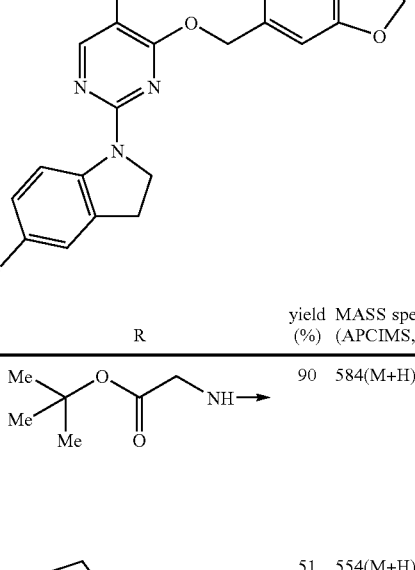

| Example No. | R | yield (%) | MASS spectrum (APCIMS, m/z) ¹H-NMR (δ ppm, CDCl₃) |
|---|---|---|---|
| 41-1 | 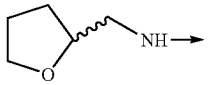 | 74 | 535(M+H)+ 1.47(9H, s), 3.20 (2H, t, J=8.4Hz), 3.81(3H, s), 4.08 (2H, d, J=4.8Hz), 4.31(2H, t, J= 8.0Hz), 5.55(2H, s), 5.98(2H, s), 6.85–6.94(3H, m), 6.96–7.07(2H, m), 7.91 (1H, t, J=7.0Hz), 8.00–8.40(1H, br), 9.09(1H, s) |
| 41-2 | 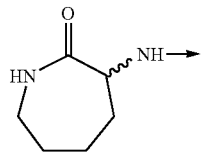 | 51 | 505(M+H)+ |
| 41-3 | 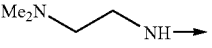 | 68 | 532(M+H)+ |
| 41-4 | 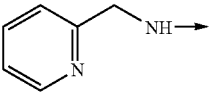 | 61 | 512(M+H)+ |

Example 42

In the same manner as in Example 1-1 using ethyl 4-[(4-methoxybenzyl)oxy]-2-(5-methoxy-2,3-dihydro-1H-indol-1-yl)-5-pyrimidinecarboxylate as a starting material, t-butyl 2-({[4-[(4-methoxybenzyl)oxy]-2-(5-methoxy-2,3-dihydro-1H-indol-1-yl)-5-pyrimidinyl]carbonyl}amino)acetate was synthesized.

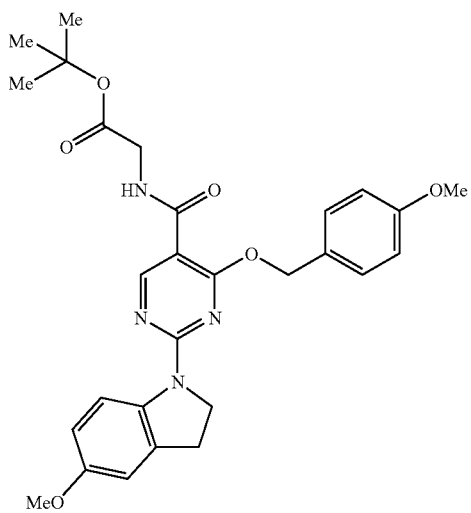

Yield 90%, MASS spectrum (APCIMS, m/z): 520

Example 43

In the same manner as in Example 1-1 using ethyl 4-[(2,5-dimethoxybenzyl)oxy]-2-(4-methoxy-2,3-dihydro-1H-indol-1-yl)-5-pyrimidinecarboxylate as a starting material, compounds of Examples 43-1 to 43-4 were synthesized.

Example 43-1: (RS)-4-[(2,5-dimethoxybenzyl)oxy]-2-(4-methoxy-2,3-dihydro-1H-indol-1-yl)-N-(2-oxo-3-azepanyl)-5-pyrimidinecarboxamide Example 43-2: t-butyl 3-({[4-[(2,5-dimethoxybenzyl)oxy]-2-(4-methoxy-2,3-dihydro-1H-indol-1-yl)-5-pyrimidinyl]carbonyl}-amino)propylcarbamate Example 43-3: 4-[(2,5-dimethoxybenzyl)oxy]-2-(4-methoxy-2,3-dihydro-1H-indol-1-yl)-N-[(5-methyl-2-pyrazinyl)methyl]-5-pyrimidinecarboxamide Example 43-4: 4-[(2,5-dimethoxybenzyl)oxy]-2-(4-methoxy-2,3-dihydro-1H-indol-1-yl)-N-(2-pyridylmethyl)-5-pyrimidinecarboxamide Respective structural formulas and MASS spectrum data are shown in the following Table.

TABLE 77

| Example No. | R | yield (%) | MASS spectrum (APCIMS, m/z) |
|---|---|---|---|
| 43-1 | (2-oxo-3-azepanyl)NH– | 35 | 548(M+H)+ |
| 43-2 | Me₃C-O-C(O)-NH-CH₂CH₂CH₂-NH– | 82 | 594(M+H)+ |
| 43-3 | (5-methyl-2-pyrazinyl)CH₂-NH– | 75 | 543(M+H)+ |
| 43-4 | (2-pyridyl)CH₂-NH– | 62 | 528(M+H)+ |

Example 44

In the same manner as in Example 1-1 using ethyl 4-[(4-methoxybenzyl)oxy]-2-(4-methoxy-2,3-dihydro-1H-indol-1-yl)-5-pyrimidinecarboxylate as a starting material, compounds of Examples 44-1 to 44-4 were synthesized.

Example 44-1: (RS)-4-[(4-methoxybenzyl)oxy]-2-(4-methoxy-2,3-dihydro-1H-indol-1-yl)-N-(2-oxo-3-azepanyl)-5-pyrimidinecarboxamide Example 44-2: t-butyl 3-({[4-[(4-methoxybenzyl)oxy]-2-(4-methoxy-2,3-dihydro-1H-indol-1-yl)-5-pyrimidinyl]carbonyl}-amino)propylcarbamate Example 44-3: 4-[(4-methoxybenzyl)oxy]-2-(4-methoxy-2,3-dihydro-1H-indol-1-yl)-N-[(5-methyl-2-pyrazinyl)methyl]-5-pyrimidinecarboxamide Example 44-4: 4-[(4-methoxybenzyl)oxy]-2-(4-methoxy-2,3-dihydro-1H-indol-1-yl)-N-(2-pyridylmethyl)-5-pyrimidinecarboxamide Respective structural formulas and MASS spectrum data are shown in the following Table.

TABLE 78

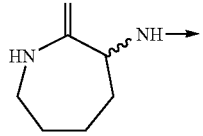

| Example No. | R | yield (%) | MASS spectrum (APCIMS, m/z) |
|---|---|---|---|
| 44-1 | 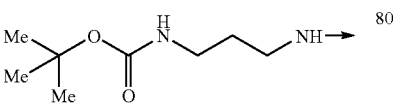 | 56 | 518(M+H)+ |
| 44-2 | 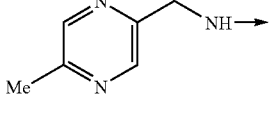 | 80 | 564(M+H)+ |
| 44-3 | 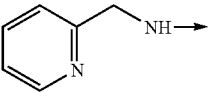 | 75 | 513(M+H)+ |
| 44-4 | 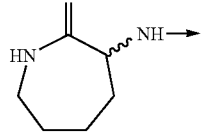 | 61 | 498(M+H)+ |

Example 45

In the same manner as in Example 1-1 using ethyl 4-[(4-methoxybenzyl)oxy]-2-(5-methyl-2,3-dihydro-1H-indol-1-yl)-5-pyrimidinecarboxylate as a starting material, compounds of Examples 45-1 to 45-6 were synthesized.

Example 45-1: (RS)-4-[(4-methoxybenzyl)oxy]-2-(5-methyl-2,3-dihydro-1H-indol-1-yl)-N-(2-oxo-3-azepanyl)-5-pyrimidinecarboxamide Example 45-2: t-butyl 3-({[4-[(4-methoxybenzyl)oxy]-2-(5-methyl-2,3-dihydro-1H-indol-1-yl)-5-pyrimidinyl]carbonyl}-amino)propylcarbamate Example 45-3: 4-[(4-methoxybenzyl)oxy]-2-(5-methyl-2,3-dihydro-1H-indol-1-yl)-N-[(5-methyl-2-pyrazinyl)methyl]-5-pyrimidinecarboxamide Example 45-4: 4-[(4-methoxybenzyl)oxy]-2-(5-methyl-2,3-dihydro-1H-indol-1-yl)-N-(2-pyridinylmethyl)-5-pyrimidinecarboxamide Example 45-5: 4-[(4-methoxybenzyl)oxy]-2-(5-methyl-2,3-dihydro-1H-indol-1-yl)-N-(3-pyridinylmethyl)-5-pyrimidinecarboxamide Example 45-6: N-(1H-benzimidazole-2-ylmethyl)-4-[(4-methoxybenzyl)oxy]-2-(5-methyl-2,3-dihydro-1H-indol-1-yl)-5-pyrimidinecarboxamide Respective structural formulas, MASS spectrum data and NMR data are shown in the following Table.

TABLE 79

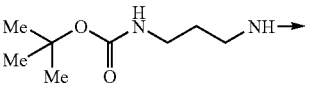

| Example No. | R | yield (%) | MASS spectrum (APCIMS, m/z) $^1$H-NMR (δ ppm, CDCl$_3$) |
|---|---|---|---|
| 45-1 | 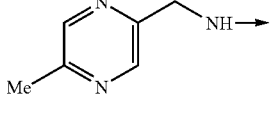 | 30 | 502(M+H)+ |
| 45-2 | 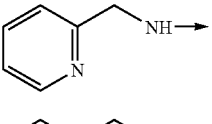 | 62 | 548(M+H)+ |
| 45-3 | 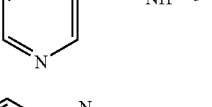 | 43 | 497(M+H)+ 2.33(3H, s), 2.54 (3H, s), 3.18(2H, t, J=8.8Hz), 3.84 (3H, s), 4.31(2H, t, J=8.4Hz), 4.69 (2H, d, J=5.2Hz), 5.54(2H, s), 6.88(2H, d, J=8.8 Hz), 7.00–7.08 (2H, m), 7.40(2H, d, J=8.4Hz), 8.13–8.32(3H, m), 8.44(1H, s), 9.13(1H, s) |
| 45-4 | 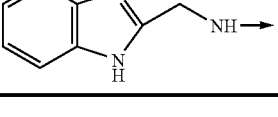 | 62 | 482(M+H)+ |
| 45-5 | | 83 | 482(M+H)+ |
| 45-6 | | 57 | 521(M+H)+ |

Example 46

In the same manner as in Example 1-1 using ethyl 4-[(2,5-dimethoxybenzyl)oxy]-2-(5-methyl-2,3-dihydro-1H-indol-1-yl)-5-pyrimidinecarboxylate as a starting material, compounds of Examples 46-1 to 46-4 were synthesized.

Example 46-1: (RS)-4-[(2,5-dimethoxybenzyl)oxy]-2-(5-methyl-2,3-dihydro-1H-indol-1-yl)-N-(2-oxo-3-azepanyl)-5-pyrimidinecarboxamide Example 46-2: t-butyl 3-({[4-[(2,5-dimethoxybenzyl)oxy]-2-(5-methyl-2,3-dihydro-1H-indol-1-yl)-5-pyrimidinyl]carbonyl}-amino)propylcarbamate Example 46-3: 4-[(2,5-dimethoxybenzyl)oxy]-2-(5-methyl-2,3-dihydro-1H-indol-1-yl)-N-[(5-methyl-2-pyrazinyl)methyl]-5-pyrimidinecarboxamide Example 46-4: 4-[(2,5-dimethoxybenzyl)oxy]-2-(5-methyl-2,3-dihydro-1H-indol-1-yl)-N-(2-pyridinylmethyl)-5-pyrimidinecarboxamide Respective structural formulas and MASS spectrum data are shown in the following Table.

TABLE 80

| Example No. | R | yield (%) | MASS spectrum (APCIMS, m/z) |
|---|---|---|---|
| 46-1 | [3-amino-2-oxo-azepanyl group] | 30 | 532(M+H)+ |
| 46-2 | [t-butyl carbamate propyl group] | 73 | 578(M+H)+ |
| 46-3 | [(5-methyl-2-pyrazinyl)methyl group] | 77 | 527(M+H)+ |
| 46-4 | [(2-pyridinyl)methyl group] | 83 | 512(M+H)+ |

Example 47

In the same manner as in Example 1-1 using ethyl (RS)-4-[(4-methoxybenzyl)oxy]-2-(2-methyl-2,3-dihydro-1H-indol-1-yl)-5-pyrimidinecarboxylate as a starting material, compounds of Examples 47-1 to 47-3 were synthesized.

Example 47-1: t-butyl (RS)-2-({[4-[(4-methoxybenzyl)oxy]-2-(2-methyl-2,3-dihydro-1H-indol-1-yl)-5-pyrimidinyl]carbonyl}-amino)acetate Example 47-2: (rac)-4-[(4-methoxybenzyl)oxy]-2-(2-methyl-2,3-dihydro-1H-indol-1-yl)-N-(tetrahydro-2-furanylmethyl)-5-pyrimidinecarboxamide Example 47-3: (rac)-4-[(4-methoxybenzyl)oxy]-2-(2-methyl-2,3-dihydro-1H-indol-1-yl)-N-(2-oxo-3-azepanyl)-5-pyrimidinecarboxamide Respective structural formulas and MASS spectrum data are shown in the following Table.

TABLE 81

| Example No. | R | yield (%) | MASS spectrum (APCIMS, m/z) |
|---|---|---|---|
| 47-1 | [t-butoxycarbonylmethyl group] | 80 | 505(M+H)+ |
| 47-2 | [(tetrahydro-2-furanyl)methyl group] | 82 | 475(M+H)+ |
| 47-3 | [3-amino-2-oxo-azepanyl group] | 65 | 502(M+H)+ |

Example 48

In the same manner as in Example 1-1 using ethyl (RS)-4-[(4-methoxybenzyl)oxy]-2-(3-methyl-2,3-dihydro-1H-indol-1-yl)-5-pyrimidinecarboxylate as a starting material, compounds of Examples 48-1 to 48-3 were synthesized.

Example 48-1: (RS)-4-[(4-methoxybenzyl)oxy]-2-(3-methyl-2,3-dihydro-1H-indol-1-yl)-N-(2-pyridinylmethyl)-5-pyrimidinecarboxamide Example 48-2: (RS)-4-[(4-methoxybenzyl)oxy]-2-(3-methyl-2,3-dihydro-1H-indol-1-yl)-N-(3-pyridinylmethyl)-5-pyrimidinecarboxamide Example 48-3: (RS)-N-(1H-benzimidazole-2-ylmethyl)-4-[(4-methoxybenzyl)oxy]-2-(3-methyl-2,3-dihydro-1H-indol-1-yl)-5-pyrimidinecarboxamide Respective structural formulas and MASS spectrum data are shown in the following Table.

TABLE 82

[Structure with R-C(=O)- group on pyrimidine bearing 4-OMe-benzyloxy and 3-methyl-2,3-dihydroindol-1-yl substituents]

| Example No. | R | yield (%) | MASS spectrum (APCIMS, m/z) |
|---|---|---|---|
| 48-1 | [2-pyridinylmethyl-NH—] | 88 | 482(M+H)⁺ |
| 48-2 | [3-pyridinylmethyl-NH—] | 35 | 482(M+H)⁺ |
| 48-3 | [benzimidazol-2-ylmethyl-NH—] | 48 | 521(M+H)⁺ |

Example 49

In the same manner as in Example 1-1 using ethyl 4-[(4-methoxybenzyl)oxy]-2-(7-methyl-2,3-dihydro-1H-indol-1-yl)-5-pyrimidinecarboxylate as a starting material, 4-[(4-methoxybenzyl)oxy]-2-(7-methyl-2,3-dihydro-1H-indol-1-yl)-N-(3-pyridinylmethyl)-5-pyrimidinecarboxamide was synthesized.

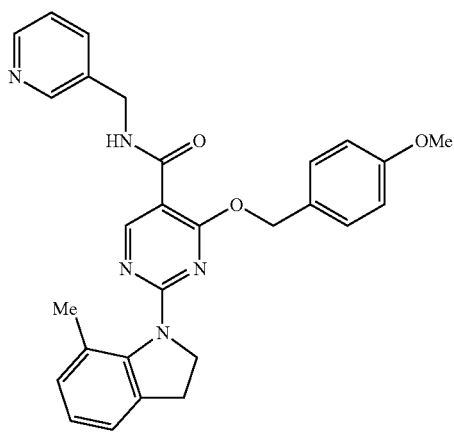

Yield 25%, MASS spectrum (APCIMS, m/z): 482

Example 50

In the same manner as in Example 1-1 using ethyl 2-(2,3-dihydro-1H-indol-1-yl)-4-{[4-(trifluoromethoxy)benzyl]oxy}-5-pyrimidinecarboxylate as a starting material, 2-(2,3-dihydro-1H-indol-1-yl)-N-(2-pyridinylmethyl)-4-{[4-(trifluoromethoxy)-benzyl]oxy}-5-pyrimidinecarboxamide was synthesized.

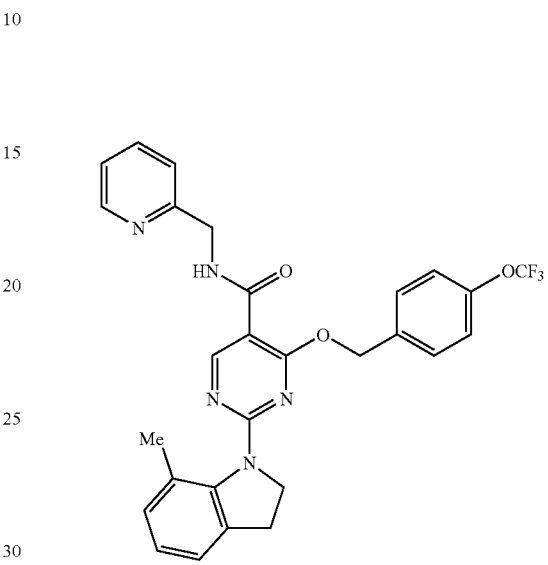

Yield 48%, MASS spectrum (APCIMS, m/z): 522

Example 51

In the same manner as in Example 1-1 using ethyl 2-(2,3-dihydro-1H-indol-1-yl)-4-[(4-fluorobenzyl)amino]-5-pyrimidinecarboxylate as a starting material, compounds of Examples 51-1 to 51-6 were synthesized.

Example 51-1: N-(cyanomethyl)-2-(2,3-dihydro-1H-indol-1-yl)-4-[(4-fluorobenzyl)amino]-5-pyrimidinecarboxamide Example 51-2: ethyl 2-[({2-(2,3-dihydro-1H-indol-1-yl)-4-[(4-fluorobenzyl)amino]-5-pyrimidinyl}carbonyl)amino]acetate Example 51-3: (RS)-2-(2,3-dihydro-1H-indol-1-yl)-4-[(4-fluorobenzyl)amino]-N-(tetrahydro-2-furanylmethyl)-5-pyrimidinecarboxamide Example 51-4: 2-(2,3-dihydro-1H-indol-1-yl)-4-[(4-fluorobenzyl)amino]-N-[3-(2-oxo-1-pyrrolizinyl)propyl]-5-pyrimidinecarboxamide Example 51-5: N-benzyl-2-(2,3-dihydro-1H-indol-1-yl)-4-[(4-fluorobenzyl)amino]-5-pyrimidinecarboxamide Example 51-6: t-butyl 2-[({2-(2,3-dihydro-1H-indol-1-yl)-4-[(4-fluorobenzyl)amino]-5-pyrimidinyl}carbonyl)amino]acetate Respective structural formulas, MASS spectrum data and NMR data are shown in the following Table.

TABLE 83

R group attached to pyrimidine scaffold with 4-fluorobenzylamino substituent and indoline substituent.

| Example No. | R | yield (%) | MASS spectrum (APCIMS, m/z) ¹H-NMR (δ ppm, CDCl₃) |
|---|---|---|---|
| 51-1 | NC–CH₂–NH→ | 35 | 403(M+H)⁺ |
| 51-2 | EtO₂C–CH₂–NH→ | 32 | 450(M+H)⁺ |
| 51-3 | (tetrahydrofuran-2-yl)methyl–NH→ | 35 | 448(M+H)⁺ |
| 51-4 | 3-(2-oxo-1-pyrrolidinyl)propyl–NH→ | 25 | 489(M+H)⁺ 1.20–1.90(5H, m), 2.07(3H, t, J=7.6Hz), 2.45(2H, t, J=8.0Hz), 3.13(2H, t, J=8.8Hz), 3.21–3.50(4H, m), 4.21(2H, t, J=8.8Hz), 4.71(2H, d, J=5.4Hz), 6.80–7.42(6H, m), 7.70(1H, br t, J=7.4Hz), 8.24(1H, dd, J=8.0Hz), 8.60(1H, s), 9.23(1H, br s) |
| 51-5 | benzyl–NH→ | 34 | 454(M+H)⁺ |
| 51-6 | Me₃C–O–C(O)–CH₂–NH→ | 60 | 478(M+H)⁺ |

Example 52

In the same manner as in Example 1-1 using ethyl 2-(2,3-dihydro-1H-indol-1-yl)-4-{[4-(trifluoromethyl)benzyl]amino}-5-pyrimidinecarboxylate as a starting material, compounds of Examples 51-1 to 52-7 were synthesized.

Example 52-1: N-(cyanomethyl)-2-(2,3-dihydro-1H-indol-1-yl)-4-([4-(trifluoromethyl)benzyl]amino}-5-pyrimidinecarboxamide Example 52-2: ethyl 2-{[(2-(2,3-dihydro-1H-indol-1-yl)-4-{[4-(trifluoromethyl)benzyl]amino}-5-pyrimidinyl)carbonyl]amino}acetate Example 52-3: (RS)-2-(2,3-dihydro-1H-indol-1-yl)-4-{[4-(trifluoromethyl)benzyl]amino}-N-(tetrahydro-2-furanylmethyl)-5-pyrimidinecarboxamide Example 52-4: 2-(2,3-dihydro-1H-indol-1-yl)-4-{[4-(trifluoromethyl)benzyl]amino}-N-[3-(2-oxo-1-pyrrolizinyl)propyl]-5-pyrimidinecarboxamide Example 52-5: N-benzyl-2-(2,3-dihydro-1H-indol-1-yl)-4-{[4-(trifluoromethyl)benzyl]amino}-5-pyrimidinecarboxamide Example 52-6: t-butyl 2-[({2-(2,3-dihydro-1H-indol-1-yl)-4-{[4-(trifluoromethyl)benzyl]amino}-5-pyrimidinyl}carbonyl)amino]acetate Example 52-7: 2-(2,3-dihydro-1H-indol-1-yl)-N-(2-ethoxyethyl)-4-{[4-(trifluoromethyl)benzyl]amino}-5-pyrimidinecarboxamide Respective structural formulas, MASS spectrum data and NMR data are shown in the following Table.

TABLE 84

R group attached to pyrimidine scaffold with 4-(trifluoromethyl)benzylamino substituent and indoline substituent.

| Example No. | R | yield (%) | MASS spectrum (APCIMS, m/z) ¹H-NMR (δ ppm, CDCl₃) |
|---|---|---|---|
| 52-1 | NC–CH₂–NH→ | 35 | 453(M+H)⁺ |
| 52-2 | EtO₂C–CH₂–NH→ | 28 | 500(M+H)⁺ |
| 52-3 | (tetrahydrofuran-2-yl)methyl–NH→ | 30 | 498(M+H)⁺ |
| 52-4 | 3-(2-oxo-1-pyrrolidinyl)propyl–NH→ | 25 | 539(M+H)⁺ |
| 52-5 | benzyl–NH→ | 45 | 504(M+H)⁺ 3.13(2H, t, J=8.0Hz), 4.17(2H, t, J=8.4Hz), 4.60(2H, d, J=5.4Hz), 4.82(2H, d, J=5.4Hz), 6.25(1H, t, J=7.0Hz), 6.91(1H, t, J=7.2Hz), 7.00–7.40(4H, m), 7.50 (2H, d, J=8.8Hz), 7.59 (2H, d, J=8.8Hz), 8.00–8.23(1H, br), 8.35(1H, s), 9.24(1H, br t, J=7.0Hz) |
| 52-6 | Me₃C–O–C(O)–CH₂–NH→ | 15 | 528(M+H)⁺ |
| 52-7 | EtO–CH₂CH₂–NH→ | 16 | 486(M+H)⁺ |

Example 53

In the same manner as in Example 1-1 using ethyl 4-[(1,3-benzodioxol-5-ylmethyl)amino]-2-(2,3-dihydro-1H-indol-1-yl)-5-pyrimidinecarboxylate as a starting material, compounds of Examples 53-1 to 53-3 were synthesized.

Example 53-1: 4-[(1,3-benzodioxol-5-ylmethyl)amino]-N-benzyl-2-(2,3-dihydro-1H-indol-1-yl)-5-pyrimidinecarboxamide Example 53-2: t-butyl 2-({[4-[(1,3-benzodioxol-5-ylmethyl)amino]-2-(2,3-dihydro-1H-indol-1-yl)-5-pyrimidinyl]carbonyl}amino)acetate Example 53-3: 4-[(1,3-benzodioxol-5-ylmethyl)amino]-2-(2,3-dihydro-1H-indol-1-yl)-N-(2-pyridinylmethyl)-5-pyrimidinecarboxamide Respective structural formulas and MASS spectrum data are shown in the following Table.

TABLE 85

| Example No. | R | yield (%) | MASS spectrum (APCIMS, m/z) |
|---|---|---|---|
| 53-1 | benzyl-NH— | 71 | 480(M+H)+ |
| 53-2 | t-butyl-O-CO-CH2-NH— | 39 | 504(M+H)+ |
| 53-3 | (2-pyridinyl)methyl-NH— | 35 | 481(M+H)+ |

Example 54

In the same manner as in Example 1-1 using ethyl 2-(2,3-dihydro-1H-indol-1-yl)-4-[(3-phenylpropyl)amino]-5-pyrimidinecarboxylate as a starting material, compounds of Examples 54-1 to 54-4 were synthesized.

Example 54-1: ethyl 2-[({2-(2,3-dihydro-1H-indol-1-yl)-4-[(3-phenylpropyl)amino]-5-pyrimidinyl}carbonyl)amino]acetate Example 54-2: N-benzyl-2-(2,3-dihydro-1H-indol-1-yl)-4-[(3-phenylpropyl)amino]-5-pyrimidinecarboxamide Example 54-3: t-butyl 2-[({2-(2,3-dihydro-1H-indol-1-yl)-4-[(3-phenylpropyl)amino]-5-pyrimidinyl}carbonyl)amino]acetate Example 54-4: 2-(2,3-dihydro-1H-indol-1-yl)-4-[(3-phenylpropyl)amino]-N-(4-pyridinylmethyl)-5-pyrimidinecarboxamide Respective structural formulas and MASS spectrum data are shown in the following Table.

TABLE 86

| Example No. | R | yield (%) | MASS spectrum (APCIMS, m/z) |
|---|---|---|---|
| 54-1 | EtO2C-CH2-NH— | 78 | 460(M+H)+ |
| 54-2 | benzyl-NH— | 69 | 464(M+H)+ |
| 54-3 | t-butyl-O-CO-CH2-NH— | 55 | 488(M+H)+ |
| 54-4 | (4-pyridinyl)methyl-NH— | 20 | 465(M+H)+ |

Example 55

In the same manner as in Example 1-1 using ethyl 2-(2,3-dihydro-1H-indol-1-yl)-4-[(4-methoxyphenethyl)amino]-5-pyrimidinecarboxylate as a starting material, compounds of Examples 55-1 to 55-4 were synthesized.

Example 55-1: ethyl 2-[({2-(2,3-dihydro-1H-indol-1-yl)-4-[(4-methoxyphenethyl)amino]-5-pyrimidinyl}carbonyl)amino]acetate Example 55-2: N-benzyl-2-(2,3-dihydro-1H-indol-1-yl)-4-[(4-methoxyphenethyl)amino]-5-pyrimidinecarboxamide Example 55-3: t-butyl 2-[({2-(2,3-dihydro-1H-indol-1-yl)-4-[(4-methoxyphenethyl)amino]-5-pyrimidinyl}carbonyl)amino]acetate Example 55-4: 2-(2,3-dihydro-1H-indol-1-yl)-4-[(4-methoxyphenethyl)amino]-N-(4-pyridinylmethyl)-5-pyrimidinecarboxamide Respective structural formulas and MASS spectrum data are shown in the following Table.

TABLE 87

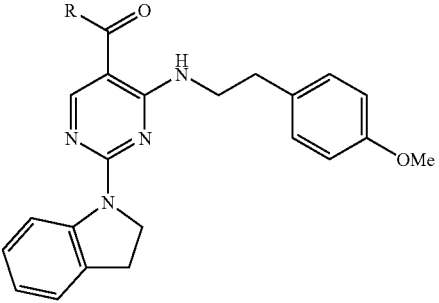

| Example No. | R | yield (%) | MASS spectrum (APCIMS, m/z) |
|---|---|---|---|
| 55-1 | 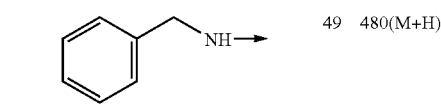 EtO₂C⁀NH→ | 73 | 476(M+H)⁺ |
| 55-2 | 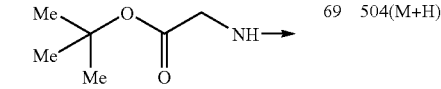 ⌬-NH→ | 49 | 480(M+H)⁺ |
| 55-3 | 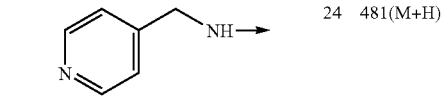 Me₃C-O-C(O)-CH₂-NH→ | 69 | 504(M+H)⁺ |
| 55-4 | 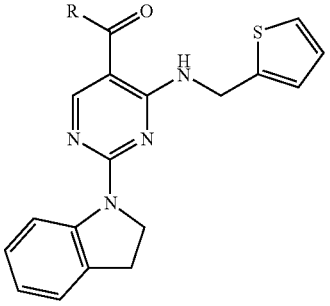 pyridyl-CH₂-NH→ | 24 | 481(M+H)⁺ |

Example 56

In the same manner as in Example 1-1 using ethyl 2-(2,3-dihydro-1H-indol-1-yl)-4-[(2-thienylmethyl)amino]-5-pyrimidinecarboxylate as a starting material, compounds of Examples 56-1 to 56-4 were synthesized.

Example 56-1: ethyl 2-[({2-(2,3-dihydro-1H-indol-1-yl)-4-[(2-thienylmethyl)amino]-5-pyrimidinyl}carbonyl)amino]acetate Example 56-2: N-benzyl-2-(2,3-dihydro-1H-indol-1-yl)-4-[(2-thienylmethyl)amino]-5-pyrimidinecarboxamide Example 56-3: t-butyl 2-[({2-(2,3-dihydro-1H-indol-1-yl)-4-[(2-thienylmethyl)amino]-5-pyrimidinyl}carbonyl)amino]acetate Example 56-4: 2-(2,3-dihydro-1H-indol-1-yl)-N-(4-pyridinylmethyl)-4-[(2-thienylmethyl)amino]-5-pyrimidinecarboxamide Respective structural formulas, MASS spectrum data and NMR data are shown in the following Table.

TABLE 88

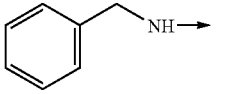

| Example No. | R | yield (%) | MASS spectrum (APCIMS, m/z) ¹H-NMR (δ ppm, CDCl₃) |
|---|---|---|---|
| 56-1 | Me₃C-O-C(O)-CH₂-NH→ | 41 | 438(M+H)⁺ |
| 56-2 | 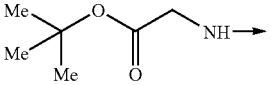 ⌬-NH→ | 45 | 442(M+H)⁺ 3.17(2H, t, J=9.2Hz), 4.28(2H, t, J=8.8Hz), 4.58(2H, d, J=5.6Hz), 4.93(2H, d, J=5.4Hz), 6.20(1H, br t, J=7.0 Hz), 6.90–7.08(3H, m), 7.10–7.40(7H, m), 8.31–8.39(2H, m), 9.00–9.10(1H, br) |
| 56-3 | Me₃C-O-C(O)-CH₂-NH→ | 49 | 466(M+H)⁺ |
| 56-4 | 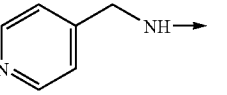 pyridyl-CH₂-NH→ | 38 | 443(M+H)⁺ |

Example 57

In the same manner as in Example 1-1 using ethyl 2-(2,3-dihydro-1H-indol-1-yl)-4-[(2-furylmethyl)amino]-5-pyrimidinecarboxylate as a starting material, compounds of Examples 57-1, 57-2 were synthesized.

Example 57-1: t-butyl 2-[({2-(2,3-dihydro-1H-indol-1-yl)-4-[(2-furylmethyl)amino]-5-pyrimidinyl}carbonyl)amino]acetate Example 57-2: (RS)-2-(2,3-dihydro-1H-indol-1-yl)-4-[(2-furylmethyl)amino]-N-(2-oxo-3-azepanyl)-5-pyrimidinecarboxamide Respective structural formulas and MASS spectrum data are shown in the following Table.

TABLE 89

| Example No. | R | yield (%) | MASS spectrum (APCIMS, m/z) |
|---|---|---|---|
| 57-1 | Me-C(Me)(Me)-O-C(=O)-CH2-NH→ | 50 | 450(M+H)+ |
| 57-2 | 3-amino-2-oxo-azepanyl-NH→ | 32 | 447(M+H)+ |

Example 58

In the same manner as in Example 1-1 using ethyl 2-(2,3-dihydro-1H-indol-1-yl)-4-[(3-fluorobenzyl)amino]-5-pyrimidinecarboxylate as a starting material, compounds of Examples 58-1 to 58-6 were synthesized.

Example 58-1: t-butyl 2-[({2-(2,3-dihydro-1H-indol-1-yl)-4-[(3-fluorobenzyl)amino]-5-pyrimidinyl}carbonyl)amino]acetate Example 58-2: N-benzyl-2-(2,3-dihydro-1H-indol-1-yl)-4-[(3-fluorobenzyl)amino]-5-pyrimidinecarboxamide Example 58-3: ethyl 2-[({2-(2,3-dihydro-1H-indol-1-yl)-4-[(3-fluorobenzyl)amino]-5-pyrimidinyl}carbonyl)amino]acetate Example 58-4: 2-(2,3-dihydro-1H-indol-1-yl)-4-[(3-fluorobenzyl)amino]-N-(4-pyridinylmethyl)-5-pyrimidinecarboxamide Example 58-5: (RS)-2-(2,3-dihydro-1H-indol-1-yl)-4-[(3-fluorobenzyl)amino]-N-(2-oxo-3-piperidinyl)-5-pyrimidinecarboxamide Example 58-6: (RS)-2-(2,3-dihydro-1H-indol-1-yl)-4-[(3-fluorobenzyl)amino]-N-(2-oxo-3-azepanyl)-5-pyrimidinecarboxamide Respective structural formulas and MASS spectrum data are shown in the following Table.

TABLE 90

| Example No. | R | yield (%) | MASS spectrum (APCIMS, m/z) |
|---|---|---|---|
| 58-1 | Me-C(Me)(Me)-O-C(=O)-CH2-NH→ | 70 | 478(M+H)+ |
| 58-2 | benzyl-NH→ | 32 | 454(M+H)+ |
| 58-3 | EtO2C-CH2-NH→ | 25 | 450(M+H)+ |
| 58-4 | 4-pyridinylmethyl-NH→ | 18 | 455(M+H)+ |
| 58-5 | 2-oxo-3-piperidinyl-NH→ | 26 | 461(M+H)+ |
| 58-6 | 3-amino-2-oxo-azepanyl-NH→ | 5 | 475(M+H)+ |

Example 59

In the same manner as in Example 1-1 using ethyl 2-(2,3-dihydro-1H-indol-1-yl)-4-[(4-methoxybenzyl)amino]-5-pyrimidinecarboxylate as a starting material, compounds of Examples 59-1 to 59-6 were synthesized.

Example 59-1: t-butyl 2-[({2-(2,3-dihydro-1H-indol-1-yl)-4-[(4-methoxybenzyl)amino]-5-pyrimidinyl}carbonyl)amino]acetate Example 59-2: N-benzyl-2-(2,3-dihydro-1H-indol-1-yl)-4-[(4-methoxybenzyl)amino]-5-pyrimidinecarboxamide Example 59-3: ethyl 2-[({2-(2,3-dihydro-1H-indol-1-yl)-4-[(4-methoxybenzyl)amino]-5-pyrimidinyl}carbonyl)amino]acetate Example 59-4: 2-(2,3-dihydro-1H-indol-1-yl)-4-[(4-methoxybenzyl)amino]-N-(4-pyridinylmethyl)-5-pyrimidinecarboxamide Example 59-5: (RS)-2-(2,3-dihydro-1H-indol-1-yl)-4-[(4-methoxybenzyl)amino]-N-(2-oxo-3-azepanyl)-5-pyrimidinecarboxamide Example 59-6: 2-(2,3-dihydro-1H-indol-1-yl)-4-[(4-methoxybenzyl)amino]-N-(2-pyridinylmethyl)-5-pyrimidinecarboxamide Respective structural formulas and MASS spectrum data are shown in the following Table.

TABLE 91

| Example No. | R | yield (%) | MASS spectrum (APCIMS, m/z) |
|---|---|---|---|
| 59-1 | Me-C(Me)(Me)-O-C(O)-CH2-NH— | 70 | 490(M+H)+ |
| 59-2 | PhCH2-NH— | 28 | 466(M+H)+ |
| 59-3 | EtO2C-CH2-NH— | 62 | 462(M+H)+ |
| 59-4 | (4-pyridyl)CH2-NH— | 12 | 467(M+H)+ |
| 59-5 | (2-oxo-azepan-3-yl)-NH— | 25 | 487(M+H)+ |
| 59-6 | (2-pyridyl)CH2-NH— | 72 | 479(M+H)+ |

Example 60

In the same manner as in Example 1-1 using ethyl 4-[(2,6-difluorobenzyl)amino]-2-(2,3-dihydro-1H-indol-1-yl)-5-pyrimidinecarboxylate as a starting material, compounds of Examples 60-1 to 60-6 were synthesized.

Example 60-1: t-butyl 2-({[4-[(2,6-difluorobenzyl)amino]-2-(2,3-dihydro-1H-indol-1-yl)-5-pyrimidinyl]carbonyl}amino)-acetate Example 60-2: N-benzyl-4-[(2,6-difluorobenzyl)amino]-2-(2,3-dihydro-1H-indol-1-yl)-5-pyrimidinecarboxamide Example 60-3: ethyl 2-({[4-[(2,6-difluorobenzyl)amino]-2-(2,3-dihydro-1H-indol-1-yl)-5-pyrimidinyl]carbonyl}amino)acetate Example 60-4: 4-[(2,6-difluorobenzyl)amino]-2-(2,3-dihydro-1H-indol-1-yl)-N-(4-pyridinylmethyl)-5-pyrimidinecarboxamide Example 60-5: (RS)-4-[(2,6-difluorobenzyl)amino]-2-(2,3-dihydro-1H-indol-1-yl)-N-(2-oxo-3-azepanyl)-5-pyrimidinecarboxamide Example 60-6: (RS)-4-[(2,6-difluorobenzyl)amino]-2-(2,3-dihydro-1H-indol-1-yl)-N-(2-oxo-3-piperidinyl)-5-pyrimidinecarboxamide Respective structural formulas and MASS spectrum data are shown in the following Table.

TABLE 92

| Example No. | R | yield (%) | MASS spectrum (APCIMS, m/z) |
|---|---|---|---|
| 60-1 | Me-C(Me)(Me)-O-C(O)-CH2-NH— | 53 | 496(M+H)+ |
| 60-2 | PhCH2-NH— | 18 | 472(M+H)+ |
| 60-3 | EtO2C-CH2-NH— | 52 | 468(M+H)+ |
| 60-4 | (4-pyridyl)CH2-NH— | 13 | 473(M+H)+ |
| 60-5 | (2-oxo-azepan-3-yl)-NH— | 25 | 493(M+H)+ |
| 60-6 | (2-oxo-piperidin-3-yl)-NH— | 10 | 479(M+H)+ |

Example 61

In the same manner as in Example 1-1 using ethyl 2-(2,3-dihydro-1H-indol-1-yl)-4-[(4-methylbenzyl)amino]-5-pyrimidinecarboxylate as a starting material, compounds of Examples 61-1 to 61-4 were synthesized.

Example 61-1: t-butyl 2-[({2-(2,3-dihydro-1H-indol-1-yl)-4-[(4-methylbenzyl)amino]-5-pyrimidinyl}carbonyl)amino]acetate Example 61-2: N-benzyl-2-(2,3-dihydro-1H-indol-1-yl)-4-[(4-methylbenzyl)amino]-5-pyrimidinecarboxamide Example 61-3: (RS)-2-(2,3-dihydro-1H-indol-1-yl)-4-[(4-methylbenzyl)amino]-N-(2-oxo-3-azepanyl)-5-pyrimidinecarboxamide Respective structural formulas and MASS spectrum data are shown in the following Table.

TABLE 93

| Example No. | R | yield (%) | MASS spectrum (APCIMS, m/z) |
|---|---|---|---|
| 61-1 | Me-C(Me)(Me)-O-C(O)-CH2-NH— | 80 | 474(M+H)+ |
| 61-2 | PhCH2-NH— | 15 | 450(M+H)+ |
| 61-3 | 2-oxo-azepan-3-yl-NH— | 7 | 471(M+H)+ |

Example 62

In the same manner as in Example 1-1 using ethyl 2-(2,3-dihydro-1H-indol-1-yl)-4-[(2-pyridinylmethyl)amino]-5-pyrimidinecarboxylate as a starting material, compounds of Examples 62-1 to 62-4 were synthesized.

Example 62-1: t-butyl 2-[({2-(2,3-dihydro-1H-indol-1-yl)-4-[(2-pyridinylmethyl)amino]-5-pyrimidinyl}carbonyl)amino]acetate Example 62-2: N-benzyl-2-(2,3-dihydro-1H-indol-1-yl)-4-[(2-pyridinylmethyl)amino]-5-pyrimidinecarboxamide Example 62-3: ethyl 2-[({2-(2,3-dihydro-1H-indol-1-yl)-4-[(2-pyridinylmethyl)amino]-5-pyrimidinyl}carbonyl)amino]acetate Example 62-4: (RS)-2-(2,3-dihydro-1H-indol-1-yl)-N-(2-oxo-3-azepanyl)-4-[(2-pyridinylmethyl)amino]-5-pyrimidinecarboxamide Respective structural formulas and MASS spectrum data are shown in the following Table.

TABLE 94

| Example No. | R | yield (%) | MASS spectrum (APCIMS, m/z) |
|---|---|---|---|
| 62-1 | Me-C(Me)(Me)-O-C(O)-CH2-NH— | 48 | 461(M+H)+ |
| 62-2 | PhCH2-NH— | 45 | 437(M+H)+ |
| 62-3 | EtO2C-CH2-NH— | 32 | 433(M+H)+ |
| 62-4 | 2-oxo-azepan-3-yl-NH— | 5 | 458(M+H)+ |

Example 63

In the same manner as in Example 1-1 using ethyl 2-(2,3-dihydro-1H-indol-1-yl)-4-[(4-pyridinylmethyl)amino]-5-pyrimidinecarboxylate as a starting material, compounds of Examples 63-1 to 63-4 were synthesized.

Example 63-1: t-butyl 2-[({2-(2,3-dihydro-1H-indol-1-yl)-4-[(4-pyridinylmethyl)amino]-5-pyrimidinyl}carbonyl)amino]acetate Example 63-2: N-benzyl-2-(2,3-dihydro-1H-indol-1-yl)-4-[(4-pyridinylmethyl)amino]-5-pyrimidinecarboxamide Example 63-3: ethyl 2-[({2-(2,3-dihydro-1H-indol-1-yl)-4-[(4-pyridinylmethyl)amino]-5-pyrimidinyl}carbonyl)amino]acetate Example 63-4: 2-(2,3-dihydro-1H-indol-1-yl)-N-(ethoxyethyl)-4-[(4-pyridinylmethyl)amino]-5-pyrimidinecarboxamide Respective structural formulas and MASS spectrum data are shown in the following Table.

TABLE 95

| Example No. | R | yield (%) | MASS spectrum (APCIMS, m/z) |
|---|---|---|---|
| 63-1 | Me-C(Me)(Me)-O-C(O)-CH2-NH— | 53 | 461(M+H)+ |
| 63-2 | PhCH2-NH— | 62 | 437(M+H)+ |
| 63-3 | EtO2C-CH2-NH— | 78 | 433(M+H)+ |
| 63-4 | EtO-CH2CH2-NH— | 45 | 419(M+H)+ |

Example 64

In the same manner as in Example 1-1 using ethyl (RS)-4-[(4-methoxybenzyl)amino]-2-(2-methyl-2,3-dihydro-1H-indol-1-yl)-5-pyrimidinecarboxylate as a starting material, (RS)-4-[(4-methoxybenzyl)amino]-2-(2-methyl-2,3-dihydro-1H-indol-1-yl)-N-(2-pyridinylmethyl)-5-pyrimidinecarboxamide was synthesized.

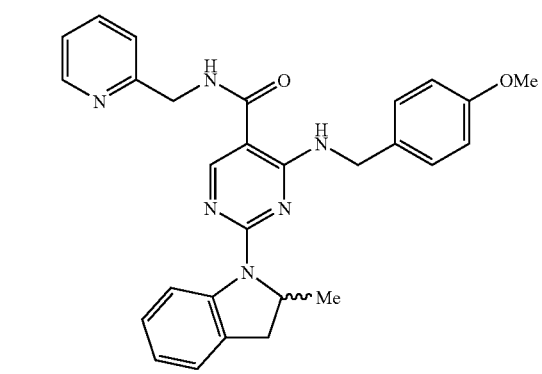

Yield 71%, MASS spectrum (APCIMS, m/z): 481

Example 65

In the same manner as in Example 1-1 using ethyl (RS)-4-[(1,3-benzodioxol-5-ylmethyl)amino]-2-(2-methyl-2,3-dihydro-1H-indol-1-yl)-5-pyrimidinecarboxylate as a starting material, (RS)-4-[(1,3-benzodioxol-5-ylmethyl)amino]-2-(2-methyl-2,3-dihydro-1H-indol-1-yl)-N-(2-pyridinylmethyl)-5-pyrimidinecarboxamide was synthesized.

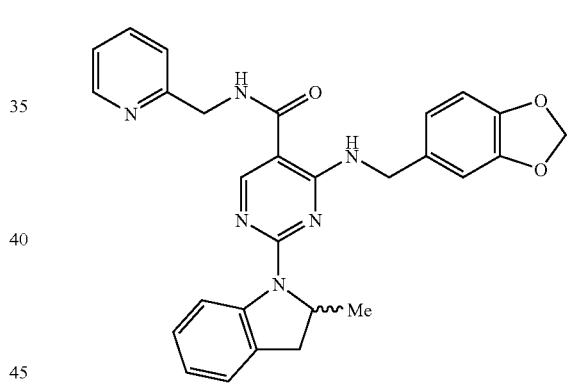

Yield 38%, MASS spectrum (APCIMS, m/z): 495

Example 66-1

2-(2,3-dihydro-1H-indol-1-yl)-4-[(4-methoxybenzyl)oxy]-N-[(3S)-2-oxoazepanyl]-5-pyrimidinecarboxamide To a suspension of ethyl 2-(2,3-dihydro-1H-indol-1-yl)-4-[(4-methoxybenzyl)oxy]-5-pyrimidinecarboxylate (5.5 g, 13.6 mmol) in ethanol (50 mL) were added 10% aqueous sodium hydroxide solution (30 mL) and tetrahydrofuran (30 mL) and the mixture was heated under reflux for 30 min. The reaction mixture was allowed to cool to room temperature and 1N hydrochloric acid was added to adjust the reaction mixture to pH 5. The precipitated crystals were collected by filtration, washed several times with water, and dried with heating under vacuum to give 2-(2,3-dihydro-1H-indol-1- yl)-4-[(4-methoxybenzyl)oxy]-5-pyrimidinecarboxylic acid (4.9 g, 96%) as crystals. A suspension of the obtained carboxylic acid (564 mg, 1.5 mmol), L-α-amino-ε-caprolactam (384 mg, 3.0 mmol), 1-ethyl-3-(3-dimethylaminopropyl)carbodiimide hydrochloride (612 mg, 3.0 mmol) and 1-hydroxybenzotriazole (408 mg, 3.0 mmol) in dichloromethane (2 mL) was stirred at room temperature for 18 h. Water and ethyl acetate were added to the reaction mixture and the organic layer was concentrated under reduced pressure. The obtained residue was subjected to silica gel chromatography and eluted with ethyl acetate to give the title compound (650 mg, 89%).

In the same manner as in Example 66-1, compounds of Examples 66-2 to 66-25 were synthesized from ethyl 2-(2,3-dihydro-1H-indol-1-yl)-4-[(4-methoxybenzyl)oxy]-5-pyrimidinecarboxylate, ethyl 4-(1,3-benzodioxol-5-ylmethoxy)-2-(2,3-dihydro-1H-indol-1-yl)-5-pyrimidinecarboxylate, ethyl 2-(2,3-dihydro-1H-indol-1-yl)-4-[(4-isopropoxybenzyl)oxy]-5-pyrimidinecarboxylate, ethyl 2-(2,3-dihydro-1H-indol-1-yl)-4-[(4-ethoxybenzyl)oxy]-5-pyrimidinecarboxylate, ethyl 2-(2,3-dihydro-1H-indol-1-yl)-4-[(3-fluoro-4-methoxybenzyl)oxy]-5-pyrimidinecarboxylate, ethyl 2-(2,3-dihydro-1H-indol-1-yl)-4-[(4-methoxy-3-methylbenzyl)oxy]-5-pyrimidinecarboxylate, ethyl 4-[(3-chloro-4-methoxybenzyl)oxy]-2-(2,3-dihydro-1H-indol-1-yl)-5-pyrimidinecarboxylate, ethyl 4-(2,3-dihydro-1-benzofuran-5-ylmethoxy)-2-(2,3-dihydro-1H-indol-1-yl)-5-pyrimidinecarboxylate, ethyl 4-[(4-methoxybenzyl)oxy]-2-(5-methyl-2,3-dihydro-1H-indol-1-yl)-5-pyrimidinecarboxylate, ethyl (RS)-4-[(4-methoxybenzyl)oxy]-2-(2-methyl-2,3-dihydro-1H-indol-1-yl)-5-pyrimidinecarboxylate, ethyl (RS)-4-[(4-methoxybenzyl)oxy]-2-(3-methyl-2,3-dihydro-1H-indol-1-yl)-5-pyrimidinecarboxylate, ethyl (R)-4-[(4-methoxybenzyl)oxy]-2-(2-methyl-2,3-dihydro-1H-indol-1-yl)-5-pyrimidinecarboxylate, ethyl (R)-4-[(3-fluoro-4-methoxybenzyl)oxy]-2-(2-methyl-2,3-dihydro-1H-indol-1-yl)-5-pyrimidinecarboxylate, ethyl (R)-4-[(3-chloro-4-methoxybenzyl)oxy]-2-(2-methyl-2,3-dihydro-1H-indol-1-yl)-5-pyrimidinecarboxylate, ethyl (R)-4-[(2-fluoro-4-methoxybenzyl)oxy]-2-(2-methyl-2,3-dihydro-1H-indol-1-yl)-5-pyrimidinecarboxylate, ethyl (R)-4-[(2-chloro-4-methoxybenzyl)oxy]-2-(2-methyl-2,3-dihydro-1H-indol-1-yl)-5-pyrimidinecarboxylate, ethyl (S)-4-[(4-methoxybenzyl)oxy]-2-(2-methyl-2,3-dihydro-1H-indol-1-yl)-5-pyrimidinecarboxylate, ethyl 4-[(1,3-benzodioxol-5-ylmethyl)amino]-2-(2,3-dihydro-1H-indol-1-yl)-5-pyrimidinecarboxylate, ethyl 2-(2,3-dihydro-1H-indol-1-yl)-4-[(4-methoxybenzyl)amino]-5-pyrimidinecarboxylate, ethyl (RS)-4-[(4-methoxybenzyl)amino]-2-(2-methyl-2,3-dihydro-1H-indol-1-yl)-5-pyrimidinecarboxylate and ethyl (RS)-4-[(1,3-benzodioxol-5-ylmethyl)amino]-2-(2-methyl-2,3-dihydro-1H-indol-1-yl)-5-pyrimidinecarboxylate.

Example 66-2: 2-(2,3-dihydro-1H-indol-1-yl)-4-[(4-methoxybenzyl)oxy]-N-[(3R)-2-oxoazepanyl]-5-pyrimidinecarboxamide Example 66-3: 4-(1,3-benzodioxol-5-ylmethoxy)-2-(2,3-dihydro-1H-indol-1-yl)-4-[(4-methoxybenzyl)oxy]-N-[(3S)-2-oxoazepanyl]-5-pyrimidinecarboxamide Example 66-4: 2-(2,3-dihydro-1H-indol-1-yl)-4-[(4-isopropoxybenzyl)oxy]-N-[(3S)-2-oxoazepanyl]-5-pyrimidinecarboxamide Example 66-5: 2-(2,3-dihydro-1H-indol-1-yl)-4-[(4-ethoxybenzyl)oxy]-N-[(3S)-2-oxoazepanyl]-5-pyrimidinecarboxamide Example 66-6: 2-(2,3-dihydro-1H-indol-1-yl)-4-[(3-fluoro-4-methoxybenzyl)oxy]-N-[(3S)-2-oxoazepanyl]-5-pyrimidinecarboxamide Example 66-7: 2-(2,3-dihydro-1H-indol-1-yl)-4-[(4-methoxy-3-methylbenzyl)oxy]-N-[(3S)-2-oxoazepanyl]-5-pyrimidinecarboxamide Example 66-8: 4-[(3-chloro-4-methoxybenzyl)oxy]-2-(2,3-dihydro-1H-indol-1-yl)-N-[(3S)-2-oxoazepanyl]-5-pyrimidinecarboxamide Example 66-9: 4-(2,3-dihydro-1-benzofuran-5-ylmethoxy)-2-(2,3-dihydro-1H-indol-1-yl)-N-[(3S)-2-oxoazepanyl]-5-pyrimidinecarboxamide Example 66-10: 4-[(4-methoxybenzyl)oxy]-2-(5-methyl-2,3-dihydro-1H-indol-1-yl)-N-[(3S)-2-oxoazepanyl]-5-pyrimidinecarboxamide Example 66-11: 4-[(4-methoxybenzyl)oxy]-2-[(2RS)-2-methyl-2,3-dihydro-1H-indol-1-yl]-N-[(3S)-2-oxoazepanyl]-5-pyrimidinecarboxamide Example 66-12: 4-[(4-methoxybenzyl)oxy]-2-[(2RS)-2-methyl-2,3-dihydro-1H-indol-1-yl]-N-[(3R)-2-oxoazepanyl]-5-pyrimidinecarboxamide Example 66-13: 4-[(4-methoxybenzyl)oxy]-2-[(3RS)-3-methyl-2,3-dihydro-1H-indol-1-yl]-N-[(3S)-2-oxoazepanyl]-5-pyrimidinecarboxamide Example 66-14: 4-[(4-methoxybenzyl)oxy]-2-[(2R)-2-methyl-2,3-dihydro-1H-indol-1-yl]-N-[(3S)-2-oxoazepanyl]-5-pyrimidinecarboxamide Example 66-15: 4-[(4-methoxybenzyl)oxy]-2-[(2R)-2-methyl-2,3-dihydro-1H-indol-1-yl]-N-[(3R)-2-oxoazepanyl]-5-pyrimidinecarboxamide Example 66-16: 2-[(2R)-2-methyl-2,3-dihydro-1H-indol-1-yl]-4-[(3-fluoro-4-methoxybenzyl)oxy]-N-[(3S)-2-oxoazepanyl]-5-pyrimidinecarboxamide Example 66-17: 4-[(3-chloro-4-methoxybenzyl)oxy]-2-[(2R)-2-methyl-2,3-dihydro-1H-indol-1-yl]-N-[(3S)-2-oxoazepanyl]-5-pyrimidinecarboxamide Example 66-18: 2-[(2R)-2-methyl-2,3-dihydro-1H-indol-1-yl]-4-[(2-fluoro-4-methoxybenzyl)oxy]-N-[(3S)-2-oxoazepanyl]-5-pyrimidinecarboxamide Example 66-19: 4-[(2-chloro-4-methoxybenzyl)oxy]-2-[(2R)-2-methyl-2,3-dihydro-1H-indol-1-yl]-N-[(3S)-2-oxoazepanyl]-5-pyrimidinecarboxamide Example 66-20: 4-[(4-methoxybenzyl)oxy]-2-[(2S)-2-methyl-2,3-dihydro-1H-indol-1-yl]-N-[(3S)-2-oxoazepanyl]-5-pyrimidinecarboxamide Example 66-21: 4-[(4-methoxybenzyl)oxy]-2-[(2S)-2-methyl-2,3-dihydro-1H-indol-1-yl]-N-[(3R)-2-oxoazepanyl]-5-pyrimidinecarboxamide Example 66-22: 4-[(1,3-benzodioxol-5-ylmethyl)amino]-2-(2,3-dihydro-1H-indol-1-yl)-4-[(4-methoxybenzyl)amino]-N-[(3S)-2-oxoazepanyl]-5-pyrimidinecarboxamide Example 66-23: 2-(2,3-dihydro-1H-indol-1-yl)-4-[(4-methoxybenzyl)amino]-N-[(3S)-2-oxoazepanyl]-5-pyrimidinecarboxamide Example 66-24: 4-[(4-methoxybenzyl)amino]-2-[(2RS)-2-methyl-2,3-dihydro-1H-indol-1-yl]-N-[(3S)-2-oxoazepanyl]-5-pyrimidinecarboxamide Example 66-25: 4-[(1,3-benzodioxol-5-ylmethyl)amino]-2-[(2RS)-2-methyl-2,3-dihydro-1H-indol-1-yl]-4-[(4-methoxybenzyl)oxy]-N-[(3S)-2-oxoazepanyl]-5-pyrimidinecarboxamide Respective structural formulas, MASS spectrum data and NMR data are shown in the following Table.

TABLE 96

| Example No. | R | X | yield (%) | MASS spectrum (APCIMS, m/z) $^1$H-NMR($\delta$ ppm, CDCl$_3$) |
|---|---|---|---|---|
| 66-1 | | -O-C₆H₄-OMe (para) | 43 | 488(M+H)⁺ |
| 66-2 | | -O-C₆H₄-OMe (para) | 29 | 488(M+H)⁺ |
| 66-3 | | -O-CH₂-(methylenedioxyphenyl) | 90 | 502(M+H)⁺ |
| 66-4 | | -O-C₆H₄-OiPr (para) | 62 | 516(M+H)⁺ |
| 66-5 | | -O-C₆H₄-OEt (para) | 96 | 502(M+H)⁺ 1.20–1.63(5H, m), 1.70–2.24(4H, m), 3.17–3.40(4H, m), 4.02(2H, q, J=7.0Hz), 4.31(2H, t, J=8.0Hz), 4.68–4.80(1H, m), 5.67(2H, s), 5.91(1H, br s), 6.82–7.03(3H, m), 7.17–7.30(2H, m), 7.50(2H, d, J=8.4Hz), 8.36(1H, br s), 8.80(1H, br d, J=6.8Hz), 9.08(1H, s) |

TABLE 96-continued

| Example No. | R | X | yield (%) | MASS spectrum (APCIMS, m/z) $^1$H-NMR(δ ppm, CDCl$_3$) |
|---|---|---|---|---|
| 66-6 | (3-aminoazepan-2-one) | 3-F-4-OMe-benzyloxy | 70 | 506(M+H)$^+$ |
| 66-7 | (3-aminoazepan-2-one) | 3-Me-4-OMe-benzyloxy | 50 | 502(M+H)$^+$ |
| 66-8 | (3-aminoazepan-2-one) | 3-Cl-4-OMe-benzyloxy | 34 | 522(M+H)$^+$ |
| 66-9 | (3-aminoazepan-2-one) | 2,3-dihydrobenzofuran-5-ylmethoxy | 63 | 500(M+H)$^+$ 1.15–2.23(6H, m), 3.14–3.32(6H, m), 4.32(2H, t, J=8.4Hz), 4.57(2H, t, J=8.8Hz), 4.70–4.80(1H, m), 5.65(2H, s), 5.89 (1H, br t, J=7.0Hz), 6.77 (1H, d, J=8.0Hz), 7.00 (1H, t, J=6.2Hz), 7.20–7.38(2H, m), 7.43(1H, br s), 8.40(1H, br d, J=7.0Hz), 8.78(1H, br d, J=7.0Hz), 9.09(1H, s) |

TABLE 97
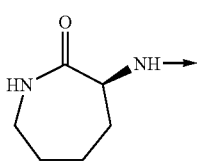
| Example No. | R | X | yield (%) | MASS spectrum (APCIMS, m/z) $^1$H-NMR($\delta$ ppm, CDCl$_3$) |
|---|---|---|---|---|
| 66-10 | 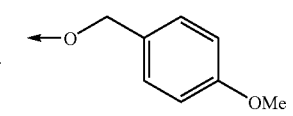 | 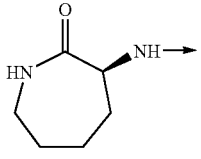 | 61 | 502(M+H)$^+$ |
TABLE 98
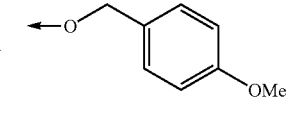
| Example No. | R | X | yield (%) | MASS spectrum (APCIMS, m/z) $^1$H-NMR($\delta$ ppm, CDCl$_3$) |
|---|---|---|---|---|
| 66-11 | 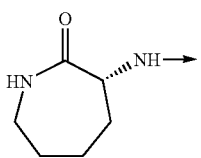 | 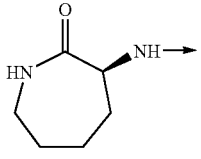 | 50 | 502(M+H)$^+$ 1.30–1.62(5H, m), 1.70–2.24(4H, m), 2.71(1H, d, J=16.2Hz), 3.20–3.50 (3H, m), 3.79(3H, s), 4.78(1H, dd, J=6.2, 9.8Hz), 5.02(1H, quintet, J=8.0Hz), 5.65(2H, s), 6.24(1H, br t, J=7.0Hz), 6.82–7.03(3H, m), 7.18–7.30(2H, m), 7.50(2H, d, J=8.8Hz), 8.31(1H, d, J=8.8Hz), 8.77(1H, d, J=4.8Hz), 9.07(1H, s) |
| 66-12 | 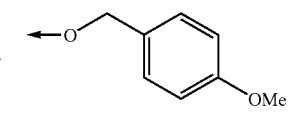 | 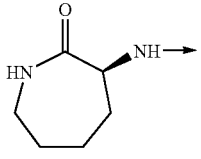 | 92 | 502(M+H)$^+$ |

TABLE 99

[Structure: pyrimidine with R-C(=O)- at position 5, X at position 4, and N-linked 3-methylindoline (wavy bond to Me) at position 2]

| Example No. | R | X | yield (%) | MASS spectrum (APCIMS, m/z) $^1$H-NMR($\delta$ ppm, CDCl$_3$) |
|---|---|---|---|---|
| 66-13 | [3-amino-azepan-2-one, NH linker] | [4-methoxybenzyloxy, -O-CH$_2$-C$_6$H$_4$-OMe] | 40 | 502(M+H)$^+$ |

TABLE 100

[Structure: pyrimidine with R-C(=O)- at position 5, X at position 4, and N-linked (2S)-2-methylindoline at position 2]

| Example No. | R | X | yield (%) | MASS spectrum (APCIMS, m/z) $^1$H-NMR($\delta$ ppm, CDCl$_3$) |
|---|---|---|---|---|
| 66-14 | [3-amino-azepan-2-one, NH linker] | [4-methoxybenzyloxy, -O-CH$_2$-C$_6$H$_4$-OMe] | 75 | 502(M+H)$^+$ 1.30–1.60(5H, m), 1.70–2.24(4H, m), 2.71(1H, d, J=15.8Hz), 3.22–3.50 (3H, m), 3.80(3H, s), 4.74(1H, dd, J=6.4, 10.0Hz), 5.03(1H, quintet, J=8.0Hz), 5.66 (2H, s), 5.90–6.02(1H br), 6.84–7.04(3H, m), 7.20–7.30(2H, m), 7.50 (2H, d, J=8.4Hz), 8.32 (1H, d, J=7.6Hz), 8.77 (1H, d, J=6.6Hz), 9.08 (1H, s) |

TABLE 100-continued

| Example No. | R | X | yield (%) | MASS spectrum (APCIMS, m/z) $^1$H-NMR($\delta$ ppm, CDCl$_3$) |
|---|---|---|---|---|
| 66-15 | (3-aminoazepan-2-one) | 4-OMe-benzyloxy | 55 | 502(M+H)$^+$ 1.30–1.70(5H, m), 1.73–2.23(4H, m), 2.71(1H, d, J=16.8Hz), 3.22–3.50 (3H, m), 3.80(3H, s), 4.75(1H, dd, J=5.8, 9.4Hz), 4.90–5.08(1H, m), 5.65(2H, s), 5.95 (1H, br t, J=7.0Hz), 6.88–7.05(3H, m), 7.18–7.30(2H, m), 7.50(2H, d, J=8.6Hz), 8.32(1H, d, J=7.6Hz), 8.77(1H, d, J=5.6Hz), 9.07(1H, s) |
| 66-16 | (3-aminoazepan-2-one) | 3-F-4-OMe-benzyloxy | 77 | 1.34(3H, d, J=6.6Hz), 1.40–1.70(3H, m), 1.80–2.28(4H, m), 2.72(1H, d, J=16.0Hz), 3.22–3.50 (3H, m), 3.80(3H, s), 4.75(1H, dd, J=6.0, 11.4Hz), 5.02(1H, quintet, J=7.0Hz), 5.63 (2H, s), 5.91(1H, t, J=6.0Hz), 6.90–7.08(2H, m), 7.19–7.37(4H, m), 8.28(1H, d, J=7.0Hz), 8.76(1H, d, J=5.0Hz), 9.08(1H, s) |
| 66-17 | (3-aminoazepan-2-one) | 3-Cl-4-OMe-benzyloxy | 79 | 1.35(3H, d, J=6.2Hz), 1.40–1.70(3H, m), 1.80–2.27(4H, m), 2.72(1H, d, J=14.6Hz), 3.25–3.50 (3H, m), 3.89(3H, s), 4.75(1H, dd, J=6.0, 10.0Hz), 5.00(1H, quintet, J=7.0Hz), 5.62 (2H, s), 5.91(1H, t, J=6.0Hz), 6.90–7.07(2H, m), 7.19–7.29(3H, m), 7.45(1H, dd, J=2.2, 8.4Hz), 7.58(1H, d, J=2.2Hz), 8.27(1H, d, J=6.6Hz), 8.75(1H, d, J=5.8Hz), 9.08(1H, s) |
| 66-18 | (3-aminoazepan-2-one) | 2-F-4-OMe-benzyloxy | 80 | 1.30–2.23(10H, m), 2.71 (1H, d, J=15.8Hz), 3.20–3.50(3H, m), 3.80(3H, s), 4.75(1H, dd, J=6.6, 11.2Hz), 4.96–5.13(1H, m), 5.70(2H, ABq), 5.90 (1H, t, J=7.0Hz), 6.63–6.76(2H, m), 7.01(1H, t, J=7.4Hz), 7.20–7.30 (2H, m), 7.50(1H, t, J=8.4Hz), 8.32(1H, d, J=7.8Hz), 8.70(1H, d, J=6.2Hz), 9.08(1H, s) |

TABLE 100-continued

| Example No. | R | X | yield (%) | MASS spectrum (APCIMS, m/z) $^1$H-NMR($\delta$ ppm, CDCl$_3$) |
|---|---|---|---|---|
| 66-19 | 3-amino-azepan-2-one (NH linker) | 2-chloro-4-methoxybenzyloxy | 79 | 1.28–1.70(6H, m), 1.71–2.26(4H, m), 2.70(1H, d, J=16.6Hz), 3.21–3.49 (3H, m), 3.80(3H, s), 4.77(1H, dd, J=6.4, 9.6Hz), 4.95–5.10(1H, m), 5.75(2H, ABq), 5.86 (1H, t, J=7.0Hz), 6.82 (1H, dd, J=2.6, 8.4Hz), 6.94–7.04(2H, m), 7.17–7.28(2H, m), 7.49(1H, d, J=8.8Hz), 8.24(1H, br d, J=5.4Hz), 8.67(1H, d, J=5.4Hz), 9.10(1H, s) |

TABLE 101

| Example No. | R | X | yield (%) | MASS spectrum (APCIMS, m/z) $^1$H-NMR($\delta$ ppm, CDCl$_3$) |
|---|---|---|---|---|
| 66-20 | 3-amino-azepan-2-one (NH linker) | 4-methoxybenzyloxy | 54 | 1.30–1.70(5H, m), 1.73–2.23(4H, m), 2.71(1H, d, J=16.8Hz), 3.22–3.50 (3H, m), 3.80(3H, s), 4.75(1H, dd, J=5.8, 9.4Hz), 4.90–5.08(1H, m), 5.65(2H, s), 5.95 (1H, br t, J=7.0Hz), 6.88–7.05(3H, m), 7.18–7.30(2H, m), 7.50(2H, d, J=8.6Hz), 8.32(1H, d, J=7.6Hz), 8.77(1H, d, J=5.6Hz), 9.07(1H, s) |

TABLE 101-continued
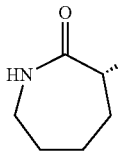
| Example No. | R | X | yield (%) | MASS spectrum (APCIMS, m/z) $^1$H-NMR($\delta$ ppm, CDCl$_3$) |
|---|---|---|---|---|
| 66-21 | 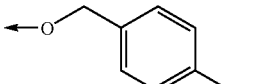 | 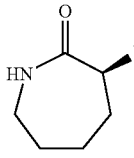 | 55 | 1.30–1.60(5H, m), 1.70–2.24(4H, m), 2.71(1H, d, J=15.8Hz), 3.22–3.50 (3H, m), 3.80(3H, s), 4.74(1H, dd, J=6.4, 10.0Hz), 5.03(1H, quintet, J=8.0Hz), 5.66 (2H, s), 5.90–6.02(1H br), 6.84–7.04(3H, m), 7.20–7.30(2H, m), 7.50 (2H, d, J=8.4Hz), 8.32 (1H, d, J=7.6Hz), 8.77 (1H, d, J=6.6Hz), 9.08 (1H, s) |
TABLE 102
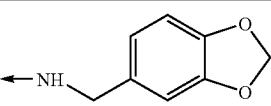
| Example No. | R | X | yield (%) | MASS spectrum (APCIMS, m/z) $^1$H-NMR($\delta$ ppm, CDCl$_3$) |
|---|---|---|---|---|
| 66-22 | 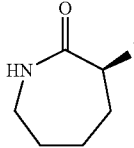 | 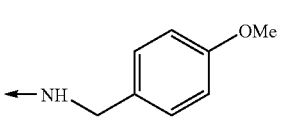 | 32 | 501(M+H)$^+$ |
| 66-23 | 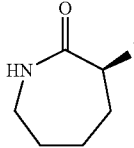 | 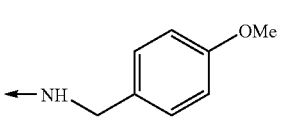 | 98 | 487(M+H)$^+$ |

TABLE 103

[Structure shown: pyrimidine core with R-C(=O) group, X substituent, and 2-methyl-2,3-dihydroindol-1-yl group]

| Example No. | R | X | yield (%) | MASS spectrum (APCIMS, m/z) $^1$H-NMR($\delta$ ppm, CDCl$_3$) |
|---|---|---|---|---|
| 66-24 | [3-amino-2-oxoazepanyl]-NH— | —NH-CH$_2$-C$_6$H$_4$-OMe | 92 | 501(M+H)$^+$ |
| 66-25 | [3-amino-2-oxoazepanyl]-NH— | —NH-CH$_2$-(benzo[1,3]dioxol-5-yl) | 32 | 515(M+H)$^+$ |

Example 67

2-(2,3-dihydro-1H-indol-1-yl)-4-hydroxy-N-[(3S)-2-oxoazepanyl]-5-pyrimidinecarboxamide

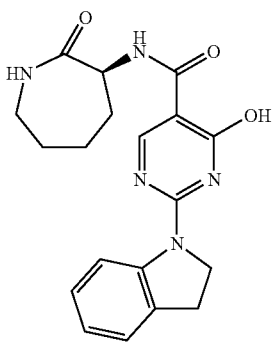

2-(2,3-Dihydro-1H-indol-1-yl)-4-[(4-methoxybenzyl)oxy]-N-[(3S)-2-oxoazepanyl]-5-pyrimidinecarboxamide (98 mg, 0.2 mmol) was dissolved in trifluoroacetic acid (0.5 mL) and the mixture was stirred at room temperature for 15 min. Water was added to the reaction mixture, and the precipitated crystals were collected by filtration, washed several times with water and ether, and dried with heating under vacuum to give the title compound (70 mg, 91%).

$^1$H-NMR ($\delta$ ppm, CDCl$_3$): 1.50–2.30 (4H, m), 3.20–3.40 (4H, m), 3.50–3.85 (2H, m), 4.32 (2H, t, J=8.0 Hz), 4.72–4.83 (1H, m), 6.63–6.74 (1H, m), 7.00–7.10 (1H, m), 7.17–7.28 (2H, m), 8.42 (1H, d, J=7.8 Hz), 8.83 (1H, s), 9.74 (1H, br s)

Example 68-1

4-({[2-(2,3-dihydro-1H-indol-1-yl)-5-({[(3S)-2-oxoazepanyl]amino}carbonyl)-4-pyrimidinyl]oxy}methyl)-phenylacetate To a solution of 2-(2,3-dihydro-1H-indol-1-yl)-4-hydroxy-N-[(3S)-2-oxoazepanyl]-5-pyrimidinecarboxamide (37 mg, 0.1 mmol) in N,N-dimethylformamide (1 mL) were added potassium carbonate (28 mg, 0.2 mmol), sodium iodide (14 mg, 0.1 mmol) and 4-chloromethylphenylacetate (0.023 mL, 0.15 mmol) and the mixture was stirred at 60° C. for 2 h. Water was added to the reaction mixture, and the precipitated crystals were collected by filtration, washed several times with water and ether, and dried with heating under vacuum to give the title compound (34 mg, 72%).

In the same manner as in Example 68-1, a compound of Example 68-2 was synthesized.

Example 68-2: 4-{[4-(acetylamino)benzyl]oxy}-2-(2,3-dihydro-1H-indol-1-yl)-N-[(3S)-2-oxoazepanyl]-5-pyrimidinecarboxamide Respective structural formulas and NMR data are shown in the following Table.

TABLE 104

[Structure: (S)-hexahydroazepinone-NH-C(O)- attached to pyrimidine with R substituent at 4-position and 2,3-dihydro-1H-indol-1-yl at 2-position]

| Example No. | R | yield (%) | ¹H-NMR (δ ppm, CDCl₃) |
|---|---|---|---|
| 68-1 | -O-CH₂-C₆H₄-OAc (para) | 72 | 1.30–1.70(6H, m), 1.70–2.35(4H, m), 3.14–3.40(3H, m), 4.29(2H, t, J=9.2Hz), 4.70–4.81(1H, m), 5.71(2H, s), 5.90(1H, br t, J=7.6Hz), 6.95–7.44(5H, m), 7.60(2H, d, J=8.4Hz), 8.28–8.40(1H, br), 8.70(1H, d, J=6.2Hz), 9.10(1H, s) |
| 68-2 | -O-CH₂-C₆H₄-NHAc (para) | 62 | 1.30–1.70(3H, m), 1.70–2.38(7H, m), 3.15–3.40(3H, m), 4.30(2H, t, J=8.0Hz), 4.70–4.85(1H, m), 5.68(2H, s), 5.83–6.00(1H, m), 6.60–6.80(1H, br), 6.85–7.32(5H, m), 7.52(2H, s), 8.20–8.40(1H, br), 8.78(1H, d, J=7.0Hz), 9.09(1H, s) |

Example 69-1

2-[({2-(2,3-dihydro-1H-indol-1-yl)-4-[(4-fluorobenzyl)oxy]-5-pyrimidinyl}carbonyl)amino]acetic acid

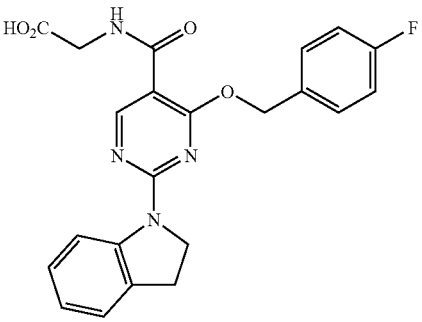

t-Butyl 2-[({2-(2,3-dihydro-1H-indol-1-yl)-4-[(4-fluorobenzyl)oxy]-5-pyrimidinyl}carbonyl)amino]acetate (210 mg, 0.4 mmol) was dissolved in trifluoroacetic acid-dichloromethane (4:1, 2 mL) and the mixture was stirred at room temperature for 15 min. The reaction mixture was concentrated under reduced pressure and the precipitated crystals were recrystallized from ethyl acetate to give the title compound (140 mg, 70%).

¹H-NMR (δ ppm, DMSO-d₆): 3.18 (3H, t, J=8.6 Hz), 3.99 (2H, d, J=5.4 Hz), 4.24 (3H, t, J=8.8 Hz), 5.68 (1H, s), 6.98 (1H, t, J=7.4 Hz), 7.14–7.30 (4H, m), 7.62 (2H, dd, J=5.6 Hz), 8.15–8.30 (2H, m), 8.55 (1H, s)

Example 70

2-(2,3-dihydro-1H-indol-1-yl)-N-[(S)-2-oxoazepanyl]-4-[(RS)-1-phenylethoxy]-5-pyrimidinecarboxamide

Example 71

2-(2,3-dihydro-1H-indol-1-yl)-4-[(RS)-1-phenylethoxy]-N-(2-pyridinylmethyl)-5-pyrimidinecarboxamide

Example 72

2-(2,3-dihydro-1H-indol-1-yl)-N-[(5-methyl-2-pyrazinyl)methyl]-4-[(RS)-1-phenylethoxy]-5-pyrimidinecarboxamide In the same manner as in Example 1-1 using ethyl 2-(2,3-dihydro-1H-indol-1-yl)-4-[(RS)-1-phenylethoxy]-5-pyrimidinecarboxylate as a starting material, compounds of Examples 70 to 72 were synthesized.

Respective structural formulas and NMR data are shown in the following Table.

TABLE 105

[Structure: pyrimidine with R-C(O)- at 5-position, -O-CH(Me)-Ph at 4-position, 2,3-dihydro-1H-indol-1-yl at 2-position]

| Example No. | R | yield (%) | ¹H-NMR (δ ppm, CDCl₃) |
|---|---|---|---|
| 70 | (S)-2-oxoazepan-3-yl-NH- | 53 | 1.32–2.19(9H, m), 2.20–2.38(1H, m), 3.05–3.40(4H, m), 4.00–4.30(2H, m), 4.78(1H, dd, J=5.8, 9.4Hz), 6.19–6.31(1H, m), 6.43(1H, br t, J=6.8Hz), 6.96(1H, t, J=7.4Hz), 7.10–7.53(6H, m), 8.00–8.40(1H, br), 9.00–9.20(2H, m) |

TABLE 105-continued

| Example No. | R | yield (%) | ¹H-NMR (δ ppm, CDCl₃) |
|---|---|---|---|
| 71 | (pyridin-2-ylmethyl)NH— | 61 | 1.87(3H, d, J=6.6Hz), 3.17(2H, t, J=8.8Hz), 4.00–4.32(3H, m), 4.84(2H, d, J=4.4Hz), 6.46(1H, q, J=6.2Hz), 6.97(1H, t, J=6.6Hz), 7.12–7.40(6H, m), 7.49(2H, dd, J=1.8, 8.0Hz), 7.70(1H, dt, J=1.4, 7.6Hz), 8.00–8.40(1H, br), 8.56(1H, d, J=4.4Hz), 9.02(1H, s), 9.15(1H, s) |
| 72 | (5-methylpyrazin-2-ylmethyl)NH— | 72 | 1.84(3H, d, J=6.6Hz), 2.58(3H, s), 3.17(2H, t, J=8.8Hz), 4.00–4.30 (3H, m), 4.83(2H, d, J=4.8Hz), 6.45(1H, q, J=6.6Hz), 6.97(1H, t, J=8.4Hz), 7.13–7.50 (6H, m), 8.00–8.35 (1H, br), 8.38(1H, s), 8.55(1H, s), 8.75(1H, t, J=5.0Hz), 9.13 (1H, s) |

Example 73

2-[(R)-2-methyl-2,3-dihydro-1H-indol-1-yl]-N-[(S)-2-oxoazepanyl]-4-[(RS)-1-phenylethoxy]-5-pyrimidinecarboxamide

Example 74

2-[(R)-2-methyl-2,3-dihydro-1H-indol-1-yl]-4-[(RS)-1-phenylethoxy]-N-(2-pyridinylmethyl)-5-pyrimidinecarboxamide

Example 75

2-[(R)-2-methyl-2,3-dihydro-1H-indol-1-yl]-N-[(5-methyl-2-pyrazinyl)methyl]-4-[(RS)-1-phenylethoxy]-5-pyrimidinecarboxamide In the same manner as in Example 1-1 using ethyl 2-[(R)-2-methyl-2,3-dihydro-1H-indol-1-yl]-4-[(RS)-1-phenylethoxy]-5-pyrimidinecarboxylate as a starting material, compounds of Examples 73 to 75 were synthesized.

Respective structural formulas and NMR data are shown in the following Table.

TABLE 106

| Example No. | R | yield (%) | ¹H-NMR (δ ppm, CDCl₃) |
|---|---|---|---|
| 73 | (S)-2-oxoazepan-3-yl-NH— | 36 | 1.20–2.15(12H, m), 2.20–2.37(1H, m), 2.65(1H, d, J=15.4Hz), 3.10–3.44 (3H, m), 4.70–5.00 (2H, m), 6.30–6.51 (1H, m), 6.52–6.70 (1H, m), 6.98(1H, t, J=7.2Hz), 7.08–7.59 (7H, m), 8.00–8.33 (1H, m), 9.00–9.20 (1H, m) |
| 74 | (pyridin-2-ylmethyl)NH— | 46 | 1.30–1.50(3H, m), 1.85(3H, d, J=6.0Hz), 2.66(1H, d, J=15.8Hz), 3.27–3.45 (1H, m), 4.70–5.05 (4H, m), 6.35–6.52 (1H, m), 6.98(1H, t, J=6.8Hz), 7.04–7.60 (8H, m), 7.69(1H, t, J=7.6Hz), 8.00–8.38 (1H, m), 8.55(1H, d, J=4.0Hz), 9.01(1H, s), 9.14(1H, s) |
| 75 | (5-methylpyrazin-2-ylmethyl)NH— | 37 | 1.20–1.40(3H, m), 1.83(3H, t, J=6.2Hz), 2.50–2.71(4H, m), 3.28–3.48(1H, m), 4.70–5.03(3H, m), 6.32–6.50(1H, m), 6.99(1H, t, J=7.0Hz), 7.01–7.50(6H, m), 8.00–8.40(3H, m), 8.55(1H, s), 8.73(1H, s), 9.13(1H, s) |

Formulation Example 1

| | | |
|---|---|---|
| (1) Example compound 66-14 | 10 mg |
| (2) lactose | 60 mg |
| (3) cornstarch | 35 mg |
| (4) gelatin | 3 mg |
| (5) magnesium stearate | 2 mg |

A mixture of Example compound 66-14 (10 mg), lactose (60 mg) and cornstarch (35 mg) was granulated using a 10% aqueous gelatin solution (0.03 ml, 3 mg of gelatin) by passing through a 1 mm mesh sieve, which granules were dried at 40° C. and passed through the sieve again. The thus-obtained granules were mixed with magnesium stearate (2 mg) and compressed. The obtained core tablet was coated with a sugar coating containing an aqueous suspension of sucrose, titanium dioxide, talc and gum arabic. The coated tablets were polished with beeswax to give coated tablets.

Formulation Example 2

| (1) Example compound 66-14 | 10 mg |
|---|---|
| (2) lactose | 70 mg |
| (3) cornstarch | 50 mg |
| (4) soluble starch | 7 mg |
| (5) magnesium stearate | 3 mg |

Example compound 66-14 (10 mg) and magnesium stearate (3 mg) were granulated using an aqueous soluble starch solution (0.07 ml, 7 mg of soluble starch), dried and mixed with lactose (70 mg) and cornstarch (50 mg). The mixture was compressed to give tablets.

Formulation Example 3

| (1) Example compound 66-14 | 5 mg |
|---|---|
| (2) common salt | 20 mg |
| (3) distilled water | to the total amount of 2 ml |

Example compound 66-14 (5 mg) and common salt (20 mg) were dissolved in distilled water. Water was added to make the total amount 2 ml. The solution was filtered and aseptically filled in 2 ml ampoules. The ampoules were sterilized and sealed to give a solution for injection.

Experimental Example 1

(1) Cloning of Gene Encoding PDE V Derived from Human Lung cDNA was cloned using a gene trapper positive selection system (Gibco BRL). The selected *Escherichia coli* was cultured and DNA was extracted, reacted using Thermo Sequenase Core Sequencing Kit (Amersham), and the nucleotide sequence of cDNA fragment was determined by SQ-3000 DNA sequencer (Hitachi). The obtained clone had a sequence consisting of 3036 bases containing a sequence consisting of 2499 bases depicted in SEQ ID No.:2. This cDNA fragment coded for novel PDE V consisting of 833 amino acids depicted in SEQ ID No.:1. The homology at the amino acid level with known bovine-derived PDE V (Linda M. McAllister et al., J. Biol. Chem. 268(30), 22863 (1993), NCBI GenBank Accession No. L16545) was 92%. A plasmid pPDE50 containing DNA encoding PDE V derived from human lung of the present invention was introduced into *Escherichia coli* (*Escherichia coli*) DH10B to give a transformant: *Escherichia coli* (*Escherichia coli*) DH10B/pPDE50.

(2) Construction of *Escherichia coli* Expression Vector

The cDNA encoding PDE V derived from human lung obtained in the above-mentioned (1) was cleaved with EcoRI and XhoI, and ligated with pGEX4T-2 (Pharmacia Biotech) treated in the same manner. Using a ligation solution, *Escherichia coli* BL21 (Funakoshi) was transformed to give *Escherichia coli* (*Escherichia coli*) BL21/pPDE51 that expresses PDE V derived from human lung of the present invention.

This transformant: *Escherichia coli* BL21/pPDE51 has been deposited at the National Institute of Bioscience and Human-Technology (NIBH) since Jul. 13, 1998 under deposit No. FERM BP-6417 and at the Institute for Fermentation, Osaka under deposit No. IFO 16185 since Jun. 18, 1998.

(3) Expression and Purification of Recombinant Type PDE V Derived from Human Lung in *Escherichia coli*

Using *Escherichia coli* BL21/pPDE51 obtained in the above-mentioned (2), recombinant type PDE V derived from human lung of the present invention was obtained. The expression and purification by *Escherichia coli* were done in accordance with the protocol attached to GST Gene Fusion System (Pharmacia Biotech). As a result, 12.5 mg of the objective ca. 100 kDa recombinant type PDE V derived from human lung was obtained from 1 L of *Escherichia coli* culture.

(4) Detection of PDE Activity of PDE V Derived from Human Lung

The PDE activity of PDE V derived from human lung was detected using Phosphodiesterase [$^3$H]cGMP SPA enzyme assay kit (Amersham). As a result, PDE activity was acknowledged in the enzyme solution obtained in the above-mentioned (2). BL21 was transformed with pGEX4T-2 and used as a control. This did not show PDE activity.

(5) Designing Inhibitor Search System

Into a 96 well plate (OPTI plate, Packard) was added a buffer [10 μl, 0.5M Tris-HCl (pH 7.5), 83 mM MgCl$_2$ and 17 mM EGTA], the recombinant type PDE V derived from human lung (10 μl, 0.025 mg/ml) obtained in the above-mentioned (3), ultrapure water (65 μl), inhibitor sample (5 μl) and [$^3$H]cGMP (10 μl), and the mixture was allowed to react at 30° C. for 30 min. After the completion of the reaction, SPA beads solution [50 μl, 18 mg/ml Yttrium silicate beads, 18 mM ZnSO$_4$] was added and the mixture was stood at room temperature for about 20 min, after which applied to measurement with a scintillation counter (Topcount, Packard). In contrast to the radioactivity (1780 cpm) without addition, the radioactivity of 10367 cpm was observed when the recombinant type PDE V derived from human lung was added. Addition of various concentrations of sildenafil (Drugs of Future 22(2), 1997), which is an inhibitor of PDE V, to this reaction resulted in the inhibition of PDE activity. About 2 nM of sildenafil inhibited the enzyme reaction by 50%. Based on such results, it was confirmed that search of PDE inhibitor is possible using this assay system.

(6) Practicing Inhibitor Search

Using the method designed in the above-mentioned (5), the representative compound of the present invention was measured for recombinant type human lung derived PDE inhibitory activity (IC$_{50}$ value). The results are shown in Table 107.

TABLE 107

| Example | PDE inhibitory activity (IC$_{50}$: nM) |
|---|---|
| 31-6 | 1.47 |
| 33-3 | 0.582 |
| 66-6 | 0.304 |

INDUSTRIAL APPLICABILITY

The compound (I), a salt thereof and a prodrug thereof of the present invention have a potent and selective cGMP-PDE, particularly cGMP-PDE V, inhibitory activity, and can be used as an agent for the prophylaxis or treatment of diseases caused by promoted metabolism of cGMP (e.g., angina pectoris, heart failure, cardiac infarction, hypertension, pulmonary hypertension, arteriosclerosis, allergic diseases, asthma, renal diseases, cerebral function disorders, immunodeficiency, ophthalmic diseases, or disorders of male or female genital function and the like).

The invention claimed is:

1. A compound of the formula

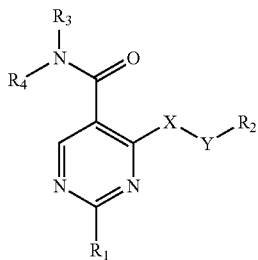

wherein

R$_1$ is a heterocycle having a skeleton consisting of 8 to 12 atoms including a nitrogen atom and optionally substituted by substituent(s) selected from the group consisting of C$_{1-8}$ alkyl, C$_{2-8}$ alkenyl, C$_{2-8}$ alkynyl, C$_{7-16}$ aralkyl, C$_{3-8}$ cycloalkyl, C$_{3-8}$ cycloalkenyl, C$_{6-14}$ aryl, C$_{1-8}$ alkoxy, C$_{1-3}$ alkylenedioxy, hydroxy, halogen atom, amino, (di or mono-(C$_{1-5}$ alkyl)amino, (C$_{1-5}$ alkoxy-carbonyl)amino, (C$_{1-5}$ acyl)amino, (C$_{1-5}$ acyl)(C$_{1-5}$ alkyl)amino, C$_{1-5}$ alkylthio, nitrile, nitro, C$_{1-5}$ alkoxy-carbonyl, carboxyl, C$_{1-5}$ alkyl-carbonyloxy, oxo, thioxo, C$_{1-6}$ acyl group, sulfamoyl and (di or mono-C$_{1-5}$ alkyl)sulfamoyl;

X is an oxygen atom, NH or a sulfur atom optionally oxidized with 1 or 2 oxygens, Y is a bond or a C$_{1-5}$ alkylene group, R$_2$ is (1) a hydrogen atom, (2) a hydroxy group, (3) a C$_{1-5}$ alkoxy group, (4) a C$_{1-5}$ alkylthio group, (5) a carbocycle having 3 to 15 carbon atoms or (6) a heterocycle having a skeleton consisting of 3 to 15 atoms including 1 to 5 heteroatom(s), provided that when Y is a bond, R$_2$ is a carbocycle having 3 to 15 carbon atoms or a heterocycle having a skeleton consisting of 3 to 15 atoms including 1 to 5 heteroatom(s) and;

one of R$_3$ and R$_4$ is a hydrogen atom or a group of the formula: —Z—R$_5$ (Z is a bond or C$_{1-10}$ alkylene group optionally having substituent(s) and R$_5$ is (1) a hydrogen atom, (2) a hydroxy group, (3) a (C$_{1-5}$ alkoxy group, (4) a nitrile group, (5) a (C$_{1-5}$ alkoxy-carbonyl group, (6) a carboxyl group, (7) a carbamoyl group, (8) a (mono or di-C$_{1-5}$ alkyl)carbamoyl group, (9) an amino group, (10) a (di or mono-C$_{1-5}$ alkyl)amino group, (11) a (C$_{1-5}$ alkoxy-carbonyl)amino group, (12) a C$_{1-5}$ alkylthio group, (13) a carbocycle having 3 to 15 carbon atoms or (14) a heterocycle having a skeleton consisting of 3 to 15 atoms including 1 to 5 heteroatom(s));

the other is a group of the formula: —Z—R$_5$ (Z and R$_5$ are as defined above);

or R$_3$ and R$_4$ may form, together with the adjacent nitrogen atom, a heterocycle having a skeleton consisting of 3 to 15 atoms, which heterocycle is attached by a secondary nitrogen atom constituting the heterocycle, wherein the above-mentioned heterocycle and a carbocycle having 3 to 15 carbon atoms are each optionally substituted by substituent(s) selected from the group consisting of C$_{1-8}$ alkyl, C$_{2-8}$ alkenyl, C$_{2-8}$ alkynyl, C$_{7-16}$ aralkyl, C$_{3-8}$ cycloalkyl, C$_{3-8}$ cycloalkenyl, C$_{6-14}$ aryl, C$_{1-8}$ alkoxy, C$_{1-3}$ alkylenedioxy, hydroxy, halogen atom, amino, (di or mono-C$_{1-5}$ alkyl)amino, (C$_{1-5}$ alkoxy-carbonyl)amino, (C$_{1-5}$ acyl)amino, (C$_{1-5}$ acyl)(C$_{1-5}$ alkyl)amino, C$_{1-5}$ alkylthio, nitrile, nitro, C$_{1-5}$ alkoxy-carbonyl, carboxyl, (C$_{1-5}$ alkyl-carbonyloxy, oxo, thioxo, $C_{1-6}$ acyl group, sulfamoyl and (di or mono-$C_{1-5}$ alkyl)sulfamoyl, or a salt thereof.

2. The compound of claim 1, wherein X is NH or a sulfur atom optionally oxidized with 1 or 2 oxygens.

3. The compound of claim 1, wherein Y is a $C_{2-5}$ alkylene group.

4. The compound of claim 1, wherein Y is a $C_{1-5}$ alkylene group, $R_2$ is a hydroxy group, a $C_{1-5}$ alkoxy group or a $C_{1-5}$ alkylthio group.

5. The compound of claim 1, wherein $R_5$ is (1) a non-aromatic carbocycle having 3 to 15 carbon atoms or (2) a non-aromatic heterocycle having a skeleton consisting of 3 to 15 atoms including 1 to 5 heteroatom(s).

6. The compound of claim 1, wherein Z is a $C_{2-10}$ alkylene group optionally having substituent(s), and $R_5$ is a hydroxy group, a nitrile group, a $C_{1-5}$ alkoxy-carbonyl, a carboxyl group, a carbamoyl group, a (mono or di-$C_{1-5}$ alkyl)carbamoyl group, a ($C_{1-5}$ alkoxy-carbonyl)amino group or a $C_{1-5}$ alkylthio group.

7. The compound of claim 1, wherein Z is a methylene group optionally having substituent(s), and $R_5$ is a nitrile group, a $C_{1-5}$ alkoxy-carbonyl group, a carboxyl group, a carbamoyl group or a (mono or di-$C_{1-5}$ alkyl)carbamoyl group.

8. The compound of claim 1, wherein the substituent(s) of the heterocycle and the carbocycle having 3 to 15 carbon atoms is selected from the group consisting of $C_{2-8}$ alkenyl, $C_{2-8}$ alkynyl, $C_{7-16}$ aralkyl, $C_{3-8}$ cycloalkyl, $C_{3-8}$ cycloalkenyl, $C_{6-14}$ aryl, $C_{1-3}$ alkylenedioxy, hydroxy, ($C_{1-5}$ alkoxy-carbonyl)amino, ($C_{1-5}$ acyl)amino, ($C_{1-5}$ acyl)($C_{1-5}$ alkyl)amino, ($C_{1-5}$ alkylthio, nitrile, ($C_{1-5}$ alkoxy-carbonyl, carboxyl, ($C_{1-5}$ alkyl-carbonyloxy, oxo, thioxo, $C_{1-6}$ acyl group, sulfamoyl and (di or mono-$C_{1-5}$ alkyl)sulfamoyl.

9. The compound of claim 1, wherein $R_1$ is 1-indolinyl optionally substituted by substituent(s) selected from the group consisting of $C_{1-8}$ alkyl, $C_{2-8}$ alkenyl, $C_{2-8}$ alkynyl, $C_{7-16}$ aralkyl, $C_{3-8}$ cycloalkyl, $C_{3-8}$ cycloalkenyl, $C_{6-14}$ aryl, $C_{1-8}$ alkoxy, $C_{1-3}$ alkylenedioxy, hydroxy, halogen atom, amino, (di or mono-$C_{1-5}$ alkyl)amino, ($C_{1-5}$ alkoxy-carbonyl)amino, ($C_{1-5}$ acyl)amino, ($C_{1-5}$ acyl)($C_{1-5}$ alkyl)amino, $C_{1-5}$ alkylthio, nitrile, nitro, $C_{1-5}$ alkoxy-carbonyl, carboxyl, $C_{1-5}$ alkyl-carbonyloxy, oxo, thioxo, $C_{1-6}$ acyl group, sulfamoyl and (di or mono-$C_{1-5}$ alkyl)sulfamoyl.

10. The compound of claim 1, wherein $R_2$ is a carbocycle having 5 to 7 carbon atoms or a heterocycle having a skeleton consisting of 5 to 7 atoms including 1 or 2 heteroatom(s), which heterocycle is optionally substituted by substituent(s) selected from the group consisting of $C_{1-8}$ alkyl, $C_{2-8}$ alkenyl, $C_{2-8}$ alkynyl, $C_{7-16}$ aralkyl, $C_{3-8}$ cycloalkyl, $C_{3-8}$ cycloalkenyl, $C_{6-14}$ aryl, $C_{1-8}$ alkoxy, $C_{1-3}$ alkylenedioxy, hydroxy, halogen atom, amino, (di or mono-$C_{1-5}$ alkyl)amino, ($C_{1-5}$ alkoxy-carbonyl)amino, ($C_{1-5}$ acyl)amino, ($C_{1-5}$ acyl)($C_{1-5}$ alkyl)amino, $C_{1-5}$ alkylthio, nitrile, nitro, $C_{1-5}$ alkoxy-carbonyl, carboxyl, $C_{1-5}$ alkyl-carbonyloxy, oxo, thioxo, $C_{1-6}$ acyl group, sulfamoyl and (di or mono-$C_{1-5}$ alkyl)sulfamoyl.

11. The compound of claim 1, wherein $R_2$ is phenyl optionally substituted by substituent(s) selected from the group consisting of $C_{1-8}$ alkyl, $C_{2-8}$ alkenyl, $C_{2-8}$ alkynyl, $C_{7-16}$ aralkyl, $C_{3-8}$ cycloalkyl, $C_{3-8}$ cycloalkenyl, $C_{6-14}$ aryl, $C_{1-8}$ alkoxy, $C_{1-3}$ alkylenedioxy, hydroxy, halogen atom, amino, (di or mono-$C_{1-5}$ alkyl)amino, ($C_{1-5}$ alkoxy-carbonyl)amino, ($C_{1-5}$ acyl)amino, ($C_{1-5}$ acyl)($C_{1-5}$ alkyl)amino, $C_{1-5}$ alkylthio, nitrile, nitro, $C_{1-5}$ alkoxy-carbonyl, carboxyl, $C_{1-5}$ alkyl-carbonyloxy, oxo, thioxo, $C_{1-6}$ acyl group, sulfamoyl and (di or mono-$C_{1-5}$ alkyl)sulfamoyl.

12. The compound of claim 1, wherein X is an oxygen atom or NH, and Y is a $C_{1-3}$ alkylene group.

13. The compound of claim 1, wherein X is an oxygen atom, and Y is a methylene group.

14. The compound of claim 1, wherein $R_3$ is a hydrogen atom and $R_4$ is a group of the formula: —Z—$R_5$.

15. The compound of claim 14, wherein Z is a bond or a $C_{1-4}$ alkylene group, $R_5$ is a carbocycle having 5 to 8 carbon atoms or a heterocycle having a skeleton consisting of 5 to 11 atoms having 1 to 5 heteroatom(s), which heterocycle is optionally substituted by substituent(s) selected from the group consisting of $C_{1-8}$ alkyl, $C_{2-8}$ alkenyl, $C_{2-8}$ alkynyl, $C_{7-16}$ aralkyl, $C_{3-8}$ cycloalkyl, $C_{3-8}$ cycloalkenyl, $C_{6-14}$ aryl, $C_{1-8}$ alkoxy, $C_{1-3}$ alkylenedioxy, hydroxy, halogen atom, amino, (di or mono-$C_{1-5}$ alkyl)amino, ($C_{1-5}$ alkoxy-carbonyl)amino, ($C_{1-5}$ acyl)amino, ($C_{1-5}$ acyl)($C_{1-5}$ alkyl)amino, $C_{1-5}$ alkylthio, nitrile, nitro, $C_{1-5}$ alkoxy-carbonyl, carboxyl, $C_{1-5}$ alkyl-carbonyloxy, oxo, thioxo, $C_{1-6}$ acyl group, sulfamoyl and (di or mono-$C_{1-5}$ alkyl)sulfamoyl.

16. The compound of claim 1, wherein $R_1$ is a group selected from

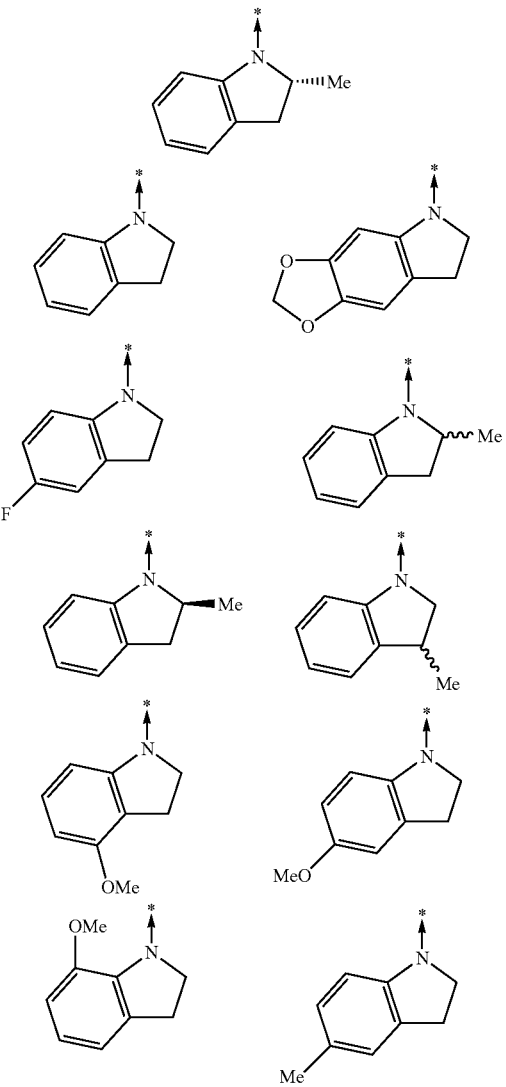

-continued
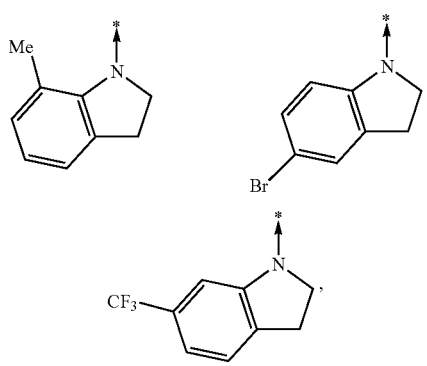
—X—Y—R$_2$ is a group selected from
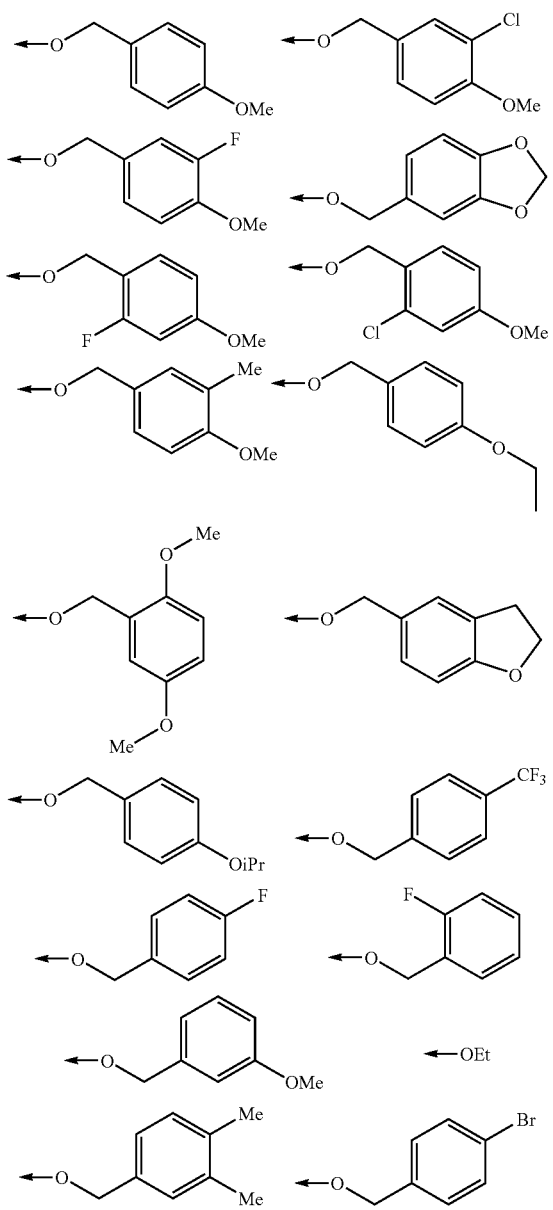
-continued
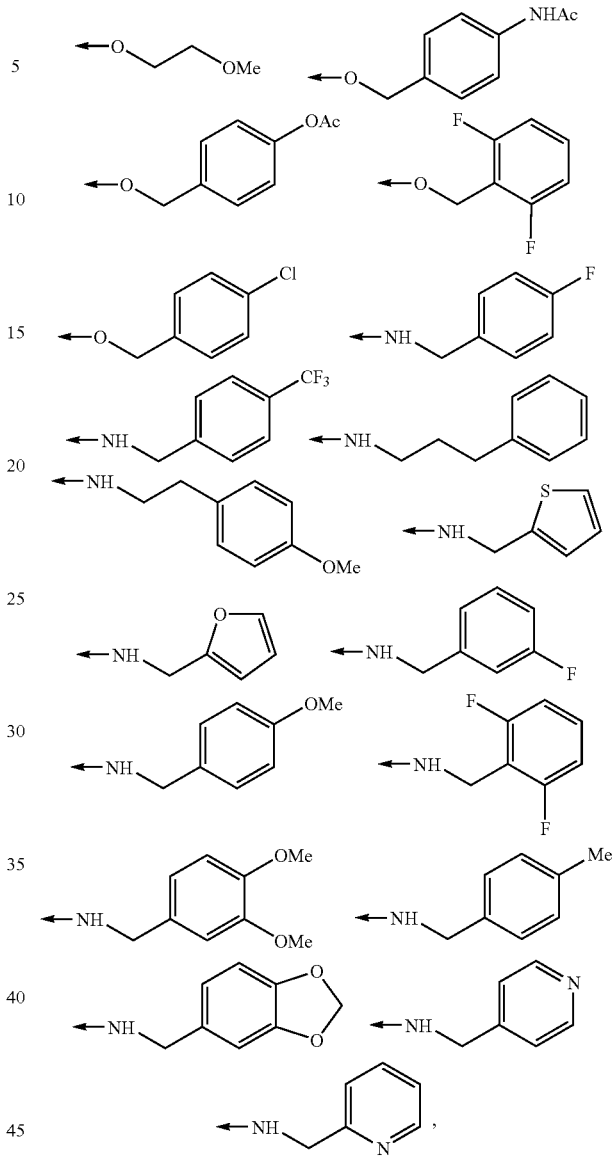
and —NR$_3$R$_4$ is a group selected from
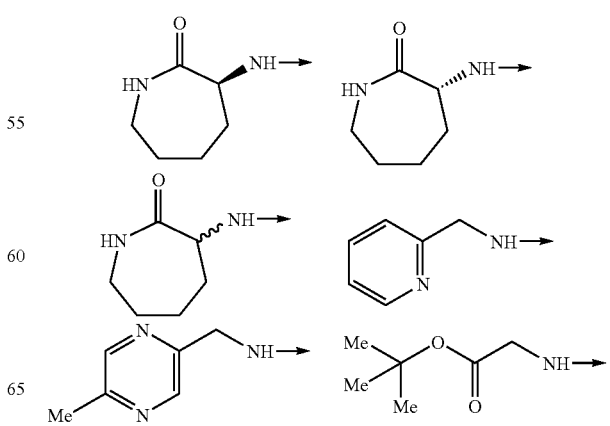

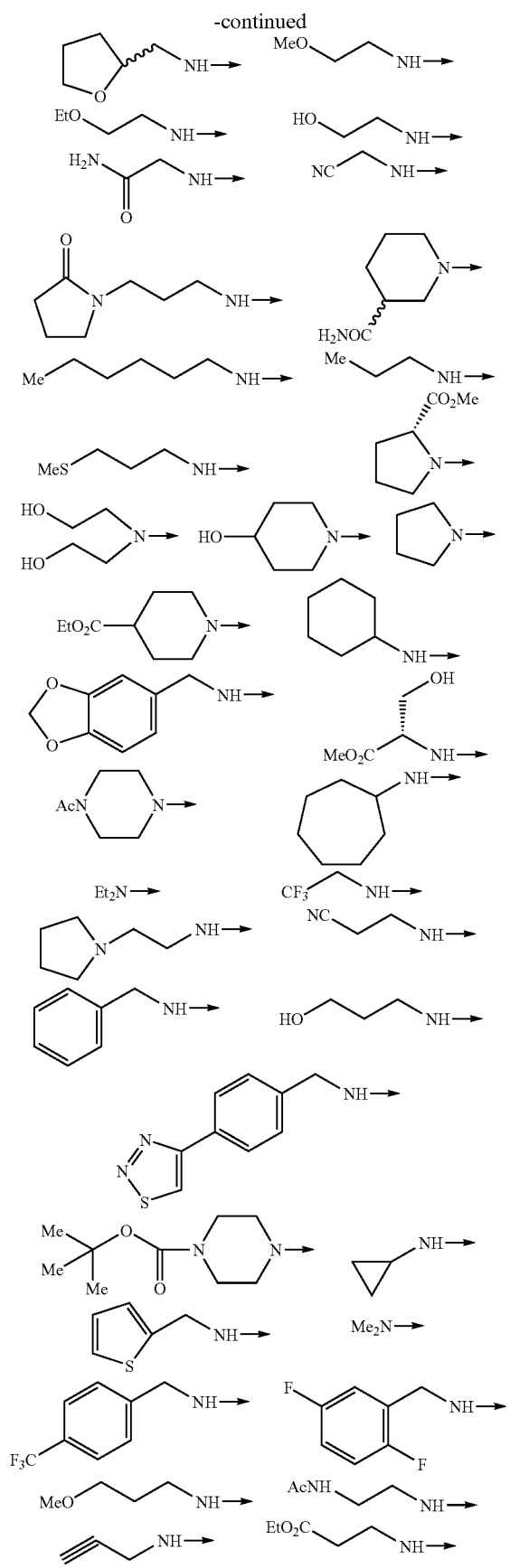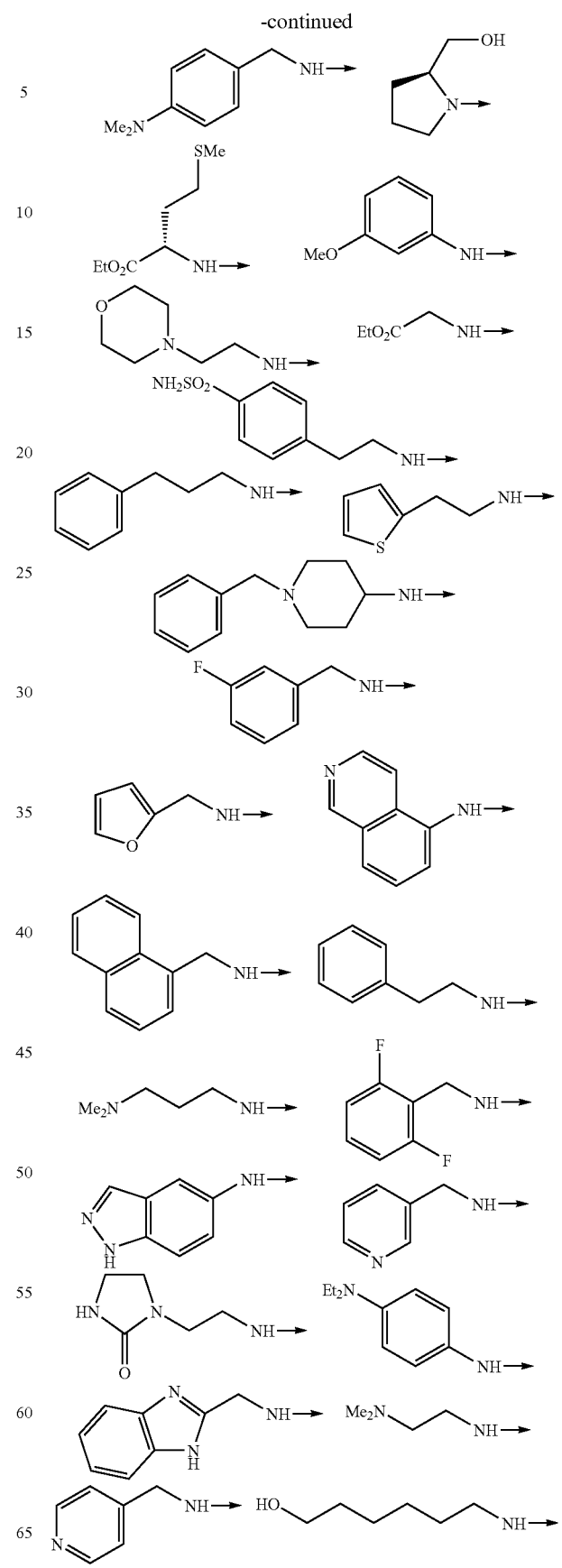

-continued
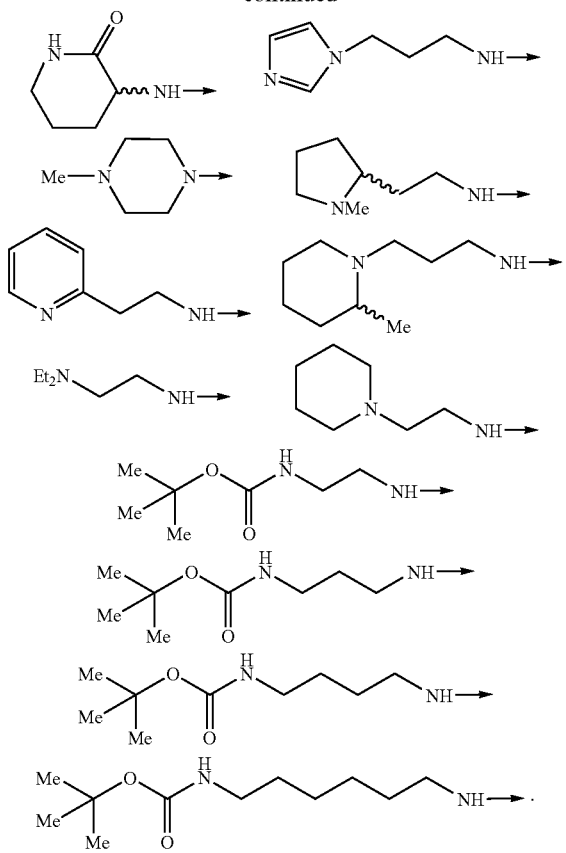
17. The compound of claim 1, wherein $R_1$ is a group selected from
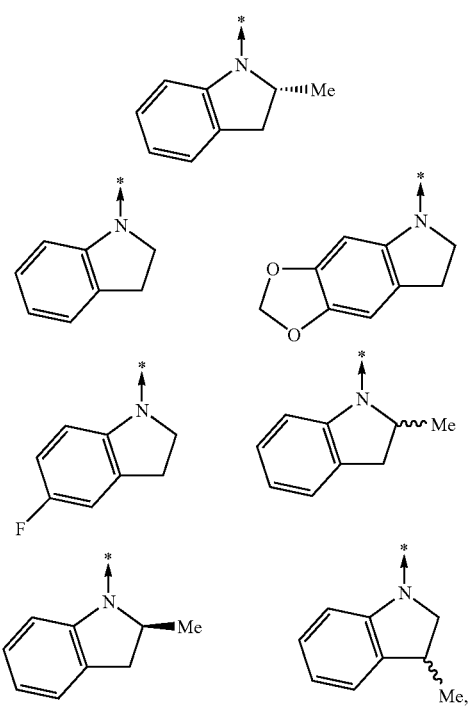
—X—Y—$R_2$ is a group selected from
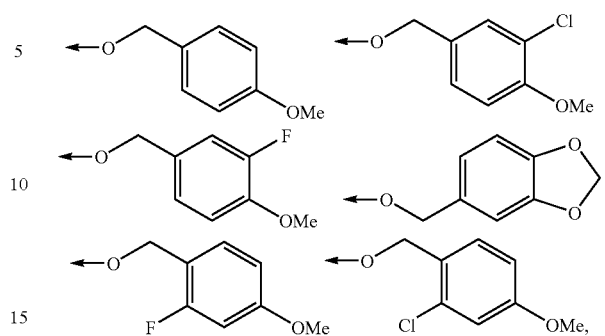
and —$NR_3R_4$ is a group selected from
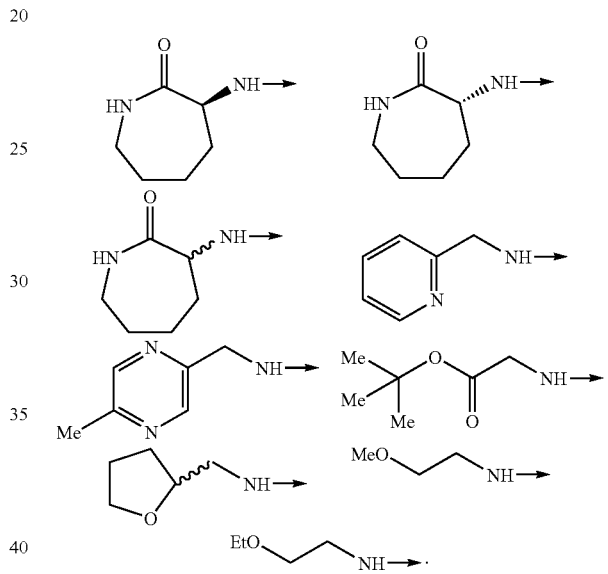
18. The compound of claim 1, wherein $R_1$ is a group selected from the group consisting of
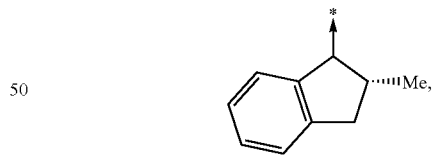
—X—Y—$R_2$ is a group selected from the group consisting of
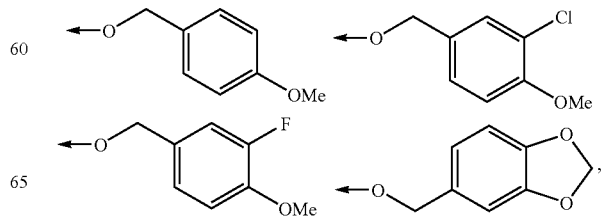

and —NR₃R₄ is a group selected from the group consisting of

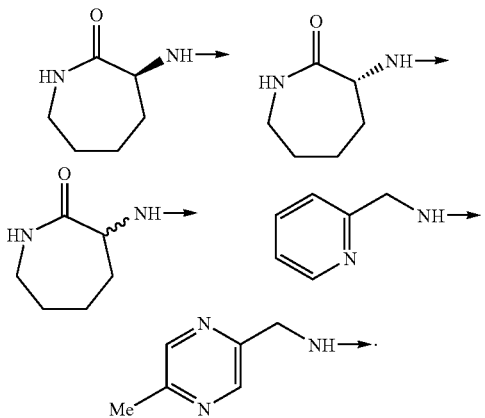

19. The compound of claim 1, wherein when Z is a $C_{2-10}$ alkylene group optionally having substituent(s), R₅ is a hydrogen atom, a hydroxy group, a $C_{1-5}$ alkoxy group, a nitrile group, a $C_{1-5}$ alkoxy-carbonyl, a carboxyl group, a carbamoyl group, a (mono or di-$C_{1-5}$ alkyl)carbamoyl group, an amino group, a (di or mono-$C_{1-5}$ alkyl)amino group, a ($C_{1-5}$ alkoxy-carbonyl)amino group, a $C_{1-5}$ alkylthio group, a carbocycle having 3 to 15 carbon atoms, or a heterocycle having a skeleton consisting of 3 to 15 atoms including 1 to 5 heteroatom(s) or when Z is a methylene group optionally having substituents, R₅ is a nitrile group, a $C_{1-5}$ alkoxy-carbonyl group, a carboxyl group, a carbamoyl group, a (mono or di-$C_{1-5}$ alkyl)carbamoyl group, a carbocycle having 3 to 15 carbon atoms, or a heterocycle having a skeleton consisting of 3 to atoms including 1 to 5 heteroatom(s).

20. (i) (RS)-2-(2,3-Dihydro-1H-indol-1-yl)-4-[(4-methoxybenzyl)oxy]-N-(2-oxo-3-azepanyl)-5-pyrimidinecarboxamide, (ii) 2-(2,3-dihydro-1H-indol-1-yl)-4-[(4-methoxybenzyl)oxy]-N-[(5-methyl-2-pyrazinyl)methyl]-5-pyrimidinecarboxamide, (iii) 2-(2,3-dihydro-1H-indol-1-yl)-4-[(4-methoxybenzyl)oxy]-N-(2-pyridinylmethyl)-5-pyrimidinecarboxamide, (iv) (RS)-4-(1,3-benzodioxol-5-ylmethoxy)-2-(2,3-dihydro-1H-indol-1-yl)-N-(2-oxo-3-azepanyl)-5-pyrimidinecarboxamide, (v) 4-(1,3-benzodioxol-5-ylmethoxy)-2-(2,3-dihydro-1H-indol-1-yl)-N-(2-pyridinylmethyl)-5-pyrimidinecarboxamide, (vi) 2-(2,3-dihydro-1H-indol-1-yl)-4-[(3-fluoro-4-methoxybenzyl)oxy]-N-(2-pyridinylmethyl)-5-pyrimidinecarboxamide, (vii) 2-(2,3-dihydro-1H-indol-1-yl)-4-[(3-fluoro-4-methoxybenzyl)oxy]-N-(2-oxo-3-azepanyl)-5-pyrimidinecarboxamide, (viii) 2-(2,3-dihydro-1H-indol-1-yl)-4-[(3-fluoro-4-methoxybenzyl)oxy]-N-[(5-methyl-2-pyrazinyl)methyl]-5-pyrimidinecarboxamide, (ix) 4-[(3-chloro-4-methoxybenzyl)oxy]-2-(2,3-dihydro-1H-indol-1-yl)-N-(2-pyridinylmethyl)-5-pyrimidinecarboxamide, (x) 4-[(3-chloro-4-methoxybenzyl)oxy]-2-(2,3-dihydro-1H-indol-1-yl)-N-(2-oxo-3-azepanyl)-5-pyrimidinecarboxamide, (xi) 4-[(3-chloro-4-methoxybenzyl)oxy]-2-(2,3-dihydro-1H-indol-1-yl)-N-[(5-methyl-2-pyrazinyl)methyl]-5-pyrimidinecarboxamide, (xii) (rac)-4-[(4-methoxybenzyl)oxy]-2-(2-methyl-2,3-dihydro-1H-indol-1-yl)-N-(2-oxo-3-azepanyl)-5-pyrimidinecarboxamide, (xiii) 2-(2,3-dihydro-1H-indol-1-yl)-4-[(4-methoxybenzyl)oxy]-N-[(3 S)-2-oxoazepanyl]-5-pyrimidinecarboxamide, (xiv) 2-(2,3-dihydro-1H-indol-1-yl)-4-[(4-methoxybenzyl)oxy]-N-[(3R)-2-oxoazepanyl]-5-pyrimidinecarboxamide, (xv) 4-(1,3-benzodioxol-5-ylmethoxy)-2-(2,3-dihydro-1H-indol-1-yl)-4-[(4-methoxybenzyl)oxy]-N-[(3S)-2-oxoazepanyl]-5-pyrimidinecarboxamide, (xvi) 2-(2,3-dihydro-1H-indol-1-yl)-4-[(3-fluoro-4-methoxybenzyl)oxy]-N-[(3S)-2-oxoazepanyl]-5-pyrimidinecarboxamide, (xvii) 4-[(3-chloro-4-methoxybenzyl)oxy]-2-(2,3-dihydro-1H-indol-1-yl)-N-[(3 S)-2-oxoazepanyl]-5-pyrimidinecarboxamide, (xviii) 4-[(4-methoxybenzyl)oxy]-2-[(2RS)-2-methyl-2,3-dihydro-1H-indol-1-yl]-N-[(3S)-2-oxoazepanyl]-5-pyrimidinecarboxamide, (xix) 4-[(4-methoxybenzyl)oxy]-2-[(2RS)-2-methyl-2,3-dihydro-1H-indol-1-yl]-N-[(3R)-2-oxoazepanyl]-5-pyrimidinecarboxamide, (xx) 4-[(4-methoxybenzyl)oxy]-2-[(2R)-2-methyl-2,3-dihydro-1H-indol-1-yl]-N-[(3 S)-2-oxoazepanyl]-5-pyrimidinecarboxamide, (xxi) 4-[(4-methoxybenzyl)oxy]-2-[(2R)-2-methyl-2,3-dihydro-1H-indol-1-yl]-N-[(3R)-2-oxoazepanyl]-5-pyrimidinecarboxamide, (xxii) 2-[(2R)-2-methyl-2,3-dihydro-1H-indol-1-yl]-4-[(3-fluoro-4-methoxybenzyl)oxy]-N-[(3S)-2-oxoazepanyl]-5-pyrimidinecarboxamide, (xxiii) 4-[(3-chloro-4-methoxybenzyl)oxy]-2-[(2R)-2-methyl-2,3-dihydro-1H-indol-1-yl]-N-[(3 S)-2-oxoazepanyl]-5-pyrimidinecarboxamide, (xxiv) 4-[(4-methoxybenzyl)oxy]-2-[(2S)-2-methyl-2,3-dihydro-1H-indol-1-yl]-N-[(3S)-2-oxoazepanyl]-5-pyrimidinecarboxamide or (xxv) 4-[(4-methoxybenzyl)oxy]-2-[(2S)-2-methyl-2,3-dihydro-1H-indol-1-yl]-N-[(3R)-2-oxoazepanyl]-5-pyrimidinecarboxamide.

21. A prodrug of the compound of the formula

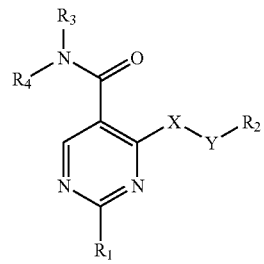

wherein

R₁ is a heterocycle having a skeleton consisting of 8 to 12 atoms including a nitrogen atom and optionally substituted by substituent(s) selected from the group consisting of $C_{1-8}$ alkyl $C_{2-8}$ alkenyl, $C_{2-8}$ alkynyl, $C_{7-16}$ aralkyl, $C_{3-8}$ cycloalkyl, $C_{3-8}$ cycloalkenyl, $C_{6-14}$ aryl, $C_{1-8}$ alkoxy, $C_{1-3}$ alkylenedioxy, hydroxy, halogen atom, amino, (di or mono-$C_{1-5}$ alkyl)amino, ($C_{1-5}$ alkoxy-carbonyl)amino, ($C_{1-5}$ acyl)amino, ($C_{1-5}$ acyl)($C_{1-5}$ alkyl)amino, $C_{1-5}$ alkylthio, nitrile, nitro, $C_{1-5}$ alkoxy-carbonyl, carboxyl, $C_{1-5}$ alkyl-carbonyloxy, oxo, thioxo, $C_{1-6}$ acyl group, sulfamoyl and (di or mono-($C_{1-5}$ alkyl)sulfamoyl;

X is an oxygen atom, NH or a sulfur atom optionally oxidized with 1 or 2 oxygens, Y is a bond or a $C_{1-5}$ alkylene group, R₂ is (1) a hydrogen atom, (2) a hydroxy group, (3) a $C_{1-5}$ alkoxy group, (4) a $C_{1-5}$ alkylthio group, (5) a carbocycle having 3 to 15 carbon atoms or (6) a heterocycle having a skeleton consisting of 3 to 15 atoms including 1 to 5 heteroatom(s), provided that when Y is a bond, $R_2$ is a carbocycle having 3 to 15 carbon atoms or a heterocycle having a skeleton consisting of 3 to 15 atoms including 1 to 5 heteroatom(s) and;

one of $R_3$ and $R_4$ is a hydrogen atom or a group of the formula: $-Z-R_5$ (Z is a bond or $C_{1-10}$ alkylene group optionally having substituent(s) and $R_5$ is (1) a hydrogen atom, (2) a hydroxy group, (3) a $C_{1-5}$ alkoxy group, (4) a nitrile group, (5) a $C_{1-5}$ alkoxy-carbonyl group, (6) a carboxyl group, (7) a carbamoyl group, (8) a (mono or di-$C_{1-5}$ alkyl)carbamoyl group, (9) an amino group, (10) a (di or mono-$C_{1-5}$ alkyl)amino group, (11) a ($C_{1-5}$ alkoxy-carbonyl)amino group, (12) a $C_{1-5}$ alkylthio group, (13) a carbocycle having 3 to 15 carbon atoms or (14) a heterocycle having a skeleton consisting of 3 to 15 atoms including 1 to 5 heteroatom(s));

the other is a group of the formula: $-Z-R_5$ (Z and $R_5$ are as defined above);

or $R_3$ and $R_4$ may form, together with the adjacent nitrogen atom, a heterocycle having a skeleton consisting of 3 to 15 atoms, which heterocycle is attached by a secondary nitrogen atom constituting the heterocycle, wherein the above-mentioned heterocycle and a carbocycle having 3 to 15 carbon atoms are each optionally substituted by substituent(s) selected from the group consisting of $C_{1-8}$ alkyl, $C_{2-8}$ alkenyl, $C_{2-8}$ alkynyl, $C_{7-16}$ aralkyl, $C_{3-8}$ cycloalkyl, $C_{3-8}$ cycloalkenyl, $C_{6-14}$ aryl, $C_{1-8}$ alkoxy, $C_{1-3}$ alkylenedioxy, hydroxy, halogen atom, amino, (di or mono-$C_{1-5}$ alkyl)amino, ($C_{1-5}$ alkoxy-carbonyl)amino, ($C_{1-5}$ acyl)amino, ($C_{1-5}$ acyl)($C_{1-5}$ alkyl)amino, $C_{1-5}$ alkylthio, nitrile, nitro, $C_{1-5}$ alkoxy-carbonyl, carboxyl, $C_{1-5}$ alkyl-carbonyloxy, oxo, thioxo, $C_{1-6}$ acyl group, sulfamoyl and (di or mono-$C_{1-5}$ alkyl)sulfamoyl, or a salt thereof;

which is selected from the group consisting of (1) a prodrug wherein an amino group of said compound is acylated, alkylated or phosphorylated; (2) a prodrug wherein a hydroxy group of said compound is acylated, alkylated, phosphorylated or borated; and (3) a prodrug wherein an esterified or amidated carboxyl group of said compound is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified or methylamidated.

22. A production method of the compound of claim 1, which comprises reacting a compound of the formula

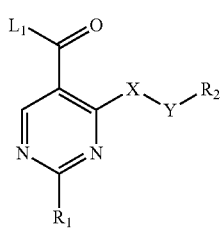

(II)

wherein $L_1$ is a leaving group and other symbols are as defined in claim 1, or a salt thereof, with an amine compound of the formula $R_3R_4NH$ wherein $R_3$ and $R_4$ are as defined in claim 1.

23. A production method of the compound of claim 1, which comprises reacting a compound of the formula

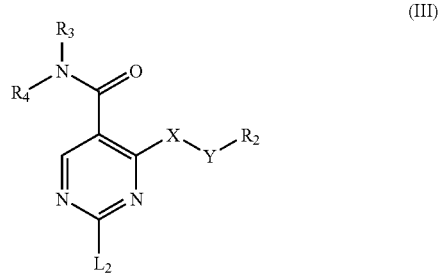

(III)

wherein $L_2$ is a leaving group and other symbols are as defined in claim 1, or a salt thereof, with a compound of the formula $R_1-H$ wherein $R_1$ is as defined in claim 1.

24. A production method of the compound of claim 1, which comprises reacting a compound of the formula

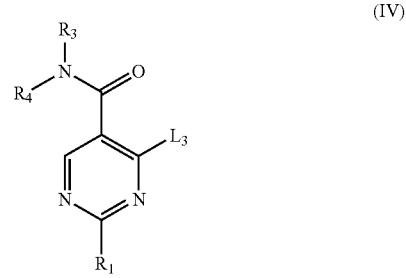

(IV)

wherein $L_3$ is a leaving group and other symbols are as defined in claim 1, or a salt thereof, with a compound of the formula $R_2-Y-X_1-H$ wherein $R_2$ and Y are as defined in claim 1 and $X_1$ is an oxygen atom, a nitrogen atom optionally substituted by a hydrocarbon group having 1 to 5 carbon atom(s) or a sulfur atom, and if desired, subjecting the resulting compound to oxidation.

25. A production method of the compound of claim 1, which comprises reacting a compound of the formula

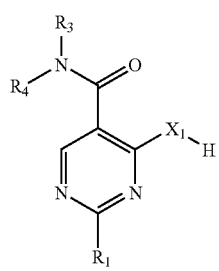

(V)

wherein symbols are as defined in claim 1, $X_1$ is an oxygen atom, a nitrogen atom optionally substituted by a hydrocarbon group having 1 to 5 carbon atom(s) or a sulfur atom, or a salt thereof, with a compound of the formula $$R_2-Y-L_4$$

wherein $R_2$ and Y are as defined in claim 1 and $L_4$ is a leaving group, and if desired, subjecting the resulting compound to oxidation.

26. A pharmaceutical composition comprising a compound of the formula

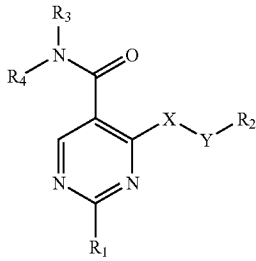

wherein symbols are as defined in claim 1, or a salt thereof or a prodrug of claim 21.

27. A method for inhibiting cGMP-PDE V which comprises administering an effective amount of the compound of claim 1 or a prodrug of claim 21 thereof to a mammal in need thereof.

28. A method for the treatment of pulmonary hypertension or disorders of male genital function in a mammal, which comprises administering an effective amount of the compound of claim 1 or a prodrug of claim 21 thereof to a mammal in need thereof.

* * * * *

UNITED STATES PATENT AND TRADEMARK OFFICE
CERTIFICATE OF CORRECTION

PATENT NO. : 7,087,597 B1
APPLICATION NO. : 10/110381
DATED : August 8, 2006
INVENTOR(S) : Tetsuo Miwa et al.

It is certified that error appears in the above-identified patent and that said Letters Patent is hereby corrected as shown below:

On the Front Page,

Under Section (54) please correct the Title to read as follows:

-- PYRIMIDINE-5-CARBOXAMIDE COMPOUNDS, PROCESS FOR PRODUCING THE SAME AND USE THEREOF --

Signed and Sealed this

Fifth Day of December, 2006

JON W. DUDAS
*Director of the United States Patent and Trademark Office*